(12) United States Patent
Bollbuck et al.

(10) Patent No.: US 7,615,562 B2
(45) Date of Patent: Nov. 10, 2009

(54) 2-AMINOPYRIMIDINE DERIVATIVES AND THEIR MEDICAL USE

(75) Inventors: Birgit Bollbuck, Weil am Rhein (DE); Alastair DenholmMritain, Horsham (GB); Jörg Eder, Rheinfelden (DE); René Hersperger, Münchenstein (CH); Philipp Janser, Basel (CH); László Révész, Therwil (CH); Achim Schlapbach, Lörrach (DE); Rudolf Wálchi, Basel (CH)

(73) Assignee: Novartis AG, Basel (CH)

( * ) Notice: Subject to any disclaimer, the term of this patent is extended or adjusted under 35 U.S.C. 154(b) by 475 days.

(21) Appl. No.: 10/552,317

(22) PCT Filed: Apr. 8, 2004

(86) PCT No.: PCT/EP2004/003819

§ 371 (c)(1),
(2), (4) Date: Jul. 6, 2006

(87) PCT Pub. No.: WO2004/089913

PCT Pub. Date: Oct. 21, 2004

(65) Prior Publication Data

US 2007/0043048 A1    Feb. 22, 2007

(30) Foreign Application Priority Data

Apr. 11, 2003   (GB)   .................. 0308466.2

(51) Int. Cl.
*C07D 239/42*   (2006.01)
*C07D 403/04*   (2006.01)
*A61K 31/506*   (2006.01)

(52) U.S. Cl. ...................... 514/275; 544/331
(58) Field of Classification Search ................. 544/331; 514/275
See application file for complete search history.

(56) References Cited

U.S. PATENT DOCUMENTS

2007/0270418 A1 * 11/2007 Ashwell et al. .......... 514/233.2

FOREIGN PATENT DOCUMENTS

| WO | 96/40143 | 12/1996 |
|----|----------|---------|
| WO | 01/12621 | 2/2001 |
| WO | 03/015776 | 2/2003 |
| WO | 03/024971 | 3/2003 |

OTHER PUBLICATIONS

Banker et al., Prodrugs, Modern Pharmaceutics, Third Edition, Revised and Expanded, pp. 451 and 596.*
Bundgaard, Design of Prodrugs, p. 1, 1985.*
Wolff, Some consideration for prodrug design, Burger's Medicinal Chemistry and Drug Discovery, 5th Edition, vol. I: Principles and Practice, pp. 975-977, 1995.*

* cited by examiner

*Primary Examiner*—Deepak Rao
(74) *Attorney, Agent, or Firm*—Hoxie and Associates LLC

(57) ABSTRACT

A compound of formula I or a pharmaceutically acceptable salt, ester or prodrug thereof wherein the variables have the meanings as defined in the specification. Further disclosed are a method of inhibiting IKK activity using a compound of formula I, a method of inhibiting production of TNF using a compound of formula I, a compound of formula I for use as a pharmaceutical, a pharmaceutical composition comprising a compound of formula I, and use of a compound of formula I in the manufacture of a medicament for use as an immunosuppressant or anti-inflammatory agent.

6 Claims, No Drawings

2-AMINOPYRIMIDINE DERIVATIVES AND THEIR MEDICAL USE

This application is a 371 of PCT/EP04/03819 filed Apr. 8, 2004.

This invention relates to 2-aminopyrimidine derivatives and to their activity as inhibitors of IKK activity and use therapeutically to treat diseases and medical conditions mediated by IKK, e.g. diseases and medical conditions involving NFκB activation of gene expression, in particular inflammatory or autoimmune diseases.

Accordingly the invention provides a compound of formula I or a pharmaceutically acceptable salt, ester or prodrug thereof

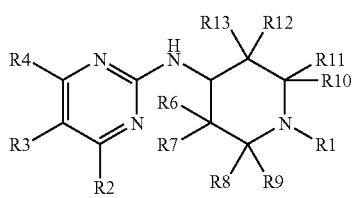

I wherein

R1 is H or optionally substituted (lower alkyl, aryl or aryl-lower alkyl, heterocycloalkyl or heterocycloalkyl-lower alkyl, —C(O)-Rx, —S(O)-Rx, —S(O)$_2$-Rx, —CH$_2$—O-Rx or —NH—C(O)-Rx where Rx is OH, lower alkoxy, aryloxy, aryl-lower alkoxy, or NH$_2$ optionally mono- or disubstituted by lower alkyl, aryl, aryl-lower alkyl, heterocycloalkyl or heterocycloalkyl-lower alkyl);

R2 is optionally substituted aryl, wherein aryl is not 4-(4-fluorophenyl)-1(1-methylpiperidin-4-yl)imidazole;

each of R3 and R4 is independently H, or optionally substituted (lower alkyl, CN, halo, hydroxy, lower alkoxy)

Each of R6 to R13 is independently H or optionally substituted (lower alkyl, lower alkoxy, —C(O)-Rx, —O—C(O)-Rx, —S(O)-Rx, —O—S(O)-Rx, —O—S(O)-Rx, —NH—C(O)-Rx or —CH$_2$—O-Rx where Rx is as defined above), and wherein at least 1 of the substituents R6 to R13 is not equal to H, or Any pair of R6 to R13 are joined to form an optionally substituted C$_1$ to C$_4$ bridge in which one or more of the bridge atoms is optionally replaced by O, S or NRy, where Ry is H or optionally substituted (lower alkyl, —C(O)-Rx, —S(O)-Rx, —S(O)$_2$-Rx, —CH$_2$—O-Rx or —NH—C(O)-Rx).

Above and elsewhere in the present description Rx is not OH or lower alkoxy when R1 or the corresponding substituent is —O—C(O)-Rx, or —O—S(O)-Rx.

It has been found in accordance with the present invention that the compounds of formula I are potent inhibitors of IKK and thus have potential for pharmaceutical use for treatment of diseases and medical conditions mediated by IKK.

Above and elsewhere in the present description the following terms have the following meanings.

Halo or halogen denote I, Br, Cl or F.

The term "lower" referred to above and hereinafter in connection with organic radicals or compounds respectively defines such as branched or unbranched with up to and including 7, preferably up to and including 4 and advantageously one or two carbon atoms.

A lower alkyl group is branched or unbranched and contains 1 to 7 carbon atoms, preferably 1-4 carbon atoms. Lower alkyl represents; for example, methyl, ethyl, propyl, butyl, isopropyl, isobutyl, or tertiary butyl.

A lower alkoxy group is branched or unbranched and contains 1 to 7 carbon atoms, preferably 1-4 carbon atoms. Lower alkoxy represents for example methoxy, ethoxy, propoxy, butoxy, isopropoxy, isobutoxy or tertiary butoxy. Di-lower alkoxy includes bridged substituents such as ethylene-dioxy or dioxolo.

A lower alkene, alkenyl or alkenyloxy group is branched or unbranched and contains 2 to 7 carbon atoms, preferably 1-4 carbon atoms and contains at least one carbon-carbon double bond. Lower alkene lower alkenyl or lower alkenyloxy represents for example vinyl, prop-1-enyl, allyl, butenyl, isopropenyl or isobutenyl and the oxy equivalents thereof.

A lower alkyne, alkynyl or alkynyloxy group is branched or unbranched and contains 2 to 7 carbon atoms, preferably 1-4 carbon atoms and contains at least one carbon-carbon triple bond. Lower alkyne or alkynyl represents for example ethynyl, prop-1-ynyl (propargyl), butynyl, isopropynyl or isobutynyl and the oxy equivalents thereof.

In the present description, oxygen containing substituents, e.g. alkoxy, alkenyloxy, alkynyloxy, carbonyl, etc. encompass their sulphur containing homologues, e.g. thioalkoxy, thioalkenyloxy, thioalkynyloxy, thiocarbonyl, sulphone, sulphoxide etc.

Aryl represents carbocyclic or heterocyclic aryl.

Carbocyclic aryl represents monocyclic, bicyclic or tricyclic aryl, for example phenyl or phenyl mono-, di- or tri-substituted by one, two or three radicals selected from lower alkyl, lower alkoxy, aryl, hydroxy, halogen, cyano, trifluoromethyl, lower alkylenedioxy and oxy-C$_2$-C$_3$-alkylene; or 1- or 2-naphthyl; or 1- or 2-phenanthrenyl. Lower alkylenedioxy is a divalent substituent attached to two adjacent carbon atoms of phenyl, e.g. methylenedioxy or ethylenedioxy. Oxy-C$_2$-C$_3$-alkylene is also a divalent substituent attached to two adjacent carbon atoms of phenyl, e.g. oxyethylene or oxypropylene. An example for oxy-C$_2$-C$_3$-alkylene-phenyl is 2,3-dihydrobenzofuran-5-yl.

Preferred as carbocyclic aryl is naphthyl, phenyl or phenyl mono- or disubstituted by lower alkoxy, phenyl, halogen, lower alkyl or trifluoromethyl, especially phenyl or phenyl mono or disubstituted by lower alkoxy, halogen or trifluoromethyl, and in particular phenyl.

Heterocyclic aryl represents monocyclic or bicyclic heteroaryl, for example pyridyl, indolyl, quinoxalinyl, quinolinyl, isoquinolinyl, benzothienyl, benzofuranyl, benzopyranyl, benzothiophenyl, benzothiopyranyl, furanyl, pyrrolyl, thiazolyl, oxazolyl, isoxazolyl, triazolyl, tetrazolyl, pyrazolyl, imidazolyl, thienyl, or any said radical substituted, especially mono or di-substituted as defined above. Preferably, heterocyclic aryl is thiophenyl, tetrahydrothiophenyl, thienopyridinyl (e.g. thieno[3,2-c]pyridinyl), benzothiophenyl (e.g. benzo)[b]thiophenyl), pyrrolyl, pyridyl, indolyl, quinolinyl, imidazolyl, or any said radical substituted, especially mono- or di- or trisubstituted as defined below.

Cycloalkyl represents a saturated cyclic hydrocarbon optionally substituted by lower alkyl which contains 3 to 10 ring carbons and is advantageously cyclopentyl, cyclohexyl, cycloheptyl or cyclooctyl optionally substituted by lower alkyl.

Heterocycloalkyl represents a mono-, di- or tricyclic moiety comprising from 3 to 18 ring atoms, at least one of which (e.g. from 1 to 3 ring atoms) is a hetero atom selected from O, S or N, and the remaining ring atoms are carbon atoms, which are saturated or comprise one or more unsaturated alkenyl or alkynyl bonds. Preferred heterocycloalkyl moieties are N-heterocycloalkyl moieties containing from 5 to 7 ring atoms and optionally containing a further hetero atom, selected from O, S or N. Heterocycloalkyl may be substituted, for instance, as hereinafter defined and including =O substitution on the heterocyclic ring e.g. as pyrrolidinone. Examples of preferred heterocycloalkyl moieties are pyrrolidine, tetrahydrothiophene, tetrahydrofuran, piperidine, pyran, dioxane, morpholino, or piperazine, especially piperidine, morpholino or piperazine.

Preferably R1 is H, OH, —C(O)-Rx, —S(O)-Rx, —S(O)$_2$-Rx or —CH$_2$—O-Rx, where Rx is as defined above or optionally substituted lower alkyl, wherein the optional substituents are preferably one or two substituents selected from OH, lower alkoxy, aryl, CN or NH$_2$ optionally mono- or disubstituted by lower alkyl, aryl, aryl-lower alkyl, heterocycloalkyl or heterocycloalkyl-lower alkyl. Most preferably R1 is H.

Each of R6, R7, R12 and R13 is preferably H. Each of R8, R9, R10 and R11 is preferably independently H, lower alkyl (e.g. butyl, propyl, ethyl or methyl), lower alkoxy, —CH$_2$—O-Rx, —C(O)-Rx, —O—C(O)-Rx, —S(O)-Rx, —O—S(O)-Rx or —NH—C(O)-Rx, where Rx is as defined above or R8 and R10 are both H and R9 and R11 are joined to form an optionally substituted C$_1$ to C$_4$ bridge in which one or more of the bridge atoms is optionally replaced by O, S or NRy, where Ry is H or optionally substituted lower alkyl. Most preferably each of R6, R7, R12 and R13 is H and each of R8, R9, R10 and R11 is lower alkyl (especially methyl).

R2 is preferably phenyl, or heteroaryl, conveniently containing from 3 to 10 ring members, including fused ring heteroaryl. For example, R2 may comprise optionally substituted pyrrole, thiophene, benzothiophene, tetrahydrobenzothiophene, furan, thienopyridine, pyridine, pyrimidine, pyrazine, triazine, imidazole, thiazole, oxazole, indole, thioindole, oxindole, purine, quinoline or isoquinoline; for instance, as disclosed in the Examples, e.g. optionally substituted phenyl, thiophenyl, benzothiophenyl, pyridinyl, naphthalenyl or indolyl.

R2 is optionally substituted by one or more substituents R20, preferably from 1-3 substituents, wherein each R20 is independently selected from OH, halogen, CN, NO$_2$, or optionally substituted (lower alkyl (including cycloalkyl), lower alkene, lower alkyne, lower alkoxy, lower alkenyloxy, lower alkynyloxy, aryl, heteroaryl or heterocycloalkyl, NH$_2$ (optionally mono- or disubstituted by lower alkyl, aryl, aryl-lower alkyl, heterocycloalkyl or heterocycloalkyl-lower alkyl), or —C(O)-Rx, —O—C(O)-Rx, —S(O)-Rx, —O—S(O)-Rx, —CH$_2$—O-Rx or —NH—C(O)-Rx, where Rx is as defined above).

R20 is further optionally substituted by one or more substituents R21, preferably from 1-4 substituents, wherein each R21 is independently selected from OH, halogen, CN, NO$_2$, or optionally substituted (lower alkyl (including cycloalkyl), lower alkene, lower alkyne, lower alkoxy, lower alkenyloxy, lower alkynyloxy, aryl, heteroaryl, heterocycloalkyl, NH$_2$ (optionally mono- or disubstituted by lower alkyl, aryl, aryl-lower alkyl, heterocycloalkyl or heterocycloalkyl-lower alkyl), or —C(O)-Rx, —O—C(O)-Rx, —S(O)-Rx, —O—S(O)-Rx, —CH$_2$—O-Rx or —NH—C(O)-Rx, where Rx is as defined above).

R21 is further optionally substituted by one or more substituents R22, preferably from 1-3 substituents, wherein each R22 is independently selected from OH, halogen, CN, NO$_2$, or lower alkyl (including cycloalkyl), lower alkoxy, aryl, heteroaryl or heterocycloalkyl, NH$_2$ (optionally mono- or disubstituted by lower alkyl, aryl, aryl-lower alkyl, heterocycloalkyl or heterocycloalkyl-lower alkyl), or —C(O)-Rx, —O—C(O)-Rx, —S(O)-Rx, —O—S(O)-Rx, —CH$_2$—O-Rx or —NH—C(O)-Rx, where Rx is as defined above).

Preferably each of R3 and R4 is independently H, CN, halo, hydroxy, lower alkyl or lower alkoxy.

Thus in a preferred embodiment the invention provides a compound of formula II

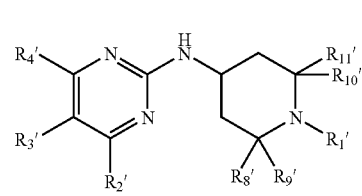

II wherein

R1' is H, OH, —C(O)-Rx, —S(O)-Rx, —S(O)$_2$-Rx or —CH$_2$—O-Rx, where Rx is as defined above or optionally substituted lower alkyl, wherein the optional substituents are preferably one or two substituents selected from OH, lower alkoxy, aryl, CN or NH$_2$ optionally mono- or disubstituted by lower alkyl, aryl, aryl-lower alkyl, heterocycloalkyl or heterocycloalkyl-lower alkyl;

R2' is optionally substituted phenyl, or heteroaryl, conveniently containing from 3 to 10 ring members, including fused ring heteroaryl, e.g. optionally substituted pyrrole, thiophene, benzothiophene, tetrahydrobenzothiophene, furan, thienopyridine, pyridine, pyrimidine, pyrazine, triazine, imidazole, thiazole, oxazole, indole, thioindole, oxindole, purine, quinoline or isoquinoline; wherein optionally substituted imidazole is not 4-(4-fluorophenyl)-1(1-methylpiperdin-4-yl)imidazole;

each R3' and R4' is independently H, CN, halo, hydroxy, lower alkyl or lower alkoxy;

each of R8', R9', R10' and R11' is independently H, lower alkyl, lower alkoxy, —CH$_2$—O-Rx, —C(O)-Rx, —O—C(O)-Rx, —S(O)-Rx, —O—S(O)-Rx or —NH—C(O)-Rx, where Rx is as defined above;

wherein at least 1 of the substituents R8' to R11' is not equal to H; or R8 and R10 are both H and R9 and R11 are joined to form an optionally substituted C$_1$ to C$_4$ bridge in which one or more of the bridge atoms is optionally replaced by O, S or NRy, where Ry is H or optionally substituted lower alkyl, or a pharmaceutically acceptable salt, ester or prodrug thereof.

Particularly preferred compounds according to the invention comprise compounds of formula IIIa or IIIb or a pharmaceutically acceptable salt, ester or prodrug thereof

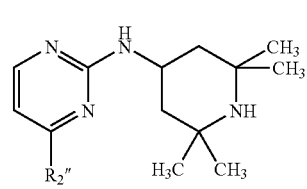

IIIa

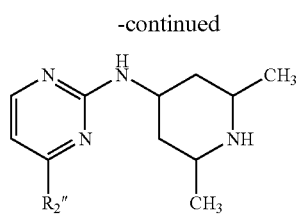

wherein

R2" is optionally substituted phenyl, thiophenyl, benzothiophenyl, pyridinyl, naphthalenyl or indolyl aryl (including heteroaryl), wherein R2 is optionally substituted by one or more substituents R20 independently selected from OH, halogen, CN, $NO_2$, or optionally substituted (lower alkyl (including cycloalkyl), lower alkene, lower alkyne, lower alkoxy, lower alkenyloxy, lower alkynyloxy, aryl, heteroaryl or heterocycloalkyl, $NH_2$ (optionally mono- or disubstituted by lower alkyl, aryl, aryl-lower alkyl, heterocycloalkyl or heterocycloalkyl-lower alkyl), or —C(O)-Rx, —O—C(O)-Rx, —S(O)-Rx, —O—S(O)-Rx, —$CH_2$—O-Rx, —$CH_2$—O-Rx or —NH—C(O)-Rx, where Rx is as defined above), wherein R20 is optionally substituted by one or more substituents R21 independently selected from OH, halogen, CN, $NO_2$, or optionally substituted (lower alkyl (including cycloalkyl), lower alkene, lower alkyne, lower alkoxy, lower alkenyloxy, lower alkynyloxy, aryl, heteroaryl, heterocycloalkyl, $NH_2$ (optionally mono- or disubstituted by lower alkyl, aryl, aryl-lower alkyl, heterocycloalkyl or heterocycloalkyl-lower alkyl), or —C(O)-Rx, —O—C(O)-Rx, —S(O)-Rx, —O—S(O)-Rx, —$CH_2$—O-Rx or —NH—C(O)-Rx, where Rx is as defined above), and wherein R21 is optionally substituted by one or more substituents R22 independently selected from OH, halogen, CN, $NO_2$, or lower alkyl (including cycloalkyl), lower alkoxy, aryl, or heterocycloalkyl, $NH_2$ (optionally mono- or disubstituted by lower alkyl, aryl, heteroaryl, aryl-lower alkyl, heterocycloalkyl or heterocycloalkyl-lower alkyl), or —C(O)-Rx, —O—C(O)-Rx, —S(O)-Rx, —O—S(O)-Rx, —$CH_2$—O-Rx or —NH—C(O)-Rx, where Rx is as defined above).

The invention includes a compound selected from the compounds of Examples 1 to 226 and pharmaceutically acceptable salts, esters or prodrugs thereof.

The compounds of formula I, II and III, and as listed above are hereinafter referred to as Agents of the Invention.

The Agents of the Invention which comprise free hydroxyl groups may also exist in the form of pharmaceutically acceptable, physiologically cleavable esters, and as such are included within the scope of the invention. Such pharmaceutically acceptable esters are preferably prodrug ester derivatives, such being convertible by solvolysis or cleavage under physiological conditions to the corresponding Agents of the Invention which comprise free hydroxyl groups. Suitable pharmaceutically acceptable prodrug esters are those derived from a carboxylic acid, a carbonic acid monoester or a carbamic acid, advantageously esters derived from an optionally substituted lower alkanoic acid or an arylcarboxylic acid.

Agents of the Invention may also exist in the form of pharmaceutically acceptable salts, and as such are included within the scope of the invention. Pharmaceutically acceptable salts include acid addition salts with conventional acids, for example, mineral acids, e.g., hydrochloric acid, sulfuric or phosphoric acid, or organic acids, for example, aliphatic or aromatic carboxylic or sulfonic acids, e.g., acetic, trifluoroacetic, propionic, succinic, glycolic, lactic, malic, tartaric, citric, ascorbic, maleic, fumaric, hydroxymaleic, pyruvic, pamoic, methanesulfonic, toluenesulfonic, naphthalenesulfonic, sulfanilic or cyclohexylsulfamic acid; also amino acids, such as arginine and lysine. For compounds of the invention having acidic groups, for example, a free carboxy group, pharmaceutically acceptable salts also represent metal or ammonium salts, such as alkali metal or alkaline earth metal salts, e.g., sodium, potassium, magnesium or calcium salts, as well as ammonium salts, which are formed with ammonia or suitable organic amines.

Agents of the Invention may also exist in the form of optical isomers; for example as hereinafter described in the Examples. Thus the invention includes both individual isomeric forms as well as mixtures, e.g. racemic and diastereoisomeric mixtures thereof, unless otherwise specified. Conveniently the invention includes compounds of formula I in purified isomeric form, e.g. comprising at least 90%, or preferably at least 95%, of a single isomeric form.

Where Agents of the Invention exist in isomeric form as aforesaid, individual isomers may be obtained in conventional manner, e.g. employing optically active starting materials or by separation of initially obtained mixtures, for example using conventional chromatographic techniques.

Agents of the Invention of formula I

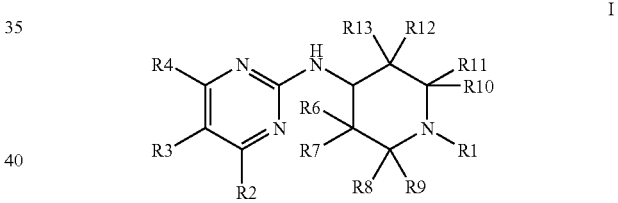

wherein the R substituents are as defined above, may be prepared by coupling of a pyrimidine derivative of formula IV, e.g. chloro-pyrimidine, 2-methylsulphinyl-pyrimidine or 2-methylsulphonyl-pyrimidine with a piperidin-4-ylamine of formula V

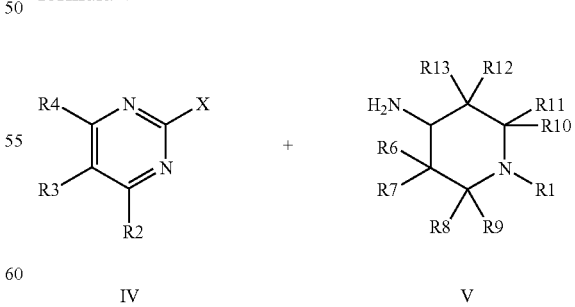

wherein the R substituents are as defined above and X is halogen, —SO—$CH_3$ or —$SO_2$—$CH_3$; for instance in the presence of DIEA at elevated temperature, e.g. ca. 120° C., conveniently as hereinafter described in the Examples.

Compounds of formula IV'

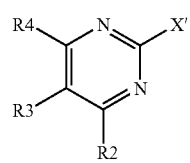

wherein the R symbols are as defined above and X' is —SO—CH$_3$ or —SO$_2$—CH$_3$ may be obtained by oxidation of the corresponding 2-methylsulphanyl derivative of formula VI

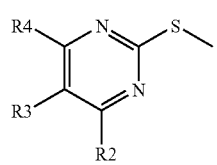

wherein the R symbols are as defined above; for instance in solution, e.g. in dichloromethane, at low temperature, e.g. at 0° C., in the presence of an oxidizing agent such as mCPBA.

Compounds of formula IV"

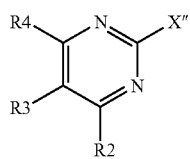

wherein the R symbols are as defined above and X" is —S—CH$_3$ or halo, e.g. Cl, may be obtained by coupling a of a 4-halo-pyrimidine of formula VII with a aryl boronic acid of formula VIII

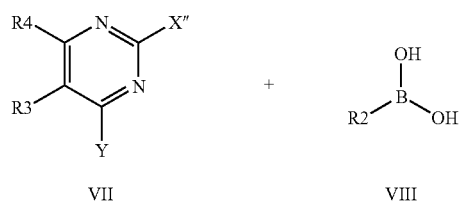

wherein the R symbols are as previously defined, Y is halo, e.g. Cl, and X" is as defined above; for instance by a Suzuki-type coupling of the aryl boronic acid derivative VIII with 4-halo-pyrimidine VII in the presence of a palladium catalyst, e.g. Pd(PPh$_3$)$_4$ or PdCl$_2$(PPh$_3$)$_2$, conveniently as hereinafter described in the Examples.

2-Methylsulphanyl pyrimidine compounds of formula VI

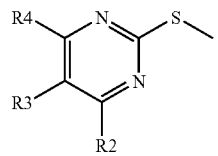

wherein the R symbols are as previously defined, may also be obtained by a Stille-type coupling of a 4-trialkyl tin- or 4-iodo-2-methylsulphanyl pyrimidine of formula IX

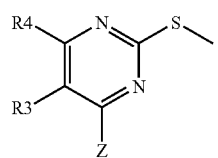

wherein R3 and R4 are as previously defined and Z is —SnBu$_3$ or —SnMe$_3$ or iodo, with a corresponding aryl iodide or aryl trialkyl tin compound respectively; for instance, in the presence of a palladium(0) catalyst system, e.g. Pd$_2$(dba)$_3$ with CuI and AsPh$_3$, conveniently as hereinafter described in the Examples.

A 2-methylsulphanyl pyrimidine compound of formula VI

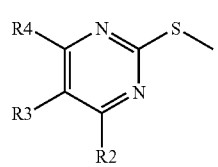

wherein the R symbols are as previously defined, may be converted to another compound of formula VI, in which the R2 substituent of the first compound is converted into a different R2 substituent as desired using standard chemical synthesis procedures and as hereinafter described in the Examples.

In a further alternative procedure Agents of the Invention of formula I may be prepared by coupling of a (4-halo-pyrimidin-2-yl)-piperidin-4-yl-amine of formula X with a aryl boronic acid of formula VIII

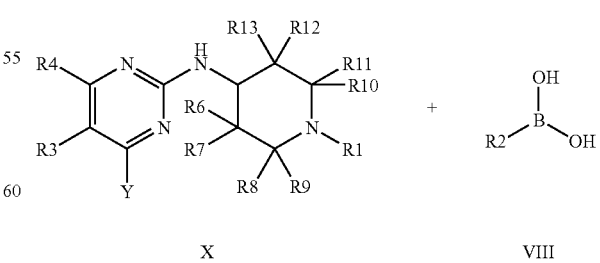

wherein the R symbols are as previously defined and Y is halo, e.g. Cl, for instance by a Suzuki-type coupling of the aryl boronic acid derivative VIII with the 4-halo-pyrimidine X in the presence of a palladium catalyst, e.g. Pd(PPh$_3$)$_4$ or PdCl$_2$(PPh$_3$)$_2$, conveniently as hereinafter described in the Examples.

In a yet further alternative procedure Agents of the Invention of formula I'

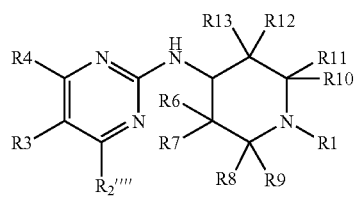

I' wherein R2'''' is N-heteroaryl attached to the pyrimidine ring via an N-atom and the other R symbols are as previously defined, may be prepared by coupling of a (4-halo-pyrimidin-2-yl)-piperidin-4-yl-amine of formula X

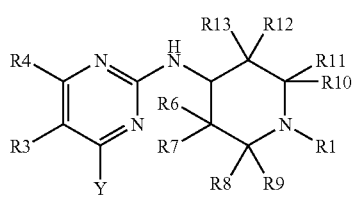

X wherein the R symbols are as previously defined and Y is halo, e.g. Cl, with the alkali metal salt, e.g. sodium or potassium salt, of the N-heteroaryl compound of R''''; for instance, by heating a mixture of X and R'''' in the presence potassium hydroxide, conveniently as hereinafter described in the Examples.

Agents of the Invention so obtained may be converted into further Agents of the Invention as desired using standard chemical synthesis procedures and as hereinafter described in the Examples.

Thus in a further aspect the invention provides a process for the preparation of an Agent of the Invention of formula I

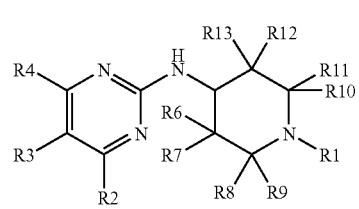

I wherein the R substituents are as defined above, comprising (i) coupling of a pyrimidine derivative of formula IV, e.g. chloro-pyrimidine, methanesulphonyl-pyrimidine or methanesulphinyl-pyrimidine with a piperidin-4-ylamine of formula V

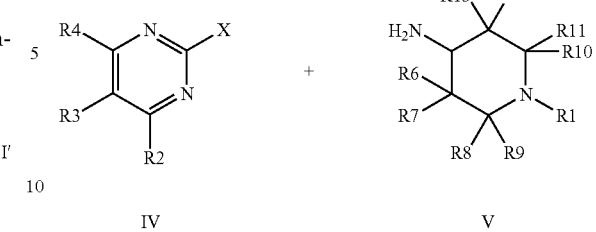

IV                          V wherein the R substituents are as defined above and X is halo, —SO—CH$_3$ or —SO$_2$—CH$_3$, (ii) coupling of a (4-halo-pyrimidin-2-yl)-piperidin-4-yl-amine of formula VII with a aryl boronic acid of formula X

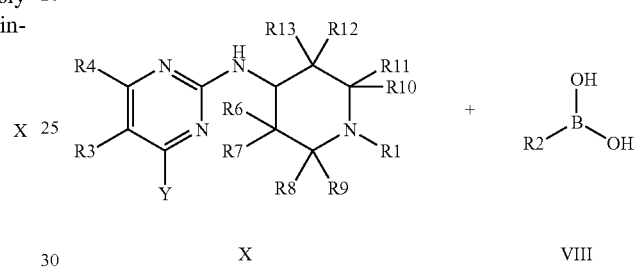

X                          VIII wherein the R symbols are as previously defined and Y is halo, or (iii) for the preparation of an Agent of the Invention of formula I wherein R2 is N-heteroaryl attached to the pyrimidine ring via an N-atom, coupling of a (4-halo-pyrimidin-2-yl)-piperidin-4-yl-amine of formula X

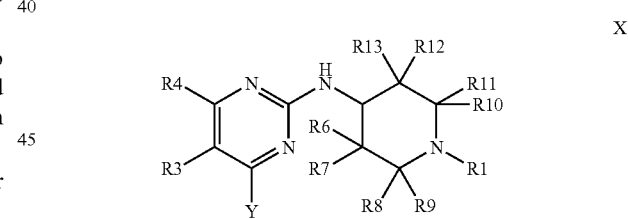

X wherein the R symbols are as previously defined and Y is halo, e.g. Cl, with the alkali metal salt, e.g. sodium or potassium salt, of the N-heteroaryl compound.

The invention is further described by way of illustration only in the following Examples

EXAMPLES

Abbreviations:
BOC: t-Butyloxycarbonyl
Boc2O: Di-t-butyl dicarbonate
DCM: Dichloromethane
DIEA: Ethyl-diisopropyl-amine
DMAP: Dimethyl-pyridin-4-yl-amine
DME: 1,2-Dimethoxy-ethane
DMF: N,N-Dimethyl formamide EDC: (3-Dimethylamino-propyl)-ethyl-carbodiimide hydrochloride
Ether: Ethoxy-ethane
EtOH: Ethanol
EtOAc: Acetic acid ethyl ester
HCl: Hydrochloric acid
HOBT: Benzotriazol-1-ol
LAH: Lithium aluminumhydride
LDA: Lithium diisopropylamine
mCPBA: 3-Chloro-benzenecarboperoxoic acid
MeOH: Methanol
NaOH: Sodium hydroxide
NMP: 1-Methyl-pyrrolidin-2-one
SEM: 2-Trimethylsilanyl-ethoxymethyl
TBAF: Tetrabutylammonium fluoride
TBME: t-Butyl-methyl ether
TBDMS: t-Butyl-dimethyl-silyl
TFA: Trifluoro-acetic acid
THF: Tetrahydrofuran $^1$H-NMR spectra were recorded on a Varian Gemini 400 MHz NMR spectrometer. Significant peaks are tabulated in the order: multiplicity (s, singlet; d, doublet; t, triplet; q, quartet; m, multiplet; br, broad) and number of protons. Electron Spray Ionization (ESI) mass spectra were recorded on a Hewlett Packard 5989A mass spectrometer. Mass spectrometry results are reported as the ratio of mass over charge. Preparative HPLC purifications were performed with XTerra™RP$_{18}$ 19×150 mm columns, using acetonitrile/water or MeOH/water as eluent systems. All reagents, starting materials and intermediates utilized in these examples are available from commercial sources or are readily prepared by methods known to those skilled in the art.

Aminopyrimidines of the formula XI were conveniently prepared by palladium(0)-catalyzed cross coupling reactions (Suzuki- or Stille-type) outlined as general Methods A to E in Scheme 1. These methods are illustrated below by representative Examples 1 to 5. The boronic acids are commercially available or were prepared in situ and used as such without further purification.

-continued
METHOD E

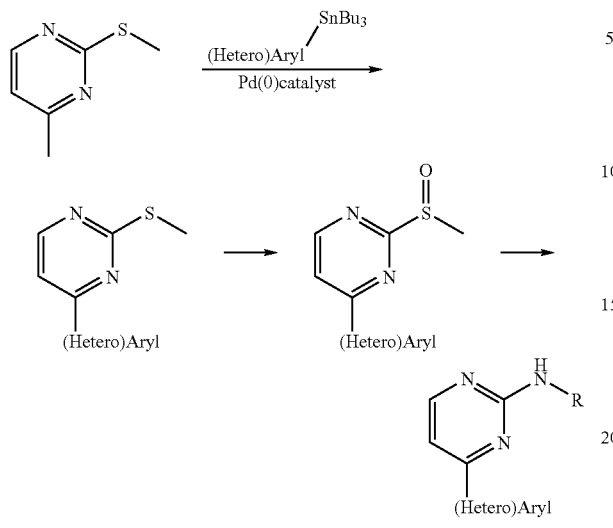

Method A is illustrated by the following representative Example 1

Example 1

2-Methyl-4-{5-[2-(2,2,6,6-tetramethyl-piperidin-4-ylamino)-pyrimidin-4-yl]-thiophen-2-yl}-butan-2-ol

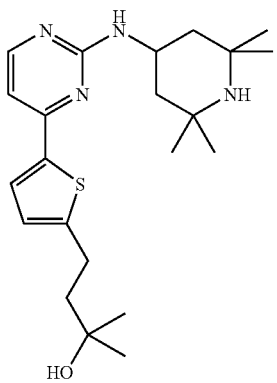

Step A: 2-Methyl-4-thiophen-2-yl-butan-2-ol

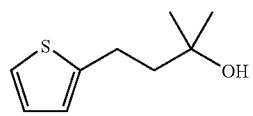

To a stirred and cooled (ice bath) solution of 3-thiophen-2-yl-propionic acid methyl ester (2 g, 11.75 mmol) in 30 ml of THF was added MeMgBr (3M solution in ether, 11.7 ml, 35.1 mmol). Stirring was continued for 2 hours. Then, the mixture was quenched with saturated ammonium chloride solution (50 ml) and extracted with EtOAc. The organic layer was washed with water and brine, dried over sodium sulfate and evaporated. Yield: 1.9 g (95%) of a pale yellow oil which was clean enough for further use.

Step B: 4-[5-(2-Chloro-pyrimidin-4-yl)-thiophen-2-yl]-2-methyl-butan-2-ol

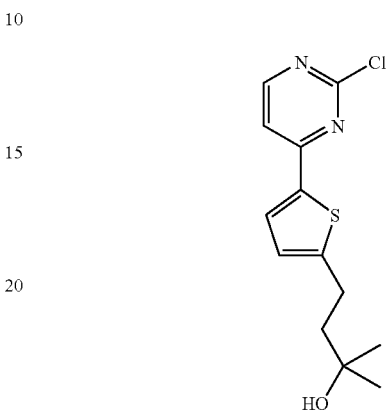

A solution of 2-methyl-4-thiophen-2-yl-butan-2-ol (630 mg, 3.7 mmol) in 10 ml of THF was treated with LDA (4.6 ml of 2M solution in THF/heptane/ethylbenzene, 9.2 mmol) at −78° C. under nitrogen and the mixture was stirred for 5 minutes. Then, trimethylborate (1 ml, 9.2 mmol) was added in one portion and the cooling bath was removed. After 15 minutes, the mixture was quenched with 50 ml of saturated ammonium chloride solution and extracted twice with EtOAc. The combined organic extracts were washed with brine and evaporated under reduced pressure at room temperature. This crude boronic acid was redissolved in 10 ml of DME and added to a stirred suspension 2,4-dichloro-pyrimidine (275 mg, 1.85 mmol), Pd(PPh$_3$)$_4$ (64 mg, 0.037 mmol), 20 ml of DME and 5 ml of a 10% solution of sodium bicarbonate. This mixture was then kept at reflux (100° C. heat bath) for 90 minutes. After cooling, most of the DME was evaporated and the crude was partitioned between water and EtOAc. The organic layer was separated, washed with 0.2N-HCl, water and brine, dried over sodium sulfate and evaporated. The crude was purified by chromatography on silicagel (EtOAc/hexane:1/1). Yield: 390 mg (77%) of 4-[5-(2-Chloro-pyrimidin-4-yl)-thiophen-2-yl]-2-methyl-butan-2-ol.

Step C: 2-Methyl-4-{5-[2-(2,2,6,6-tetramethyl-piperidin-4-ylamino)-pyrimidin-4-yl]-thiophen-2-yl}-butan-2-ol To the above chloro-pyrimidine (100 mg, 0.35 mmol) was added 2,2,6,6-tetramethyl-piperidin-4-ylamine (0.22 μl, 1.27 mmol), DIEA (0.42 ml) and the mixture was stirred for 2 hours at 120° C., then evaporated. The residue was purified by preparative HPLC to give the title compound. Yield: 104 mg (73%) of a white solid.

MS (ESI): 403.0 [M+H]$^+$ $^1$H-NMR (CDCl$_3$): δ (ppm) 8.24 (d, 1H), 7.53 (d, 1H), 6.87 (d, 1H), 6.82 (d, 1H), 4.93 (br d, 1H), 4.42 (m, 1H), 3.0 (m, 2H), 2.13 (m, 2H), 1.94 (m, 2H), 1.42 (br s, 6H), 1.34 (s, 6H), 1.23 (br s, 6H), 1.07 (m, 2H).

Method B is illustrated by the following representative Example 2

Example 2

4-{5-[5-Methoxy-2-(2,2,6,6-tetramethyl-piperidin-4-ylamino)-pyrimidin-4-yl]-thiophen-2-yl}-2-methyl-butan-2-ol

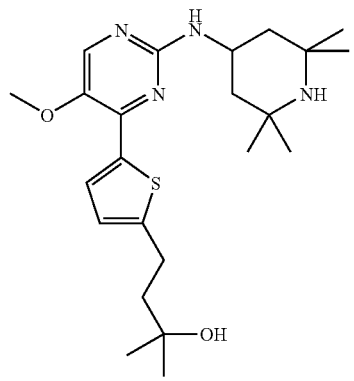

Step A: 4-[5-(5-Methoxy-2-methylsulfanyl-pyrimidin-4-yl)-thiophen-2-yl]-2-methyl-butan-2-ol

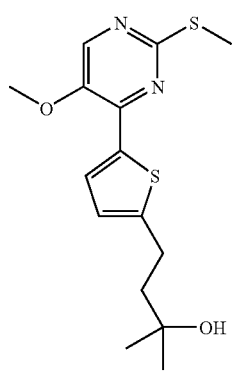

A solution of 2-methyl-4-thiophen-2-yl-butan-2-ol (340 mg, 2 mmol)—synthesis see Step A of Example 1—in 20 ml of THF was treated with LDA (2M in THF/heptane/ethylbenzene, 5 ml, 10 mmol) at −78° C. under nitrogen and the mixture was stirred for 5 minutes. Then, trimethylborate (1.1 ml, 10 mmol) was added in one portion and the cooling bath was removed. After 15 minutes, the mixture was quenched with 50 ml of saturated ammonium chloride solution and extracted twice with ether. The aqueous layer was then acidified with 2N-HCl and extracted once more with ether. The combined organic extracts were washed with brine and evaporated. This crude boronic acid was redissolved in 10 ml of DME and added to a stirred suspension 4-chloro-5-methoxy-2-methylsulfanyl-pyrimidine (190 mg, 1 mmol), Pd(PPh$_3$)$_4$ (23 mg, 0.02 mmol), 20 ml of DME and 3 ml of a 10% solution of sodium bicarbonate. This mixture was then kept at reflux (100° C. heat bath) for 90 minutes. After cooling, most of the DME was evaporated and the crude was partitioned between water and ether. The organic layer was separated, washed with 0.2N-HCl, water and brine, dried over sodium sulfate and evaporated. The crude was purified by chromatography on silicagel (EtOAc/hexane:1/1) to give 4-[5-(5-methoxy-2-methylsulfanyl-pyrimidin-4-yl)-thiophen-2-yl]-2-methyl-butan-2-ol. Yield: 275 mg (85%).

Step B: 4-[5-(2-Methanesulfonyl-5-methoxy-pyrimidin-4-yl)-thiophen-2-yl]-2-methyl-butan-2-ol

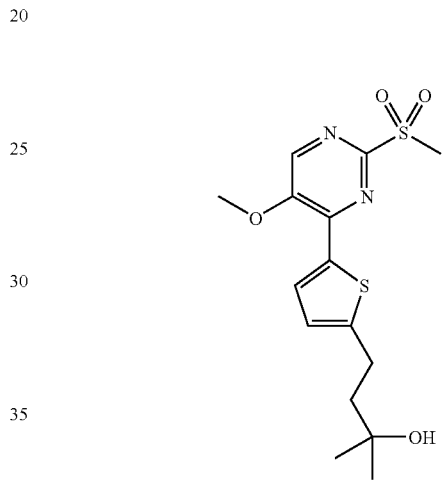

4-[5-(5-methoxy-2-methylsulfanyl-pyrimidin-4-yl)-thiophen-2-yl]-2-methyl-butan-2-ol (270 mg, 0.832 mmol) was dissolved in 5 ml of chloroform. Solid mCPBA (content 50%, 631 mg, 1.83 mmol) was added and it was stirred for 1 hour. The mixture was then diluted with DCM (25 ml) and extracted successively with saturated solutions of sodium bisulfite and sodium bicarbonate and brine. Drying over sodium sulfate and evaporation gave crude 4-[5-(2-methanesulfonyl-5-methoxy-pyrimidin-4-yl)-thiophen-2-yl]-2-methyl-butan-2-ol. Yield: 245 mg (83%).

Step C: 4-{5-[5-Methoxy-2-(2,2,6,6-tetramethyl-piperidin-4-ylamino)-pyrimidin-4-yl]-thiophen-2-yl}-2-methyl-butan-2-ol 4-[5-(2-Methanesulfonyl-5-methoxy-pyrimidin-4-yl)-thiophen-2-yl]-2-methyl-butan-2-ol (240 mg, 0.673 mmol) was mixed with 2,2,6,6-Tetramethyl-piperidin-4-ylamine (0.5 ml, 2.86 mmol) and DIEA (0.5 ml, 2.92 mmol) and heated to 120° C. in a closed flask for 2 hours. The residue was then diluted with MeOH and purified by preparative HPLC to give the title compound. Yield: 8 mg (3%).

MS (ESI): 433.0 [M+H]$^{+1}$H-NMR (CDCl$_3$): δ (ppm) 8.05 (s, 1H), 7.88 (d, 1H), 6.84 (d, 1H), 4.63 (d, 1H), 4.3 (m, 1H), 3.92 (s, 3H), 2.96 (m, 2H), 2.11 (m, 2H), 1.92 (m, 2H), 1.36 (s, 6H), 1.31 (s, 6H), 1.16 (br s, 6H), 0.98 (m, 2H).

Method C is illustrated by the following representative Example 3

Example 3

{4-[5-(4-Methoxy-butyl)-thiophen-2-yl]-pyrimidin-2-yl}-(2,2,6,6-tetramethyl-piperidin-4-yl)-amine hydrochloride

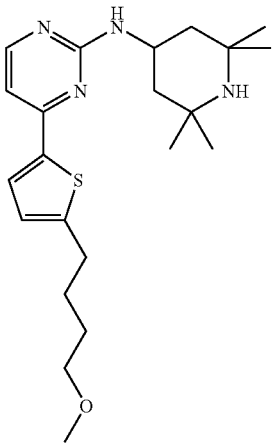

Step A: (4-Chloro-pyrimidin-2-yl)-(2,2,6,6-tetramethyl-piperidin-4-yl)-amine

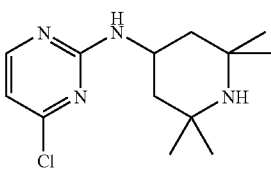

Neat 2-methylsulfanyl-pyrimidin-4-ol (5 g, 35 mmol) and 2,2,6,6-tetramethyl-piperidin-4-ylamine (8.243 g, 52.75 mmol) were heated to 170° C. with stirring for 2 hours. After cooling, the brown solid was triturated with ether. Filtration gave 8.16 g (93%) of 2-(2,2,6,6-Tetramethyl-piperidin-4-ylamino)-pyrimidin-4-ol. This crude (8 g, 32 mmol) was suspended in 160 ml of acetonitrile. Then, 4N-HCl in dioxane (24 ml, 96 mmol) and POCl$_3$ (7.32 ml, 80 mmol) were added successively and the suspension was heated to reflux (105° C. heat bath) for 2 hours. After that, the mixture was cooled, diluted with EtOAc and washed twice with 2N-NaOH, then brine, dried over sodium sulfate and evaporated. Chromatography on silicagel (EtOAc/MeOH/ammonia:2/1/0.02) gave (4-chloro-pyrimidin-2-yl)-(2,2,6,6-tetramethyl-piperidin-4-yl)-amine as a beige solid. Yield: 7.68 g (89%).

Step B: 2-(4-Methoxy-butyl)-thiophene

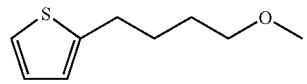

A solution of 4-thiophen-2-yl-butan-1-ol (4.55 g, 29.09 mmol) in 20 ml of THF was carefully added to a stirred suspension of oil-free sodium hydride (1.05 g, 43.75 mmol) in 15 ml of THF. When the addition was complete, the mixture was heated to 50° C. and stirring continued for 1 hour. Iodomethane (2.7 ml, 43.75 mmol) was then added and the turbid solution was stirred at 50° C. for another 2 hours. After cooling, a few drops of water were added and the mixture was partitioned between 1N-HCl and ether. The organic layer was washed with saturated sodium bicarbonate solution and brine. Drying over sodium sulfate and careful evaporation (product is volatile) gave a pale yellow oil. Yield: 4.45 g (90%).

Step C: {4-[5-(4-Methoxy-butyl)-thiophen-2-yl]-pyrimidin-2-yl}-(2,2,6,6-tetramethyl-piperidin-4-yl)-amine hydrochloride A solution of 2-(4-methoxy-butyl)-thiophene (527 mg, 3.1 mmol) in 10 ml of THF was treated with LDA (2.3 ml of 1.5M solution in cyclohexane, 3.4 mmol) at −78° C. under nitrogen and the mixture was stirred for 5 minutes. Then, trimethylborate (0.379 ml, 3.4 mmol) was added in one portion and the cooling bath was removed. After 15 minutes, the mixture was quenched with 10 ml of saturated ammonium chloride solution and extracted twice with ether. The aqueous layer was then acidified with 2N-HCl and extracted once more with ether. The combined organic extracts were washed with water and brine and evaporated. This crude boronic acid was redissolved in 5 ml of DME and added to a stirred suspension of (4-chloro-pyrimidin-2-yl)-(2,2,6,6-tetramethyl-piperidin-4-yl)-amine (416 mg, 1.55 mmol), Pd(PPh$_3$)$_4$ (36 mg, 0.031 mmol), 10 ml of DME and 5 ml of a 10% solution of sodium bicarbonate. This mixture was then kept at reflux (100° C. heat bath) for 90 minutes. After cooling, most of the DME was evaporated and the crude was partitioned between 2N-HCl and ether. The aqueous layer was separated, made basic with 2N-NaOH and extracted twice with ether and once with DCM. The combined organic layers were washed with water and brine, dried over sodium sulfate and evaporated. The crude oil was purified by preparative HPLC and converted into its hydrochloride salt by addition of excess of 3M-HCl solution in EtOAc. Yield: 494 mg (73%).

MS (ESI): 403.0 [M+H]$^{+1}$H-NMR (CDCl$_3$): δ (ppm) 8.19 (br d, 1H), 7.48 (d, 1H), 6.80 (d, 1H), 6.77 (d, 1H), 5.55 (b s, 1H), 4.38 (m, 1H), 3.39 (t, 2H), 3.31 (s, 3H), 2.86 (t, 2H), 2.08 (m, 2H), 1.76 (m, 2H), 1.66 (m, 2H), 1.35 (br s, 6H), 1.14 (br s, 6H), 0.97 (m, 2H).

Method D is illustrated by the following representative Example 4

Example 4

(E)-4-{5-[2-(2,2,6,6-Tetramethyl-piperidin-4-ylamino)-pyrimidin-4-yl]-thiophen-2-yl}-but-3-en-2-ol

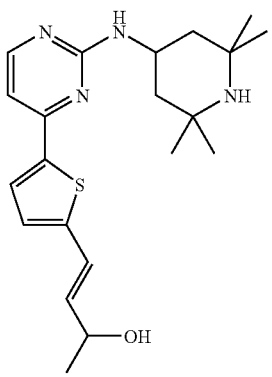

Step A: (E)-4-[5-(2-Methylsulfanyl-pyrimidin-4-yl)-thiophen-2-yl]-but-3-en-2-one

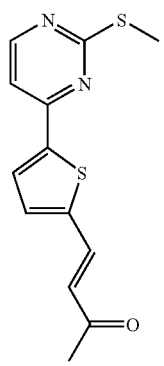

A mixture of (E)-4-(5-bromo-thiophen-2-yl)-but-3-en-2-one (1 g, 4.34 mmol), triphenylarsine (319 mg, 1.04 mmol), cuprous iodide (99 mg, 0.52 mmol) and Pd$_2$(dba)$_3$ (119 mg, 0.13 mmol) in 25 ml of NMP was heated to 80° C. To this hot solution 2-methylsulfanyl-4-tributylstannanyl-pyrimidine (1.8 g, 4.34 mmol) dissolved in 10 ml of NMP was added dropwise over a period of 10 minutes. Stirring was continued for 24 hours. The solvent was then removed in vacuo and the residue partitioned between water and EtOAc. The aqueous layer was separated and extracted once more with EtOAc. The combined organic extracts were washed with water and brine, dried over sodium sulfate and evaporated. The crude was purified by chromatography on silicagel (EtOAc/hexane: 2/3) to give a yellow solid. Yield: 480 mg (40%).

Step B: (E)-4-[5-(2-Methylsulfanyl-pyrimidin-4-yl)-thiophen-2-yl]-but-3-en-2-ol

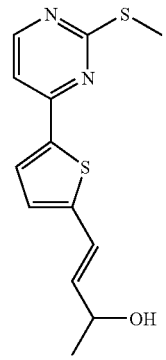

Solid sodium borohydride (25 mg, 0.66 mmol) was added to a solution of (E)-4-[5-(2-methylsulfanyl-pyrimidin-4-yl)-thiophen-2-yl]-but-3-en-2-one (120 mg, 0.43 mmol) in 8 ml of MeOH. After stirring for 3 hours, the MeOH was evaporated and the residue was partitioned between water and EtOAc. The aqueous layer was separated and extracted once more with EtOAc. The combined organic extracts were washed with brine, dried over sodium sulfate and evaporated to give a yellow solid which was used without further purification. Yield: 112 mg (93%).

Step C: (E)-4-[5-(2-Methanesulfonyl-pyrimidin-4-yl)-thiophen-2-yl]-but-3-en-2-ol

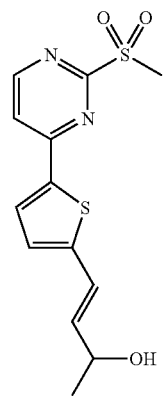

A solution of (E)-4-[5-(2-methylsulfanyl-pyrimidin-4-yl)-thiophen-2-yl]-but-3-en-2-ol (100 mg, 0.36 mmol) in 5 ml of chloroform was treated with mCPBA (content 50%, 272 mg, 0.79 mmol) at room temperature for 2 hours. The mixture was then diluted with DCM (25 ml) and extracted successively with saturated solutions of sodium bisulfite and sodium bicarbonate and brine. Drying over sodium sulfate and evaporation gave (E)-4-[5-(2-methanesulfonyl-pyrimidin-4-yl)-thiophen-2-yl]-but-3-en-2-ol which was used directly in the next step. Yield: 108 mg (97%).

Step D: (E)-4-{5-[2-(2,2,6,6-Tetramethyl-piperidin-4-ylamino)-pyrimidin-4-yl]-thiophen-2-yl}-but-3-en-2-ol (E)-4-[5-(2-Methanesulfonyl-pyrimidin-4-yl)-thiophen-2-yl]-but-3-en-2-ol (100 mg, 0.32 mmol) was mixed with 2,2,6,6-tetramethyl-piperidin-4-ylamine (0.2 ml, 1.15 mmol) and DIEA (0.2 ml, 1.17 mmol) and heated to 120° C. in a closed flask for 2 hours. The residue was then diluted with MeOH and purified by preparative HPLC to give the title compound. Yield: 25 mg (20%).

MS (ESI): 387.0 [M+H]$^{+1}$H-NMR (DMSO-d$_6$): δ (ppm) 8.25 (br s, 1H), 7.76 (d, 1H), 7.12 (d, 1H), 7.0 (d, 1H), 6.68 (d 1H), 6.14 (m, 1H), 4.95 (br s, 1H), 4.15-4.35 (m, 2H), 1.7-1.9 (br m, 2H), 0.9-1.35 (m, 17H).

Method E is illustrated by the following representative Example 5

Example 5

{4-[5-(3-Amino-3-methyl-but-1-ynyl)-thiophen-2-yl]-pyrimidin-2-yl}-(2,2,6,6-tetramethyl-piperidin-4-yl)-amine

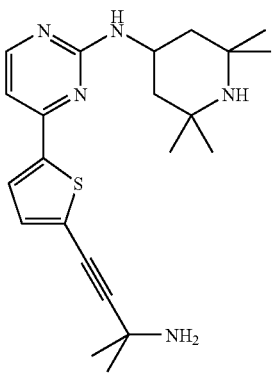

Step A: 4-(5-Bromo-thiophen-2-yl)-2-methylsulfanyl-pyrimidine

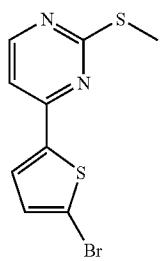

4-Iodo-2-methylsulfanyl-pyrimidine (2.5 g, 10 mmol), (5-Bromo-thiophen-2-yl)-tributyl-stannane (4.9 g, 11 mmol) and PdCl$_2$ (702 mg, 1 mmol) were heated to 105° C. in toluene (30 ml) for 2 hours. The reaction mixture was poured on water and extracted three times with EtOAc. The combined organic phases were dried over sodium sulfate, filtered, evaporated to dryness and purified via chromatography on silicagel (acetone/hexanes:0/100 to 3/97) to give the title compound as colourless foam. Yield: 1.6 g (55%).

Step B: 4-(5-Bromo-thiophen-2-yl)-2-methanesulfinyl-pyrimidine

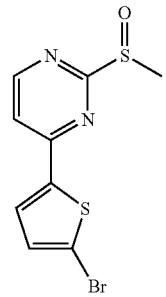

4-(5-Bromo-thiophen-2-yl)-2-methylsulfanyl-pyrimidine (144 mg, 0.5 mmol) was dissolved in DCM (5 ml) and treated at 0° C. with mCPBA (content 70%, 112 mg, 0.65 mmol) for 15 minutes. The reaction mixture was washed with 2N-solution of sodium carbonate, the organic phase dried over sodium sulfate, filtered and evaporated to dryness and purified via chromatography on silicagel (acetone/hexanes:20/80 to 40/60) to give the title compound as white crystals. Yield: 120 mg (80%).

Step C: [4-(5-Bromo-thiophen-2-yl)-pyrimidin-2-yl]-(2,2,6,6-tetramethyl-piperidin-4-yl)-amine

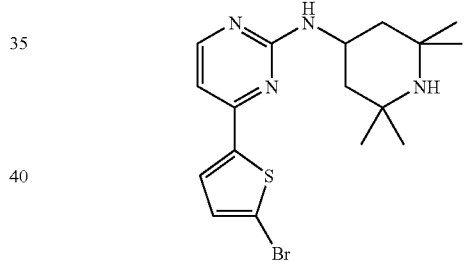

4-(5-Bromo-thiophen-2-yl)-2-methanesulfinyl-pyrimidine (110 mg, 0.36 mmol) and 4-amino-2,2,6,6,-tetramethyl piperidine (0.6 ml) were heated to 130° C. for 45 minutes. Evaporation and chromatography on silicagel (TBDME/MeOH/ammonia:90/9/1) gave the title compound as slightly coloured crystals. Yield: 100 mg (70%).

Step D: {4-[5-(3-Amino-3-methyl-but-1-ynyl)-thiophen-2-yl]-pyrimidin-2-yl}-(2,2,6,6-tetramethyl-piperidin-4-yl)-amine {4-[5-Bromothiophen-2-yl]-pyrimidin-2-yl}-(2,2,6,6-tetramethyl-piperidin-4-yl)-amine (100 mg, 0.253 mmol), PdCl$_2$(PPh$_3$)$_2$ (18 mg, 0.025 mmol), 1,1-dimethyl-prop-2-ynylamine (0.03 ml, 0.253 mmol) and CuI (15 mg) were dissolved in triethylamine (25 ml) and refluxed for 1 hour. The reaction mixture was filtered, evaporated to dryness and taken up in DCM, filtered and evaporated again and the residue crystallized from ether to give the title compound as red-yellow crystals. Yield: 50 mg (50%).

MS (ESI): 398 [M+H]$^{+1}$H-NMR (CDCl$_3$): δ (ppm) 8.30 (br s, 1H), 7.50 (d, 1H), 7.13 (d, 1H), 6.83 (br s, 1H), 5.45 (br s, 1H, NH), 4.45 (m, 1H), 3.78 (br s, 2H, NH2), 2.33 (br s, 1H, NH), 2.12 (br d, 2H), 1.53 (s, 12H), 1.43 (br t, 2H), 1.38 (s, 6H).

Thiophenes

Example 6

(E)-2-Methyl-4-{5-[2-(2,2,6,6-tetramethyl-piperidin-4-ylamino)-pyrimidin-4-yl]-thiophen-2-yl}-but-3-en-2-ol

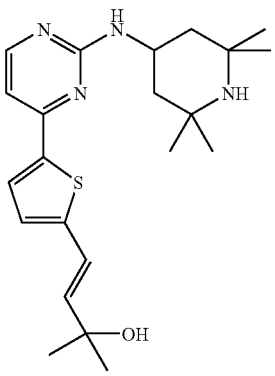

The title compound was prepared analogous to Step A of Method D, using 2-methylsulfanyl-4-tributylstannanyl-pyrimidine and (E)-3-(5-bromo-thiophen-2-yl)-acrylic acid methyl ester, followed by reaction with MeMgBr (Step A of Method A), mCPBA (Step C of Method D) and added 2,2,6,6-tetramethyl-piperidin-4-ylamine (Step D of Method D).

MS (ESI): 401.0 [M+H]$^{+1}$H-NMR (DMSO-d$_6$) δ (ppm) 8.24 (br d, 1H), 7.54 (d, 1H), 6.98 (d, 1H), 6.83 (d, 1H), 6.74 (d, 1H), 6.31 (d, 1H), 4.93 (br d, 1H), 4.4 (m, 1H), 2.12 (m, 2H), 1.44 (s, 6H), 1.4 (s, 6H), 1.2 (s, 6H), 1.05 (m, 2H).

Example 7

4-{5-[2-(2,2,6,6-Tetramethyl-piperidin-4-ylamino)-pyrimidin-4-yl]-thiophen-2-yl}-pyrrolidin-2-one

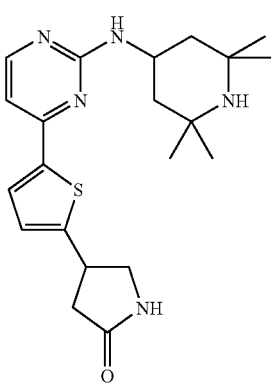

Step A: (E)-3-[5-(2-Methylsulfanyl-pyrimidin-4-yl)-thiophen-2-yl]-acrylic acid methyl ester

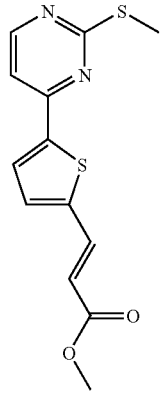

(E)-3-[5-(2-Methylsulfanyl-pyrimidin-4-yl)-thiophen-2-yl]-acrylic acid methyl ester was prepared analogous to Step A of Method D, using (E)-3-(5-bromo-thiophen-2-yl)-acrylic acid methyl ester and 2-methylsulfanyl-4-tributylstannanyl-pyrimidine. Yield: 45%.

Step B: 3-[5-(2-Methylsulfanyl-pyrimidin-4-yl)-thiophen-2-yl]-4-nitro-butyric acid methyl ester

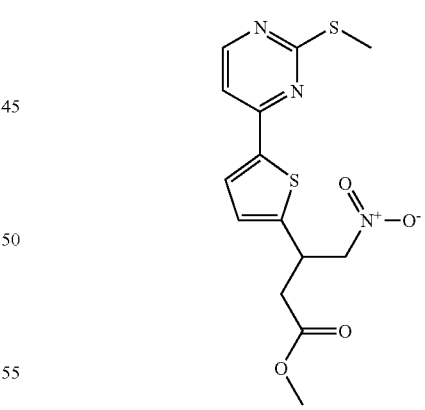

A solution of (E)-3-[5-(2-methylsulfanyl-pyrimidin-4-yl)-thiophen-2-yl]-acrylic acid methyl ester (200 mg, 0.684 mmol), nitromethane (3 ml) and Triton B (0.3 ml) was heated to 80° C. for 4 hours. After cooling, the mixture was diluted with EtOAc and washed with saturated ammonium chloride solution, water and brine. Drying over sodium sulfate and evaporation gave a red-brown oil. Yield: 100 mg (41%)

Step C: 4-[5-(2-Methylsulfanyl-pyrimidin-4-yl)-thiophen-2-yl]-pyrrolidin-2-one

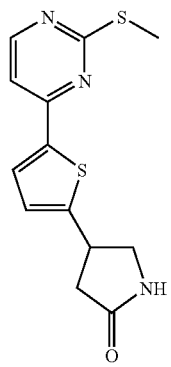

The nitro derivative from Step B (100 mg, 0.283 mmol) was dissolved in 10 ml of ethanol and hydrogenated with Raney-nickel for 18 hours. The catalyst was then filtered off and the solution was heated to reflux for 3 hours. After evaporation, the crude product was purified by preparative HPLC. Yield: 19 mg (23%).

Step D: 4-[5-(2-Methanesulfonyl-pyrimidin-4-yl)-thiophen-2-yl]-pyrrolidin-2-one

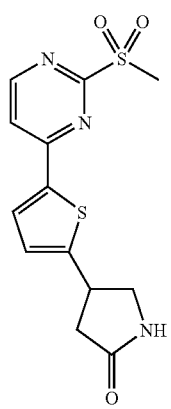

The sulfane from Step C was oxidized with mCPBA (Step C of Method D). Yield: 17 mg (80%).

Step E: 4-{5-[2-(2,2,6,6-Tetramethyl-piperidin-4-ylamino)-pyrimidin-4-yl]-thiophen-2-yl}-pyrrolidin-2-one The title compound was prepared analogous to Step D of Method D, using the above sulfone. Yield: 13 mg (62%).
MS (ESI): 400.0 [M+H]$^{+1}$H-NMR (CDCl$_3$): δ (ppm) 8.23 (d, 1H), 7.52 (d, 1H), 6.92 (d, 1H), 6.8 (d, 1H), 6.07 (br s, 1H), 4.99 (br d, 1H), 4.36 (m, 1H), 3.96 (m, 1H), 3.82 (m, 1H), 3.48 (m 1H), 2.8 (m, 1H), 2.55 (m 1H), 2.09 (m, 2H), 1.35 (s, 6H), 1.15 (s, 6H), 1.0 (m, 2H).

Example 8

4-{5-[5-Methyl-2-(2,2,6,6-tetramethyl-piperidin-4-ylamino)-pyrimidin-4-yl]-thiophen-2-yl}-butan-1-ol

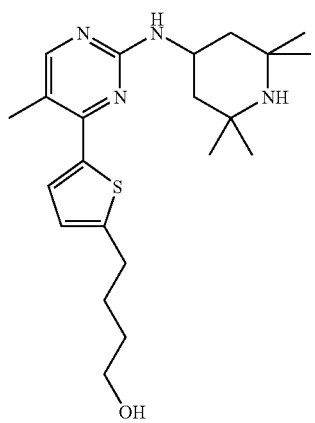

Step A: 4-[5-(2-Chloro-5-methyl-pyrimidin-4-yl)-thiophen-2-yl]-butyric acid methyl ester

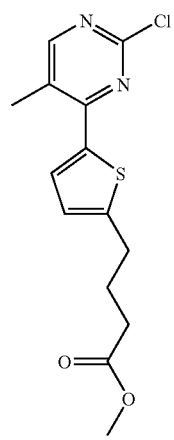

4-[5-(2-Chloro-5-methyl-pyrimidin-4-yl)-thiophen-2-yl]-butyric acid methyl ester was prepared analogous to Step B of Method A, starting from 4-thiophen-2-yl-butyric acid methyl ester and 2,4-dichloro-5-methyl-pyrimidine. Yield: 12%.

Step B: 4-{5-[5-Methyl-2-(2,2,6,6-tetramethyl-piperidin-4-ylamino)-pyrimidin-4-yl]-thiophen-2-yl}-butyric acid methyl ester

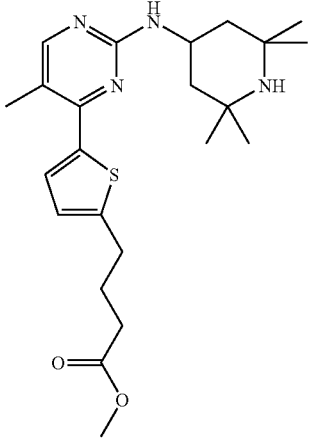

4-{5-[5-Methyl-2-(2,2,6,6-tetramethyl-piperidin-4-ylamino)-pyrimidin-4-yl]-thiophen-2-yl}-butyric acid methyl ester was prepared analogous to Step C of Method A, starting from 4-[5-(2-chloro-5-methyl-pyrimidin-4-yl)-thiophen-2-yl]-butyric acid methyl ester and added 2,2,6,6-tetramethyl-piperidin-4-ylamine. Yield: 60%.

Step C: 4-{5-[5-Methyl-2-(2,2,6,6-tetramethyl-piperidin-4-ylamino)-pyrimidin-4-yl]-thiophen-2-yl}-butan-1-ol The ester from Step B (37 mg, 0.09 mmol) was dissolved in 1 ml of THF and LAH (1M in THF, 0.22 ml, 0.22 mmol) was added. After 30 minutes, the mixture was quenched with water and extracted with ether. The organic layers were washed with brine, dried over sodium sulfate and evaporated. The crude product was purified by preparative HPLC. Yield: 15 mg (43%).

MS (ESI): 403.0 [M+H]$^{+1}$H-NMR (DMSO-$d_6$) δ (ppm) 8.13 (br s, 1H), 7.51 (d, 1H), 6.94 (d, 1H), 6.7 (br d, 1H), 4.49 (br t, 1H), 4.2 (m, 1H), 3.42 (m, 2H), 2.82 (t, 2H), 2.3 (s, 3H), 1.8 (br m, 2H), 1.66 (m, 2H), 1.5 (m, 2H), 1.23 (br s, 6H), 1.08 (m, 2H), 1.02 (br s, 6H).

Example 9a

1-{5-[2-(2,2,6,6-Tetramethyl-piperidin-4-ylamino)-pyrimidin-4-yl]-thiophen-2-yl}-propan-2-ol

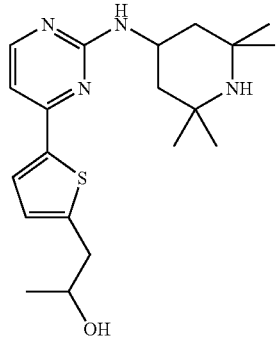

The title compound was prepared analogous to Steps B and C of Method A, starting from 1-thiophen-2-yl-propan-2-ol, 2,4-dichloro-pyrimidine and 2,2,6,6-tetramethyl-piperidin-4-ylamine.

MS (ESI): 375.0 [M+H]$^{+1}$H-NMR (DMSO-$d_6$) δ (ppm) 8.24 (br m, 1H), 7.71 (d, 1H), 6.96 (d, 1H), 6.93 (d, 1H), 4.82 (br d, 1H), 4.25 (m, 1H), 3.85 (s, 1H), 2.87 (d, 2H), 1.8 (br m, 2H), 1.0-1.35 (m, 17H).

Example 9b

2-Methyl-1-{5-[2-(2,2,6,6-tetramethyl-piperidin-4-ylamino)-pyrimidin-4-yl]-thiophen-2-yl}-propan-2-ol

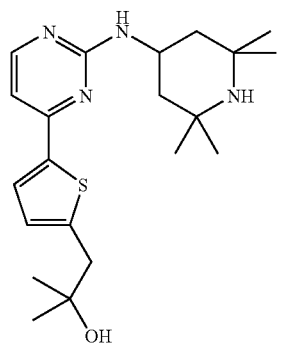

The title compound was prepared analogous to Method C, starting from (4-chloro-pyrimidin-2-yl)-(2,2,6,6-tetramethyl-piperidin-4-yl)-amine and 2-methyl-1-thiophen-2-yl-propan-2-ol.

MS (ESI): 389.2 [M+H]$^+$

Example 10

2,2,N-Trimethyl-3-{5-[2-(2,2,6,6-tetramethyl-piperidin-4-ylamino)-pyrimidin-4-yl]-thiophen-2-yl}-propionamide

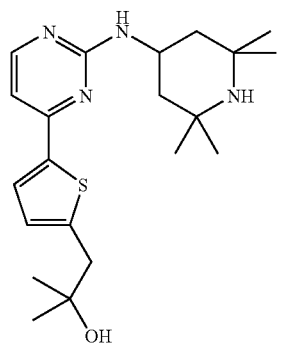

Step A:
2,2,N-Trimethyl-3-thiophen-2-yl-propionaide

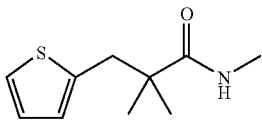

A solution of 2,2-dimethyl-3-thiophen-2-yl-propionic acid (315 mg, 1.589 mmol) in 10 ml of dichloromethane was treated successively with HOBt (257 mg, 1.9 mmol), EDC (364 mg, 1.9 mmol) and triethylamine (0.223 ml, 1.6 mmol). The mixture was stirred for 20 minutes, then methylamine (0.621 ml, 8 mmol) was added and stirring was continued for 18 hours. The solvent was then evaporated and the crude was redissolved in ether, washed with 2N-HCl, saturated sodium bicarbonate and brine. Drying over sodium sulfate and evaporation gave a yellow-brown oil which was used without further purification. Yield: 244 mg (78%).

Step B: 2,2,N-Trimethyl-3-{5-[2-(2,2,6,6-tetramethyl-piperidin-4-ylamino)-pyrimidin-4-yl]-thiophen-2-yl}-propionamide The title compound was prepared analogous to Steps B and C of Method A, starting from 2,2,N-trimethyl-3-thiophen-2-yl-propionamide, 2,4-dichloro-pyrimidine and 2,2,6,6-tetramethyl-piperidin-4-ylamine.

MS (ESI): 430.4 [M+H]$^{+1}$H-NMR (DMSO-d$_6$) δ (ppm) 8.23 (br m, 1H), 7.66 (d, 1H), 7.52 (m, 1H), 6.94 (d, 1H), 6.83 (d, 1H), 4.25 (m, 1H), 2.99 (s, 2H), 2.58 (d, 3H), 1.77 (br m, 2H), 0.95-1.35 (m, 20H).

Example 11

2-Methyl-4-{3-[2-(2,2,6,6-tetramethyl-piperidin-4-ylamino)-pyrimidin-4-yl]-pyrrol-1-yl}-butan-2-ol

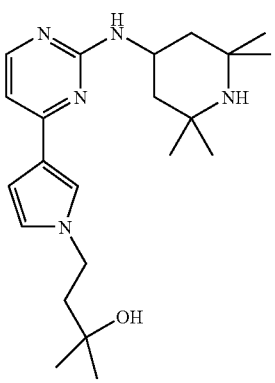

Step A:
2-Methylsulfanyl-4-(1H-pyrrol-3-yl)-pyrimidine

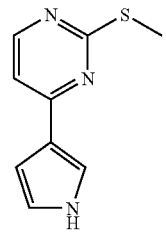

The title compound was prepared analogous to Step A of Method B, starting from [1-[tris(1-methylethyl)silyl]-1H-pyrrol-3-yl]-boronic acid and 4-chloro-2-methylsulfanyl-pyrimidine. Under the reaction conditions, the triisopropylsilyl protecting group was cleaved. Yield: 95%.

Step B: 3-[3-(2-Methylsulfanyl-pyrimidin-4-yl)-pyrrol-1-yl]-propionic acid methyl ester

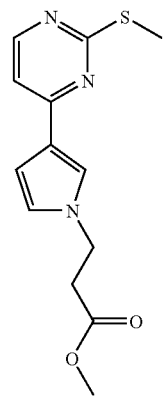

2-Methylsulfanyl-4-(1H-pyrrol-3-yl)-pyrimidine (260 mg, 1.36 mmol) was added to a suspension of fat free sodium hydride (39 mg, 1.63 mmol) in 5 ml of THF. The mixture was heated to 50° C. for 20 minutes. Then, 3-bromo-propionic acid methyl ester (0.156 ml, 1.36 mmol) was added and the temperature was increased to 80° C. After 14 hours, the mixture was cooled, quenched with water and extracted with ether. The combined organic layers were washed with brine, dried over sodium sulfate and evaporated. The crude product was used without further purification. Yield: 302 mg (80%).

Step C: 2-Methyl-4-{3-[2-(2,2,6,6-tetramethyl-piperidin-4-ylamino)-pyrimidin-4-yl]-pyrrol-1-yl}-butan-2-ol The title compound was prepared from 3-[3-(2-Methylsulfanyl-pyrimidin-4-yl)-pyrrol-1-yl]-propionic acid methyl ester by reaction with MeMgBr (Step A of Method A), followed by mCPBA (Steps C and D) and (2,2,6,6-tetramethyl-piperidin-4-yl)-amine (Step D of Method D).

MS (ESI): 386.0 [M+H]$^{+1}$H-NMR (DMSO-d$_6$) δ (ppm) 8.18 (br d, 1H), 7.48 (br s, 1H), 6.65-6.75 (m, 3H), 4.82 (br d, 1H), 4.43 (m, 1H), 4.1 (m, H), 2.14 (m, 2H), 2.05 (m, 2H), 1.47 (s, 6H), 1.43 (s, 6H), 1.2 (s, 6H), 1.03 (m, 2H).

Example 12a 2-(2-{5-[2-(2,2,6,6-Tetramethyl-piperidin-4-ylamino)-pyrimidin-4-yl]-thiophen-2-ylmethyl}-cyclopropyl)-propan-2-ol

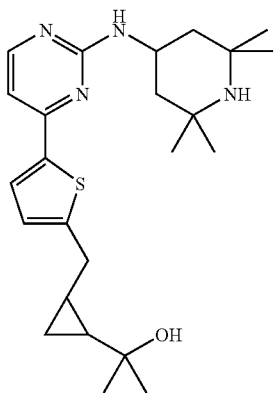

Step A:
2-(2-Thiophen-2-ylmethyl-cyclopropyl)-propan-2-ol

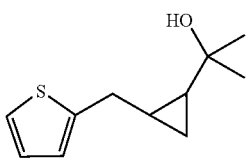

The title compound was prepared in 4 steps from thiophene. First, thiophene was acylated with 3-oxa-bicyclo[3.1.0]hexane-2,4-dione, followed by carbonyl reduction to give 2-thiophen-2-ylmethyl-cyclopropanecarboxylic acid (both steps analogous to *Eur. J. Med. Chem.* 1998, 867) which was converted into its methyl ester using diazomethane. Finally, the methyl ester was converted to the gem-dimethyl alcohol by reaction with MeMgBr (Step A of Method A).

Step B: 2-(2-{5-[2-(2,2,6,6-Tetramethyl-piperidin-4-ylamino)-pyrimidin-4-yl]-thiophen-2-ylmethyl}-cyclopropyl)-propan-2-ol The title compound was prepared analogous to Method C, starting from 2-(2-thiophen-2-ylmethyl-cyclopropyl)-propan-2-ol and (4-chloro-pyrimidin-2-yl)-(2,2,6,6-tetramethyl-piperidin-4-yl)-amine. Yield: 20%.

MS (ESI): 429.0 [M+H]$^{+1}$H-NMR (DMSO-d$_6$) δ (ppm) 8.25 (br s, 1H), 7.7 (d, 1H), 6.9-7.0 (m, 3H), 4.25 (m, 1H), 3.95 (s, 1H), 2.65-2.85 (m, 2H), 1.7 (br m, 2H), 0.95-1.45 (m, 21H), 0.79 (m, 1H), 0.6 (m, 1H), 0.25 (m, 1H).

Example 12b 2,3,3-Trimethyl-5-{5-[2-(2,2,6,6-tetramethyl-piperidin-4-ylamino)-pyrimidin-4-yl]-thiophen-2-yl}-pentan-2-ol

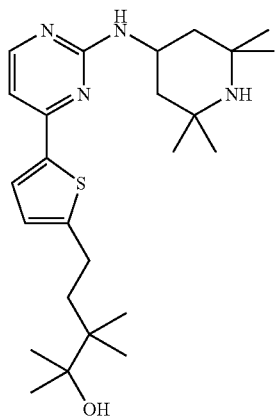

Step A: 2,3,3-Trimethyl-5-thiophen-2-yl-pentan-2-ol

The title compound was prepared in 4 steps from thiophene. First, thiophene was acylated with 3,3-dimethyl-dihydro-furan-2,5-dione, followed by carbonyl reduction to give 2,2-dimethyl-4-thiophen-2-yl-butyric acid (both steps analogous to *Eur. J. Med. Chem.* 1998, 867) which was converted into its methyl ester using diazomethane. Finally, the methyl ester was converted to the gem-dimethyl alcohol by reaction with MeMgBr (Step A of Method A).

Step B: 2,3,3-Trimethyl-5-{5-[2-(2,2,6,6-tetramethyl-piperidin-4-ylamino)-pyrimidin-4-yl]-thiophen-2-yl}-pentan-2-ol The title compound was prepared analogous to Method C, starting from (4-chloro-pyrimidin-2-yl)-(2,2,6,6-tetramethyl-piperidin-4-yl)-amine and 2,3,3-trimethyl-5-thiophen-2-yl-pentan-2-ol from Step A.

MS (ESI): 445.3 [M+H]$^{+1}$H-NMR (DMSO-d$_6$): δ (ppm) 8.22 (br d, 1H), 7.6 (br d, 1H), 6.85-6.95 (m, 2H), 6.16 (br m, 1H), 4.35 (br m, 1H), 3.43 (br s, 1H), 2.84-2.95 (m, 2H), 1.86-1.98 (m, 2H), 1.74-1.83 (m, 2H), 0.9-1.4 (m, 26H).

Example 13a 2-((1R,2R)-2-{5-[2-(2,2,6,6-Tetramethyl-piperidin-4-ylamino)-pyrimidin-4-yl]-thiophen-2-yl}-cyclopropyl)-propan-2-ol

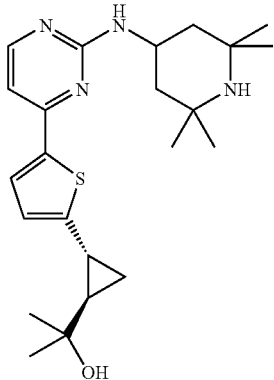

Step A: 2-((1R,2R)-2-Thiophen-2-yl-cyclopropyl)-propan-2-ol

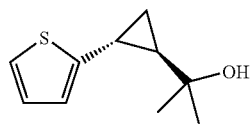

The title compound was prepared from (1R,2R)-2-thiophen-2-yl-cyclopropanecarboxylic acid (*J. Med. Chem.* 39, 1485) by successive treatment with diazomethane and MeMgBr (Step A of Method A).

Step B: 2-((1R,2R)-2-{5-[2-(2,2,6,6-Tetramethyl-piperidin-4-ylamino)-pyrimidin-4-yl]-thiophen-2-yl}-cyclopropyl)-propan-2-ol The title compound was prepared analogous to Method C, starting from 2-((1R,2R)-2-thiophen-2-yl-cyclopropyl)-propan-2-ol and (4-chloro-pyrimidin-2-yl)-(2,2,6,6-tetramethyl-piperidin-4-yl)-amine. Yield: 63%.

MS (ESI): 415.0 $[M+H]^+$ $^1$H-NMR (DMSO-$d_6$) δ (ppm) 8.22 (br s, 1H), 7.65 (d, 1H), 6.98 (br s, 1H), 6.93 (d, 1H), 6.82 (d, 1H), 4.25 (br m, 1H), 4.21 (s, 1H), 2.13 (m, 1H), 1.8 (br m, 2H), 0.95-1.45 (m, 22H), 0.78 (m, 1H).

Example 13b 2-((1S,2S)-2-{5-[2-(2,2,6,6-Tetramethyl-piperidin-4-ylamino)-pyrimidin-4-yl]-thiophen-2-yl}-cyclopropyl)-propan-2-ol

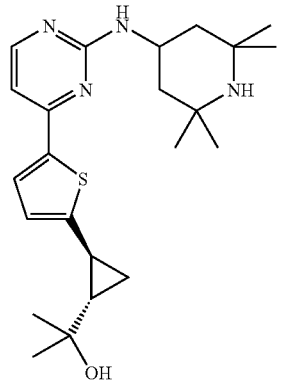

The title compound was prepared as described for Example 13a, starting from the enantiomeric (1R,2R)-2-thiophen-2-yl-cyclopropanecarboxylic acid.

MS (ESI): 415.0 $[M+H]^+$ $^1$H-NMR (DMSO-$d_6$) δ (ppm) 8.22 (br s, 1H), 7.65 (d, 1H), 6.98 (br s, 1H), 6.93 (d, 1H), 6.82 (d, 1H), 4.25 (br m, 1H), 4.21 (s, 1H), 2.13 (m, 1H), 1.8 (br m, 2H), 0.95-1.45 (m, 22H), 0.78 (m, 1H).

Example 14

2-Ethoxy-2-methyl-1-{5-[2-(2,2,6,6-tetramethyl-piperidin-4-ylamino)-pyrimidin-4-yl]-thiophen-2-yl}-propan-1-one

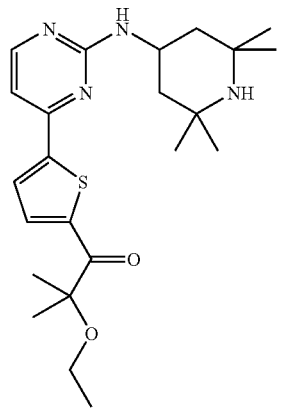

The title compound was prepared analogous to Method C, starting from (4-chloro-pyrimidin-2-yl)-(2,2,6,6-tetramethyl-piperidin-4-yl)-amine and 2-ethoxy-2-methyl-1-thiophen-2-yl-propan-1-one.

MS (EI): 430 $[M]^+$, 415 $[M-CH_3]^+$ $^1$H-NMR (DMSO-$d_6$): δ (ppm) 8.37 (br s, 1H), 8.07 (br d, 1H), 7.94 (br d, 1H), 7.23 (br s, 1H), 7.15 (br d, 1H), 4.26 (br m, 1H), 3.38 (q, 2H), 1.7-1.9 (m, 2H), 1.0-1.35 (m, 14H) overlapping 1.13 (t, 3H).

Example 15

{4-[5-(3-Methoxy-propyl)-thiophen-2-yl]-pyrimidin-2-yl}-(2,2,6,6-tetramethyl-piperidin-4-yl)-amine

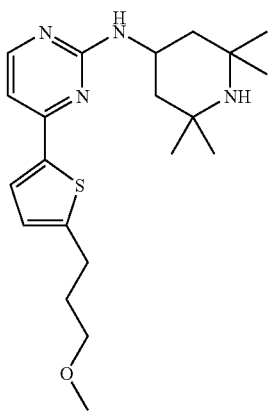

The title compound was prepared analogous to Method C, starting from (4-chloro-pyrimidin-2-yl)(2,2,6,6-tetramethyl-piperidin-4-yl)-amine and 3-thiophen-2-yl-propan-1-ol.

MS (ESI): 389.0 [M+H]$^{+1}$H-NMR (DMSO-d$_6$) δ (ppm) 8.35 (br m, 1H), 7.95 (br m, 1H), 7.35 (br m, 1H), 7.05 (br m, 1H), 4.4 (br m, 1H), 3.37 (t, 2H), 3.25 (s, 3H), 2.9 (t, 2H), 2.05 (m, 2H), 1.87 (m, 2H), 1.65 (m, 2H), 1.54 (br s, 6H), 1.46 (br s, 6H).

Example 16

2'-{5-[2-(2,2,6,6-Tetramethyl-piperidin-4-ylamino)-pyrimidin-4-yl]-thiophen-2-yl}-bicyclopropyl-1-ol

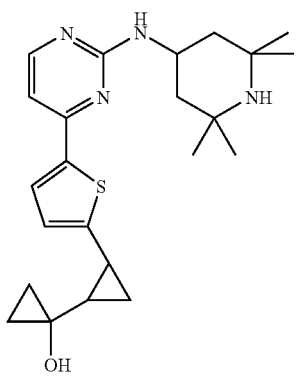

The title compound was prepared analogous to Method C, starting from (4-chloro-pyrimidin-2-yl)-(2,2,6,6-tetramethyl-piperidin-4-yl)-amine and 2'-thiophen-2-yl-bicyclopropyl-1-ol (prepared by cyclopropanation of 2-thiophen-2-yl-cyclopropanecarboxylic acid methyl ester, *J. Org. Chem.* 1993, 502).

MS (ESI): 413.0 [M+H]$^{+1}$H-NMR (DMSO-d$_6$) δ (ppm) 8.21 (br m, 1H), 7.66 (d, 1H), 6.94 (d 1H), 6.93 (d, 1H), 6.85 (d, 1H), 5.33 (s, 1H), 4.24 (m, 1H), 2.1 (m, 1H), 1.78 (b m, 2H), 1.39 (m, 1H), 0.95-1.35 (m, 16H), 0.85 (m, 1H), 0.35-0.65 (m, 4H).

Example 17

4-{3-Methoxy-5-[2-(2,2,6,6-tetramethyl-piperidin-4-ylamino)-pyrimidin-4-yl]-thiophen-2-yl}-2-methyl-butan-2-ol

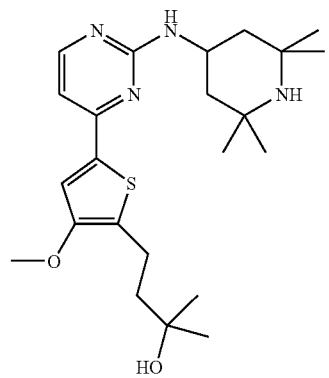

The title compound was prepared analogous to Method C, starting from (4-chloro-pyrimidin-2-yl)-(2,2,6,6-tetramethyl-piperidin-4-yl)-amine and 4-(3-methoxy-thiophen-2-yl)-2-methyl-butan-2-ol (prepared by Pd/C hydrogenation of (E)-3-(3-Methoxy-thiophen-2-yl)-acrylic acid methyl ester, followed by reaction with MeMgBr (Step A of Method A)).

MS (ESI): 433.0 [M+H]$^{+1}$H-NMR (DMSO-d$_6$) δ (ppm) 8.25 (br m, 1H), 7.76 (s, 1H), 6.98 (d, 1H), 4.32 (s, 1H), 4.24 (m, 1H), 3.85 (s, 3H), 2.71 (m, 2H), 1.8 (br m, 2H), 1.65 (m, 2H), 1.0-1.35 (m, 20H).

Example 18

{4-[5-(2-Amino-2-methyl-propyl)-thiophen-2-yl]-pyrimidin-2-yl}-(2,2,6,6-tetramethyl-piperidin-4-yl)-amine

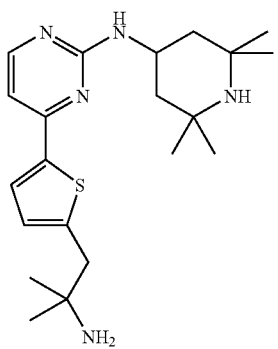

The title compound was prepared analogous to Method C, starting from (4-chloro-pyrimidin-2-yl)-(2,2,6,6-tetramethyl-piperidin-4-yl)-amine and (1,1-Dimethyl-2-thiophen-2-yl-ethyl)-carbamic acid tert-butyl ester (prepared by BOC protection of 1,1-Dimethyl-2-thiophen-2-yl-ethylamine), followed by BOC cleavage with HCl in dioxane.

MS (ESI): 388.0 [M+H]$^{+1}$H-NMR (DMSO-d$_6$) δ (ppm) 8.25 (br m, 1H), 7.72 (d, 1H), 6.98 (d, 1H), 6.92 (d, 1H), 4.26 (m, 1H), 2.82 (s, 2H), 2.07 (m, 2H), 1.8 (br m, 2H), 1.0-1.35 (m, 20H).

Example 19

2,2-Difluoro-3-methyl-1-{5-[2-(2,2,6,6-tetramethyl-piperidin-4-ylamino)-pyrimidin-4-yl]-thiophen-2-yl}-butane-1,3-diol

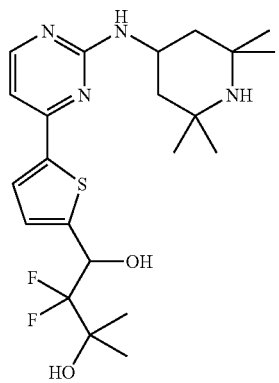

The title compound was prepared analogous to Method C, starting from (4-chloro-pyrimidin-2-yl)-(2,2,6,6-tetramethyl-piperidin-4-yl)-amine and 2-[1,3-Bis-(tert-butyl-dimethyl-silanyloxy)-2,2-difluoro-3-methyl-butyl]-thiophene (prepared from 2,2-Difluoro-3-hydroxy-3-thiophen-2-yl-propionic acid ethyl ester by treatment with MeMgBr (Step A of Method A) and TBDMS protection), followed by TBDMS cleavage with TBAF in THF.

MS (ESI): 455.0 [M+H]$^{+1}$H-NMR (CDCl$_3$) δ (ppm) 8.2 (br m, 1H), 7.55 (d, 1H), 7.13 (d, 1H), 6.85 (d, 1H), 5.42 (m, 1H), 5.0 (br m, 1H), 4.37 (m, 1H), 2.07 (m, 2H), 0.95-1.55 (m, 20H).

Example 20

2,3,3-Trimethyl-4-{5-[2-(2,2,6,6-tetramethyl-piperidin-4-ylamino)-pyrimidin-4-yl]-thiophen-2-yl}-butan-2-ol

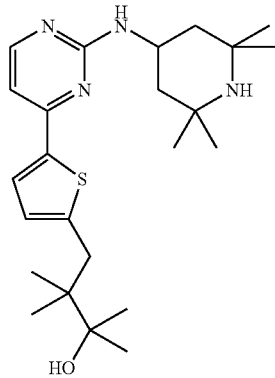

The title compound was prepared analogous to Method C, starting from (4-chloro-pyrimidin-2-yl)-(2,2,6,6-tetramethyl-piperidin-4-yl)-amine and 2,3,3-trimethyl-4-thiophen-2-yl-butan-2-ol (prepared from 2,2-dimethyl-3-thiophen-2-yl-propionic acid by esterification with diazomethane and treatment with MeMgBr (Step A of Method A)).

MS (ESI): 431.0 [M+H]$^{+1}$H-NMR (DMSO-d$_6$) δ (ppm) 8.25 (br m, 1H), 7.72 (d, 1H), 6.97 (d, 1H), 6.89 (d, 1H), 4.26 (m, 1H), 4.22 (s, 1H), 2.86 (s, 2H), 1.82 (br m, 2H), 1.0-1.35 (m, 20H), 0.85 (s, 6H).

Example 21

[4-(5-Benzyloxy-thiophen-2-yl)-pyrimidin-2-yl]-(2,2,6,6-tetramethyl-piperidin-4-yl)-amine

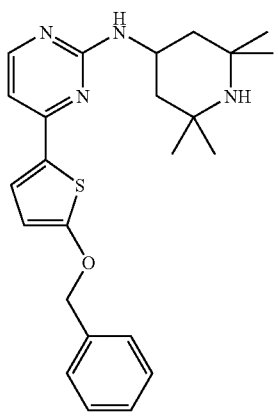

The title compound was prepared analogous to Method C, starting from (4-chloro-pyrimidin-2-yl)-(2,2,6,6-tetramethyl-piperidin-4-yl)-amine and 2-benzyloxy-thiophene.

MS (ESI): 423.0 [M+H]$^{+1}$H-NMR (DMSO-d$_6$) δ (ppm) 8.18 (br m, 1H), 7.62 (d, 1H), 7.35-7.55 (m, 5H), 6.94 (d, 1H), 6.52 (d, 1H), 5.23 (s, 2H), 4.23 (m, 1H), 1.77 (br m, 2H), 1.0-1.3 (m, 14H).

Example 22

[4-(5-Butyl-thiophen-2-yl)-pyrimidin-2-yl]-(2,2,6,6-tetramethyl-piperidin-4-yl)-amine

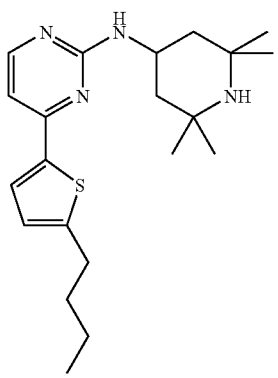

The title compound was prepared analogous to Method C, starting from (4-chloro-pyrimidin-2-yl)-(2,2,6,6-tetramethyl-piperidin-4-yl)-amine and 2-butyl-thiophene.

MS (ESI): 373.0 [M+H]⁺ ¹H-NMR (DMSO-$d_6$) δ (ppm) 8.25 (br m, 1H), 7.71 (d, 1H), 6.97 (d, 1H), 6.93 (d, 1H), 4.25 (m, 1H), 2.84 (t, 2H), 1.8 (br m, 2H), 1.64 (m, 2H), 1.38 (m, 2H), 1.0-1.3 (m, 14H), 0.93 (t, 3H).

Example 23

[4-(5-Proxy-thiophen-2-yl)-pyrimidin-2-yl]-(2,2,6,6-tetramethyl-piperidin-4-yl)-amine

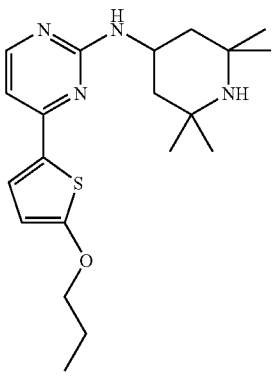

The title compound was prepared analogous to Method C, starting from (4-chloro-pyrimidin-2-yl)-(2,2,6,6-tetramethyl-piperidin-4-yl)-amine and 2-propoxy-thiophene.

MS (ESI): 375.0 [M+H]⁺ ¹H-NMR (DMSO-$d_6$) δ (ppm) 8.18 (br m, 1H), 7.62 (d, 1H), 6.94 (d, 1H), 6.4 (d, 1H), 4.24 (m, 1H), 4.08 (t, 2H), 1.7-1.85 (m, 4H), 1.0-1.35 (m, 14H), 0.97 (t, 3H).

Example 24a

{4-[5-(2-Methoxy-ethoxy)-thiophen-2-yl]-pyrimidin-2-yl}-(2,2,6,6-tetramethyl-piperidin-4-yl)-amine

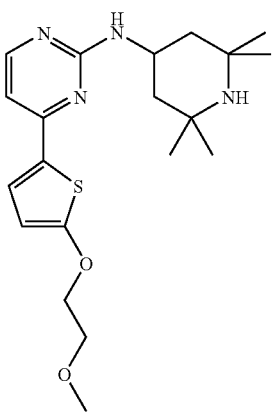

The title compound was prepared analogous to Method C, starting from (4-chloro-pyrimidin-2-yl)-(2,2,6,6-tetramethyl-piperidin-4-yl)-amine and 2-(2-methoxy-ethoxy)-thiophene (prepared by cupric oxide-mediated coupling of 2-methoxy-ethanol and 2-iodo-thiophene, *J. Am. Chem. Soc.* 1953, 3697).

MS (ESI): 391.4 [M+H]⁺ ¹H-NMR (DMSO-$d_6$) δ (ppm) 8.29 (br m, 1H), 7.61 (d, 1H), 6.95 (d, 1H), 6.43 (d, 1H), 4.25 (m, 3H), 3.69 (m, 2H), 3.33 (s, 3H), 1.8 (br m, 2H), 0.95-1.35 (m, 14H).

Example 24b

{4-[5-(2-Dimethylamino-ethoxy)-thiophen-2-yl]-pyrimidin-2-yl}-(2,2,6,6-tetramethyl-piperidin-4-yl)-amine(dihydrochloride)

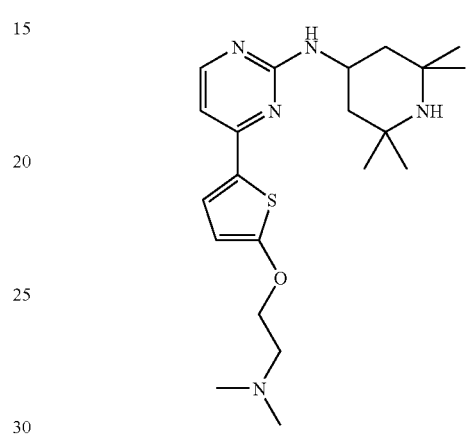

The title compound was prepared analogous to Method C, starting from (4-chloro-pyrimidin-2-yl)-(2,2,6,6-tetramethyl-piperidin-4-yl)-amine and dimethyl-[2-(thiophen-2-yloxy)-ethyl]-amine (prepared by cupric oxide-mediated coupling of 2-dimethylamino-ethanol and 2-iodo-thiophene, *J. Am. Chem. Soc.* 1953, 3697).

MS (ESI): 404.3 [M+H]⁺ ¹H-NMR (DMSO-$d_6$, 120° C.): δ (ppm) 8.25 (d, 1H), 7.9 (br s, 1H), 7.6 (d, 1H), 6.96 (d, 1H), 6.55 (d, 1H), 4.57 (br t, 2H), 4.38 (br m, 1H), 3.54 (br t, 2H), 2.85 (s, 6H), 2.03-2.12 (m, 2H), 1.64-1.75 (m, 2H), 1.58 (s, 6H), 1.52 (s, 6H).

Example 25

[4-(5-Pyridin-4-yl-thiophen-2-yl)-pyrimidin-2-yl]-(2,2,6,6-tetramethyl-piperidin-4-yl)-amine

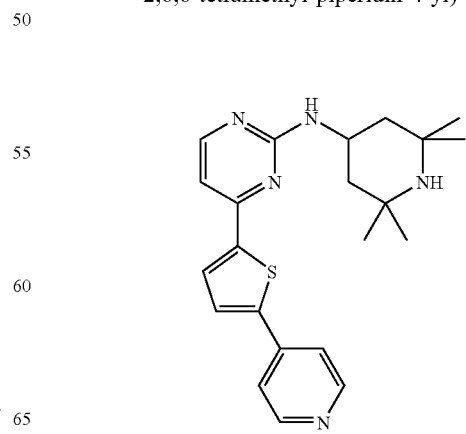

[4-(5-Bromo-thiophen-2-yl)-pyrimidin-2-yl]-(2,2,6,6-tetramethyl-piperidin-4-yl)-amine (Step C of Example 5, 100 mg, 0.253 mmol), 4-trimethylstannylpyridine (186 mg, 0.506 mol) and PdCl$_2$(PPh$_3$)$_2$ (18 mg, 0.025 mmol) were dissolved in xylene (5 ml) and heated to 120° C. for 30 minutes. The reaction mixture was poured on 1N-NaOH and extracted three times with EtOAc. The combined organic phases were dried over sodium sulfate, filtered, evaporated to dryness and purified via preparative HPLC to give the title compound as yellow crystals. Yield: 23 mg (23%)

MS (ESI): 394 [M+H]$^{+1}$H-NMR (CDCl$_3$): δ (ppm) 8.65 (d, 2H), 8.31 (d, 1H), 7.69 (d, 1H), 7.52 (t, 2H), 6.90 (d, 1H), 4.98 (d, 1H), 4.43 (m, 1H), 2.14 (br d, 2H), 1.42 (s, 6H), 1.21 (s, 6H), 1.05 (br t, 2H).

Example 26

1-Methyl-4-{5-[2-(2,2,6,6-tetramethyl-piperidin-4-ylamino)-pyrimidin-4-yl]-thiophen-2-yl}-piperidin-4-ol

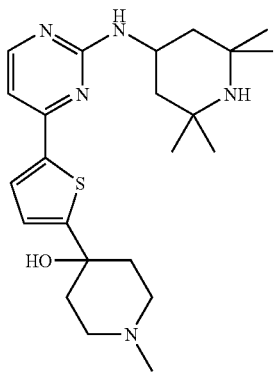

[4-(5-Bromo-thiophen-2-yl)-pyrimidin-2-yl]-(2,2,6,6-tetramethyl-piperidin-4-yl)-amine (Step C of Example 5, 198 mg, 0.5 mmol) was dissolved in THF (10 ml), cooled to −78° C. and treated with nBuLi (1.6M in hexane, 0.94 ml, 1.5 mmol) for 15 minutes. N-methyl-4-piperidone (231 µl, 2 mmol) in THF (0.2 ml) was added rapidly and the reaction mixture stirred for 15 minutes at −78° C., then poured on water and extracted three times with EtOAc. The combined organic phases were dried over sodium sulfate, filtered, evaporated to dryness and purified via preparative HPLC to give the title compound as colorless crystals, which crystallized from ether. Yield: 40 mg (19%).

MS (EI): 429 [M]$^{+1}$H-NMR (CDCl$_3$): δ (ppm) 8.23 (d, 1H), 7.55 (d, 1H), 7.02 (d, 1H), 6.83 (d, 1H), 4.90 (d, 1H, NH), 4.40 (m, 1H), 2.73 (br d, 2H), 2.48 (br t, 2H), 2.36 (s, 3H), 2.21 (dt, 2H), 2.10 (dd, 2H), 1.98 (d, 2H), 1.48 (br s, 1H, NH), 1.36 (s, 6H), 1.17 (s, 6H), 1.00 (t, 2H).

Example 27

[4-(5-Pyridin-3-yl-thiophen-2-yl)-pyrimidin-2-yl]-(2,2,6,6-tetramethyl-piperidin-4-yl)-amine

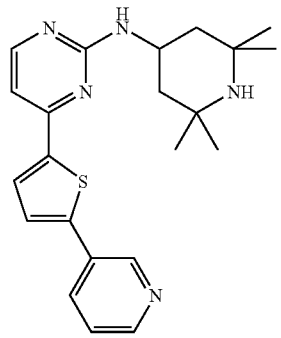

The title compound was prepared as described for Example 25, using [4-(5-bromo-thiophen-2-yl)-pyrimidin-2-yl]-(2,2,6,6-tetramethyl-piperidin-4-yl)-amine (Step C of Example 5) and 3-tributylstannylpyridine. Yield: 38%.

MS (ESI): 394 [M+H]$^{+1}$H-NMR (CDCl$_3$): δ (ppm) 8.95 (d, 1H), 8.58 (d, 1H), 8.29 (d, 1H), 7.92 (d, 1H), 7.68 (d, 1H), 7.41 (t, 1H), 7.36 (dd, 1H), 6.88 (d, 1H), 4.95 (d, 1H), 4.43 (m, 1H), 2.13 (br d, 2H), 1.55 (br s, 1H, NH), 1.39 (s, 6H), 1.18 (s, 6H), 1.03 (br t, 2H).

Example 28

[4-(5-Pyridin-2-yl-thiophen-2-yl)-pyrimidin-2-yl]-(2,2,6,6-tetramethyl-piperidin-4-yl)-amine

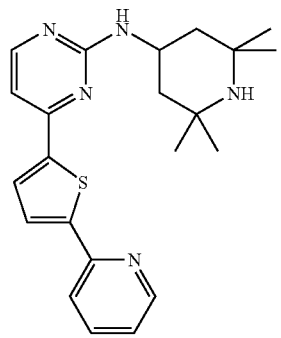

The title compound was prepared as described for Example 25, using [4-(5-bromo-thiophen-2-yl)-pyrimidin-2-yl]-(2,2,6,6-tetramethyl-piperidin-4-yl)-amine (Step C of Example 5) and 3-tributylstannylpyridine. Yield: 13%.

MS (ESI): 394 [M+H]$^{+1}$H-NMR (CDCl$_3$): δ (ppm) 8.62 (d, 1H), 8.29 (d, 1H), 7.71 (m, 3H), 7.64 (d, 1H), 7.21 (dd, 1H), 6.88 (d, 1H), 4.92 (d, 1H), 4.43 (m, 1H), 2.15 (dd, 2H), 1.60 (br s 1H), 1.41 (s, 6H), 1.20 (s, 6H), 1.04 (br t, 2H).

Example 29

[4-(5-Piperazin-4-yl-thiophen-2-yl)-pyrimidin-2-yl]-(2,2,6,6-tetramethyl-piperidin-4-yl)-amine

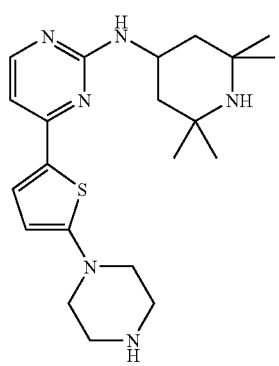

Step A: 4-{5-[2-(2,2,6,6-Tetramethyl-piperidin-4-ylamino)-pyrimidin-4-yl]-thiophen-2-yl}-piperazine-1-carboxylic acid ethyl ester

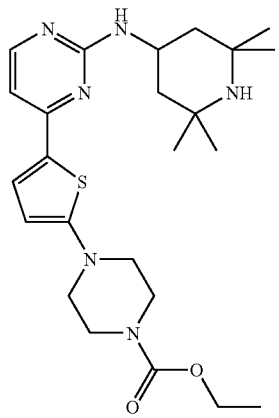

[4-(5-Bromo-thiophen-2-yl)-pyrimidin-2-yl]-(2,2,6,6-tetramethyl-piperidin-4-yl)-amine (Step C of Example 5, 198 mg, 0.5 mmol), NaOtBu (53 mg, 0.55 mmol), R-(+)-BINAP (6.2 mg, 0.01 mmol), Pd(OAc)$_2$ (6.2 mg, 0.027 mol) and N-ethoxycarbonylpiperazine (158 mg, 1.0 mmol) were refluxed in 1,4-dioxan for 18 hours. The reaction mixture was poured on water and extracted three times with EtOAc. The combined organic phases were dried over sodium sulfate, filtered, and purified via chromatography on silicagel (TBME/MeOH/ammonia:98/1.8/0.2 to 95/4.5/0.5) to give the title compound as yellow solid. Yield: 120 mg (50%).

Step B: [4-(5-Piperazin-4-yl-thiophen-2-yl)-pyrimidin-2-yl]-(2,2,6,6-tetramethyl-piperidin-4-yl)-amine 4-{5-[2-(2,2,6,6-Tetramethyl-piperidin-4-ylamino)-pyrimidin-4-yl]-thiophen-2-yl}-piperazine-1-carboxylic acid ethyl ester (120 mg, 0.25 mmol) in chloroform (5 ml) was treated with Me$_3$SiI (0.34 ml, 2.5 mmol) at 60° C. for 4 hours. 6N-HCl in propanol (5 ml) was added and stirred for 30 minutes at room temperature. The reaction mixture was poured on 2N-NaOH and extracted 5 times with EtOAc. The combined organic phases were dried over sodium sulfate, filtered, and purified via chromatography on silicagel (TBME/MeOH/ammonia:95/4.5/0/5 to 80/18/2) to give the title compound as yellow crystals. Yield: 20 mg (20%).

MS (ESI): 401 [M+H]$^{+1}$ H-NMR (CDCl$_3$): δ (ppm) 8.12 (d, 1H), 7.43 (d, 1H), 6.72 (d, 1H), 6.10 (d, 1H), 4.85 (d, 1H), 4.43 (m, 1H), 3.23 (m, 4H), 3.06 (m, 4H), 2.15 (dd, 2H), 1.61 (br s 1H), 1.40 (s, 6H), 1.21 (s, 6H), 1.03 (br t, 2H).

Example 30

4-(5-{2-[(8-Aza-bicyclo[3.2.1]oct-3-yl) exo-amino]-pyrimidin-4-yl}-thiophen-2-yl)-1-methyl-piperidin-4-ol

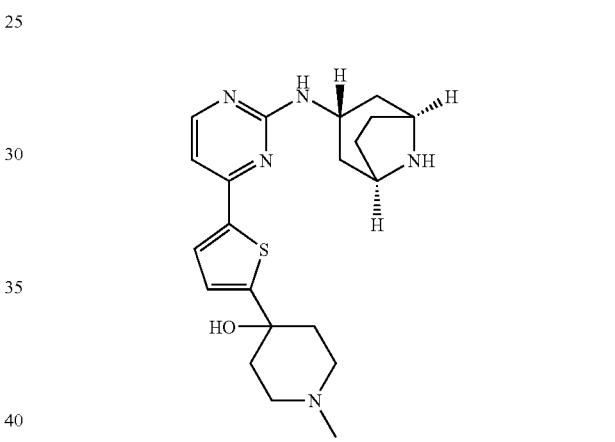

5-Bromo-{2-[(8-aza-bicyclo[3.2.1]oct-3-yl)exo-amino]-pyrimidin-4-yl}-thiophen (prepared analogous to Method E, using 4-iodo-2-methylsulfanyl-pyrimidine, (5-bromo-thiophen-2-yl)-tributyl-stannane and (1R,5S)-3-amino-8-aza-bicyclo[3.2.1]octane-8-carboxylic acid tert-butyl ester (WO 99/36424)), (183 mg, 0.5 mmol) in THF (10 ml) was cooled to −78° C. and treated with nBuLi (1.6M in hexane, 0.94 ml, 1.5 mmol) for 15 minutes. N-methyl-4-piperidone (231 μl, 2 mmol) was added in THF (0.2 ml) within 10 minutes and the resulting mixture stirred for 15 minutes at −78° C. The reaction mixture was poured on water and extracted 4 times with EtOAc. The combined organic phases were dried over sodium sulfate, filtered, and purified via chromatography on silicagel (TBME/MeOH/ammonia:80/18/2 to 60/36/4) to give the title compound as brownish solid. Yield: 80 mg (40%).

MS (ESI): 400 [M+H]$^{+1}$ H-NMR (DMSO-d$_6$, 120° C.): δ (ppm) 8.20 (d, 1H), 7.61 (d, 1H), 7.01 (d, 1H), 6.86 (d, 1H), 6.13 (br d, 1H, NH), 4.84 (br s, 1H, OH), 4.23 (m, 1H), 3.48 (br s, 2H), 2.88 (br s, 1H, NH), 2.41-2.58 (m, 4H), 2.23 (s, 3H), 1.71-2.07 (m, 10H), 1.51 (br t, 2H).

Example 31

8-Aza-bicyclo[3.2.1]oct-3-yl-[4-(5-piperazin-1-yl-thiophen-2-yl)-pyrimidin-2-yl]-exo-amine

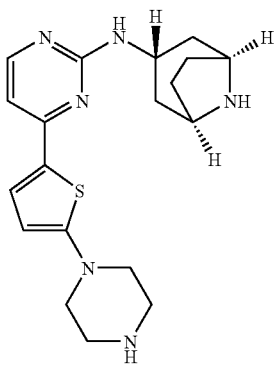

Step A: 8-Aza-bicyclo[3.2.1]oct-3-yl-[4-(5-(4-ethoxycarbonyl)piperazin-1-yl-thiophen-2-yl)-pyrimidin-2-yl]-exo-amine

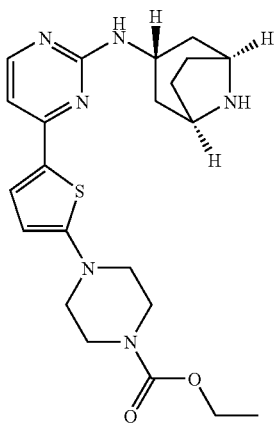

5-Bromo-{2-[(8-aza-bicyclo[3.2.1]oct-3-yl) exo-amino]-pyrimidin-4-yl}-thiophen (prepared as described in Example 30) (183 mg, 0.5 mmol), N-ethoxycarbonylpiperazine (158 mg, 0.55 mmol), Pd(OAc)$_2$ (6.2 mg, 0.027 mmol), R-(+)-BINAP (6.2 mg, 0.01 mmol) and NaOtBu (53 mg, 0.55 mmol) were dissolved in 1,4-dioxane and heated to 110° C. for 18 hours. The reaction mixture was poured on water and extracted three times with TBME. The combined organic phases were dried over sodium sulfate, filtered, and purified via chromatography on silicagel (TBME/MeOH/ammonia: 90/9/1 to 80/18/2) to give the title compound as brownish solid. Yield: 20 mg (9%).

Step B: 8-Aza-bicyclo[3.2.1]oct-3-yl-[4-(5-piperazin-1-yl-thiophen-2-yl)-pyrimidin-2-yl]-exo-amine 8-Aza-bicyclo[3.2.1]oct-3-yl-[4-(5-(4-ethoxycarbonyl)piperazin-1-yl-thiophen-2-yl)-pyrimidin-2-yl]-exo-amine (20 mg, 0.04 mmol) was dissolved in chloroform (0.4 ml) and treated with Me$_3$SiI (0.4 ml) at 60° C. for 5 hours. 6M-HCl in propanol (4 ml) was added and stirred for 30 minutes at room temperature. The reaction mixture was poured on 2N-NaOH and extracted 5 times with EtOAc. The combined organic phases were dried over sodium sulfate, filtered, and purified via preparative HPLC to give the title compound as yellow crystals. Yield: 5 mg (15%).

MS (ESI): 371 [M+H]$^+$

Example 32

{4-[5-((E)-3-Amino-3-methyl-but-1-enyl)-thiophen-2-yl]-pyrimidin-2-yl}-(2,2,6,6-tetramethyl-piperidin-4-yl)-amine

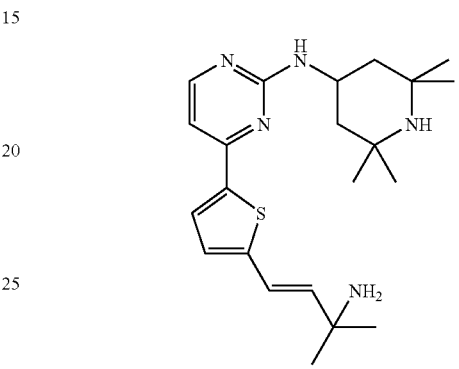

A solution of {4-[5-(3-Amino-3-methyl-but-1-ynyl)-thiophen-2-yl]-pyrimidin-2-yl}-(2,2,6,6-tetramethyl-piperidin-4-yl)-amine (Example 5, 100 mg, 0.252 mmol) in 10 ml of THF and LAH (1M in THF, 0.25 ml, 0.25 mmol) was refluxed for 3 hours, poured on water and extracted 3 times with TBME. The combined organic phases were dried over sodium sulfate, filtered and purified via chromatography on silicagel (DCM/MeOH/ammonia:90/10/1 to 85/15/2) to give the title compound as yellow solid. Yield: 20 mg (20%).

MS (ESI): 400 [M+H]$^{+1}$H-NMR (CDCl$_3$): δ (ppm) 8.23 (d, 1H), 7.55 (d, 1H), 6.96 (d, 1H), 6.82 (d, 1H), 6.61 (d, 1H), 6.28(d, 1H), 4.89 (d, 1H), 4.42 (m, 1H), 2.11 (br d, 2H), 1.52 (br s, 3H, NH2/NH), 1.40 (s, 6H), 1.32 (s, 6H), 1.20 (s, 6H), 1.05 (br t, 2H).

Example 33

{4-[5-(3-Amino-3-methyl-butyl)-thiophen-2-yl]-pyrimidin-2-yl}-(2,2,6,6-tetramethyl-piperidin-4-yl)-amine

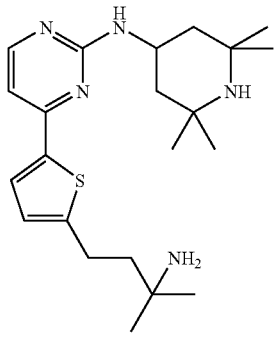

{4-[5-(3-Amino-3-methyl-but-1-ynyl)-thiophen-2-yl]-pyrimidin-2-yl}-(2,2,6,6-tetramethyl-piperidin-4-yl)-amine (Example 5, 100 mg, 0.252 mmol) in MeOH (100 ml) was hydrogenated over Pd/C (10%, 50 mg) at 1 atm for 2 hours. The reaction mixture was filtered, evaporated to dryness and purified via chromatography on silicagel (DCM/MeOH/ammonia: 95/5/1 to 90/10/1) to give the title compound as colorless solid, which crystallized from ether.

Yield: 20 mg (20%).

MS (ESI): 402 [M+H]$^{+1}$H-NMR (CDCl$_3$): δ (ppm) 8.21 (d, 1H), 7.52 (d, 1H), 6.84 (d, 1H), 6.80 (d, 1H), 4.87 (d, 1H, NH), 4.40 (m, 1H), 2.93 (m, 2H), 2.12 (br d, 2H), 1.81 (m, 2H), 1.52 (br s, 3H, NH2/NH), 1.39 (s, 6H), 1.20 (s, 12H), 1.03 (br t, 2H).

Example 34

2-Methyl-4-{5-[2-(2,2,6,6-tetramethyl-piperidin-4-ylamino)-pyrimidin-4-yl]-thiophen-2-yl}-but-3-yn-2-ol

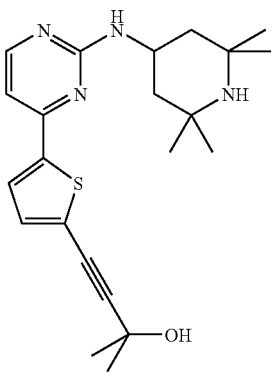

{4-[5-Bromothiophen-2-yl]-pyrimidin-2-yl}-(2,2,6,6-tetramethyl-piperidin-4-yl)-amine, described in Example 5, (300 mg, 0.76 mmol), PdCl$_2$(PPh$_3$)$_2$ (18 mg, 0.025 mmol), 2-methyl-but-3-yn-2-ol (0.3 ml, 2.53 mmol) and CuI (15 mg) were dissolved in triethylamine (25 ml) and refluxed for 1 hour. The reaction mixture was evaporated, taken up in water and extracted 3 times with TBME. The combined organic phases were dried over sodium sulfate, filtered, and purified via chromatography on silicagel (DCM/MeOH/ammonia:95/5/1 to 90/10/1) to give the title compound as white solid, which was crystallized as HCl-salt from EtOH/HCl. Yield: 150 mg (32%).

MS (ESI): 399 [M+H]$^{+1}$H-NMR (DMSO-d$_6$): δ (ppm) 8.98 (br s 1H, NH), 8.37 (d, 1H), 7.88 (d, 1H), 7.32 (d, 1H), 7.17 (d, 1H), 4.32 (m, 1H), 2.05 (br d, 2H), 1.53 (m, 3H), 1.48 (s, 12H), 1.42 (s, 6H).

Example 35

{4-[5-(3-RS-Methyl-piperazin-1-yl)-thiophen-2-yl]-pyrimidin-2-yl}-(2,2,6,6-tetramethyl-piperidin-4-yl)-amine

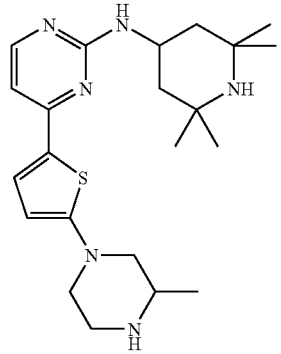

{4-[5-Bromothiophen-2-yl]-pyrimidin-2-yl}-(2,2,6,6-tetramethyl-piperidin-4-yl)-amine, (Step C of Example 5, 395 mg, 1 mmol), Pd(OAc)$_2$ (20 mg), R-(+)-BINAP (20 mg), 2-methylpiperazine (500 mg, 5 mmol) and NaOtBu (400 mg, 4 mmol) were dissolved in 1,4-dioxan (6 ml) and refluxed for 3 hours. The reaction mixture was poured on water and extracted 3 times with EtOAc. The combined organic phases were dried over sodium sulfate, filtered through a bed of silicagel (TBME/MeOH/ammonia:90/10/1) and purified via preparative HPLC to give the title compound as yellow crystals. Yield: 10 mg (2%).

MS (ESI): 415 [M+H]$^{+1}$H-NMR (CDCl$_3$): δ (ppm) 8.12 (d, 1H), 7.43 (d, 1H), 6.73 (d, 1H), 6.10 (d, 1H), 4.88 (br d, 1H), 4.45 (m, 1H), 3.48 (br d, 2H), 2.90-3.17 (m, 5H), 2.59 (br t, 1H), 2.13 (br d, 2H), 1.41-1.79 (m, 14H), 1.18 (d, 3H).

Example 36

5-[2-(2,2,6,6-Tetramethyl-piperidin-4-ylamino)-pyrimidin-4-yl]-thiophene-2-sulfonic acid amide

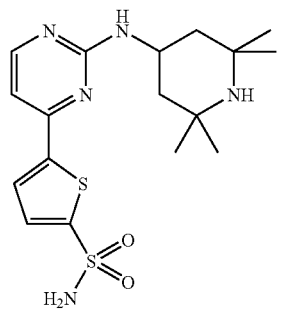

Step A: 5-Trimethylstannanyl-thiophene-2-sulfonic acid amide

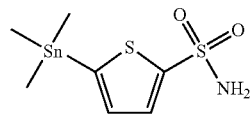

To a degassed suspension of 5-bromo-thiophene-2-sulfonic acid amide (500 mg, 2.07 mmol) in 10 ml toluene were added bis(dibenzylideneacetone)palladium (47 mg, 0.083 mmol), triphenylphosphine (87 mg, 0.33 mmol) and hexamethyldistannane (812 mg, 2.48 mmol). The mixture was stirred at 120° C. for 2 hours. The reaction mixture was filtered through Celite, washed with water, dried and concentrated. The residue was purified by chromatography on silica gel (cyclohexane/EtOAc:2/1). Yield: 190 mg (28%).

Example 37

5-[2-(2,2,6,6-Tetramethyl-piperidin-4-ylamino)-pyrimidin-4-yl]-thiophene-2-carboxylic acid ((S)-1-carbamoyl-2-phenyl-ethyl)-amide

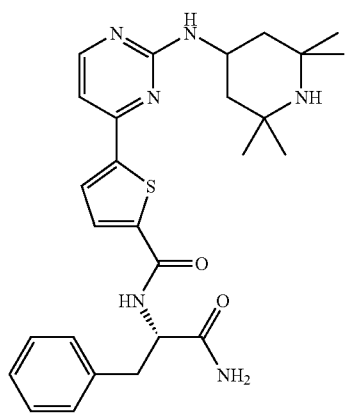

Step A: 5-[2-(2,2,6,6-Tetramethyl-piperidin-4-ylamino)-pyrimidin-4-yl]-thiophene-2-carboxylic acid ethyl ester

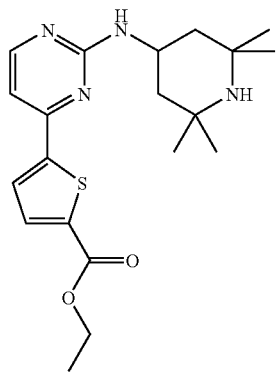

Thiophene-2-carboxylic acid ester (5.0 g, 32.0 mmol), LDA (1.6M in THF, 22.0 ml, 35 mmol), trimethylborate (6.65 g, 64 mmol) and (4-chloro-pyrimidin-2-yl)-(2,2,6,6-tetramethyl-piperidin-4-yl)-amine (8.33 g, 31.0 mmol) were reacted following the procedure given in Step C of Example 3 to give 4.93 g (12.7 mmol, 41%) product as a pale yellow solid.

MS (ESI): 389 [M+H]$^{+1}$H NMR (DMSO-d$_6$) δ (ppm): 8.38 (d, 1H), 7.95 (d, 1H), 7.82 (d, 1H), 7.23-7.30 (m, 1H), 7.16 (d, 1H), 4.32 (q, 2H), 4.20-4.30 (m, 1H), 1.70-1.90 (m, 2H), 1.32 (t, 3H), 1.28 (br s, 6H), 1.08-1.25 (m, 2H), 1.07 (s, 6H).

Step B: 5-[2-(2,2,6,6-Tetramethyl-piperidin-4-ylamino)-pyrimidin-4-yl]-thiophene-2-carboxylic acid

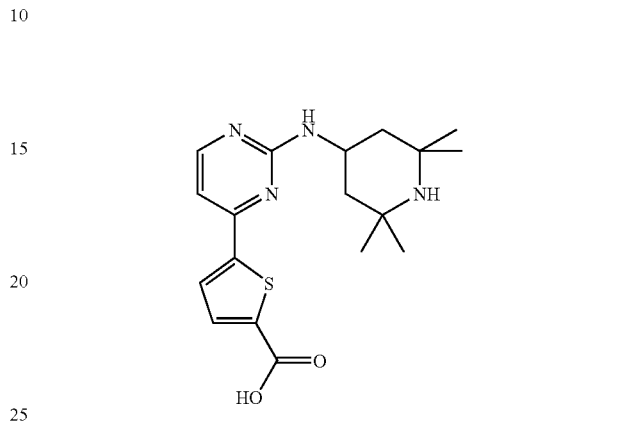

5-[2-(2,2,6,6-Tetramethyl-piperidin-4-ylamino)-pyrimidin-4-yl]-thiophene-2-carboxylic acid ethyl ester (4.90 g, 12.6 mmol) were dissolved in methanol (50 ml). After addition of sodium hydroxide (31 ml of a 40% solution) the mixture was stirred at room temperature overnight. The reaction mixture was acidified using 1N HCl and the product was collected by filtration (4.50 g, 12.5 mmol).

MS (ESI): 361 [M+H]$^{+1}$H NMR (DMSO-d$_6$, 120° C.) δ (ppm): 8.29 (d, 1H), 7.70 (d, 1H), 7.49 (d, 1H), 6.95 (d, 1H), 6.32-6.38 (m, 1H), 4.30-4.41 (m, 1H), 1.94 (dd, 2H), 1.33 (s, 6H), 1.21 (dd, 2H), 1.14 (s, 6H).

Step C: 5-[2-(2,2,6,6-Tetramethyl-piperidin-4-ylamino)-pyrimidin-4-yl]-thiophene-2-carboxylic acid ((S)-1-carbamoyl-2-phenyl-ethyl)-amide 5-[2-(2,2,6,6-Tetramethyl-piperidin-4-ylamino)-pyrimidin-4-yl]-thiophene-2-carboxylic acid (100 mg, 0.28 mmol) and phenylalanin amide (50.1 mg, 0.31 mmol) was dissolved in 5 ml dimethylformamide. After Addition of diisopropyl ethylamine (48 μl, 0.28 mmol) and HATU (105 mg, 0.28 mmol) the mixture was stirred at room temperature overnight. Ethylacetate (100 ml) was added and the solution was washed with NaHCO$_3$, water and brine. The crude product was further purified by HPLC to give 84 mg (0.166 mmol, 60%) of pure product.

MS (ESI): 507 [M+H]$^{+1}$H NMR (DMSO-d$_6$, 120° C.) δ (ppm): 8.37 (d, 1H), 8.05 (d, 1H), 7.79 (d, 1H), 7.74 (d, 1H), 7.16-7.38 (m, 5H), 7.07 (d, 1H), 6.88 (br s, 2H), 4.67-4.75 (m, 1H), 4.30-4.47 (m, 1H), 3.24 (dd, 1H), 3.06 (dd, 1H), 2.10-2.18 (m, 2H), 1.60-1.7 (m, 2H), 1.56 (s, 6H, 1.46 (s, 6H).

The following compounds (Example 38 to Example 43c) were prepared analogous to Step C of Example 37, using 5-[2-(2,2,6,6-tetramethyl-piperidin-4-ylamino)-pyrimidin-4-yl]-thiophene-2-carboxylic acid and the appropriate amines.

Example 38

(S)-3-Phenyl-2-({5-[2-(2,2,6,6-tetramethyl-piperidin-4-ylamino)-pyrimidin-4-yl]-thiophene-2-carbonyl}-amino)-propionic acid methyl ester

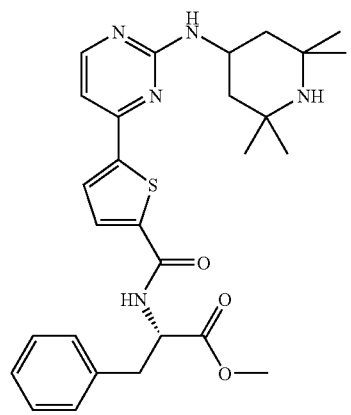

MS (ESI): 522 [M+H]$^{+1}$ H NMR (DMSO-d$_6$) δ (ppm): 9.05 (d, 1H), 8.39 (d, 1H), 7.93 (d, 1H), 7.88 (d, 1H), 7.20-735 (m, 6H), 7.16 (d, 1H), 4.61-4.70 (m, 1H), 4.25-4.37 (m, 1H), 3.68 (s, 3H), 3.20 (dd, 1H), 3.10 (dd, 1H), 1.90-2.06 (m, 4H), 1.46 (br s, 6H), 1.32 (br s, 6H).

Example 39

(R)-3-Phenyl-2-({5-[2-(2,2,6,6-tetramethyl-piperidin-4-ylamino)-pyrimidin-4-yl]-thiophene-2-carbonyl}-amino)-propionic acid methyl ester

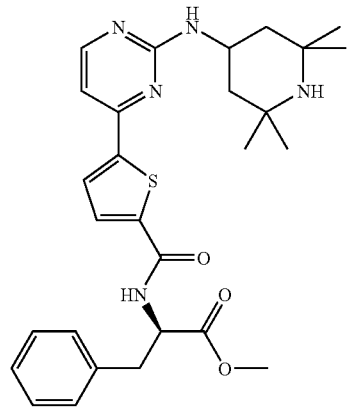

Spectroscopic data are identical to those of the enantiomer given in Example 38.

Example 40

2-Benzyl-1-{5-[2-(2,2,6,6-tetramethyl-piperidin-4-ylamino)-pyrimidin-4-yl]-thiophene-2-carbonyl}-piperidin-4-one

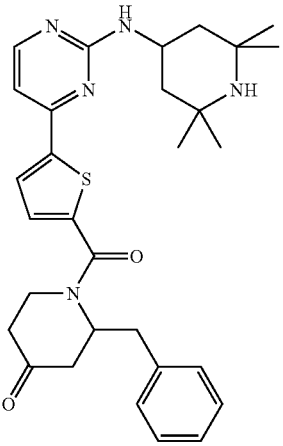

MS (ESI): 532 [M+H]$^{+1}$ H NMR (DMSO-d$_6$) δ (ppm): 8.33 (d, 1H), 7.84 (d, 1H), 7.15-7.31 (m, 8H), 7.10 (d, 1H), 4.95-5.05 (m, 1H), 4.38-4.45 (m, 1H), 4.20-4.32 (m, 1H), 3.60-3.72 (m, 1H), 2.95 (dd, 1H), 2.82-2.90 (m, 2H), 2.63-2.74 (m, 1H), 2.30-2.40 (m, 2H), 1.72-1.85 (m, 2H), 1.26 (br s, 6H), 1.17-1.25 (m, 2H), 1.06 (s, 6H).

Example 41

1-{5-[2-(2,2,6,6-Tetramethyl-piperidin-4-ylamino)-pyrimidin-4-yl]-thiophene-2-carbonyl}-piperidine-4-carboxylic acid isopropylamide

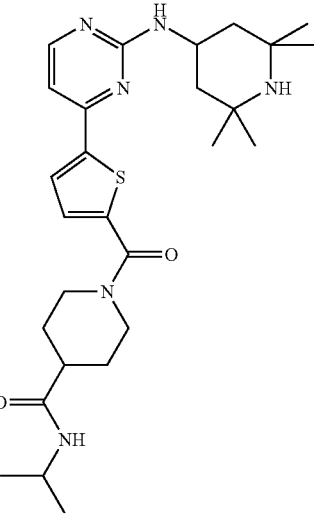

MS (ESI): 513 [M+H]$^{+1}$ H NMR (DMSO-d$_6$) δ (ppm): 8.24 (d, 1H), 7.87 (d, 1H), 7.68 (d, 1H), 7.42 (d, 1H), 7.15-7.22 (m, 1H), 7.12 (d, 1H), 4.20-4.34 (m, 4H), 3.84 (sept, 1H), 2.98-3.10 (m, 1H), 2.35-2.46 (m, 1H), 1.72-1.88 (m, 4H), 1.50-1.64 (m, 2H), 1.28 (br s, 6H), 1.10-1.25 (m, 2H), 1.06 (d, 6H), 1.06 (s, 6H).

Example 42

Biphenyl-4-yl-({5-[2-(2,2,6,6-tetramethyl-piperidin-4-ylamino)-pyrimidin-4-yl]-thiophene-2-carbonyl}-amino)-acetic acid methyl ester

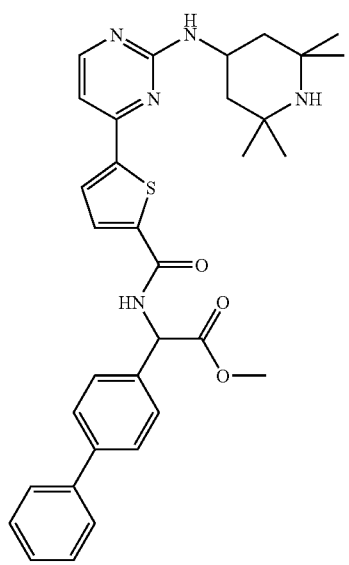

MS (ESI): 584 [M+H]$^+$ $^1$H NMR (DMSO-d$_6$) δ (ppm): 9.48 (br s, 1H), 9.42 (d, 1H), 8.39 (br s, 1H), 8.07 (d, 1H), 7.95 (d, 1H), 7.72 (d, 2H), 7.68 (d, 2H), 7.57 (d, 2H), 7.48 (t, 2H), 7.39 (t, 1H), 7.17 (d, 1H), 5.70 (d, 1H), 4.26-4.38 (m, 1H), 3.70 (s, 3H), 1.92-2.08 (m, 2H), 1.55-1.64 (m, 2H), 1.55 (s, 6H), 1.45 (s, 6H).

Example 43a (2S,4R)-4-Hydroxy-1-{5-[2-(2,2,6,6-tetramethyl-piperidin-4-ylamino)-pyrimidin-4-yl]-thiophene-2-carbonyl}-pyrrolidine-2-carboxylic acid benzyl ester

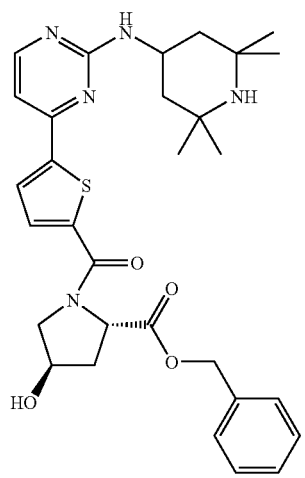

MS (ESI): 564 [M+H]$^+$ $^1$H NMR (DMSO-d$_6$) δ (ppm): 8.39 (d, 1H), 7.96 (d, 1H), 7.70 (d, 1H), 7.58 (br s, 1H), 7.30-7.40 (m, 5H), 7.23 (d, 1H), 5.11-5.30 (m, 4H), 4.64 (t, 1H), 4.43 (br s, 1H), 4.04 (dd, 1H), 2.18-2.27 (m, 1H), 1.94-2.08 (m, 3H), 1.54 (s, 6H), 1.44-1.52 (m, 2H), 1.40 (s, 6H).

Example 43b

5-[2-(2,2,6,6-Tetramethyl-piperidin-4-ylamino)-pyrimidin-4-yl]-thiophene-2-carboxylic acid phenethyl-amide

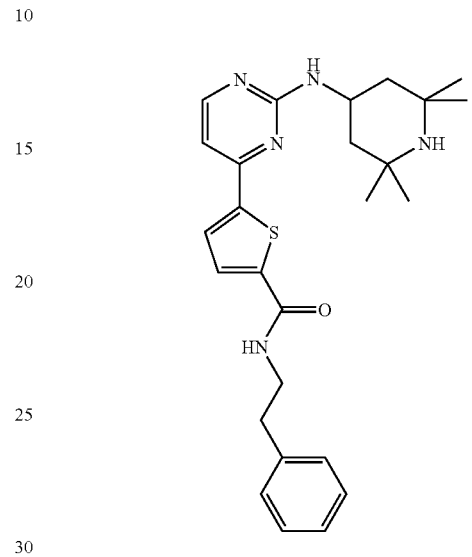

MS (ESI$^+$): 464 [M+H]$^+$ $^1$H-NMR (DMSO-d$_6$): δ (ppm) 8.71 (t, 1H), 8.34 (s, 1H), 7.89 (d, 1H), 7.75 (d, 1H), 7.46-7.20 (m, 5H), 7.08 (d, 1H), 4.34-4.22 (m, 1H), 3.48 (q, 2H), 2.87 (t, 2H), 1.87-1.73 (m, 2H), 1.28 (s, 6H), 1.25-1.08 (m, 3H), 1.06 (s, 6H).

Example 43c

[4-(1H-Indol-3-yl)-piperidin-1-yl]-{5-[2-(2,2,6,6-tetramethyl-piperidin-4-ylamino)-pyrimidin-4-yl]-thiophen-2-yl}-methanone

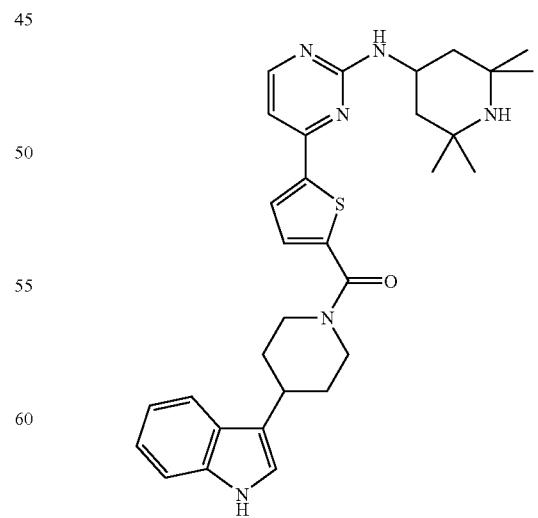

MS (ESI$^+$): 543 [M+H]$^+$ $^1$H-NMR (DMSO-d$_6$) δ (ppm) 10.85 (s, 1H), 8.34 (s, 1H), 7.89 (d, 1H), 7.62 (d, 1H), 7.47 (d, 1H), 7.36 (d, 1H), 7.20-6.96 (m, 5H), 4.47-4.22 (m, 3H), 3.28-3.12 (m, 3H), 2.13-2.04 (m, 2H), 1.86-1.64 (m, 4H), 1.26 (s, 6H), 1.20-1.07 (m, 2H), 1.05 (s, 6H).

Example 44

(4-[2,2']Bithiophenyl-5-yl-5-methyl-pyrimidin-2-yl)-(2,2,6,6-tetramethyl-piperidin-4-yl)-amine

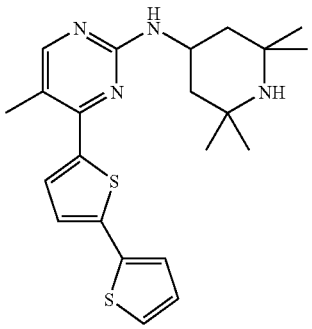

The title compound was prepared analogous to Method A, starting from [2,2']bithiophenyl, 2,4-dichloro-5-methyl-pyrimidine and 4-amino-2,2,6,6-tetramethylpiperidine.

MS (ESI): 413 [M+H]$^{+1}$H-NMR (DMSO-d$_6$) δ (ppm) 8.17 (s, 1H), 7.61 (d, 1H), 7.56 (d, 1H), 7.38 (d, 1H), 7.35 (br d, 1H), 7.13 (dd, 1H), 2.90 (m, 1H), 2.33 (s, 3H), 1.58 (dd, 2H), 1.08 (br s, 6H), 1.04 (br s, 6H), 0.74 (t, 2H).

Example 45

1-{5'-[5-Methyl-2-(2,2,6,6-tetramethyl-piperidin-4-ylamino)-pyrimidin-4-yl]-[2,2']bithiophenyl-5-yl}-ethanone

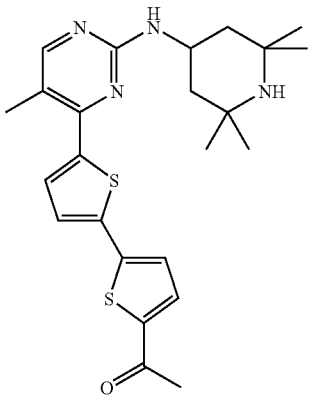

The title compound was prepared analogous to Method A, starting from 1-[2,2']bithiophenyl-5-yl-ethanone, 2,4-dichloro-5-methyl-pyrimidine and 4-amino-2,2,6,6-tetramethylpiperidine.

MS (ESI): 455 [M+H]$^{+1}$H-NMR (DMSO-d$_6$) δ (ppm) 8.20 (br s, 1H), 7.93 (d, 1H), 7.65 (d, 1H), 7.61 (d, 1H), 7.47 (br t, 1H), 4.20 (m, 1H), 2.54 (s, 3H), 2.33 (s, 3H), 1.88 (m, 2H), 1.21 (br t, 2H), 1.07 (br s, 12H).

Example 46

{4-[5'-(1-Amino-ethyl)-[2,2']bithiophenyl-5-yl]-5-methyl-pyrimidin-2-yl}-(2,2,6,6-tetramethyl-piperidin-4-yl)-amine

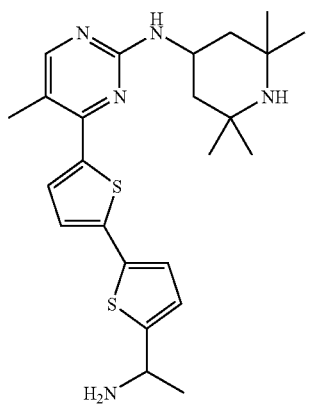

Step, A: 1-{5'-[5-methyl-2-(2,2,6,6-tetramethyl-piperidin-4-ylamino)-pyrimidin-4-yl]-[2,2']bithiophenyl-5-yl}-ethanone.O-methyl-oxime

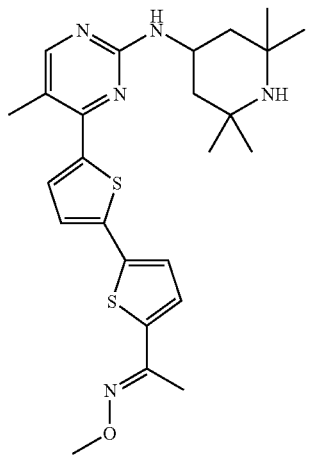

O-Methylhydroxylamine hydrochloride (122 mg, 1.5 mmol) was added to 1-{5'-[5-methyl-2-(2,2,6,6-tetramethyl-piperidin-4-ylamino)-pyrimidin-4-yl]-[2,2']bithiophenyl-5-yl}-ethanone, Example 45, (102 mg, 0.22 mmol) in MeOH (25 mL) and the reaction was heated at 80° C. for 3 hours then allowed to cool to room temperature. 2N-NaOH was added and the solution was evaporated under reduced pressure. Water was added, the aqueous layer was extracted with EtOAc and the organic layer was evaporated under reduced pressure. The crude residue was purified by chromatography on silicagel (1% ammonia, 5-15% MeOH in EtOAc) to give 1-{5'-[5-methyl-2-(2,2,6,6-tetramethyl-piperidin-4-ylamino)-pyrimidin-4-yl]-[2,2']bithiophenyl-5-yl}-ethanone.O-methyl-oxime. Yield: 97 mg (91%).

Step B: {4-[5'-(1-Amino-ethyl)-[2,2']bithiophenyl-5-yl]-5-methyl-pyrimidin-2-yl}-(2,2,6,6-tetramethyl-piperidin-4-yl)-amine Borane (1M in THF, 0.18 ml, 0.18 mmol) was added dropwise to a solution of 1-{5'-[5-methyl-2-(2,2,6,6-tetramethyl-piperidin-4-ylamino)-pyrimidin-4-yl]-[2,2']bithiophenyl-5-yl}-ethanone.O-methyl-oxime (43 mg, 0.09 mmol) in THF (2 mL). The reaction was heated at 80° C. for 18 hours. Another portion of borane (0.18 mL, 0.18 mmol) was added and heating was continued for 3 hours. The reaction mixture was allowed to cool to room temperature and was concentrated under reduced pressure. A mixture of 1N-HCl (2 mL) and isopropanol (2 mL) was added dropwise and the mixture was heated at 85° C. for 4 hours, allowed to cool to room temperature, and concentrated under reduced pressure. Water was added to the residue and the pH was adjusted to 12 with 1N-NaOH. The mixture was extracted with DCM and the organic extract was concentrated under reduced pressure. The crude residue was purified by chromatography on silicagel (1% ammonia, 9% MeOH in DCM) to give {4-[5'-(1-Amino-ethyl)-[2,2']bithiophenyl-5-yl]-5-methyl-pyrimidin-2-yl}-(2,2,6,6-tetramethyl-piperidin-4-yl)-amine.

Yield: 39 mg (95%).

MS (ESI): 456 [M+H]$^{+1}$H-NMR (DMSO-d$_6$) δ (ppm) 8.20 (br s, 1H), 7.93 (d, 1H), 7.67 (d, 1H), 7.61 (d, 1H), 7.47 (br m, 1H), 4.20 (m, 1H), 2.53 (s, 3H), 2.34 (s, 3H), 1.87 (br m, 2H), 1.35 (br s, 6H), 1.31 (br m, 2H), 1.22 (br s, 6H).

Example 47

[5-Bromo-4-(4,5,6,7-tetrahydro-benzo[b]thiophen-2-yl)-pyrimidin-2-yl]-(2,2,6,6-tetramethyl-piperidin-4-yl)-amine

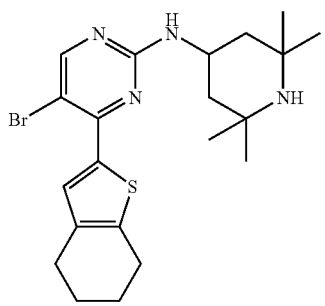

Compound of Example 96 (83 mg, 0,23 mmol) was dissolved in 3 ml acetic acid/water 1/1 and cooled to 0° C. and 12 μl (0.23 mmol) bromine dissolved in 2 ml acetic acid/water 1/1 was added dropwise. This mixture was stirred for 1 hour at 0° C. and was then poured to 20 ml water, the pH was adjusted to 14 by addition of 2N-NaOH and afterwards extracted with EtOAc. The crude was purified by chromatography on silicagel (DCM/MeOH/ammonia:9/1/0.1). Yield: 70 mg (70%).

MS (ESI): 449 [M+H]$^{+1}$H-NMR (DMSO-d$_6$): δ (ppm) 8.40 (s, 1H), 8.00 (s, 1H), 7.35-7.25 (m, 1NH), 4.30-4.15 (m, 1H), 2.80-2.70 (m, 2H), 2.65-2.55 (m, 2H), 1.95-1.70 (m, 6H), 1.35-1.00 (m, 14H).

Example 48

N-(2-{5-[5-Bromo-2-(2,2,6,6-tetramethyl-piperidin-4-ylamino)-pyrimidin-4-yl]-thiophen-2-yl}-ethyl)-acetamide

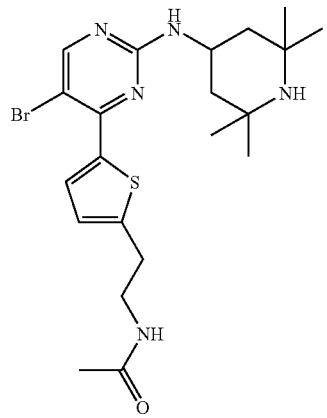

Compound of Example 101 was brominated analogous to Example 47

MS (ESI): 480 [M+H]$^{+1}$H-NMR (DMSO-d$_6$): δ (ppm) 8.40 (m, 1H), 8.15 (m, 1H), 8.00 (m, 1NH), 7.35 (m, 1NH), 7.00 (m, 1H), 4.25-4.10 (m, 1H), 3.35-3.25 (m, 2H), 2.95-2.85 (m, 2H), 1.90-1.80 (m, 5H), 1.35-1.05 (m, 14H).

Example 49

{4-[5-(2-Amino-ethyl)-thiophen-2-yl]-5-bromo-pyrimidin-2-yl}-(2,2,6,6-tetramethyl-piperidin-4-yl)-amine

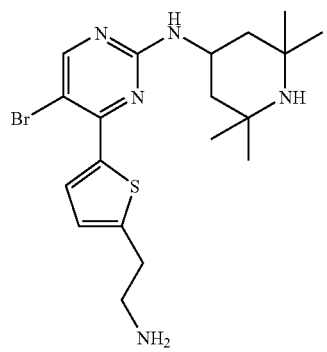

Compound of Example 95 was brominated analogous to Example 47

MS (ESI): 438.2 [M+H]$^{+1}$H-NMR (DMSO-d$_6$, 120° C.): δ (ppm) 8.40 (s, 1H), 8.15 (d, 1H), 7.10 (d, 1H), 4.35-4.25 (m, 1H), 3.35 (t, 2H), 3.15 (t, 2H), 2.05-2.00 (m, 2H), 1.80-1.70 (m, 2H), 1.60 (s, 6H), 1.50 (s, 6H).

Example 50

{5-Bromo-4-[5-(2-dimethylamino-ethyl)-thiophen-2-yl]-pyrimidin-2-yl}-(2,2,6,6-tetramethyl-piperidin-4-yl)-amine

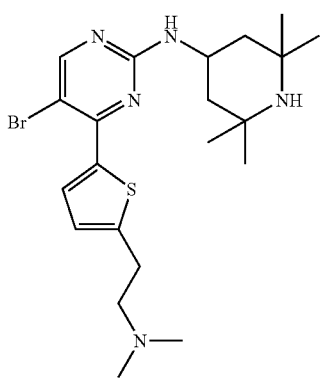

Compound of Example 102 was brominated analogous to Example 47

MS (EI): 467 [M+] $^1$H-NMR (DMSO-$d_6$): δ (ppm) 8.45 (m, 1H), 8.15 (m, 1H), 7.10 (d, 1H), 4.30-4.20 (m, 1H), 3.45-3.35 (m, 4H0, 2.80 (m, 6H), 2.05-1.95 (m, 2H), 1.60-1.40 (m, 14H).

Example 51

1-(4-{5-[2-(2,2,6,6-Tetramethyl-piperidin-4-ylamino)-pyrimidin-4-yl]-thiophen-2-yl}-phenyl)-ethanone O-methyl-oxime

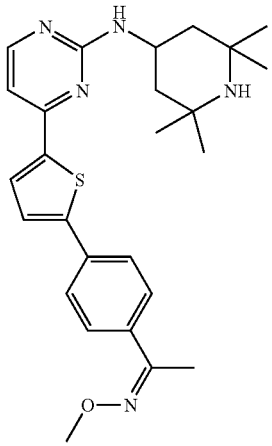

Compound of Example 103 (421 mg, 0.97 mmol) was dissolved in 5 ml of MeOH, then O-methylhydroxylamine hydrochloride (174 mg, 2.1 mmol) was added. This mixture was refluxed for 3 hours and then evaporated. The residue was dissolved in 50 ml water and basified with 2N NaOH solution and afterwards extracted with EtOAc. The crude was purified by chromatography on silicagel (DCM/MeOH/ammonia:9/1/0.1). Yield: 426 mg (95%).

MS (ESI): 464.5 [M+H]+ $^1$H-NMR (DMSO-$d_6$, 120° C.): δ (ppm) 8.30 (d, 1H), 7.85 (d, 1H), 7.75-7.65 (m, 4H), 7.55 (d, 1H), 6.95 (d, 1H), 6.65-6.60 (m, 1NH), 4.35-4.25 (m, 1H), 3.95 (s, 3H), 2.20 (s, 3H), 1.90-1.85 (m, 2H), 1.30 (s, 6H), 1.15-1.10 (m, 2H), 1.05 (s, 6H).

Example 52

(4-{5-[4-((Z)-1-Methyl-propenyl)-phenyl]-thiophen-2-yl}-pyrimidin-2-yl(2,2,6,6-tetramethyl-Piperidin-4-yl)-amine

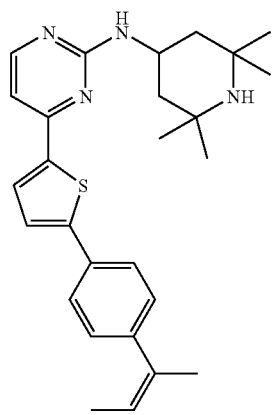

Ethyltriphenylphosphonium bromide+sodium amide (0.5 g, 1.2 mmol) was suspended in 2 ml of THF and 130 mg (0.3 mmol) of compound of Example 103 were added. This mixture was stirred at room temperature for 2 hours and then poured on saturated ammonium chloride solution and afterwards extracted with EtOAc. The crude was purified by chromatography on silicagel (DCM/MeOH/ammonia:95/5/0.5). Yield: 68 mg (50%).

MS (ESI): 447 [M+H]+ $^1$H-NMR (DMSO-$d_6$, 120° C.): 3 (ppm) 8.30 (m, 1H), 7.80 (m, 1H), 7.65 (d, 2H), 7.50 (d, 1H), 7.45 (d, 2H), 6.95 (d, 1H), 4.35-4.20 (m, 1H), 2.05 (s, 3H), 1.90-1.85 (m, 2H), 1.80 (d, 3H), 1.30 (s, 6H), 1.25-1.10 (m, 2H), 1.10 (s, 6H).

Example 53

(4-{5-[4-(1-Amino-ethyl)-phenyl]-thiophen-2-yl}-pyrimidin-2-yl)-(2,2,6,6-tetramethyl-piperidin-4-yl)-amine

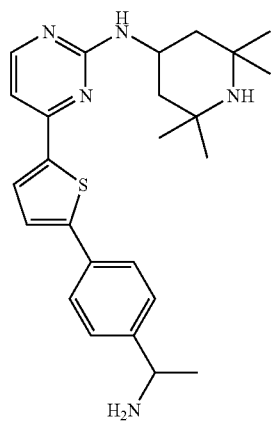

Compound of Example 51 (366 mg, 0.79 mmol) was dissolved in 20 ml THF and 0.35 ml of LAH (~2.3 M suspension in THF) added dropwise at room temperature. Afterwards this mixture was stirred for 2 hours at 60° C. After cooling to room temperature 40 ml of saturated sodium sulfate solution was added and stirred for 15 minutes. The title compound was isolated by extraction with EtOAc and purified by chromatography on silicagel (DCM/MeOH/ammonia:95/5/0.5). Yield: 160 mg (47%).

MS (ESI): 436 [M+H]$^{+1}$H-NMR (DMSO-d$_6$, 120° C.): δ (ppm) 8.35 (d, 1H), 7.85 (d, 1H), 7.75 (d, 2H), 7.65 (d, 2H), 7.55 (d, 1H), 7.05 (d, 1H), 4.45-4.35 (m, 2H), 2.10-2.05 (m, 2H), 1.75-1.65 (m, 2H), 1.65-1.60 (m, 9H), 1.55 (s, 6H).

Example 54

[5-Bromo-4-(5-chloro-thiophen-2-yl)-pyrimidin-2-yl]-(2,2,6,6-tetramethyl-piperidin-4-yl)-amine

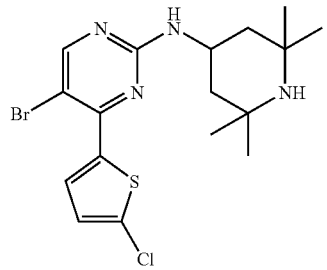

Compound of Example 105 was brominated analogous to Example 47

MS (ESI): 431 [M+H]$^{+1}$H-NMR (DMSO-d$_6$): δ (ppm) 8.45 (m, 1H), 8.15 (m, 1H), 7.30 (m, 1H), 4.30-4.10 (m, 1H), 1.90-1.70 (m, 2H), 1.35-1.05 (m, 14H).

Example 55

4-{5-[5-Bromo-2-(2,2,6,6-tetramethyl-piperidin-4-ylamino)-pyrimidin-4-yl]-thiophen-2-yl}-butyric acid methyl ester

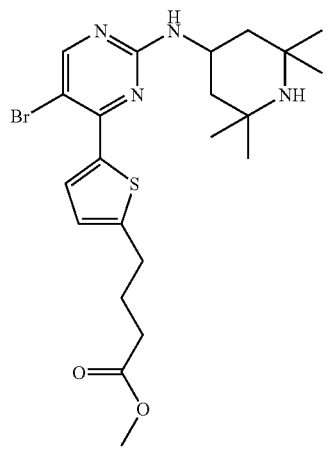

Compound of Example 106 was brominated analogous to Example 47.

MS (ESI): 497 [M+H]$^{+1}$H-NMR (DMSO-d$_6$): δ (ppm) 8.40 (m, 1H), 8.15 (m, 1H), 6.95 (m, 1H), 4.30-4.15 (m, 1H), 2.90 (t, 2H), 2.40 (t, 2H), 1.95 1.75 (m, 4H), 1.35-1.05 (m, 14H).

Example 56

4-{5-[5-Bromo-2-(2,2,6,6-tetramethyl-piperidin-4-ylamino)-pyrimidin-4-yl]-thiophen-2-yl}-butan-1-ol

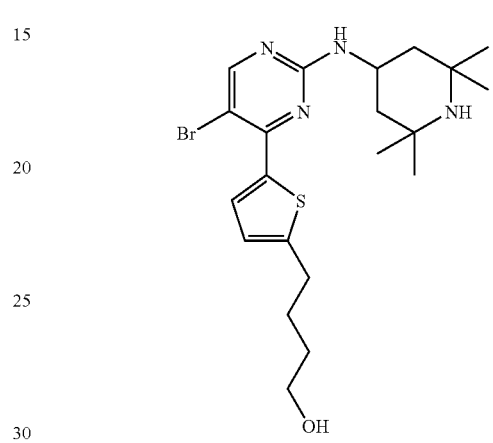

Compound of Example 116 was brominated analogous to Example 47

MS (ESI): 467 [M+H]$^{+1}$H-NMR (DMSO-d$_6$, 120° C.): δ (ppm) 8.35 (s, 1H), 8.10 (d, 1H), 6.95 (d, 1H), 6.60-6.55 (m, 1NH), 4.30-4.20 (m, 1H), 3.90-3.80 (m, 1OH), 3.50-3.45 (m, 2H), 2.90 (t, 2H), 1.95-1.85 (m, 2H), 1.80-1.70 (q, 2H), 1.60-1.50 (q, 2H), 1.30 (s, 6H), 1.25-1.15 (m, 2H), 1.10 (s, 6H).

Example 57

{4-[5'-(1-Amino-ethyl)-[2,2']bithiophenyl-5-yl]-pyrimidin-2-yl}-(2,2,6,6-tetramethyl-piperidin-4-yl)-amine

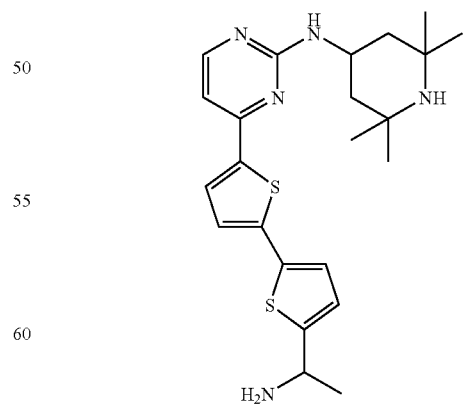

The title compound was prepared from Example 112 by O-methyloxime formation followed by LAH reduction analogous to Example 51 and Example 53.

MS (ESI): 443 [M+H]⁺ ¹H-NMR (DMSO-d₆, 120° C.): δ (ppm) 8.35 (d, 1H), 7.85 (d, 1H), 7.35 (d, 1H), 7.30 (s, 2H), 7.05 (d, 1H), 4.45-4.35 (m, 1H), 3.20-3.10 (m, 1H), 2.15-2.10 (m, 2H), 1.75-1.65 (m, 5H), 1.60 (s, 6H), 1.50 (s, 6H).

Example 58

{4-[5-(3-Aminomethyl-phenyl)-thiophen-2-yl]-pyrimidin-2-yl}-(2,2,6,6-tetramethyl-piperidin-4-yl)-amine

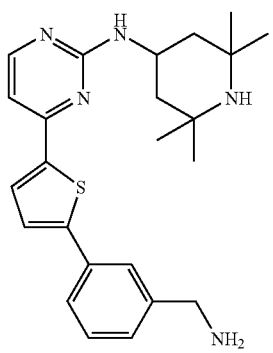

Compound of Example 119 was reduced analogous to Example 1621

MS (ESI): 422 [M+H]⁺ ¹H-NMR (DMSO-d₆, 120° C.): δ (ppm) 8.35 (d, 1H), 7.90 (m, 1H), 7.85 (d, 1H), 7.70-7.60 (m, 1H), 7.55 (d, 1H), 7.45 (m, 1H), 7.05 (d, 1H), 4.45-4.35 (m, 1H), 3.55-3.45 (m, 2H), 2.15-2.05 (m, 2H), 1.75-1.65 (m, 2H), 1.65 (s, 6H), 1.55 (s, 6H).

Example 59

{4-[5-(4-Dimethylaminomethyl-phenyl)-thiophen-2-yl]-pyrimidin-2-yl}-(2,2,6,6-tetramethyl-piperidin-4-yl)-amine

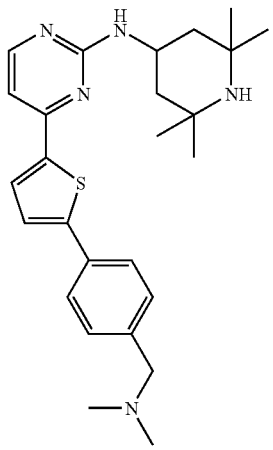

Compound of Example 133 (64 mg, 0.15 mmol) was dissolved in 3 ml MeOH/acetic acid (93/7), then 9 mg (0.3 mmol) formaldehyde solution 37% followed by 22 mg (0.3 mmol) sodium cyanoborohydride were added. This mixture was stirred at room temperature for 2 hours. Afterwards 2 ml 2N hydrochloric acid were added and 20 minutes stirred at room temperature. After addition of 40% NaOH to basify the solution, the title compound was extracted with EtOAc. The crude was purified by chromatography on silicagel (DCM/MeOH/ammonia:95/5/0.5). Yield: 56 mg (80%).

MS (ESI): 450.1 [M+H]⁺ ¹H-NMR (DMSO-d₆, 120° C.): δ (ppm) 8.35 (d, 1H), 7.85 (d, 1H), 7.75-7.65 (m, 4H), 7.60 (d, 1H), 7.05 (d, 1H), 4.45-4.35 (m, 1H), 4.30 (s, 2H), 2.75 (s, 6H), 2.15-2.05 (m, 2H), 1.75-1.65 (m, 2H), 1.60 (s, 6H), 1.50 (s, 6H).

Example 60

(4-{5-[(2-Piperidin-1-yl-ethylamino)-methyl]-thiophen-2-yl}-pyrimidin-2-yl)(2,2,6,6-tetramethyl-piperidin-4-yl)-amine

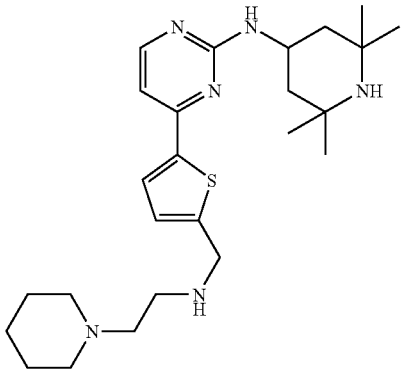

Dess-Martin reagent (16.3 g, 37 mmol) was suspended in 100 ml of DCM and at room temperature compound of Example 114 suspended in 100 ml DCM was quickly added. Stirring was continued for 2 hours at room temperature. Then the reaction was poured on ice/150 ml 1N sodium bicarbonate solution/150 ml 10% sodium bisulfite solution. The solution was basified with 40% NaOH and extracted with DCM. The crude aldehyde was used directly together with 1-(2-Aminoethyl)-piperidine for the reductive amination step analogous to the procedure used in Example 59. Yield: 62%.

MS (ESI): 457 [M+H]⁺ ¹H-NMR (DMSO-d₆, 120° C.): δ (ppm) 8.35 (d, 1H), 7.90 (d, 1H), 7.50 (d, 1H), 7.15 (d, 1H), 4.50 (s, 2H), 4.45-4.35 (m, 1H), 3.55-3.45 (m, 4H), 3.30-3.00 (m, 4H), 2.10-2.05 (m, 2H), 1.90-1.80 (m, 4H), 1.75-166 (m, 2H), 1.65-1.55 (m, 8H), 1.50 (s, 6H).

Example 61

[4-(5-{[Methyl-(2-piperidin-1-yl-ethyl)-amino]-methyl}-thiophen-2-yl)-pyrimidin-2-yl]-(2,2,6,6-tetramethyl-piperidin-4-yl)-amine

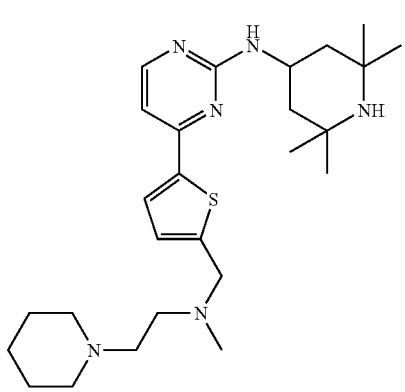

Compound of Example 60 was N-methylated using an analogous protocol to Example 59.

MS (ESI): 471 [M+H]$^{+1}$H-NMR (DMSO-d$_6$, 120° C.): δ (ppm) 8.35 (d, 1H), 7.85 (d, 1H), 7.45 (d, 1H), 7.10 (d, 1H), 4.50-4.35 (m, 3H), 3.50 (m, 4H), 3.25-3.15 (m, 4H), 2.70 (s, 3H), 2.10-2.05 (m, 2H), 1.95-1.85 (m, 4H), 1.80-1.70 (m, 2H), 1.65-1.60 (m, 8H), 1.55 (s, 6H).

Example 62

2-Methyl-5-{5-[2-(2,2,6,6-tetramethyl-piperidin-4-ylamino)-pyrimidin-4-yl]-thiophen-2-yl}-pentan-2-ol

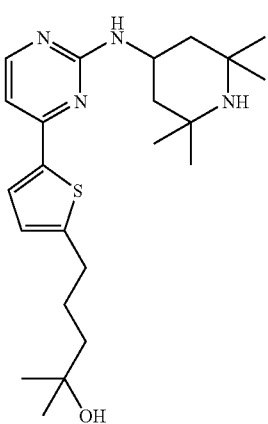

The title compound was prepared analogous to Step A of Method A, starting with compound from Example 106.

MS (ESI): 417 [M+H]$^{+1}$H-NMR (DMSO-d$_6$): δ (ppm) 8.30 (m, 1H), 7.85 (m, 1H), 7.15 (m, 1H), 6.95 (m, 1H), 4.45-4.35 (m, 1H), 2.85-2.80 (t, 2H), 2.10-1.95 (m, 2H), 1.75-1.40 (m, 18H), 1.05 (s, 6H).

Example 63

{4-[5-(2-Isopropylamino-ethyl)-thiophen-2-yl]-pyrimidin-2-yl}-(2,2,6,6-tetramethyl-piperidin-4-yl)-amine

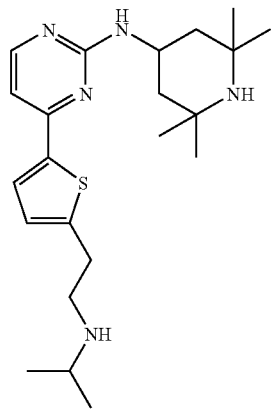

The title compound was prepared from Example 96 by reductive amination analogous to Example 59.

MS (ESI): 402 [M+H]$^{+1}$H-NMR (DMSO-d$_6$, 120° C.): δ (ppm) 8.30 (d, 1H), 7.75 (d, 1H), 7.10 (d, 1H), 7.00 (d, 1H), 4.45-4.35 (m, 1H), 3.50-3.42 (m, 1H), 3.40-3.35 (m, 2H), 3.25-3.15 (m, 2H), 2.10-2.05 (m, 2H), 1.80-1.70 (m, 2H), 1.60 (s, 6H), 1.50 (s, 6H), 1.35 (d, 6H).

Example 64

N-(2-{5-[2-(2,2,6,6-Tetramethyl-piperidin-4-ylamino)-pyrimidin-4-yl]-thiophen-2-yl}-ethyl)-methanesulfonamide

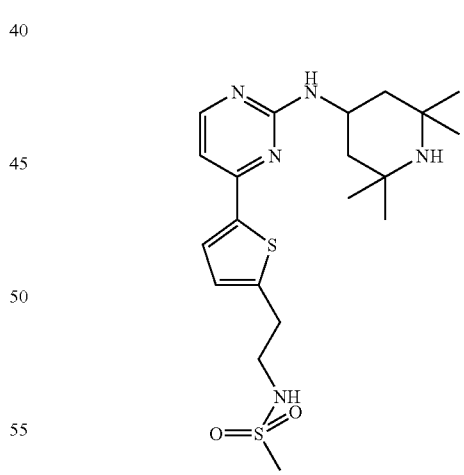

Compound of Example 95 (90 mg, 0.25 mmol) was dissolved in 10 ml THF and 0.2 ml triethylamine and 22 μl (0.28 mmol) methansulfochloride were added. This mixture was stirred for 2 hours at room temperature. Afterwards the solution was diluted with 100 ml water and extracted with EtOAc. The crude was purified by chromatography on silicagel (DCM/MeOH/ammonia:9/1/0.1). Yield: 60 mg (55%).

MS (ESI): 438 [M+H]$^{+1}$H-NMR (DMSO-d$_6$, 120° C.): δ (ppm) 8.30 (d, 1H), 7.70 (d, 1H), 7.00 (m, 2H), 4.45-4.35 (m, 1H), 3.30 (t, 2H), 3.05 (t, 2H), 2.90 (s, 3H), 2.10-2.00 (m, 2H), 1.75-1.65 (m, 2H), 1.60 (s, 6H), 1.50 (s, 6H).

Example 65

(2-{5-[2-(2,2,6,6-Tetramethyl-piperidin-4-ylamino)-pyrimidin-4-yl]-thiophen-2-yl}-ethyl)-urea

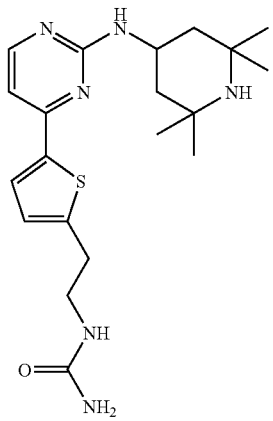

Compound of Example 95 (90 mg, 0.25 mmol) was dissolved in 10 ml water and 0.5 ml 1N hydrochloric acid and 32 mg (0.5 mmol) sodium cyanate were added. This mixture was stirred at 50° C. for 16 hours. Afterwards the solution was basified with 40% NaOH and extracted with EtOAc. The crude was purified by chromatography on silicagel (DCM/MeOH/ammonia:9/1/0.1). Yield: 70 mg (70%).

MS (ESI): 403 [M+H]$^{+1}$H-NMR (DMSO-d$_6$, 120° C.): δ (ppm) 8.30 (d, 1H), 7.70 (d, 1H), 7.00 (d, 1H), 6.95 (d, 1H), 4.45-4.35 (m, 1H), 3.35 (t, 2H), 3.00 (t, 2H), 2.10-2.00 (m, 2H), 1.75-1.65 (m, 2H), 1.60 (s, 6H), 1.50 (s, 6H).

Example 66

{5-[2-(2,2,6,6-Tetramethyl-piperidin-4-ylamino)-pyrimidin-4-yl]-thiophen-2-ylmethyl}-urea

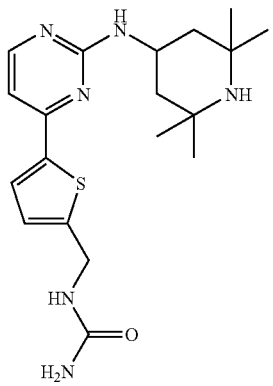

The title compound was prepared starting with compound from Example 132 using an analogous procedure as in Example 65.

MS (ESI): 389 [M+H]$^{+1}$H-NMR (DMSO-d$_6$): δ (ppm) 8.35 (m, 1H), 7.70 (d, 1H), 7.05-7.00 (m, 1NH+2H), 6.55-6.50 (m, 1NH), 5.65-5.55 (m, 2NH), 4.35 (d, 2H), 4.30-4.20 (m, 1H), 1.90-1.70 (m, 2H), 1.35-1.05 (m, 14H).

Example 67

N-{5-[2-(2,2,6,6-Tetramethyl-piperidin-4-ylamino)-pyrimidin-4-yl]-thiophen-2-ylmethyl}-methanesulfonamide

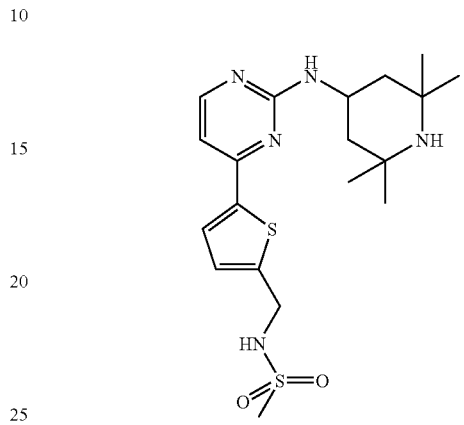

The title compound was prepared starting with compound from Example 132 using an analogous procedure as in Example 64.

MS (ESI): 424 [M+H]$^{+1}$H-NMR (DMSO-d$_6$): δ (ppm) 8.25 (m, 1H), 7.70 (d, 1H), 7.05 (d, 1H), 6.95 (d, 1H), 4.40-4.35 (m, 2H), 4.30-4.20 (m, 1H), 2.90 (s, 3H), 1.85-1.75 (m, 2H), 1.35-1.05 (m, 14H).

Example 68

N-{5'-[2-(2,2,6,6-Tetramethyl-piperidin-4-ylamino)-pyrimidin-4-yl]-[2,2']bithiophenyl-5-ylmethyl}-methanesulfonamide

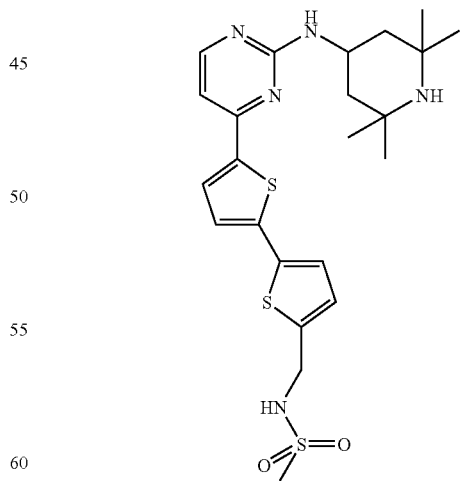

The title compound was prepared starting with compound from Example 68 using an analogous procedure as in Example 64.

MS (ESI): 506 [M+H]$^{+1}$H-NMR (DMSO-d$_6$): δ (ppm) 8.35 (d, 1H), 7.95 (m, 1H), 7.80 (t, 1NH), 7.45 (m, 1H), 7.30

(m, 1H), 7.25 (m, 1H), 7.05 (m, 1H), 4.45-4.35 (m, 3H), 2.90 (s, 3H), 2.15-2.00 (m, 2H), 1.65-1.45 (m, 14H).

Example 69

[4-(5'-Dimethylaminomethyl-[2,2']bithiophenyl-5-yl)-pyrimidin-2-yl]-(2,2,6,6-tetramethyl-piperidin-4-yl)-amine

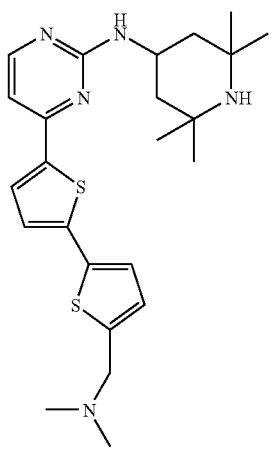

The title compound was prepared from Example 68 by reductive amination analogous to Example 59.

MS (ESI): 456 [M+H]$^{+1}$H-NMR (DMSO-d$_6$): δ (ppm) 8.35 (d, 1H), 7.95 (d, 1H), 7.45 (d, 1H), 7.40 (d, 1H), 7.35 (d, 1H), 7.15 (d, 1H), 4.55 (s, 2H), 4.35-4.25 (m, 1H), 2.75 (m, 6H), 2.15-2.00 (m, 2H), 1.65-1.45 (m, 14H).

Example 70

{5'-[2-(2,2,6,6-Tetramethyl-piperidin-4-ylamino)-pyrimidin-4-yl]-[2,2']bithiophenyl-5-ylmethyl}-urea

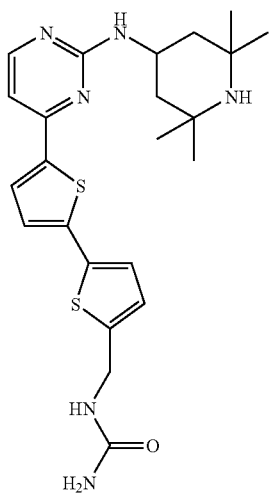

The title compound was prepared starting with compound from Example 68 using an analogous procedure as in Example 65.

MS (ESI): 471 [M+H]$^{+1}$H-NMR (DMSO-d$_6$): δ (ppm) 8.35 (m, 1H), 7.85 (d, 1H), 7.30 (d, 1H), 7.15 (m, 1H), 7.05 (d, 1H), 6.95 (d, 1H), 6.55 (t, 1NH), 5.60 (s, 2NH), 4.35 (d, 2H), 4.35-4.20 (m, 1H), 1.90-1.70 (m, 2H), 1.35-1.05 (m, 14H).

Example 71

2-Methoxy-N-{5'-[2-(2,2,6,6-tetramethyl-piperidin-4-ylamino)-pyrimidin-4-yl]-[2,2']bithiophenyl-5-ylmethyl}-acetamide

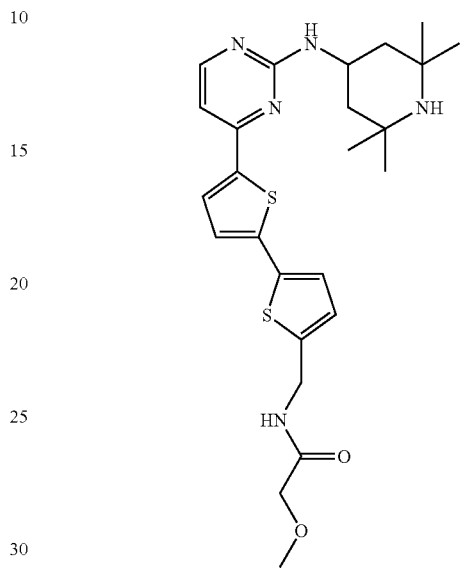

Compound of Example 68 (133 mg, 0.31 mmol) was dissolved in 7 ml THF and 0.2 ml triethylamine and 37 mg (0.35 mmol) methoxyacetylchloride added. This mixture was stirred at room temperature for 3 hours. Afterwards the solution was evaporated and the crude was purified by chromatography on silicagel (DCM/MeOH/ammonia:95/5/0.5). Yield: 137 mg (88%).

MS (ESI): 500 [M+H]$^{+1}$H-NMR (DMSO-d$_6$): δ (ppm) 8.55 (t, 1NH), 8.35 (m, 1H), 8.00 (m, 1H), 7.40 (m, 1H), 7.30 (m, 2H), 6.95 (m, 1H), 4.50-4.30 (m, 3H), 3.85 (s, 2H), 3.30 (5, 3H), 2.15-2.00 (m, 2H), 1.70-1.45 (m, 14H).

Example 72

3-{3-Methyl-5-[2-(2,2,6,6-tetramethyl-piperidin-4-ylamino)-pyrimidin-4-yl]-thiophen-2-yl}-propionamide

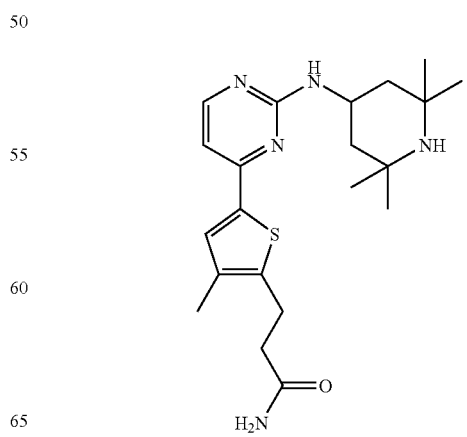

Compound of Example 140 was saponified analogous to Step B of Example 37. 180 mg (0.41 mmol) of this acid derivative were suspended in 12 ml THF and 0.17 ml triethylamine added. The mixture is cooled to −10° C. and 56 mg (0.41 mmol) isobutylchloroformate were added. After stirring for 15 minutes at −10° C., 0.12 ml ammonia 25% in 5 ml THF were added dropwise at −10° C. and stirring continued for 30 minutes at −10° C. Afterwards this mixture was poured to 100 ml water and 40% NaOH added to reach pH~13-14. The title compound was isolated by extraction with EtOAc. The crude was purified by chromatography on silicagel (DCM/MeOH/ammonia:9/1/0.1). Yield: 118 mg (72%).

MS (ESI): 402 [M+H]$^{+1}$H-NMR (DMSO-d$_6$): δ (ppm) 8.35-8.30 (m, 1H), 7.90-7.80 (m, 1H), 7.45-7.40 (m, 1CONH), 7.25-7.15 (m, 1H), 6.90-6.85 (m, 1CONH), 4.45-4.35 (m, 1H), 3.00 (t, 2H), 2.40 (t, 2H), 2.20 (s, 3H), 2.10-2.00 (m, 2H), 1.65-1.40 (m, 14H).

Example 73

{4-[5-(3-Amino-3-ethyl-pentyl)-thiophen-2-yl]-pyrimidin-2-yl}-(2,2,6,6-tetramethyl-piperidin-4-yl)-amine

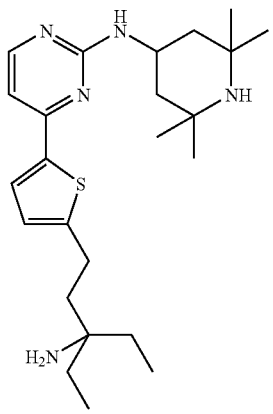

The title compound was prepared analogous to Example 79a.

MS (ESI): [M+H]$^{+1}$H-NMR (DMSO-d$_6$): δ (ppm) 8.25 (m, 1H), 7.70 (d, 1H), 6.95 (d, 1H), 6.90 (d, 1H), 4.30-4.20 (m, 1H), 2.85-2.75 (m, 2H), 1.85-1.75 (m, 2H), 1.60-1.55 (m, 2H), 1.35-1.20 (m, 12H), 1.05 (s, 6H), 0.80 (t, 6H).

Example 74

{4-[5-(2-Methanesulfinyl-ethyl)-thiophen-2-yl]-pyrimidin-2-yl}-(2,2,6,6-tetramethyl-piperidin-4-yl)-amine

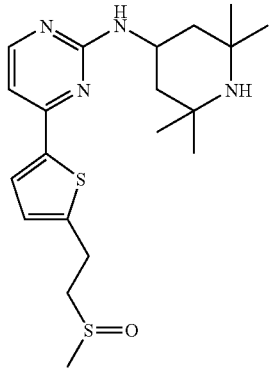

The title compound was prepared analogous to Steps A to D of Example 76.

MS (ESI): 407 [M+H]$^{+1}$H-NMR (DMSO-d$_6$, 120° C.): δ (ppm) 8.30 (d, 1H), 7.75 (m, 1H), 7.05 (d, 1H), 7.00 (d, 1H), 4.45-4.35 (m, 1H), 3.30 (t, 2H), 3.20-2.95 (m, 2H), 2.60 (s, 3H), 2.15-2.05 (m, 2H), 1.75-1.65 (m, 2H), 1.60 (s, 6H), 1.50 (s, 6H).

Example 75

{4-[5-(3-Methylsulfanyl-propyl)-thiophen-2-yl]-pyrimidin-2-yl}-(2,2,6,6-tetramethyl-piperidin-4-yl)-amine

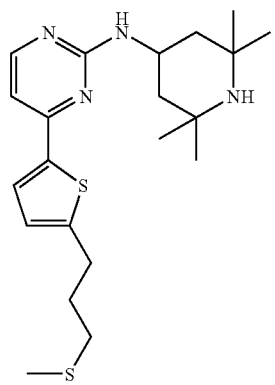

The title compound was prepared analogous to Steps A to C of Example 76.

MS (ESI): 405 [M+H]$^{+1}$H-NMR (DMSO-d$_6$, 120° C.): δ (ppm) 8.25 (d, 1H), 7.65 (d, 1H), 6.95 (m, 2H), 4.40-4.30 (m, 1H), 2.95 (t, 2H), 2.60 (t, 2H), 2.10 (s, 3H), 2.10-1.95 (m, 4H), 1.50-1.20 (m, 14H).

Example 76

{4-[5-(4-Methanesulfonyl-butyl)-thiophen-2-yl]-pyrimidin-2-yl}-(2,2,6,6-tetramethyl-piperidin-4-yl)-amine

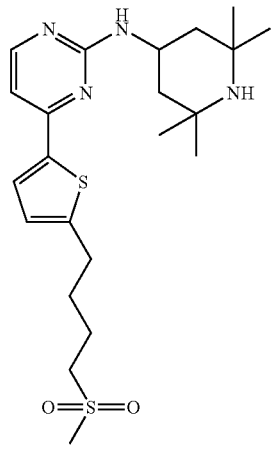

Step A: Toluene-4-sulfonic acid-4-{5-[2-(2,2,6,6-tetramethyl-piperidin-4-ylamino)-pyrimidinyl-4-yl]-thiophen-2-yl}-butylester

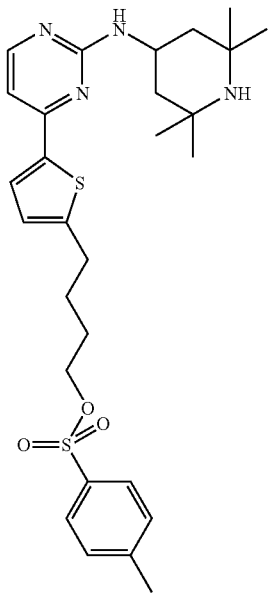

Compound of Example 116 (4.0 g, 10.3 mmol) were dissolved in 80 ml DCM and 2.6 ml triethylamine and 5.6 g (29.3 mmol) 4-toluolsulfochloride were added. This mixture was stirred over night at room temperature. Afterwards 300 ml of water were added and the mixture was extracted with DCM. The crude was purified by chromatography on silicagel (DCM/MeOH/ammonia:9/1/0.1). Yield: 3.0 g (54%).

Step B: {4-[5-(4-Iodo-butyl)-thiophen-2-yl]-pyrimidin-2-yl}-(2,2,6,6-tetramethyl-piperidin-4-yl)-amine.

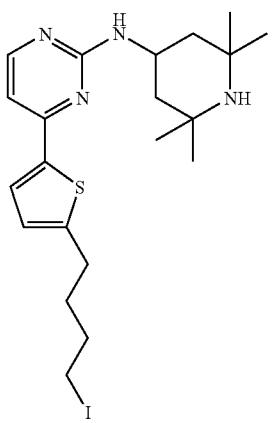

Compound of Step A (2.8 g, 5.1 mmol) was dissolved in 70 ml acetone and 1.2 g (7.8 mmol) sodium iodide were added. This mixture was refluxed for 16 hours. Afterwards the mixture was evaporated and the crude iodide derivative was used without further purification.

Step C: {4-[5-(4-Methylsulfanyl-butyl)-thiophen-2-yl]-pyrimidin-2-yl}-(2,2,6,6-tetramethyl-piperidin-4-yl)-amine

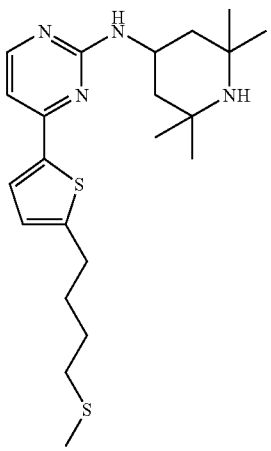

Crude compound of Step B (1.4 g, 2.8 mmol) was dissolved in 10 ml MeOH and 0.4 g (5.6 mmol) sodiumthiomethylate were added. This mixture was refluxed for 7 hours. After evaporation the title compound was purified by chromatography on silicagel (DCM/MeOH/ammonia:9/1/0.1). Yield: 0.82 g (68%).

Step D: {4-[5-(Methanesulfinyl-butyl)-thiophen-2-yl]-pyrimidin-2-yl}-(2,2,6,6-tetramethyl-piperidin-4-yl)-amine

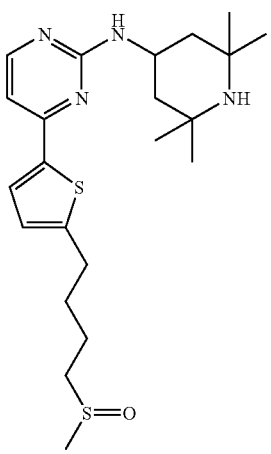

Compound of Step C (650 mg, 1.55 mmol) was dissolved in 5 ml TFA and 3 ml DCM. At room temperature 79 mg (2.3 mmol) hydroperoxide 30% were added. This mixture was stirred at room temperature for 2 hours. Afterwards 10 ml 10% sodium bisulfite solution was added and stirring continued for 15 minutes. The solution was basified with 40% NaOH and extracted with EtOAc. The crude was purified by chromatography on silicagel (DCM/MeOH/ammonia:9/1/0.1). Yield: 0.35 g (50%).

Step E: {4-[5-(4-Methanesulfonyl-butyl)-thiophen-2-yl]-pyrimidin-2-yl}-(2,2,6,6-tetramethyl-piperidin-4-yl)-amine Compound of Step D (192 mg, 0.43 mmol) was dissolved in 5 ml TFA and 3 ml DCM. At room temperature 22 mg (0.64 mmol) hydroperoxide 30% were added. This mixture was stirred at room temperature for 4 hours. Afterwards 10 ml 10% sodium bisulfite solution was added and stirring continued for 15 minutes. The solution was basified with 40% NaOH and extracted with EtOAc. The crude was purified by chromatography on silicagel (DCM/MeOH/ammonia:9/1/0.1). Yield: 75 mg (37%).

MS (ESI): 451 [M+H]$^{+1}$H-NMR (DMSO-d$_6$): δ (ppm) 8.35 (m, 1H), 7.75 (m, 1H), 7.05 (m, 1H), 6.95 (m, 1H), 4.35-4.25 (m, 1H), 3.20-3.10 (m, 2H), 2.95 (s, 3H), 2.90-2.85 (m, 2H), 1.80-1.70 (m, 4H), 1.60-1.00 (m, 16H).

Example 77

1-{5-[2-(2,2,6,6-Tetramethyl-piperidin-4-ylamino)-pyrimidin-4-yl]-thiophen-2-yl}-pentan-3-ol

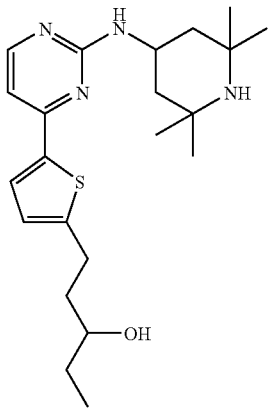

The title compound is produced by reduction of compound from Example 144 analogous to Example 53.

MS (ESI): 403 [M+H]$^{+1}$H-NMR (DMSO-d$_6$): δ (ppm) 8.35 (m, 1H), 7.70 (d, 1H), 6.95 (d, 1H), 6.90 (d, 1H), 4.35-4.20 (m, 1H), 4.10 (m, 1H), 2.95-2.80 (m, 2H), 1.85-1.65 (m, 4H), 1.45-1.35 (m, 2H), 1.35-1.05 (m, 14H), 0.85 (t, 3H).

Example 78

{4-[5-(1-Amino-cyclohexylethynyl)-thiophen-2-yl]-pyrimidin-2-yl}-(2,2,6,6-tetramethyl-piperidin-4-yl)-amine

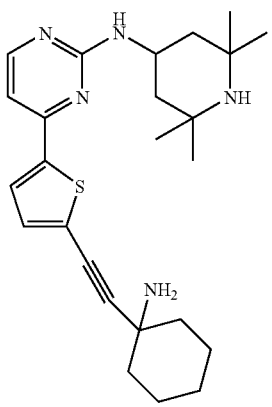

The title compound was prepared following the procedure given in Example 5.

MS (ESI): 438 [M+H]$^{+1}$H-NMR (DMSO-d$_6$): δ (ppm) 8.35 (m, 1H), 7.85 (d, 1H), 7.30 (d, 1H), 7.10 (d, 1H), 4.35-4.20 (m, 1H), 1.95-1.80 (m, 4H), 1.70-1.65 (m, 2H), 1.60-1.15 (m, 20H).

Example 79a (4-{5-[2-(1-Amino-cyclohexyl)-ethyl]-thiophen-2-yl}-pyrimidin-2-yl)-(2,2,6,6-tetramethyl-piperidin-4-yl)-amine

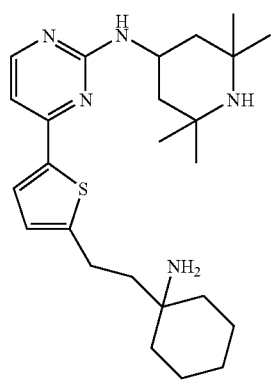

Compound of Example 78 (2.5 g, 5.7 mmol) was dissolved in 200 ml MeOH and 0.8 g palladium on charcoal 10% were added. Hydrogenation was performed at room temperature and 1 bar hydrogen pressure for 8 hours. Afterwards the mixture was filtered through Hyflo and evaporated. The crude was purified by chromatography on silicagel (DCM/MeOH/ammonia:85/15/1.5). Yield: 1.6 g (64%).

MS (ESI): 442 [M+H]$^{+1}$H-NMR (DMSO-d$_6$, 120° C.): δ (ppm) 8.25 (d, 1H), 7.65 (d, 1H), 6.95 (d, 1H), 6.90 (d, 1H), 4.40-4.30 (m, 1H), 2.95-2.85 (m, 2H), 1.95-1.90 (m, 2H), 1.80-1.70 (m, 2H), 1.65-1.60 (m, 3H), 1.50-1.40 (m, 8H), 1.35 (s, 6H), 1.25-1.15 (m, 2H), 1.10 (s, 6H).

Example 79b 1-(2-{5-[2-(2,2,6,6-Tetramethyl-piperidin-4-ylamino)-pyrimidin-4-yl]-thiophen-2-yl}-ethyl)-cyclobutanol

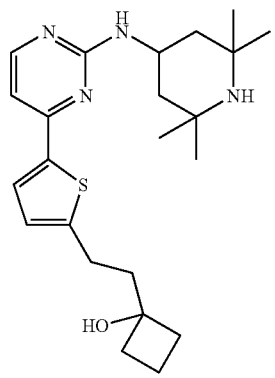

Step A: 1-{5-[2-(2,2,6,6-Tetramethyl-piperidin-4-ylamino)-pyrimidin-4-yl]-thiophen-2-ylethynyl}-cyclobutanol

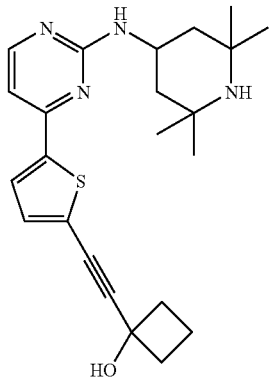

The title compound was prepared following the procedure given in Example 5.

Step B: 1-(2-{5-[2-(2,2,6,6-Tetramethyl-piperidin-4-ylamino)-pyrimidin-4-yl]-thiophen-2-yl}-ethyl)-cyclobutanol The title compound was prepared as described in Example 79a.

MS (ESI): 415 [M+H]$^{+1}$H-NMR (DMSO-d$_6$): δ (ppm) 8.35-8.30 (m, 1H), 7.75 (d, 1H), 7.00-6.90 (m, 2H), 5.00 (s, 1OH), 4.30-4.15 (m, 1H), 2.90-2.80 (m, 2H), 2.05-1.95 (m, 2H), 1.90-1.75 (m, 4H), 1.70-1.60 (m, 1H), 1.55-1.45 (m, 1H), 1.30-1.15 (m, 8H), 1.10-1.05 (m, 8H).

Example 80

Phenyl-(4-{5-[2-(2,2,6,6-tetramethyl-piperidin-4-ylamino)-pyrimidin-4-yl]-thiophen-2-yl}-butyrylamino)-acetic acid methyl ester

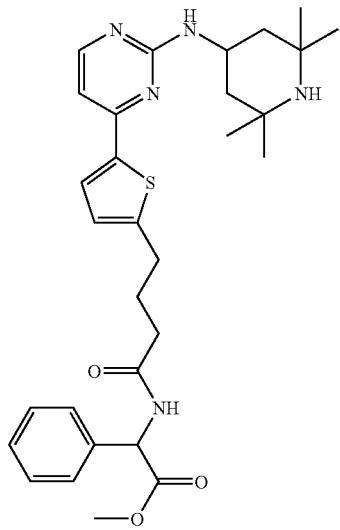

The title compound was prepared analogous to Step C of Example 37.

MS (ESI): 550 [M+H]$^{+1}$H-NMR (DMSO-d$_6$, 120° C.): δ (ppm) 8.30 (m, 1H), 7.70 (m, 1H), 7.40-7.30 (m, 5H), 6.95 (m, 1H), 6.90 (m, 1H), 5.55 (m, 1H), 4.45-4.35 (m, 1H), 2.90 (t, 2H), 2.35 (m, 2H), 2.15-2.10 (m, 2H), 2.00-1.95 (m, 2H), 1.75-1.65 (m, 2H), 1.60 (s, 6H), 1.50 (s, 6H).

Example 81

{4-[5-(5-Phenyl-pentyl)-thiophen-2-yl]-pyrimidin-2-yl}-(2,2,6,6-tetramethyl-piperidin-4-yl)-amine

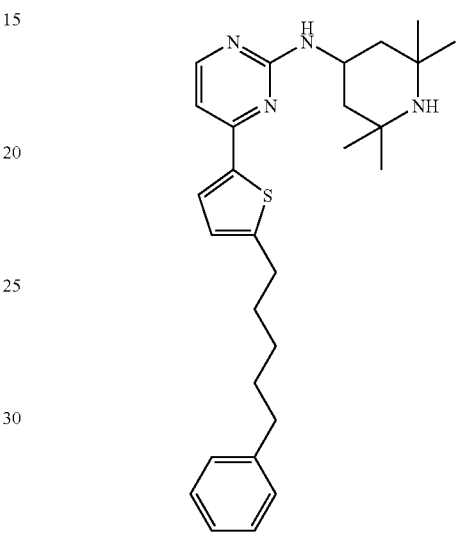

The title compound was prepared analogous to Example 73.

MS (ESI): 463 [M+H]$^{+1}$H-NMR (DMSO-d$_6$): δ (ppm) 8.35 (m, 1H), 7.95 (m, 1H), 7.35-7.15 (m, 6H), 7.00 (m, 1H), 4.45-4.35 (m, 1H), 2.90 (t, 2H), 2.60 (t, 2H), 2.15-2.00 (m, 2H), 1.75-1.35 (m, 20H).

Example 82

(Benzyl-{5-[2-(2,2,6,6-tetramethyl-piperidin-4-ylamino)-pyrimidin-4-yl]-thiophen-2-ylmethyl}-amino)-acetic acid ethyl ester

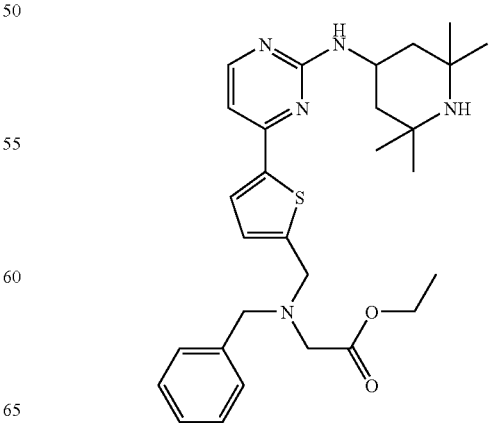

The title compound was prepared analogous to the procedure described in Example 60.

MS (ESI): 522.4 [M+H]$^{+1}$H-NMR (DMSO-d$_6$): δ (ppm) 8.35 (m, 1H), 8.00 (m, 1H), 7.45-7.15 (m, 7H), 4.50-4.35 (m, 1H), 4.25 (m, 2H), 4.15 (t, 2H), 3.95 (m, 2H), 3.50 (m, 2H), 2.15-2.00 (m, 2H), 1.75-1.45 (m, 14H), 1.20 (t, 3H).

Example 83

1-(Benzyl-{5-[2-(2,2,6,6-tetramethyl-piperidin-4-ylamino)-pyrimidin-4-yl]-thiophen-2-ylmethyl}-amino)-2-methyl-propan-2-ol

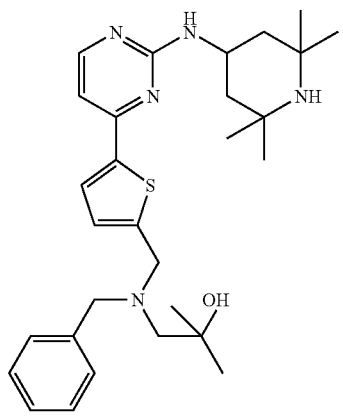

The title compound was prepared analogous to Step A of Method A, starting with compound from Example 82.

MS (ESI): 508 [M+H]$^{+1}$H-NMR (DMSO-d$_6$, 120° C.): δ (ppm) 8.30 (m, 1H), 7.75 (m, 1H), 7.45-7.40 (m, 2H), 7.35-7.25 (m, 3H), 7.05 (m, 1H), 7.00 (m, 1H), 4.45-4.40 (m, 1H), 4.10 (s, 2H), 3.85 (s, 2H), 2.65 (s, 2H), 2.15-2.05 (m, 2H), 1.75-1.65 (m, 2H), 1.65 (s, 6H), 1.55 (s, 6H), 1.15 (s, 6H).

Example 84

1-Phenyl-3-{5-[2-(2,2,6,6-tetramethyl-piperidin-4-ylamino-pyrimidin-4-yl]-thiophen-2-yl}-propan-1-ol

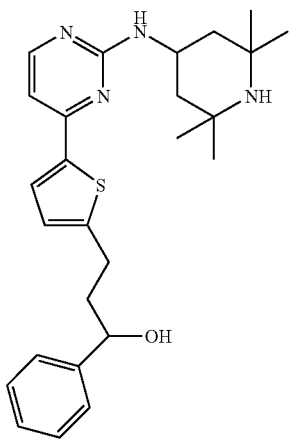

The title compound is produced by reduction of compound from Example 145 analogous to Example 53.

MS (ESI): 451 [M+H]$^{+1}$H-NMR (DMSO-d$_6$): δ (ppm) 8.25 (m, 1H), 7.70 (d, 1H), 7.40-7.30 (m, 4H), 7.30-7.25 (m, 1H), 6.95 (d, 1H), 6.90 (d, 1H), 5.35 (d, 1OH), 4.65-4.55 (m, 1H), 4.35-4.20 (m, 1H), 2.90 (t, 2H), 2.05-1.95 (m, 2H), 1.95-1.70 (m, 2H), 1.35-1.05 (m, 14H).

Example 85

3-Ethyl-1-{5-[2-(2,2,6,6-tetramethyl-piperidin-4-ylamino)-pyrimidin-4-yl]-thiophen-2-yl}-pentan-3-ol

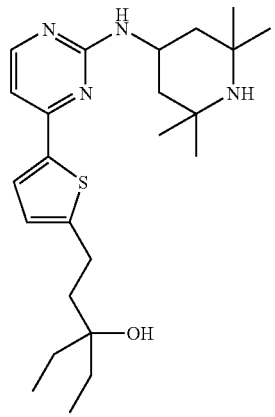

The title compound was prepared analogous to Example 79a

MS (ESI): 431.4 [M+H]$^{+1}$H-NMR (DMSO-d$_6$, 120° C.): δ (ppm) 8.25 (d, 1H), 7.65 (d, 1H), 6.95-6.90 (m, 2H), 4.35-4.20 (m, 1H), 2.90 (m, 2H), 1.95-1.90 (m, 2H), 1.80 (m, 2H), 1.50 (qa, 4H), 1.30 (s, 6H), 1.20-1.10 (m, 2H), 1.10 (s, 6H), 0.90 (t, 6H).

Example 86

3-({5-[2-(2,2,6,6-Tetramethyl-piperidin-4-ylamino)-pyrimidin-4-yl]-thiophen-2-ylmethyl}-amino)-propionitrile

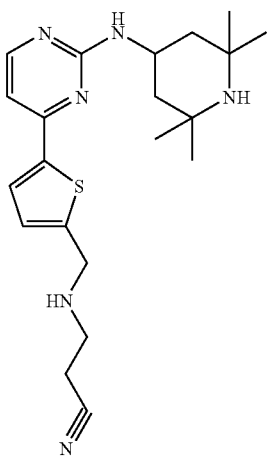

Compound of Example 132 (483 mg, 1.4 mmol) was dissolved in 25 ml MeOH and 110 µl (1.7 mmol) acrylonitrile were added. This mixture was stirred at room temperature for 24 hours. After evaporation the crude was purified by chromatography on silicagel (DCM/MeOH/ammonia:9/1/0.1). Yield: 0.55 g (98%).

MS (ESI): 399 [M+H]$^{+1}$H-NMR (DMSO-d$_6$): δ (ppm) 8.40 (m, 1H), 7.95 (m, 1H), 7.45 (m, 1H), 7.25 (m, 1H), 4.45-4.30 (m, 3H), 3.35-3.25 (m, 2H), 3.10 (t, 2H), 2.15-1.95 (m, 2H), 1.70-1.45 (m, 14H).

Example 87

3-(Benzyl-{5-[2-(2,2,6,6-tetramethyl-piperidin-4-ylamino)-pyrimidin-4-yl]-thiophen-2-ylmethyl}-amino)-propionitrile

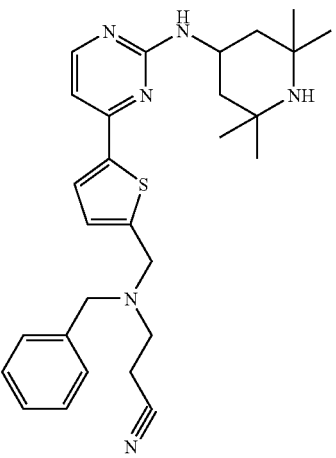

The title compound was prepared analogous to the procedure described in Example 59, using benzaldehyde in place of formaldehyde.

MS (ESI): 489 [M+H]$^{+1}$H-NMR (DMSO-d$_6$, 120° C.): δ (ppm) 8.30 (d, 1H), 7.75 (d, 1H), 7.45 (m, 2H), 7.35 (t, 2H), 7.25 (m, 1H), 7.10 (d, 1H), 7.05 (d, 1H), 4.45-4.35 (m, 1H), 3.95 (s, 2H), 3.80 (m, 2H), 2.90 (t, 2H), 2.65 (t, 2H), 2.15-2.05 (m, 2H), 1.75-1.65 (m, 2H), 1.60 (s, 6H), 1.50 (s, 6H).

Example 88

3-(Methyl-{5-[2-(1,2,2,6,6-pentamethyl-piperidin-4-ylamino)-pyrimidin-4-yl]-thiophen-2-ylmethyl}-amino)-propionitrile

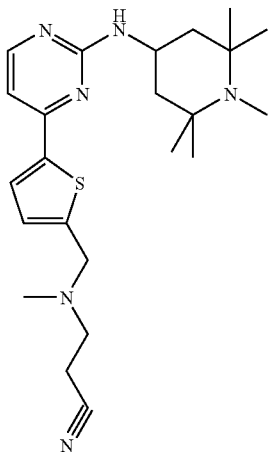

The title compound was prepared analogous to the procedure described in Example 59.

MS (ESI): 427 [M+H]$^{+1}$H-NMR (DMSO-d$_6$): δ (ppm) 8.40 (d, 1H), 8.05 (m, 1H), 7.50 (m, 1H), 7.30 (m, 1H), 4.60 (m, 2H), 4.45-4.35 (m, 1H), 3.45-3.35 (m, 2H), 3.25 (t, 2H), 2.75 (s, 6H), 2.20-1.95 (m, 4H), 1.60-1.40 (m, 12H).

Example 89

N-(2-Cyano-ethyl)-N-{5-[2-(2,2,6,6-tetramethyl-piperidin-4-ylamino)-pyrimidin-4-yl]-thiophen-2-ylmethyl}-acetamide

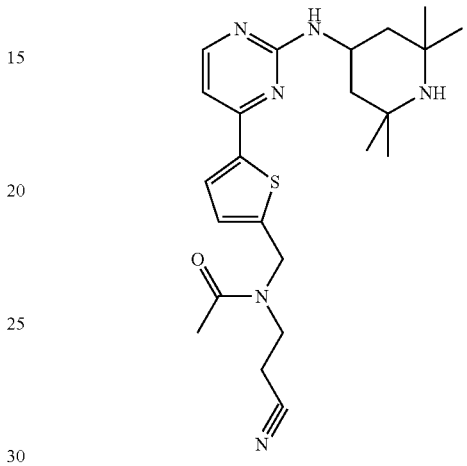

Compound of Example 86 (119 mg, 0.3 mmol) was dissolved in 5 ml THF and 0.5 ml triethylamine and 36 µl (0.33 mmol) acetic anhydride were added. This mixture was stirred at room temperature for 16 hours. Afterwards the solution was diluted with 100 ml water and extracted with EtOAc. The crude was purified by chromatography on silicagel (DCM/MeOH/ammonia:9/1/0.1). Yield: 103 mg (78%).

MS (ESI): 441 [M+H]$^{+1}$H-NMR (DMSO-d$_6$, 120° C.): δ (ppm) 8.30 (d, 1H), 7.75 (d, 1H), 7.15 (d, 1H), 7.00 (d, 1H), 4.80 (s, 2H), 3.65 (t, 2H), 2.80 (t, 2H), 2.15 (s, 3H), 2.10-2.05 (m, 2H), 1.75-1.65 (m, 2H), 1.60 (s, 6H), 1.50 (s, 6H).

The following compounds (Example 90 to Example 145) were prepared analogous to Method C, starting from the appropriate known thiophene derivatives and (4-chloro-pyrimidin-2-yl)-(2,2,6,6-tetramethyl-piperidin-4-yl)-amine. Functional groups were protected prior to boronic acid formation and deprotected after Suzuki-coupling, using standard methods described in literature.

Example 90

1-{5-[2-(2,2,6,6-Tetramethyl-piperidin-4-ylamino)-pyrimidin-4-yl]-thiophen-2-yl}-ethanone

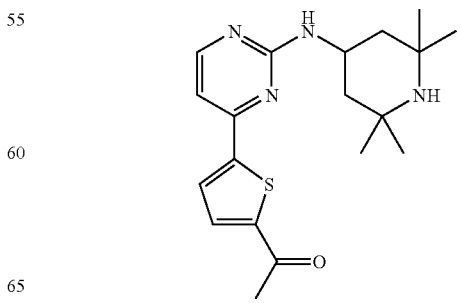

MS (EI): 343 [M-CH$_3$]$^+$ $^1$H-NMR (DMSO-d$_6$): δ (ppm) 8.40-8.35 (m, 1H), 8.00 (s, 2H), 7.30-7.25 (m, 1NH), 7.15 (m, 1H), 4.35-4.20 (m, 1H), 2.55 (s, 3H), 1.90-1.75 (m, 1H), 1.35-1.05 (m, 14H).

Example 91

{4-[5-(4-Chloro-phenyl)-thiophen-2-yl}-pyrimidin-2-yl]-(2,2,6,6-tetramethyl-piperidin-4-yl)-amine

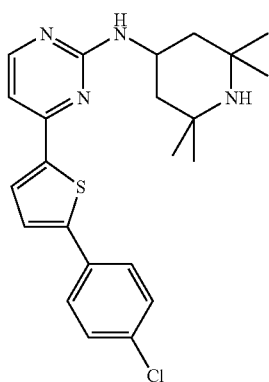

$^1$H-NMR (DMSO-d$_6$, 120° C.): δ (ppm) 8.35 (d, 1H), 7.85 (m, 1H), 7.70 (d, 2H), 7.55 (m, 1H), 7.45 (d, 2H), 7.05 (m, 1H), 4.45-4.35 (m, 1H), 2.15-2.05 (m, 2H), 1.80-1.70 (m, 2H), 1.60 (s, 6H), 1.50 (s, 6H).

Example 92

3-Methyl-5-[2-(2,2,6,6-tetramethyl-piperidin-4-ylamino)-pyrimidin-4-yl]-thiophene-2-carbonitrile

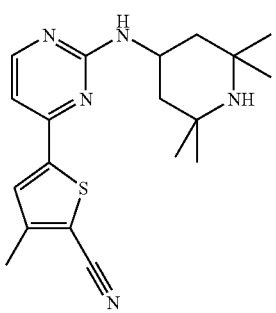

MS (ESI): 356.2 [M+H]$^+$ $^1$H-NMR (DMSO-d$_6$): δ (ppm) 8.45 (m, 1H), 7.95 (s, 1H), 7.15 (d, 1H), 4.35-4.15 (m, 1H), 2.40 (s, 3H), 1.85-1.75 (m, 2H), 1.30-1.05 (m, 14H).

Example 93

(4-[2,2']Bithiophenyl-5-yl-pyrimidin-2-yl)-(2,2,6,6-tetramethyl-piperidin-4-yl)-amine

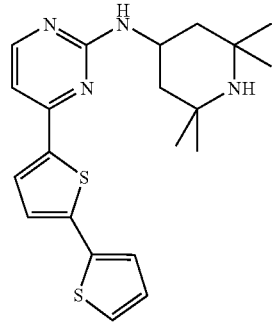

MS (ESI): 399.2 [M+H]$^+$ $^1$H-NMR (DMSO-d$_6$, 120° C.): δ (ppm) 8.30 (d, 1H), 7.75 (d, 1H), 7.50 (m, 1H), 7.35 (m, 1H), 7.30 (d, 1H), 7.15-7.10 (m, 1H), 7.00 (d, 1H), 4.40-4.30 (m, 1H), 2.05-1.95 (m, 2H), 1.45 (s, 6H), 1.45-1.35 (m, 2H), 1.30 (s, 6H).

Example 94

[4-(5-Isopropenyl-thiophen-2-yl)-pyrimidin-2-yl]-(2,2,6,6-tetramethyl-piperidin-4-yl)-amine

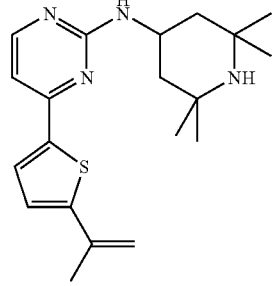

MS (ESI): 357.2 [M+H]$^+$ $^1$H-NMR (DMSO-d$_6$, 120° C.): δ (ppm) 8.30 (d, 1H), 7.75 (d, 1H), 7.30 (d, 1H), 7.00 (d, 1H, 5.45 (s, 1H), 5.10 (s, 1H), 4.45-4.35 (m, 1H), 2.15 (s, 3H), 2.10-2.05 (m, 2H), 1.75-1.50 (m, 14H).

Example 95

{4-[5-(2-Amino-ethyl)-thiophen-2-yl]-pyrimidin-2-yl}-(2,2,6,6-tetramethyl-piperidin-4-yl)-amine

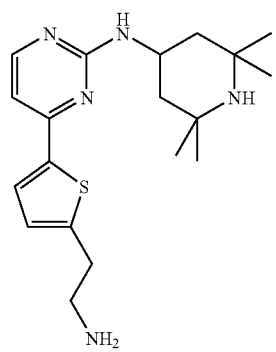

MS (ESI): 360.2 [M+H]+ 1H-NMR (DMSO-d6, 120° C.): δ (ppm) 8.30 (d, 1H), 7.70 (d, 1H), 7.05 (d, 1H), 6.95 (d, 1H), 4.45-4.30 (m, 1H), 3.25-3.20 (m, 2H), 3.15-3.10 (m, 2H), 2.10-2.00 (m, 2H), 1.75-1.65 (m, 2H), 1.60 (s, 6H0, 1.50 (s, 6H).

Example 96

[4-(4,5,6,7-Tetrahydro-benzo[b]thiophen-2-yl)-pyrimidin-2-yl]-(2,2,6,6-tetramethyl-piperidin-4-yl)-amine

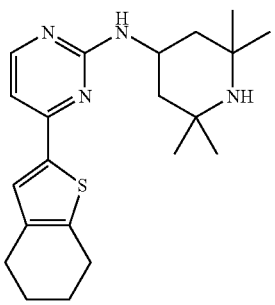

MS (ESI): 371.2 [M+H]+ 1H-NMR (DMSO-d6, 120° C.): δ (ppm) 8.35 (d, 1H), 7.50 (s, 1H), 6.95 (d, 1H), 4.45-4.35 (m, 1H), 2.80 (t, 2H), 2.65 (t, 2H), 2.10-2.05 (m, 2H), 1.90-1.75 (m, 4H), 1.75-1.65 (m, 2H), 1.55 (s, 6H), 1.50 (s, 6H).

Example 97

4-Chloro-2-((E)-2-{5-[2-(2,2,6,6-tetramethyl-piperidin-4-ylamino)-pyrimidin-4-yl]-thiophen-2-yl}-vinyl)-benzonitrile

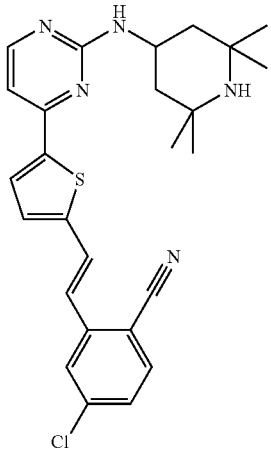

MS (ESI): 478.3 [M+H]+ 1H-NMR (DMSO-d6, 120° C.), cis/trans mixture 3:7: δ (ppm) 8.35-8.25 (m, 1H), 8.05 (m, 1H), 7.80-7.75 (m, 3H), 7.50-7.45 (m, 1H), 7.40 (m, 1H), 7.20-7.10 (m, 1H), 7.05 (m, 1H), 4.40-4.30 (m, 1H), 2.05-1.95 (m, 2H), 1.50-1.15 (m, 14H).

Example 98

2-[2-(2,2,6,6-Tetramethyl-piperidin-4-ylamino)-pyrimidin-4-yl]-4,5,6,7-tetrahydro-benzo[b]thiophen-4-ol

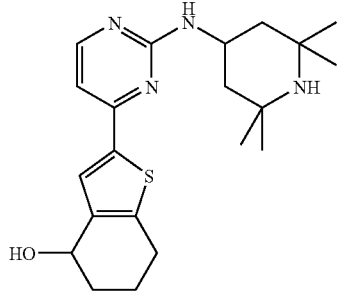

MS (ESI): 387.2 [M+H]+ 1H-NMR (DMSO-d6): δ (ppm): 8.35-8.30 (m, 1H), 7.75 (s, 1H), 6.95 (m, 1H), 5.15 (m, 1OH), 4.60-4.50 (m, 1H), 4.30-4.20 (m, 1H), 2.80-2.60 (m, 2H), 2.00-1.60 (m, 6H), 1.30-1.05 (m, 14H).

Example 99

(2,2,6,6-Tetramethyl-piperidin-4-yl)-(4-thieno[3,2-c]pyridin-2-yl-pyrimidin-2-yl)-amine

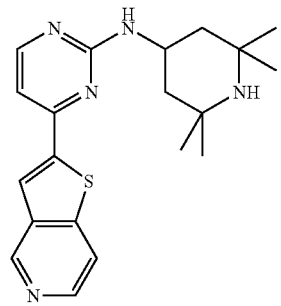

MS (ESI): 368 [M+H]+ 1H-NMR (DMSO-d6, 120° C.): δ (ppm) 9.25 (s, 1H), 8.50 (d, 1H), 8.40 (d, 1H), 8.15 (m, 1NH), 7.25 (d, 1H), 4.45-4.35 (m, 1H), 2.10-2.00 (m, 2H), 1.80-1.70 (m, 2H), 1.65 (s, 6H), 1.55 (s, 6H).

Example 100

(4-Chloro-phenyl)-{5-[2-(2,2,6,6-tetramethyl-piperidin-4-ylamino)-pyrimidin-4-yl]-thiophen-2-yl}-methanol

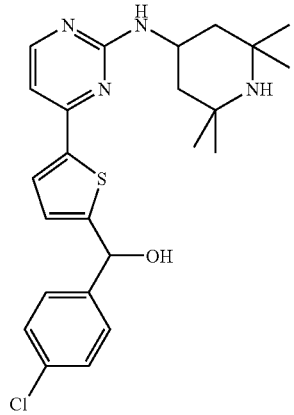

MS (ESI): 457 [M+H]+ 1H-NMR (DMSO-d6, 120° C.): δ (ppm) 8.25 (d, 1H), 7.65 (d, 1H), 7.45 (d, 2H), 7.35 (d, 2H), 7.00 (d, 1H), 6.95 (d, 1H), 5.95 (s, 1H), 4.35-4.25 (m, 1H), 2.10-2.05 (d, 2H), 1.75-1.65 (m, 2H), 1.55 (s, 6H), 1.50 (s, 6H).

Example 101

N-(2-{5-[2-(2,2,6,6-Tetramethyl-piperidin-4-ylamino)-pyrimidin-4-yl]-thiophen-2-yl}-ethyl)-acetamide

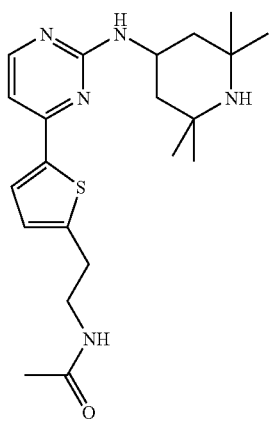

MS (ESI): 402.1 [M+H]+ 1H-NMR (DMSO-d6): δ (ppm) 8.35 (m, 1H), 8.10 (m, 1NH), 7.95 (m, 1H), 7.20 (m, 1H), 7.05 (m, 1H), 4.45-4.35 (m, 1H), 3.35-3.30 (m, 2H), 3.05-2.95 (m, 2H), 2.15-1.95 (m, 2H), 1.85 (s, 3H), 1.65-1.45 (m, 14H).

Example 102

{4-[5-(2-Dimethylamino-ethyl)-thiophen-2-yl]-pyrimidin-2-yl}-(2,2,6,6-tetramethyl-piperidin-4-yl)-amine

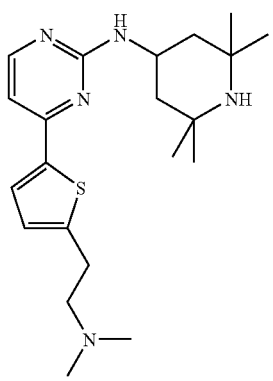

MS (ESI): 388.1 [M+H]+ 1H-NMR (DMSO-d6): δ (ppm) 8.35 (m, 1H), 7.70 (d, 1H), 6.95-6.90 (m, 2H), 4.35-4.20 (m, 1H), 2.95 (t, 2H), 2.55 (t, 2H), 2.20 (s, 6H), 1.85-1.75 (m, 2H), 1.35-1.05 (m, 14H).

Example 103

1-(4-{5-[2-(2,2,6,6-Tetramethyl-piperidin-4-ylamino)-pyrimidin-4-yl]-thiophen-2-yl}-phenyl)-ethanone

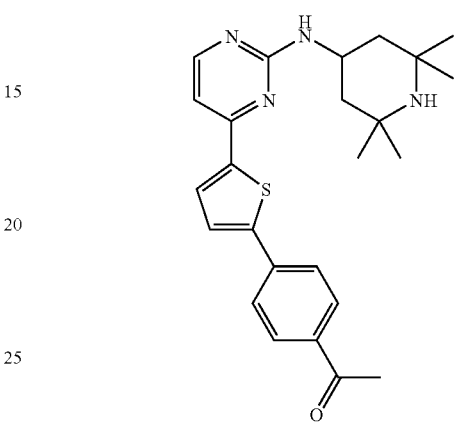

MS (EI): 343 [M+]1H-NMR (DMSO-d6): δ (ppm) 8.35 (m, 1H), 8.10-8.00 (m, 2H), 7.95 (m, 1H), 7.85-7.80 (m, 2H), 7.75 (m, 1H), 7.05 (d, 1H), 4.35-4.20 (m, 1H), 2.60 (s, 3H), 1.95-1.80 (m, 2H), 1.45-1.05 (m, 14H).

Example 104

3-Methyl-5-[2-(2,2,6,6-tetramethyl-piperidin-4-ylamino)-pyrimidin-4-yl]-thiophene-2-carboxylic acid methyl ester

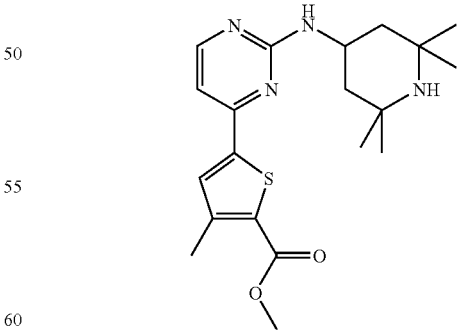

MS (ESI): 389 [M+H]+ 1H-NMR (DMSO-d6): δ (ppm) 8.45 (d, 1H), 7.90 (s, 1H), 7.25 (d, 1H), 4.40-4.30 (m, 1H), 3.85 (s, 3H), 2.15-2.00 (m, 2H), 1.65-1.40 (m, 17H).

Example 105

[4-(5-Chloro-thiophen-2-yl)-pyrimidin-2-yl]-(2,2,6,6-tetramethyl-piperidin-4-yl)-amine

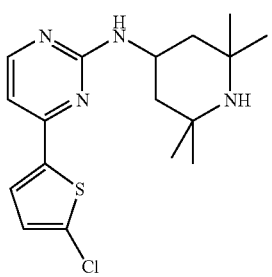

MS (ESI): 351 [M+H]$^{+1}$H-NMR (DMSO-d$_6$): δ (ppm) 8.30 (m, 1H), 7.80 (m, 1H), 7.20 (m, 1H), 7.00 (m, 1H1, 4.30-4.15 (m, 1H), 1.90-1.75 (m, 2H), 1.30-1.05 (m, 14H).

Example 106

4-{5-[2-(2,2,66-Tetramethyl-piperidin-4-ylamino)-pyrimidin-4-yl]-thiophen-2-yl}-butyric acid methyl ester

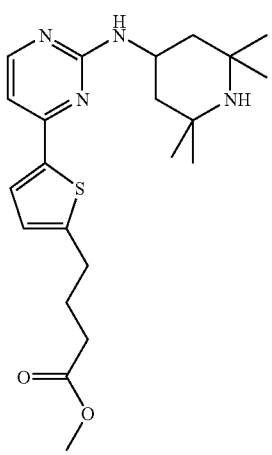

MS (ESI): 417 [M+H]$^{+1}$H-NMR (DMSO-d$_6$, 120° C.): δ (ppm) 8.25 (d, 1H), 7.70 (d, 1H), 7.00 (d, 1H), 6.95 (d, 1H), 4.40-4.35 (m, 1H), 3.65 (s, 3H), 2.90 (t, 2H), 2.40 (t, 2H), 2.10-2.05 (m, 2H), 1.95 (q, 2H), 1.75-1.65 (m, 2H), 1.60 (s, 6H), 1.50 (s, 6H).

Example 107

4-{5-[2-(2,2,6,6-Tetramethyl-piperidin-4-ylamino)-pyrimidin-4-yl]-thiophen-2-yl}-butyric acid

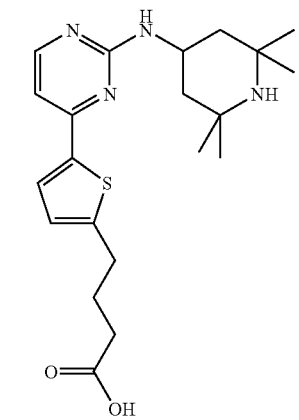

MS (ESI): 401 [M-H]$^{+1}$H-NMR (DMSO-d$_6$): 8.20 (m, 1H), 7.70 (m, 1H), 6.95 (m, 1H), 6.90 (m, 1H), 4.30-4.20 (m, 1H), 2.80 (m, 2H), 2.05-1.95 (m, 2), 1.85-1.70 (m, 4H), 1.35-1.00 (m, 14H).

Example 108

5-[2-(2,2,6,6-Tetramethyl-piperidin-4-ylamino)-pyrimidin-4-yl]-thiophene-2-caboxylic acid benzylamide

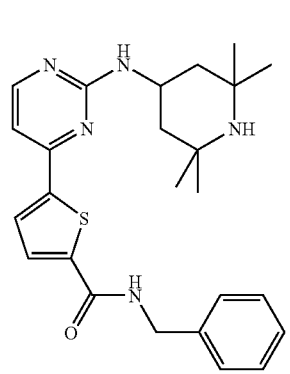

MS (ESI): 450 [M+H]$^{+1}$H-NMR (DMSO-d$_6$): δ (ppm) 9.30-9.22 (m, 1H), 9.20-9.10 (m, 1H), 8.40-8.35 (m, 1H), 8.10-7.80 (m, 4H), 7.40-7.20 (m, 6H), 4.50-4.30 (m, 3H), 2.15-1.95 (m, 2H), 1.65-1.35 (m, 14H).

Example 109

[4-(5-Nitro-thiophen-2-yl)-pyrimidin-2-yl]-(2,2,6,6-tetramethyl-piperidin-4-yl)-amine

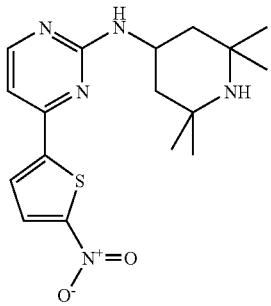

MS (ESI): 362 [M+H]$^+$ $^1$H-NMR (DMSO-d$_6$): δ (ppm) 8.45 (m, 1H), 8.20 (m, 1H), 8.00 (m, 1H0, 7.25 (m, 1H), 4.35-4.15 9m, 1H), 1.90-1.75 (m, 1H0, 1.35-1.05 (m, 14H).

Example 110

{4-[5-(4-Methoxy-phenyl)-thiophen-2-yl]-pyrimidin-2-yl}-(2,2,6,6-tetramethyl-piperidin-4-yl)-amine

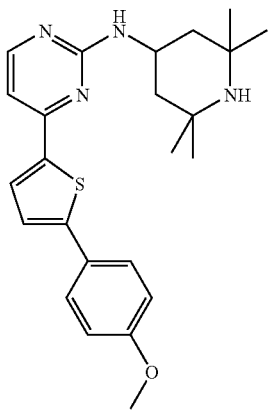

MS (ESI): 423 [M+H]$^+$ $^1$H-NMR (DMSO-d$_6$, 120° C.): δ (ppm) 8.30 (d, 1H), 7.80 (d, 1H), 7.60 (d, 2H), 7.40 (d, 1H), 7.05-7.00 (m, 3H), 4.45-4.35 (m, 1H), 3.85 (s, 3H), 2.15-2.05 (m, 2H), 1.75-1.65 (m, 2H), 1.60 (s, 6H), 1.50 (s, 6H).

Example 111

4-{5-[2-(2,2,6,6-Tetramethyl-piperidin-4-ylamino)-pyrimidin-4-yl]-thiophen-2-yl}-phenol

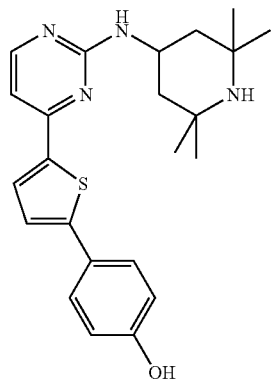

MS (ESI): 409 [M+H]$^+$ $^1$H-NMR (DMSO-d$_6$, 120° C.): δ (ppm) 9.15-9.00 (m, 1H), 8.30 (d, 1H), 7.75 (d, 1H), 7.50 (d, 2H), 7.30 (d, 1H), 7.00 (d, 1H), 6.85 (d, 2H), 4.45-4.35 (m, 1H), 2.15-2.05 (d, 2H), 1.75-1.65 (m, 2H), 1.60 (s, 6H), 1.50 (s, 6H).

Example 112

1-{5'-[2-(2,2,6,6-Tetramethyl-piperidin-4-ylamino)-pyrimidin-4-yl]-[2,2']bithiophenyl-5-yl}-ethanone

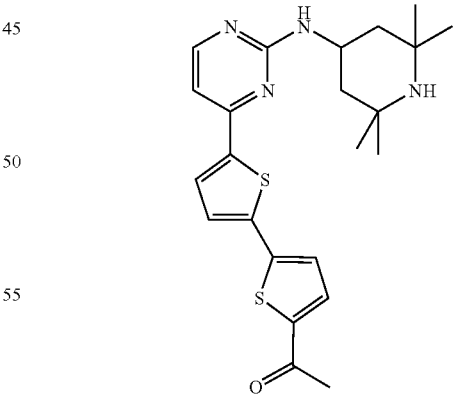

MS (ESI): 441 [M+H]$^+$ $^1$H-NMR (DMSO-d$_6$): δ (ppm) 8.35 (m, 1H), 7.95-7.90 (m, 2H), 7.65 (m, 1H), 7.45 (m, 1H), 7.05 (m, 1H), 4.35-4.15 (m, 1H), 2.55 (s, 3H), 1.95-1.80 (m, 2H), 1.35-1.05 (m, 14H).

Example 113

{4-[5-(2-Methoxy-phenyl)-thiophen-2-yl]-pyrimidin-2-yl}-(2,2,6,6-tetramethyl-piperidin-4-yl)-amine

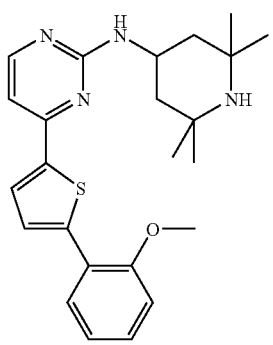

MS (ESI): 423 [M+H]+ 1H-NMR (DMSO-d6, 120° C.): δ (ppm) 8.30 (d, 1H), 7.85 (d, 1H), 7.75 (m, 1H), 7.60 (d, 1H), 7.40-7.35 (m, 1H), 7.20 (d, 1H), 7.10-7.05 (m, 2H), 4.50-4.40 (m, 1H), 3.95 (s, 3H), 2.15-2.05 (m, 2H), 1.75-1.65 (m, 2H), 1.65 (s, 6H), 1.55 (s, 6H).

Example 114

{5-[2-(2,2,6,6-Tetramethyl-piperidin-4-ylamino)-pyrimidin-4-yl]-thiophen-2-yl}-methanol

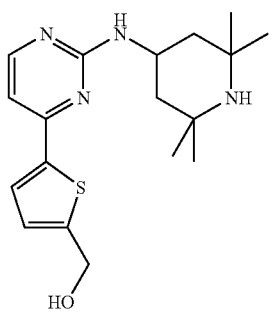

MS (ESI): 347 [M+H]+ 1H-NMR (DMSO-d6, 120° C.): δ (ppm) 8.30 (d, 1H), 7.70 (m, 1H), 7.05-7.00 (m, 2H), 4.70 (s, 2H), 4.45-4.35 (m, 1H), 2.15-2.05 (m, 2H), 1.75-1.65 (m, 2H), 1.60 (s, 6H), 1.50 (s, 6H).

Example 115

5-[2-(2,2,6,6-Tetramethyl-piperidin-4-ylamino)-pyrimidin-4-yl]-thiophene-2-carboxylic acid (2-amino-ethyl)-amide

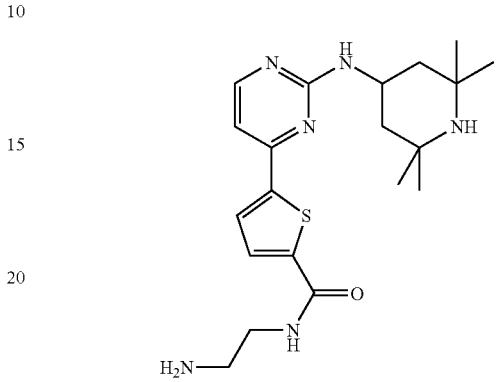

MS (ESI): 403 [M+H]+ 1H-NMR (DMSO-d6): δ (ppm) 8.90-8.85 (m, 1NH), 8.40 (m, 1H), 7.95 (m, 1H), 7.80 (m, 1H), 7.15 9m, 1H), 4.40-4.30 (m, 1H), 3.55-3.45 (m, 2H), 3.05-2.95 (m, 2H), 2.15-1.95 (m, 2H), 1.60-1.40 (m, 14H).

Example 116

4-{5-[2-(2,2,6,6-Tetramethyl-piperidin-4-ylamino)-pyrimidin-4-yl]-thiophen-2-yl}-butan-1-ol

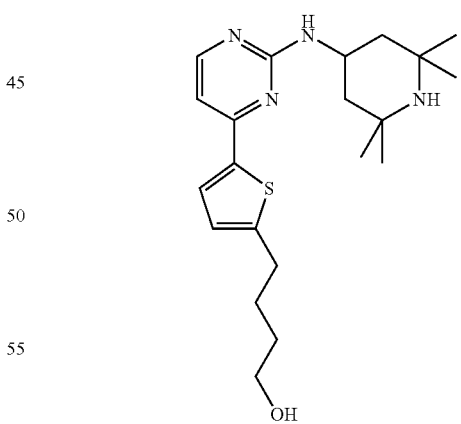

MS (ESI): 389 [M+H]+ 1H-NMR (DMSO-d6, 120° C.): δ (ppm) 8.25 (d, 1H), 7.65 (m, 1H), 6.95-6.85 (m, 2H), 6.35-6.25 (m, 1NH), 4.40-4.20 (m, 1H), 3.50-3.45 (t, 2H), 3.00-2.80 (M, 2H), 1.95-1.85 (m, 2H), 1.80-1.70 (q, 2H), 1.60-1.50 (q, 2H), 1.35-1.10 (m, 14H).

Example 117

{4-[5-(3-Methoxy-phenyl)-thiophen-2-yl]-pyrimidin-2-yl}-(2,2,6,6-tetramethyl-piperidin-4-yl)-amine

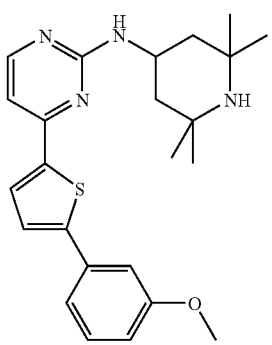

MS (ESI): 423 [M+H]$^+$ $^1$H-NMR (DMSO-d$_6$): δ (ppm) 8.30 (m, 1H), 7.90 (m, 1H), 7.65 (d, 1H), 7.35 (t, 1H), 7.30-7.20 (m, 2H), 7.05 (d, 1H), 6.95 (m, 1H), 4.35-4.20 (m, 1H), 3.85 (s, 3H), 1.95-1.85 (m, 2H), 1.35-1.05 (m, 14H).

Example 118

4-{5-[2-(2,2,6,6-Tetramethyl-piperidin-4-ylamino)-pyrimidin-4-yl]-thiophen-2-yl}-benzenesulfonamide

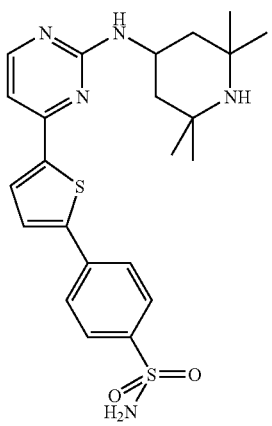

MS (ESI): 472 [M+H]$^+$ $^1$H-NMR (DMSO-d$_6$): δ (ppm) 8.40 (d, 1H), 8.10 (m, 1H), 7.95-7.90 (m, 4H), 7.80 (m, 1H), 7.30 (m, 1H), 4.45-4.30 (m, 1H), 2.15-1.95 (m, 2H), 1.65-1.45 (m, 14H).

Example 119

3-{5-[2-(2,2,6,6-Tetramethyl-piperidin-4-ylamino)-pyrimidin-4-yl]-thiophen-2-yl}-benzonitrile

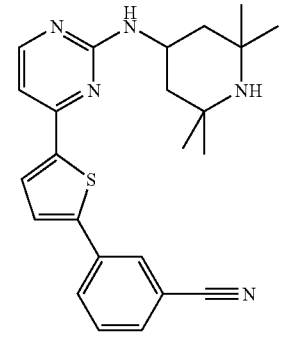

MS (ESI): 418 [M+H]$^+$ $^1$H-NMR (DMSO-d$_6$): δ (ppm) 8.35 (m, 1H), 8.25 (m, 1H), 7.95 (d, 1H), 7.85 (d, 1H), 7.75 (d, 1H), 7.65 (t, 1H), 7.05 (d, 1H), 4.35-4.20 (m, 1H), 1.90-1.75 (m, 2H), 1.35-1.05 (m, 14H).

Example 120

4-{5-[2-(2,2,6,6-Tetramethyl-piperidin-4-ylamino)-pyrimidin-4-yl]-thiophen-2-yl}-benzoic acid methyl ester

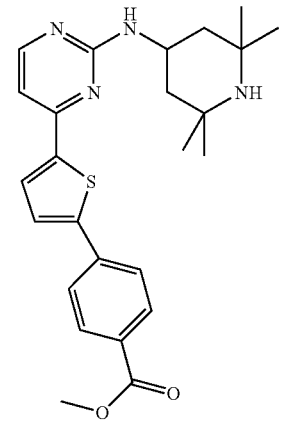

MS (ESI): 451 [M+H]$^+$ $^1$H-NMR (DMSO-d$_6$): δ (ppm) 8.40 (d, 1H), 8.15-8.00 (m, 3H), 7.90 (d, 2H), 7.85 (d, 1H), 7.30-7.25 (m, 1H), 4.45-4.35 (m, 1H), 3.85 (s, 3H), 2.15-1.95 (, 2H), 1.65-1.35 (m, 14H).

Example 121

(4-{5-[2-(2,2,6,6-Tetramethyl-piperidin-4-ylamino)-pyrimidin-4-yl]-thiophen-2-yl}-phenyl)-methanol

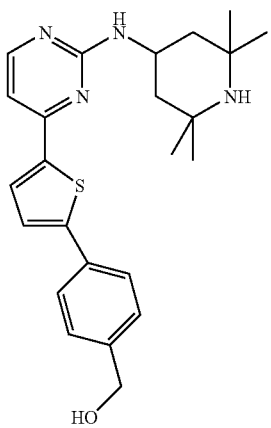

MS (ESI): 423 [M+H]$^{+1}$H-NMR (DMSO-d$_6$, 120° C.): δ (ppm) 8.35 (d, 1H), 7.85 (d, 1H), 7.56 (d, 2H), 7.50 (d, 1H), 7.40 (d, 2H), 4.55 (s, 2H), 4.45-4.35 (m, 1H), 2.15-2.05 (m, 2H), 1.75-1.65 (m, 2H), 1.65 (s, 6H), 1.55 (s, 6H).

Example 122

(3-{5-[2-(2,2,6,6-Tetramethyl-piperidin-4-ylamino)pyrimidin-4-yl]-thiophen-2-yl}-phenyl)-methanol

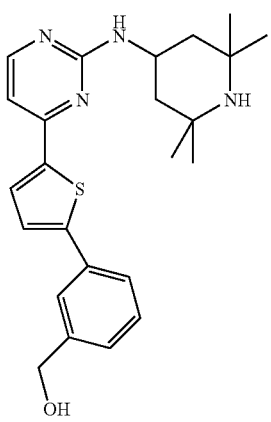

MS (ESI): 423 [M+H]$^{+1}$H-NMR (DMSO-d$_6$, 120° C.): δ (ppm) 8.35 (d, 1H), 7.85 (d, 1H), 7.65 (m, 1H), 7.55 (d, 1H), 7.50 (d, 1H), 7.45 (t, 1H), 7.35 (d, 1H), 7.05 (d, 1H), 4.60 (s, 2H), 4.45-4.35 (m, 1H), 2.15-2.10 (m, 2H), 1.75-1.65 (m, 2H), 1.65 (s, 6H), 1.55 (s, 6H).

Example 123

N-(3-{5-[2-(2,2,6,6-Tetramethyl-piperidin-4-ylamino)-pyrimidin-4-yl]-thiophen-2-yl}-phenyl)-acetamide

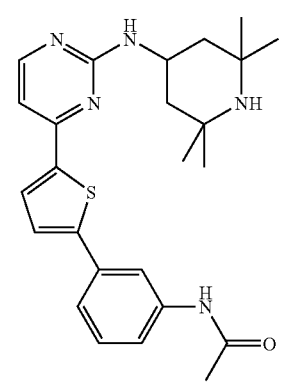

MS (ESI): 450 [M+H]$^{+1}$H-NMR (DMSO-d$_6$, 120° C.): δ (ppm) 9.60 (m, 1NH), 8.30 (d, 1H), 8.00 (m, 1H), 7.80 (d, 1H), 7.55-7.45 (m, 1H), 7.40 (m, 1H), 7.35 (m, 2H), 6.95 (d, 1H), 6.35-6.30 (m, 1NH), 4.45-4.30 (m, 1H), 2.10 (s, 3H), 1.35 (s, 6H), 1.25-1.15 (m, 2H), 1.10 (s, 6H).

Example 124

{4-[5-(3-Amino-phenyl)-thiophen-2-yl]-pyrimidin-2-yl}-(2,2,6,6-tetramethyl-piperidin-4-yl)-amine

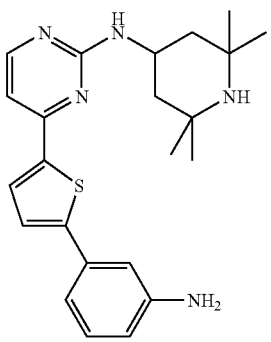

MS (ESI): 408 [M+H]$^{+1}$H-NMR (DMSO-d$_6$): δ (ppm) 8.35 (m, 1H), 7.85 (m, 1H), 7.40 (m, 1H), 7.15-7.00 (m, 2H), 6.90-6.80 (m, 2H), 6.55 (m, 1H), 5.25 (m, 2NH), 4.35-4.20 (m, 1H), 1.90-1.70 (m, 2H), 1.35-1.05 (m, 14H).

Example 125

1-(3-{5-[2-(2,2,6,6-Tetramethyl-piperidin-4-ylamino)-pyrimidin-4-yl]-thiophen-2-yl}-phenyl)-ethanone

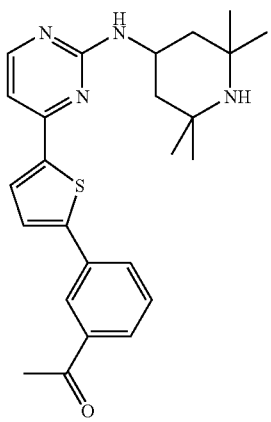

MS (ESI): 435 [M+H]$^{+1}$H-NMR (DMSO-d$_6$): δ (ppm) 8.35 (m, 1H), 8.20 (m, 1H), 8.05-7.95 (m, 3H), 7.75 (d, 1H), 7.60 (t, 1H), 7.05 (d, 1H), 4.35-4.20 (m, 1H), 2.65 (s, 3H), 1.95-1.70 (m, 2H0, 1.35-1.05 (m, 14H).

Example 126

5'-[2-(2,2,6,6-Tetramethyl-piperidin-4-ylamino)-pyrimidin-4-yl]-[2,2']bithiophenyl-5-sulfonic acid amide

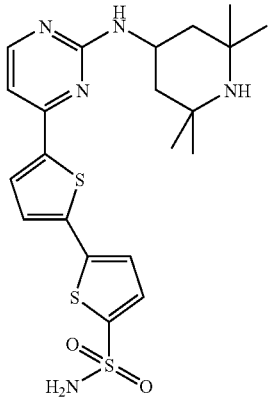

MS (ESI): 478 [M+H]$^{+1}$H-NMR (DMSO-d$_6$): δ (ppm) 8.36 (d, 1H), 7.95 (d, 1H), 7.80 (s, 2NH), 7.55 (d, 1H), 7.02 (d, 1H), 7.40 (d, 1H), 7.20 (d, 1H), 4.40-4.25 (m, 1H), 2.15-1.95 (m, 2H), 1.65-1.35 (m, 14H).

Example 127

{4-[5-(1-Amino-ethyl)-thiophen-2-yl]-pyrimidin-2-yl}-(2,2,6,6-tetramethyl-piperidin-4-yl)-amine

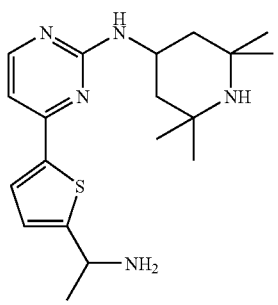

MS (ESI): 359 [M+H]$^{+1}$H-NMR (DMSO-d$_6$, 120° C.): δ (ppm) 8.30 (d, 1H), 7.80 (d, 1H), 7.40 (, 1H), 7.05 (d, 1H), 4.70 (qa, 1H), 4.45-4.30 (m, 1H), 2.10-2.00 (m, 2H), 1.75-1.70 (m, 2H), 1.68 (d, 3H), 1.60 (s, 6H), 1.50 (s, 6H).

Example 128

3-{5-[2-(2,2,6,6-Tetramethyl-piperidin-4-ylamino)-pyrimidin-4-yl]-thiophen-2-yl}-propan-1-ol

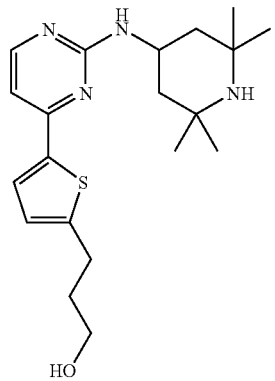

MS (ESI): 375 [M+H]$^{+1}$H-NMR (DMSO-d$_6$, 120° C.): δ (ppm) 8.30 (d, 1H), 7.70 (d, 1H), 7.00 (d, 1H), 6.95 (d, 1H), 4.45-4.35 (m, 1H), 3.55 (t, 2H), 2.95 (t, 2H), 2.10-2.05 (m, 2H), 1.90-1.80 (q, 2H), 1.75-1.65 (m, 2H), 1.60 (s, 6H), 1.50 (s, 6H).

Example 129

3-{5-[2-(2,2,6,6-Tetramethyl-piperidin-4-ylamino)-pyrimidin-4-yl]-thiophen-2-yl}-propionic acid methyl ester

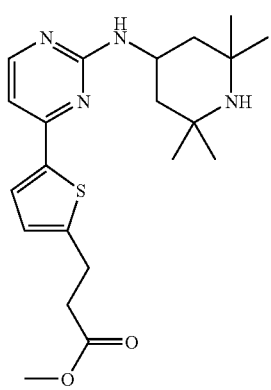

MS (ESI): 403 [M+H]$^{+1}$H-NMR (DMSO-d$_6$): δ (ppm) 8.30 (m, 1H), 7.75 (d, 1H), 7.05 (d, 1H), 6.95 (d, 1H), 4.40-4.25 (m, 1H), 3.60 (s, 3H), 3.10 (t, 2H), 2.70 (t, 2H), 2.05-1.95 (m, 2H), 1.65-1.40 (m, 14H).

Example 130

{4-[5-(4-Amino-butyl)-thiophen-2-yl]-pyrimidin-2-yl}-(2,2,6,6-tetramethyl-piperidin-4-yl)-amine

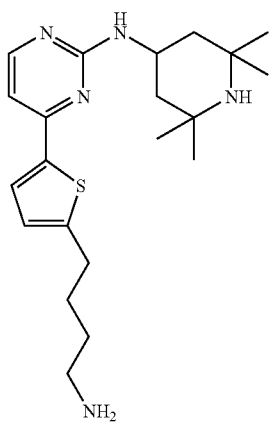

MS (EI): 387 [M$^+$]$^1$H-NMR (DMSO-d$_6$, 120° C.): δ (ppm) 8.32 (d, 1H), 7.80 (d, 1H), 7.15 (d, 1H0, 7.00 (d, 1H), 4.45-4.35 (m, 1H), 3.10-3.05 (m 2H), 2.90 (t, 2H), 2.10-2.00 (m, 2H), 1.85-1.65 (m, 6H), 1.60 (s, 6H), 1.50 (s, 6H).

Example 131

5-[2-(2,2,6,6-Tetramethyl-piperidin-4-ylamino)-pyrimidin-4-yl]-thiophene-2-carbonitrile

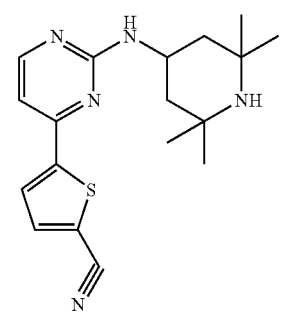

MS (ESI): 342 [M+H]$^{+1}$H-NMR (DMSO-d$_6$): δ (ppm) 8.45 (d, 1H), 8.10 (d, 1H), 8.05 (d, 1H), 7.30 (d, 1H), 4.35-4.25 (m, 1H), 2.05-1.95 (m, 2H), 1.65-1.45 (m, 14H).

Example 132

[4-(5-Aminomethyl-thiophen-2-yl)-pyrimidin-2-yl]-(2,2,6,6-tetramethyl-piperidin-4-yl)-amine

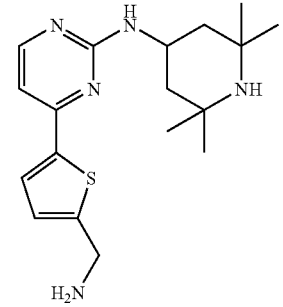

MS (EI): 345 [M$^+$]$^1$H-NMR (DMSO-d$_6$): δ (ppm) 8.35 (m, 1H), 7.95 (m, 1H), 7.40 (m,1H), 7.25 (m, 1H), 4.45-4.35 (m, 1H), 4.30-4.25 (m, 2H), 2.15-2.00 (m, 2H), 1.70-1.45 (m, 14H).

Example 133

{4-[5-(4-Aminomethyl-phenyl)-thiophen-2-yl]-pyrimidin-2-yl}-(2,2,6,6-tetramethyl-piperidin-4-yl)-amine

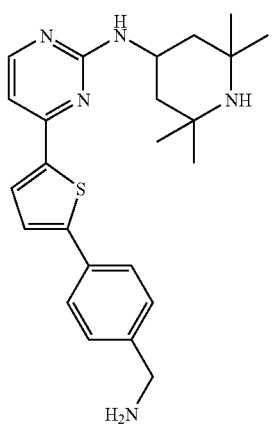

MS (ESI): 422.1 [M+H]$^{+1}$H-NMR (DMSO-d$_6$): δ (ppm) 8.40 (m, 1H), 8.10 (m, 1H), 7.80 (d, 2H), 7.70 (m, 1H), 7.60 (d, 2H), 7.25 (m, 1H), 4.45-4.35 (m, 1H), 4.10-4.00 (m, 2H), 2.15-2.00 (m, 2H0, 1.70-1.45 (m, 14H).

Example 134

{5'-[2-(2,2,6,6-Tetramethyl-piperidin-4-ylamino)-pyridin-4-yl]-[2,2']bithiophenyl-5-yl}-methanol

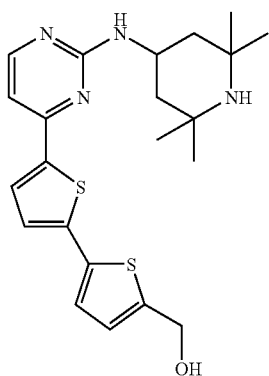

MS (ESI): 429 [M+H]$^{+1}$H-NMR (DMSO-d$_6$): δ (ppm) 8.30 (m, 1H), 7.85 (d, 1H), 7.35 (d, 1H), 7.20 (m, 1H), 7.05 (d, 1H), 6.95 (d, 1H), 5.55 (t, 1OH), 4.65 (d, 2H), 4.35-4.20 (m, 1H), 1.90-1.70 (m, 2H), 1.35-1.05 (m, 14H).

Example 135

2-Methyl-1-{5-[2-(2,2,6,6-tetramethyl-piperidin-4-ylamino)-pyrimidin-4-yl]-thiophen-2-yl}-propan-1-ol

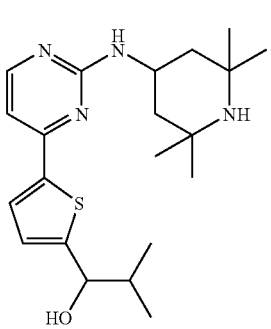

MS (ESI): 389 [M+H]$^{+1}$H-NMR (DMSO-d$_6$, 120° C.): δ (ppm) 8.30 (d, 1H), 7.70 (d, 1H), 7.00-6.95 (m, 2H), 4.60 (d, 1H), 4.45-4.35 (m, 1H), 2.15-2.10 (m, 2H), 2.03-1.90 (m, 1H), 1.80-1.70 (m, 2H), 1.60 (s, 6H), 1.50 (s, 6H), 0.97 (d, 3H), 0.93 (d, 3H).

Example 136

3-{5-[2-(2,2,6,6-Tetramethyl-piperidin-4-ylamino)-pyrimidin-4-yl]-thiophen-2-yl}-propionamide

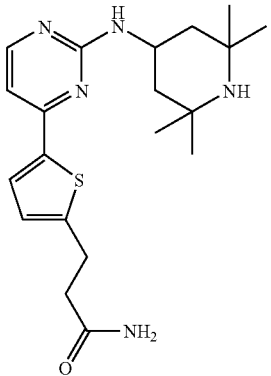

MS (ESI): 388 [M+H]$^{+1}$H-NMR (DMSO-d$_6$, 120° C.): δ (ppm) 8.25 (m, 1H), 7.70 (m, 1H), 7.00-6.90 (m, 2H), 4.45-4.35 (m, 1H), 3.10 (t, 2H), 2.45 (t, 2H), 2.15-2.05 (m, 2H), 1.70-1.60 (m, 2H), 1.60 (s, 6H), 1.50 (s, 6H).

Example 137

{4-[5-(3-Amino-propyl)-thiophen-2-yl]-pyrimidin-2-yl}-(2,2,6,6-tetramethyl-piperidin-4-yl)-amine

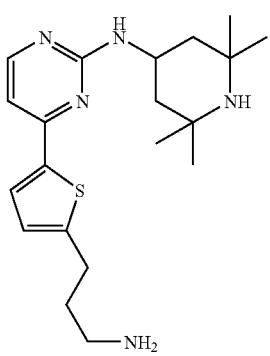

MS (ESI): 374 [M+H]$^{+1}$H-NMR (DMSO-d$_6$, 120° C.): δ (ppm) 8.30 (d, 1H), 7.65 (d, 1H), 7.00-6.95 (m, 2H), 4.45-4.35 (m, 1H), 3.20-3.10 (m, 2H), 3.00 (t, 2H), 2.20-2.10 (m, 2H), 2.10-2.00 (m, 2H), 1.75-1.65 (m, 2H), 1.60 (s, 6H0, 1.50 (s, 6H).

Example 138

4-{5-[2-(2,2,6,6-Tetramethyl-piperidin-4-ylamino)-pyrimidin-4-yl]-thiophen-2-yl}-butan-2-ol

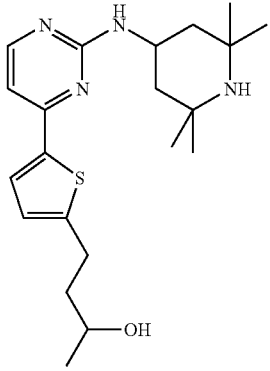

MS (ESI): 389 [M+H]$^{+1}$H-NMR (DMSO-d$_6$): δ (ppm) 8.25-8.15 (m, 1H), 7.70 (d, 1H), 7.00-6.90 (m, 2H), 4.55 (d, 1OH), 4.30-4.20 (m, 1H), 3.70-3.60 (m, 1H), 2.95-2.80 (m, 2H), 1.90-1.75 (m,2H), 1.70 (qa, 2H), 1.30-1.00 (m, 17H).

Example 139

[4-(5'-Aminomethyl-[2,2']bithiophenyl-5-yl)-pyrimidin-2-yl]-(2,2,6,6-tetramethyl-piperidin-4-yl)-amine

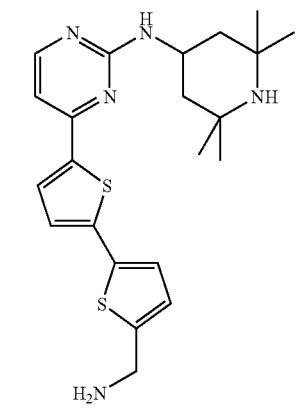

MS (ESI): 498 [M+HCl+Cl]$^{-1}$H-NMR (DMSO-d$_6$, 120° C.): δ (ppm) 8.35 (d, 1H), 7.80 (d, 1H), 7.35 (d, 1H), 7.30-7.25 (m, 2H), 7.05 (d, 1H), 4.45-4.35 (m, 1H), 4.25 (s, 2H), 2.15-2.05 (m, 2H), 1.75-1.68 (m, 2H), 1.65 (s, 6H0, 1.55 (s, 6H).

Example 140

3-{3-Methyl-5-[2-(2,2,6,6-tetramethyl-piperidin-4-ylamino)-pyrimidin-4-yl]-thiophen-2-yl}-propionic acid methyl ester

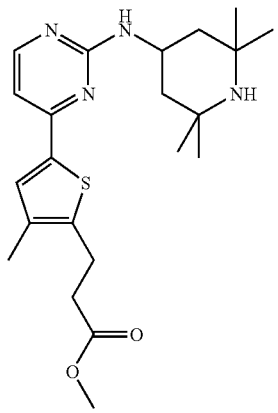

MS (ESI): 417 [M+H]$^{+1}$H-NMR (DMSO-d$_6$): δ (ppm) 8.30 (m, 1H), 7.85 (m, 1H), 7.15 (m, 1H), 4.45-4.30 (m, 1H), 3.65 (s, 3H), 3.05 (t, 2H), 2.70 (t, 2H), 2.20 (s, 3H), 2.15-2.00 (m, 1H), 1.65-1.45 (m, 14H).

Example 141

Acetic acid 2-methyl-2-nitro-1-{5-[2-(2,2,6,6-tetramethyl-piperidin-4-ylamino)-pyrimidin-4-yl]-thiophen-2-yl}-propyl ester

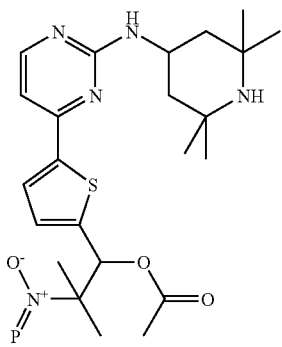

MS (ESI): 476 [M+H]+ 1H-NMR (DMSO-d$_6$): δ (ppm) 8.40 (m 1H), 7.95 (m, 1H), 7.35 (m, 1H), 7.25 (m, 1H), 6.55 (s, 1H), 4.45-4.30 (m, 1H), 2.15 (s, 3H), 2.15-1.95 (m, 2H), 1.65-1.45 (m, 20H). 6-{5-[2-(2,2,6,6-Tetramethyl-piperidin-4-ylamino)-pyrimidin-4-yl]-thiophen-2-yl}-hexanenitrile

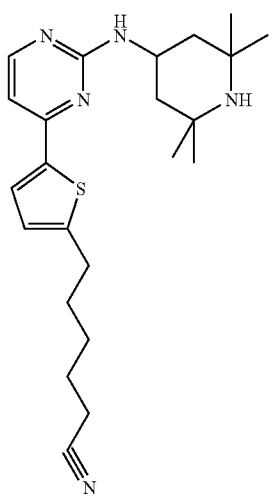

MS (ESI): 412 [M+H]+ 1H-NMR (DMSO-d$_6$): δ (ppm) 8.35 (m,1H), 7.70 (d, 1H), 6.95 (d, 1H), 6.90 (d, 1H), 4.35-4.25 (m, 1H), 2.85 (t, 2H), 2.50 (t, 2H), 1.90-1.60 (m, 6H), 1.50-1.40 (m, 2H), 1.45-1.05 (m, 14H).

Example 143

{4-[5-(6-Amino-hexyl)-thiophen-2-yl]-pyrimidin-2-yl}-(2,2,6,6-tetramethyl-piperidin-4-yl)-amine

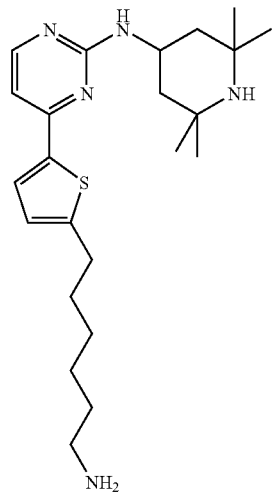

MS (ESI): 416 [M+H]+ 1H-NMR (DMSO-d$_6$, 120° C.): δ (ppm) 8.30 (d, 1H), 7.65 (d, 1H), 6.95 (d, 1H), 6.90 (d, 1H), 4.45-4.35 (m, 1H), 2.90 (t, 2H), 2.85 (t, 2H), 2.10-2.00 (m, 2H), 1.75-1.40 (m, 20H).

Example 144

1-{5-[2-(2,2,6,6-Tetramethyl-piperidin-4-ylamino)-pyrimidin-4-yl]-thiophen-2-yl}-pentan-3-one

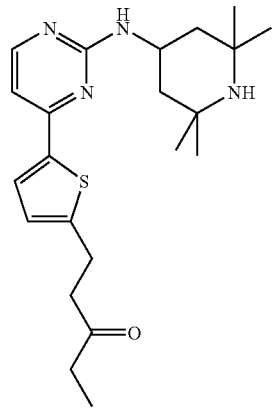

MS (ESI): 401 [M+H]+ 1H-NMR (DMSO-d$_6$): δ (ppm) 8.35 (m, 1H), 7.95 (m, 1H), 7.30 (m, 1H), 7.05 (m, 1H), 4.45-4.35 (m, 1H), 3.05 (t, 2H), 2.85 (t, 2H), 2.45 (qa, 2H), 2.15-2.00 (m,2H), 1.75-1.45 (m, 14H), 0.95 (t, 3H).

Example 145

1-Phenyl-3-{5-[2-(2,2,6,6-tetramethyl-piperidin-4-ylamino)-pyrimidin-4-yl]-thiophen-2-yl}-propan-1-one

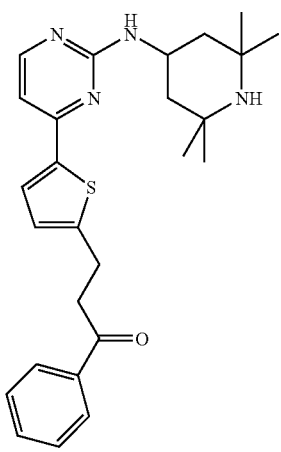

MS (ESI): 449.3 [M+H]$^{+1}$H-NMR (DMSO-d$_6$): δ (ppm) 8.25 (m, 1H), 8.05-8.00 (m, 2H), 7.75-7.65 (m, 2H), 7.60-7.50 (m, 2H), 7.05 (d, 1H), 7.00 (d, 1H), 4.35-4.20 (m,1H), 3.50 (t, 2H), 3.20 (t, 2H), 1.90-1.75 (m, 2H), 1.35-1.05 (m, 14H).

Benzthiophenes

Example 146

4-(4-Benzo[b]thiophen-2-yl-pyrimidin-2-ylamino)-piperidine-1-carboxylic acid ethyl ester

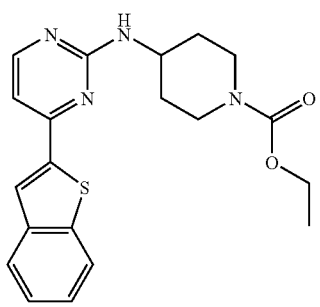

The title compound was prepared analogous to Method A, starting from 2,4-dichloro-pyrimidine, benzo[b]thiophen-2-boronic acid and ethyl-4-amino-1-piperidinecarboxylate.

MS (EI): 382 M$^{+1}$H-NMR (DMSO-d$_6$, 120° C.): δ (ppm) 8.40 (d, 1H), 8.20 (s, 1H), 8.00-7.90 (m, 2H), 7.45-7.40 (m, 2H), 7.10 (d, 1H), 4.10 (qa, 2H), 4.05-3.90 (m, 3H), 3.10-3.00 (m, 2H), 2.00-1.95 (m, 2H), 1.60-1.50 (m, 2H), 1.20 (t, 3H).

Example 147

4-(4-Benzo[b]thiophen-2-yl-pyrimidin-2-ylamino)-2,2,6,6-tetramethyl-piperidin-1-ol

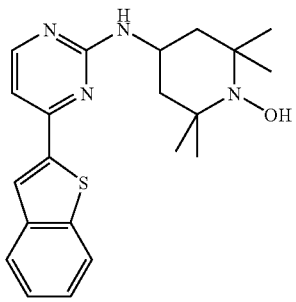

The title compound was prepared analogous to Method A, starting from 2,4-dichloro-pyrimidine, benzo[b]thiophen-2-boronic acid and 4-amino-2,2,6,6-tetramethylpiperidine-1-ol.

MS (ESI): 383.2 [M+H]$^{+1}$H-NMR (DMSO-d$_6$, 120° C.): δ (ppm) 8.35 (d, 1H), 8.10 (s, 1H), 7.95-7.85 (m, 2H), 7.45-7.40 (m, 2H), 7.10 (d, 1H), 6.55 (s, 1OH), 6.45-6.35 (m, 1NH), 4.35-4.20 (m, 1H), 1.95-1.85 (m, 2H), 1.60-1.50 (m, 2H), 1.25 (s, 6H), 1.15 (s, 6H).

Example 148

(4-Benzo[b]thiophen-2-yl-pyrimidin-2-yl)(1,2,2,6,6-pentamethyl-piperidin-4-yl)-amine

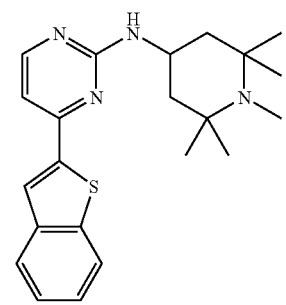

The title compound was prepared analogous to Method A, starting from 2,4-dichloro-pyrimidine, benzo[b]thiophen-2-boronic acid and 4-amino-1,2,2,6,6-pentamethylpiperidine.

MS (ESI): 381.2 [M+H]$^{+1}$H-NMR (DMSO-d$_6$, 120° C.): δ (ppm) 8.35 (d, 1H), 8.15 (s, 1H), 7.95-7.85 (m, 2H), 7.45-7.40 (m, 2H), 7.15 (d, 1H), 4.35-4.20 (m, 1H), 2.30 (s, 3H), 1.95-1.85 (m, 2H), 1.55-1.45 (m, 2H), 1.20-1.10 (2 s, 12H).

Example 149

(4-Benzo[b]thiophen-2-yl-pyrimidin-2-yl)-(1-benzyl-piperidin-4-yl)-amine

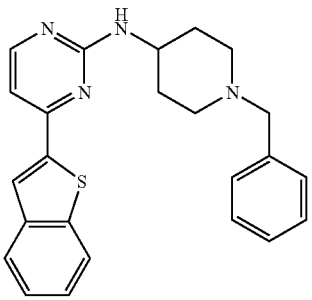

The title compound was prepared analogous to Method A, starting from 2,4-dichloro-pyrimidine, benzo[b]thiophen-2-boronic acid and 4-amino-1-benzyl-piperidine.

MS (EI): 400 [M+] $^1$H-NMR (DMSO-d$_6$): δ (ppm) 8.35 (m, 1H), 8.25 (s, 1H), 8.10-8.00 (m, 2H), 7.95 (m, 1H), 7.45-7.40 (m, 3H), 7.35-7.20 (m, 5H), 3.85-3.70 (m, 1H), 3.50 (s, 2H), 2.85-2.70 (m, 2H), 2.15-1.85 (m, 4H), 1.60-1.50 (m, 2H).

Example 150

(4-Benzo[b]thiophen-2-yl-pyrimidin-2-yl)-piperidin-4-yl-amine

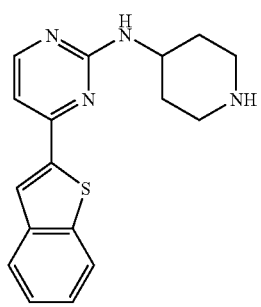

Compound of Example 149 (4.0 g, 10.0 mmol) was dissolved in 100 ml of EtOH and hydrogenated in the presence of 200 mg palladium on charcoal 10% at room temperature and 1 bar for 5 hours. Then the mixture was filtered through Hyflo and evaporated. The crude was purified by chromatography on silicagel (DCM/MeOH/ammonia:8/2/0.2). Yield: 2.76 g (89%).

MS (ESI): 311.1 [M+H]$^{+1}$H-NMR (DMSO-d$_6$): δ (ppm) 8.70-8.55 (m, 1H), 8.45-8.25 (m, 2H), 8.05-8.00 (m, 1H), 7.95-7.90 (m, 1H), 7.65-7.60 (m, 1H), 7.50-7.40 (m, 2H), 7.30 (m, 1H), 4.10-4.00 (m, 1H), 3.40-3.30 (m, 2H), 3.15-3.00 (m, 2H), 2.20-2.05 (m, 2H), 1.85-1.70 (m, 2H).

Example 151

3-[4-(4-Benzo[b]thiophen-2-yl-pyrimidin-2-ylamino)-piperidin-1-yl]-propionitrile The title compound was prepared starting from Example 150 analogous to Example 86.

MS (ESI): 364 [M+H]$^{+1}$H-NMR (DMSO-d$_6$): δ (ppm) 8.35 (d, 1H), 8.25 (s, 1H), 8.05-8.00 (m, 1H), 7.95-7.90 (m, 1H), 7.45-7.40 (m, 2H), 7.25 (d, 1H), 3.85-3.70 (m, 1H), 3.00-2.90 (m, 2H), 2.75-2.70 (m, 2H), 2.65-2.60 (m, 2H), 2.20-2.10 (m, 2H), 2.00-1.85 (m, 2H), 1.65-1.50 (m, 2H).

Example 152

[4-(6-Methoxy-benzo[b]thiophen-2-yl)-pyrimidin-2-yl]-(2,2,6,6-tetramethyl-piperidin-4-yl)-amine

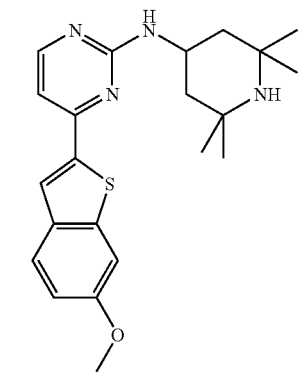

The title compound was prepared analogous to Method C, starting 6-methoxy-benzo[b]thiophen-2-boronic acid and (4-Chloro-pyrimidin-2-yl)-(2,2,6,6-tetramethyl-piperidin-4-yl)-amine.

MS (ESI): 397.2 [M+H]$^{+1}$H-NMR (DMSO-d$_6$): δ (ppm) 8.35-8.25 (m, 1H), 8.17 (s, 1H), 7.80 (d, 1H), 7.60-7.55 (m, 1H), 7.20-7.15 (m, 1H), 7.05-7.00 (m, 1H), 4.40-4.25 (m, 1H), 3.86 (s, 3H), 1.90-1.75 (m, 2H), 1.40-1.00 (m, 16H).

Example 153

2-[2-(2,2,6,6-Tetramethyl-piperidin-4-ylamino)-pyrimidin-4-yl]-benzo[b]thiophen-6-ol

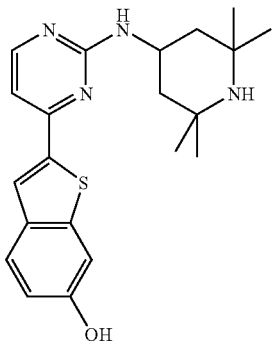

Compound of Example 152 (200 mg, 0.5 mmol) was dissolved in 10 ml hydrobromic acid 48% and stirred at 120° C. for 20 hours. Afterwards the mixture was evaporated and the crude was purified by chromatography on silicagel (DCM/MeOH/ammonia:8/2/0.2). Yield: 120 mg (62%).

MS (ESI): 383.1 [M+H]$^{+1}$H-NMR (DMSO-d$_6$): δ (ppm) 8.45 (m, 1H), 8.10 (s, 1H), 7.70 (d, 1H), 7.25 (m, 1H), 7.10 (d, 1H), 6.90 (d, 1H), 4.35-4.25 (m, 1H), 1.95-1.70 (m, 2H), 1.40-1.05 (m, 14H).

Example 154

[4-(6-Ethoxy-benzo[b]thiophen-2-yl)-pyrimidin-2-yl]-(2,2,6,6-tetramethyl-piperidin-4-yl)-amine

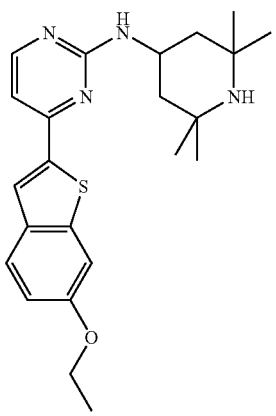

Compound of Example 153 (76 mg, 0.2 mmol), triphenylphosphine (80 mg, 0.3 mmol) and EtOH (30 mg, 0.65 mmol) were suspended in 8 ml of THF, then diethylazodicarboxylate (52 mg, 0.3 mmol) dissolved in 4 ml THF was added dropwise. This mixture was stirred at room temperature over night and afterwards evaporated. The crude was purified by chromatography on silicagel (DCM/MeOH/ammonia:9/1/0.1). Yield: 33 mg (40%).

MS (ESI): 411 [M+H]$^{+1}$H-NMR (DMSO-d$_6$, 120° C.): δ (ppm) 8.35 (d, 1H), 8.10 (s, 1H), 7.75 (d, 1H), 7.50 (m, 1H), 7.15 (m, 1H), 7.05 (m, 1H), 4.45-4.40 (m, 1H), 4.15 (qa, 2H), 2.15-2.10 (m, 2H), 1.75-1.65 (m, 2H), 1.65 (s, 6H), 1.55 (s, 6H), 1.40 (t, 3H).

Example 155

[4-(6-Allyloxy-benzo[b]thiophen-2-yl)-pyrimidin-2-yl]-(2,2,6,6-tetramethyl-piperidin-4-yl)-amine

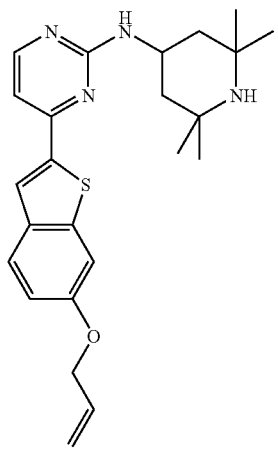

Compound of Example 153 (191 mg, 0.5 mmol) was suspended in 2 ml dimethylformamide. 24 mg (0.5 mmol) sodium hydride was added in small portions at room temperature. After 15 minutes 72 mg (0.6 mmol) allylbromide was added and the mixture was stirred at 100° C. for 2 hours. Then the cooled solution was poured on 200 ml water and extracted with EtOAc. The crude was purified by chromatography on silicagel (DCM/MeOH/ammonia:9/1/0.1). Yield: 110 mg (52%).

MS (ESI): 423 [M+H]$^{+1}$H-NMR (DMSO-d$_6$, 120° C.): δ (ppm) 8.35 (d, 1H), 8.10 (s, 1H), 7.80 (d, 1H), 7.55 (m, 1H), 7.15 (d, 1H), 7.05 (m, 1H), 6.15-6.05 (m, 1H), 5.45-5.40 (m, 1H), 5.30-5.25 (m, 1H), 4.70 (m, 2H), 4.45-4.35 (m, 1H), 2.15-2.10 (m, 2H), 1.75-1.65 (m, 2H), 1.65 (s, 6H), 1.55 (s, 6H).

Example 156

[4-(6-Oxiranylmethoxy-benzo[b]thiophen-2-yl)-pyrimidin-2-yl]-(2,2,6,6-tetramethyl-piperidin-4-yl)-amine

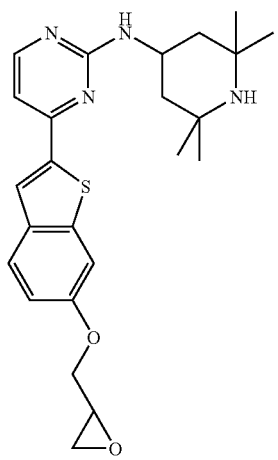

Starting from title compound of Example 153 this compound was O-alkylated analogous to Example 155.

MS (ESI): 475 [M+HCl+H]$^{+1}$H-NMR (DMSO-d$_6$, 120° C.): δ (ppm) 8.35 (d, 1H), 8.10 (s, 1H), 7.80 (d, 1H), 7.55 (m, 1H), 7.15 (d, 1H), 7.05 (m, 1H), 4.45-4.40 (m, 1H), 4.15-4.10 (m, 2H), 3.80-3.65 (m, 2H), 2.15-2.05 (m, 2H), 1.75-1.70 (m, 2H), 1.65 (s, 6H), 1.55 (s, 6H).

Example 157

1-Isopropylamino-3-{2-[2-(2,2,6,6-tetramethyl-piperidin-4-ylamino)-pyrimidin-4-yl]-benzo[b]thiophen-6-yloxy}-propan-2-ol

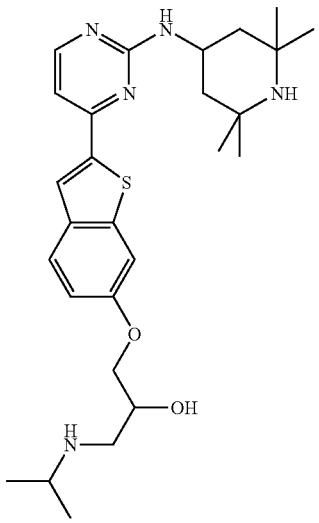

Compound of Example 156 (44 mg, 0.1 mmol) was dissolved in 2 ml ethanol and 100 mg (1.7 mmol) isopropylamine added. This mixture was stirred for 24 hours at 70° C. After evaporation the crude was purified by chromatography on silicagel (DCM/MeOH/ammonia:85/15/1.5). Yield: 38 mg (78%).

MS (ESI): 498 [M+H]$^{+1}$H-NMR (DMSO-d$_6$, 120° C.): δ (ppm) 8.35 (d, 1H), 8.10 (s, 1H), 7.80 (d, 1H), 7.55 (m, 1H), 7.15-7.05 (m, 2H), 4.45-4.40 (m, 1H), 4.40-4.30 (m, 1H), 4.20-4.15 (m, 2H), 3.45-3.35 (m, 1H), 3.25-3.15 (m, 1H), 3.05-3.00 (m, 1H), 2.15-2.05 (m, 2H), 1.80-1.70 (m, 2H), 1.65 (s, 6H), 1.55 (s, 6H), 1.35-1.30 (m, 6H).

Example 158

[4-(6-Methoxy-benzo[b]thiophen-2-yl)-5-methyl-pyrimidin-2-yl]-(2,2,6,6-tetramethyl-piperidin-4-yl)-amine

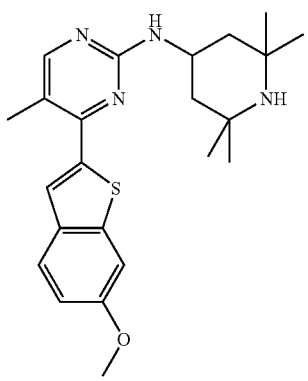

The title compound was prepared analogous to Method A, starting 6-methoxy-benzo[b]thiophene-2-boronic acid, 2,4-dichloro-5-methyl-pyrimidine and 4-amino-2,2,6,6-tetramethylpiperidine.

MS (ESI): 411 [M+H]$^{+1}$H-NMR (DMSO-d$_6$, 120° C.): δ (ppm) 8.20 (s, 1H), 7.90 (s, 1H), 7.80 (d, 1H), 7.45 (m, 1H), 7.05-7.00 (m, 1H), 4.40-4.30 (m, 1H), 3.90 (s, 3H), 2.45 (s, 3H), 1.95-1.90 (m, 2H), 1.35 (s, 6H), 1.25-1.15 (m, 2H0, 1.10 (s, 6H).

Example 159

1-Isopropylamino-3-{2-[5-methyl-2-(2,2,6,6-tetramethyl-piperidin-4-ylamino)-pyrimidin-4-yl]-benzo[b]thiophen-6-yloxy}-propan-2-ol

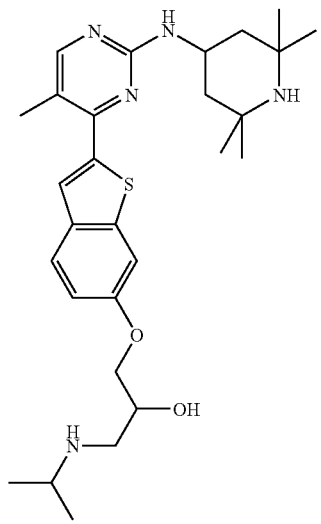

The title compound was prepared starting with compound from Example 158 using analogous procedures as described in Example 153 for the demethylation step, Example 156 for the o-alkylation step and Example 157 for epoxide opening.

MS (ESI): 512 [M+H]$^{+1}$H-NMR (DMSO-d$_6$, 120° C.): δ (ppm) 8.25 (s, 1H), 8.10 (s, 1H), 7.90-7.85 (m, 1H), 7.60 (m, 1H), 7.10-7.05 (m, 1H), 4.45-4.35 (m, 1H), 4.35-4.25 (m, 1H), 4.15-4.10 (m, 2H), 3.40-3.30 (m, 1H), 3.20-3.15 (m, 1H), 3.05-2.95 (m, 1H), 2.45 (s, 3H), 2.10-2.00 (m, 2H), 1.65-1.50 (m, 14H), 1.30 (dxd, 6H).

Example 160

[1-(3-Amino-propyl)-piperidin-4-yl]-(4-benzo[b]thiophen-2-yl-pyrimidin-2-yl)-amine

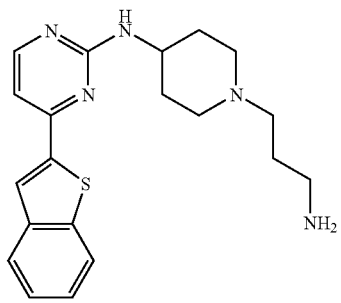

Compound of Example 151 was reduced with LAH in THF at 60° C. analogous to Example 53.

MS (ESI): 368 [M+H]$^{+1}$H-NMR (DMSO-d$_6$, 120° C.): δ (ppm) 8.40 (d, 1H), 8.15 (s, 1H), 8.00-7.90 (m, 2H), 7.45-7.40 (m, 2H), 7.20 (d, 1H), 4.20-4.10 (m, 1H), 3.60-3.30 (m, 6H), 3.05 (t, 2H), 2.35-2.05 (m, 6H).

Example 161a (4-Benzo[b]thiophen-2-yl-pyrimidin-2-yl)-(2,2,6-trimethyl-piperiin-4-yl)-amine

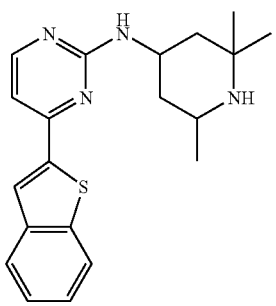

Step A: 2,2,6-Trimethyl-piperidin-4-ylamine

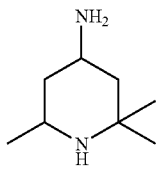

A solution of 2,2,6-trimethyl-piperidin-4-one (790 mg, 5.6 mmol) in 23 ml of MeOH was treated with ammonium acetate (4.6 g, 56.0 mmol) and sodium cyanoborohydride (0.27 g, 3.9 mmol). This mixture was stirred at room temperature for 24 hours. Afterwards 5 ml 1N-HCl were added and stirring continued for 20 minutes. For extraction with EtOAc the solution was basified with 40% NaOH. The crude was purified by chromatography on silicagel (DCM/MeOH/ammonia:6/4/0.4). Yield: 0.39 g (49%).

Step B: (4-Benzo[b]thiophen-2-yl-pyrimidin-2-yl)-(2,2,6-trimethyl-piperidin-4-yl)-amine The title compound was prepared analogous to Method A, starting from 2,4-dichloro-pyrimidine, benzo[b]thiophen-2-boronic acid and 2,2,6-trimethyl-piperidin-4-ylamine.

MS (ESI): 353 [M+H]$^{+1}$H-NMR (DMSO-d$_6$, 120° C., diastereomeric mixture): δ (ppm) 8.45-8.40 (m, 1H), 8.20 (m, 1H), 8.00-7.95 (m, 1H), 7.95-7.90 (m, 1H), 7.45-7.40 (m, 2H), 7.25-7.20 (m, 1H), 4.30-4.25 (m, 1H), 3.90-3.80 (m, 1H), 2.30-2.20 (m, 1H), 2.15-1.95 (m, 2H), 1.90-1.85 (m, 1H), 1.50-1.35 (m, 9H).

Example 161b (5-Aza-spiro[3.5]non-8-yl)-(4-benzo[b]thiophen-2-yl-pyrimidin-2-yl)-amine

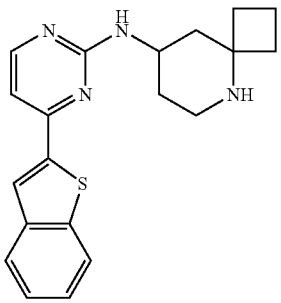

Step A:
8-Amino-5-aza-spiro[3.5]nonane-5-carboxylic acid tert-butyl ester

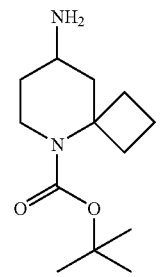

A of solution 8-Oxo-5-aza-spiro[3.5]nonane-5-carboxylic acid tert-butyl ester (Tetrahedron Letters 42, 4815 (2001)) (488 mg, 2.04 mmol) in 11 ml of MeOH was treated with ammonium acetate (1.5 g, 20.4 mmol) and sodium cyanoborohydride (100 mg, 1.6 mmol). This mixture was stirred at room temperature for 72 hours. Afterwards 0.8 ml 1N-HCl were added and stirring continued for 10 minutes. For extraction with EtOAc the solution was basified with 1N-NaOH. The crude was purified by chromatography on silicagel (DCM/MeOH/ammonia:9/1/0.1). Yield: 0.27 g (55%).

Step B: (5-Aza-spiro[3.5]non-8-yl)-(4-benzo[b]thiophen-2-yl-pyrimidin-2-yl)-amine The racemic title compound was prepared analogous to Method A, starting from 2,4-dichloro-pyrimidine, benzo[b]thiophen-2-boronic acid and 8-Amino-5-aza-spiro[3.5]nonane-5-carboxylic acid tert-butyl ester followed by BOC-deprotection with 4N-HCl in dioxane.

MS (ESI): 351 [M+H]$^{+1}$H-NMR (DMSO-d$_6$, 120° C.): δ (ppm) 8.45 (d, 1H), 8.20 (s, 1H), 8.00-7.90 (m, 2H), 7.45-7.40 (m, 2H), 7.25 (d, 1H), 4.15-4.05 (m, 1H), 3.35-3.30 (m, 1H), 3.00-2.95 (m, 1H), 2.50-2.30 (m, 4H), 2.15-1.95 (m, 4H), 1.85-1.75 (m, 2H).

Example 161c (4-Benzo[b]thiophen-2-yl-pyrimidin-2-yl)-trans-(2,6-dimethyl-piperidin-4-yl)-amine

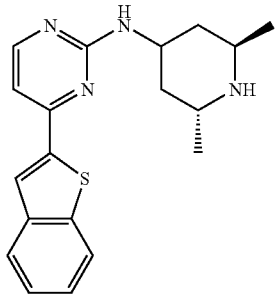

Step A: trans-(2,6-Dimethyl-piperidin-4-yl)-amine

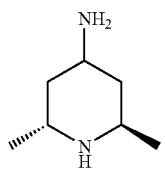

The title compound was prepared from trans-(2,6-dimethyl-piperidin-4-yl)-carbamic acid tert-butyl ester (separated by chromatography from its cis-isomer as described in WO-97/36871) followed by BOC-deprotection with 4N-HCl in dioxane.

Step B: (4-Benzo[b]thiophen-2-yl-pyrimidin-2-yl)-trans-(2,6-dimethyl-piperidin-yl)-amine The racemic title compound was prepared analogous to Method A, starting from 2,4-dichloro-pyrimidine, benzo[b]thiophen-2-boronic acid and trans-(2,6-dimethyl-piperidin-4-yl)-amine from step A.

MS (ESI): 339 [M+H]$^{+1}$H-NMR (DMSO-d$_6$): δ (ppm) 8.37 (d, 1H), 8.3 (s, 1H), 8.03 (m, 1H), 7.93 (m, 1H), 7.4-7.5 (m, 2H), 7.28 (d, 1H), 4.25 (br m, 1H), 3.75 (br m, 1H), 3.52 (br m, 1H), 2.05-2.17 (m, 2H), 1.8-2.0 (m, 8H).

The following compounds (Examples 162 to 167) were prepared analogous to Method C, starting from the appropriate known benzthiophene derivatives and (4-chloro-pyrimidin-2-yl)-(2,2,6,6-tetramethyl-piperidin-4-yl)-amine. Functional groups were protected prior to boronic acid formation and deprotected after Suzuki-coupling, using standard methods described in literature.

Example 162

[4-(3-Methyl-benzo[b]thiophen-2-yl)-pyrimidin-2-yl]-(2,2,6,6-tetramethyl-piperidin-4-yl)-amine

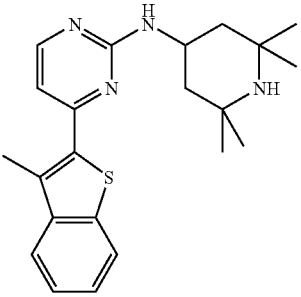

MS (ESI): 381.3 [M+H]$^{+1}$H-NMR (DMSO-d$_6$): δ (ppm) 8.45-8.40 (m, 1H), 8.00-7.90 (m, 2H), 7.60-7.50 (m, 1NH), 7.50-7.45 (m, 2H), 4.45-4.35 (m, 1H), 2.75 (s, 3H), 2.10-2.00 (m, 2H), 1.65-1.45 (m, 14H).

Example 163

[4-(5-Methyl-benzo[b]thiophen-2-yl)-pyrimidin-2-yl]-(2,2,6,6-tetramethyl-piperidin-4-yl)-amine

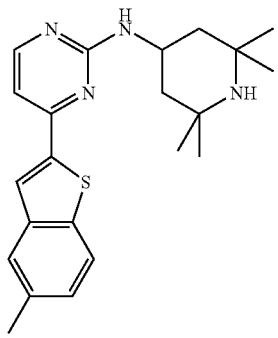

MS (ESI): 381.1 [M+H]$^{+1}$H-NMR (DMSO-d$_6$): δ (ppm) 8.45-8.40 (m,1H), 8.20 (s, 1H), 7.85 (d, 1H), 7.70 (s, 1H), 7.25 (d, 1H0, 7.10 (m, 1H), 4.40-4.30 (m, 1H), 2.45 (s, 3H), 1.95-1.75 (m, 2H), 1.54-1.05 (m, 14H).

Example 164

[4-(7-Methoxy-benzo[b]thiophen-2-pyrimidin-2-yl]-(2,2,6,6-tetramethyl-piperidin-4-yl)-amine

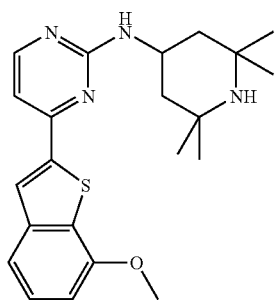

MS (ESI): 397 [M+H]$^{+1}$H-NMR (DMSO-d$_6$): δ (ppm) 8.45-8.35 (m, 1H), 8.25 (br.,s, 1H), 7.55-7.48 (m, 1H), 7.45-7.35 (t, 1H), 7.30-7.20 (m, 1H), 7.05-7.00 (m, 1H), 4.40-4.30 (m, 1H), 3.97 (s, 3H), 2.10-1.80 (m, 2H), 1.60-1.00 (m, 16H).

Example 165

(4-Benzo[b]thiophen-5-yl-pyrimidin-2-yl)-(2,2,6,6-tetramethyl-piperidin-4-yl)-amine

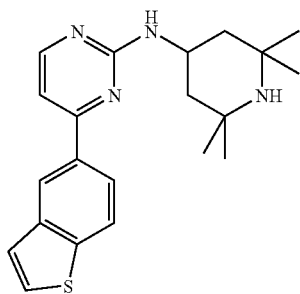

MS (ESI): 366 [M+H]$^{+1}$H-NMR (DMSO-d$_6$, 120° C.): δ (ppm) 8.35 (d, 1H), 8.10-8.05 (m, 2H), 7.95 (d, 1H), 7.55 (m, 1H), 7.10 (d, 1H), 4.40-4.30 (m, 1H), 1.95-1.90 (m, 2H), 1.35 (s, 6H), 1.30-1.20 (m, 2H), 1.10 (s, 6H).

Example 166

(4-Benzo[b]thiophen-2-yl-pyrimidin-2-yl)-(2,2,6,6-tetramethyl-piperidin-4-yl)-amine

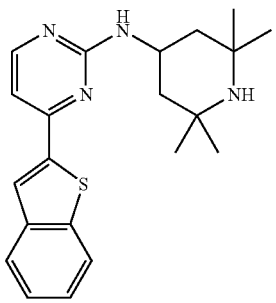

MS (ESI): 367 [M+H]$^{+1}$H-NMR (DMSO-d$_6$): δ (ppm) 9.45-9.35 (m, 1NH), 8.40 (d, 1H), 8.35 (s, 1H), 8.05-8.00 (m, 1H), 7.95-7.90 (m, 1H), 7.50-7.40 (m, 2H), 7.35 (d, 1H), 4.50-4.40 (m 1H), 2.10-2.00 (m, 2H), 1.70-1.55 (m, 8H), 1.50 (s, 6H).

Example 167

2-[2-(2,2,6,6-Tetramethyl-piperidin-4-ylamino)-pyrimidin-4-yl]-benzo[b]thiophene-7-carboxylic acid (2-diethylamino-ethyl)-amide

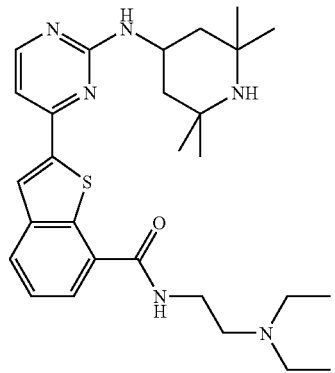

MS (ESI): 509 [M+H]$^{+1}$H-NMR (DMSO-d$_6$, 120° C.): δ (ppm) 8.40 (d, 1H), 8.20-8.15 (m, 2H), 8.05 (d, 1H), 7.50 (t, 1H), 7.20 (d, 1H), 4.45-4.40 (m, 1H), 3.85 (qa, 2H), 3.35 (t, 2H), 3.25 (qa, 4H), 2.15-2.10 (m, 2H), 1.75-1.65 (m, 2H), 1.65 (s, 6H), 1.55 (s, 6H), 1.35 (t, 6H).

Example 168

8-Aza-bicyclo[3.2.1]oct-3-yl-(4-benzo[b]thiophen-2-yl-pyrimidin-2-yl)-endo-amine

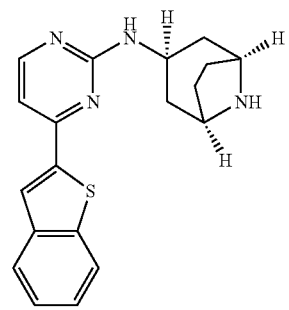

The title compound was prepared analogous to Method B, using benzo[b]thiophen-2-boronic acid, 4-chloro-2-methylthiopyrimidine and (1R,5S)-3-amino-8-aza-bicyclo[3.2.1]octane-8-carboxylic acid tert-butyl ester (WO 99/36424). Finally, the BOC group was cleaved with HCl/ethanol.

MS (EI): 336 [M+]$^1$H-NMR (DMSO-d$_6$): δ (ppm) 8.36 (d, 1H), 8.27 (s, 1H), 8.03 (m, 1H), 7.91 (m, 1H), 7.43 (m, 2H), 7.23 (d, 1H), 6.93 (br s, 1H), 3.98 (m, 1H), 3.35 (m, 2H), 2.00 (m, 4H), 1.82 (m, 2H), 1.66 (m, 2H).

Example 169

8-Aza-bicyclo[3.2.1]oct-3-yl-(4-benzo[.b.]thiophen-2-yl-pyrimidin-2-yl)-exo-amine

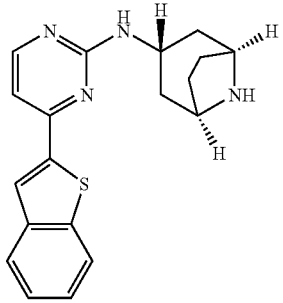

The title compound was prepared analogous to Method B, using benzo[b]thiophen-2-boronic acid, 4-chloro-2-methylthiopyrimidine and (1R,5S)-3-amino-8-aza-bicyclo[3.2.1]octane-8-carboxylic acid tert-butyl ester (WO 99/36424). Finally, the BOC group was cleaved with HCl/ethanol.

MS (EI): 336 [M+]$^1$H-NMR (DMSO-$d_6$): δ (ppm) 8.33 (br s, 1H), 8.25 (s, 1H), 8.02 (br s, 1H), 7.92 (m. 1H), 7.42 (m, 2H), 7.20 (d, 2H), 7.11 (br s, 1H, NH), 4.20 (m, 1H), 3.46 (br s, 2H), 1.60-2.12 (m, 6H), 1.48 (br t, 2H).

Example 170

(2R,4R)-4-(4-Benzo[b]thiophen-2-yl-pyrimidin-2-ylamino)-piperidine-2-carboxylic acid methyl ester

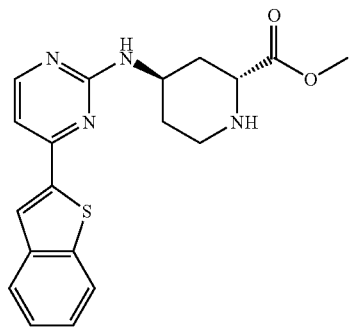

The title compound was prepared from 4-benzo[b]thiophen-2-yl-2-chloro-pyrimidine and (2R,4R)-4-amino-piperidine-1,2-dicarboxylic acid 1-tert-butyl ester 2-methyl ester according to Step C of Method A. Yield 45 mg (45%).

MS (ESI): 369.0 [M+H]$^{+1}$H-NMR (DMSO-$d_6$): δ (ppm) 8.38 (d, 1H), 8.29 (s, 1H), 8.05 (m, 1H), 7.93 (m, 1H), 7.45 (m, 2H), 7.32 (br d, 1H), 7.25 (d, 1H), 3.99 (m, 1H), 3.77 (m, 1H), 3.71 (s, 3H), 2.88 (m, 2H), 2.06 (m, 1H), 1.85 (m, 2H), 1.51 (m, 1H).

Example 171

(4-Benzo[b]thiophen-2-yl-5-methyl-pyrimidin-2-yl)-(2,2,6,6-tetramethyl-piperidin-4-yl)-amine

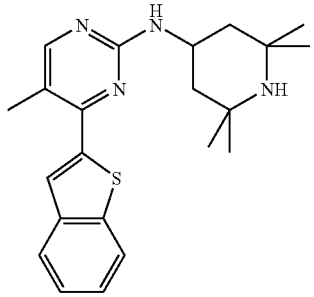

The title compound was prepared analogous to Steps B and C of Method A, starting from benzo[b]thiophene-2-boronic acid, 2,4-dichloro-5-methyl-pyrimidine and 4-amino-2,2,6,6-tetramethylpiperidine.

MS (ESI): 381 [M+H]$^{+1}$H-NMR (CDCl$_3$) δ (ppm) 8.09 (br s, 1H), 7.78 (br m, 3H), 7.31 (br m, 2H), 4.74 (d, 1H), 4.34 (m, 1H), 2.42 (s, 3H), 2.06 (dd, 2H), 1.18 (br s, 6H), 1.12 (br s, 6H), 0.97 (br t, 2H).

Phenyls

Example 172

[4-(4-Pyridin-4-yl-phenyl)-pyrimidin-2-yl]-(2,2,6,6-tetramethyl-piperidin-4-yl)-amine

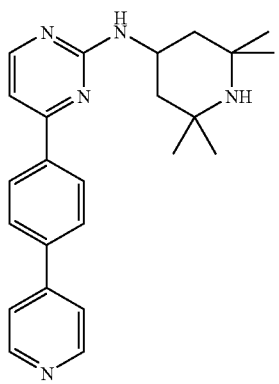

Step A:
4-(4-Bromo-phenyl)-2-methylsulfanyl-pyrimidine

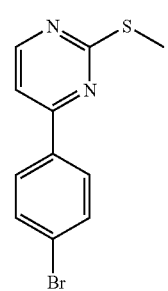

2-Methylthio-4-tributylstannylpyrimidine (3.5 g, 7.5 mmol), PdCl$_2$ (525 mg, 0.75 mmol) and 1,4-dibromobenzene (5.3 g, 22.5 mmol) were refluxed in xylene (75 ml) for 30 minutes, filtered and poured directly on a column of silicagel. Chromatography (acetone/hexanes:3/97 to 5/95) gave the title compound as white solid, which was crystallized from hexanes. Yield: 1.1 g (52%).

Step B:
4-(4-Bromo-phenyl)-2-methanesulfinyl-pyrimidine

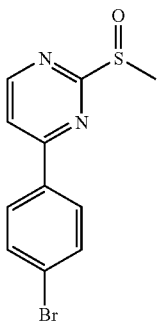

A solution of 4-(4-Bromo-phenyl)-2-methylsulfanyl-pyrimidine (1.1 g, 3.91 mmol) in DCM (33 ml) was cooled to 0° C. and treated within 1 hour with several portions of mCPBA (content 70%, 1.1 g, 4.46 mmol) under TLC-control. The reaction mixture was washed with 2N-solution of sodium carbonate, the organic phase dried over sodium sulfate, filtered and evaporated to dryness and purified by chromatography on silicagel (acetone/hexanes:50/50 to 75/25) to give the title compound as white crystals. Yield: 700 mg (60%).

Step C: [4-(4-Bromophenyl)-pyrimidin-2-yl]-(2,2,6,6-tetramethyl-piperidin-4-yl)-amine

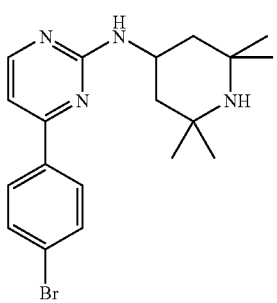

4-(4-Bromo-phenyl)-2-methanesulfinyl-pyrimidine (0.25 g, 0.84 mmol) and 4-amino-2,2,6,6,-tetramethylpiperidine (1 ml) were heated for 45 minutes at 130° C. Evaporation and chromatography on silicagel (EtOAc/MeOH/ammonia:95/4.5/0.5 to 90/9/1) gave the title compound as white crystals. Yield: 260 mg (78%).

Step D: [4-(4-Pyridin-4-yl-phenyl)-pyrimidin-2-yl]-(2,2,6,6-tetramethyl-piperidin-4-yl)-amine

[4-(4-Bromophenyl (pyrimidin-2-yl]-(2,2,6,6-tetramethyl-piperidin-4-yl)-amine (116 mg; 0.3 mmol), PdCl$_2$(PPh$_3$)$_2$ (21 mg; 0.03 mmol) and 4-tributylstannanyl-pyridine (221 mg; 0.6 mmol) were heated in xylene (3 ml) at 100° C. for 1 hour. The reaction mixture was filtered, evaporated and purified by preparative HPLC to give the title compound as a white solid. Yield: 20 mg (17%).

MS (ESI): 388 [M+H]$^{+1}$ H-NMR (CDCl$_3$): δ (ppm) 8.72 (d, 2H), 8.40 (d, 1H), 8.20 (d, 2H), 7.78 (d, 2H), 7.59 (d, 2H), 7.05 (d, 1H), 5.00 (d, 1H, NH), 4.50 (bs, 1H), 2.16 (dd, 2H), 1.37 (s, 6H), 1.30 (m, 1H, NH), 1.20 (s, 6H), 1.07 (br t, 2H).

Example 173

1-Methyl-4-{4-[2-(2,2,6,6-tetramethyl-piperidin-4-ylamino)-pyrimidin-4-yl]-phenyl}-piperidin-4-ol

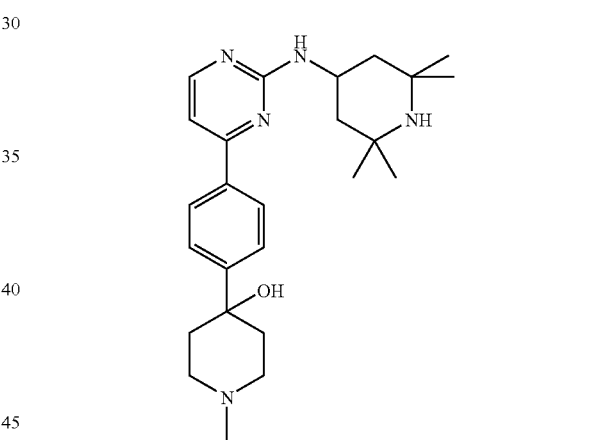

[4-(4-Bromophenyl)-pyrimidin-2-yl]-(2,2,6,6-tetramethyl-piperidin-4-yl)-amine (116 mg; 0.3 mmol) in THF/isopentane (3 ml/0.6 ml) was cooled to −100° C. nBuLi (1.6M in hexane, 0.56 ml; 0.9 mmol) was added within 5 minutes and the reaction mixture stirred for 15 minutes at this temperature. N-methyl-4-piperidone (71 µl, 0.6 mmol) was added in THF (71 µl), the reaction mixture stirred for 10 minutes at −100° C., poured on water and extracted three times with EtOAc. The combined organic phases were dried over sodium sulfate, filtered, evaporated to dryness and purified via chromatography on silicagel (EtOAc/MeOH/ammonia:90/9/1 to 80/18/2) to give the title compound as a white solid. Yield: 25 mg (17%).

MS (ESI): 424 [M+H]$^{+1}$ H-NMR (CDCl$_3$): δ (ppm) (mixture of tautomers) 8.33 (d, 1H), 8.07 (d, 2H), 7.63 (d, 2H), 7.00 (m, 1H), 4.95 (d, 1H), 4.45 (m, 1H), 3.25 (s, 1H, OH), 2.43 (d, 3H, NMe), 2.30-3.00 (m, 4H), 1.27-2.18 (m, 9H), 1.21 (s, 12H).

Example 174

[4-(4-Pyridin-3-yl-phenyl)-pyrimidin-2-yl]-(2,2,6,6-tetramethyl-piperidin-4-yl)-amine

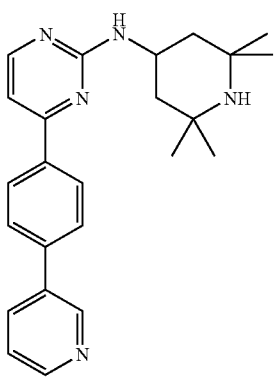

The title compound was prepared analogous to Step D of Example 172, starting from [4-(4-bromophenyl)-pyrimidin-2-yl]-(2,2,6,6-tetramethyl-piperidin-4-yl)-amine and 3-tributylstannanyl-pyridine. Yield: 45 mg (24%).

MS (ESI): 388 [M+H]$^+$ $^1$H-NMR (CDCl$_3$): δ (ppm) 8.93 (d, 1H), 8.65 (dd, 1H), 8.38 (d, 1H), 8.18 (d, 2H), 7.97 (dt, 1H), 7.73 (d, 2H), 7.42 (dd, 1H), 7.04 (d, 1H), 4.97 (d, 1H), 4.50 (m, 1H), 2.16 (dd, 2H), 1.40 (s, 6H), 1.20 (s, 6H+ NH), 1.06 (t, 2H).

Example 175

[4-(4-Pyridin-2-yl-phenyl)-pyrimidin-2-yl]-(2,2,6,6-tetramethyl-piperidin-4-yl)-amine

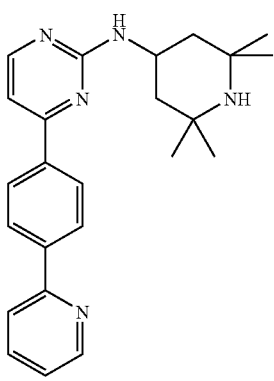

The title compound was prepared analogous to Step D of Example 172, starting from [4-(4-bromophenyl)-pyrimidin-2-yl]-(2,2,6,6-tetramethyl-piperidin-4-yl)-amine and 2-tributylstannanyl-pyridine. Yield: 85 mg (44%).

MS (ESI): 388 [M+H]$^+$ $^1$H-NMR (CDCl$_3$): δ (ppm) 8.75 (d, 1H), 8.38 (d, 1H), 8.19 (d, 2H), 8.12 (d, 2H), 7.82 (m, 2H), 7.28 (m, 1H), 7.05 (d, 1H), 4.97 (d, 1H, NH), 4.50 (m, 1H), 2.16 (dd, 2H), 1.40 (s, 6H), 1.20 (s, 6H+NH), 1.06 (t, 2H).

Example 176

{4-[4-(4-Methyl-piperazin-1-yl)-phenyl]-pyrimidin-2-yl}-2,2,6,6-tetramethyl-piperidin-4-yl)-amine

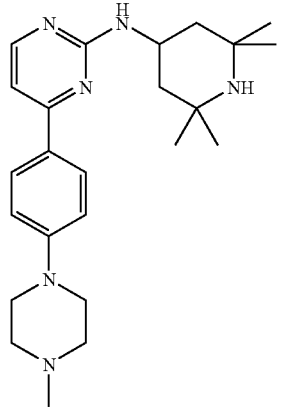

[4-(4-Bromophenyl)-pyrimidin-2-yl]-(2,2,6,6-tetramethyl-piperidin-4-yl)-amine (Step C of Example 172, 286 mg, 0.73 mmol), NaOtBu (78 mg, 0.8 mmol), N-methylpiperazine (90 μl, 0.8 mmol), R-(+)-BINAP (6 mg, 0.009 mmol) and Pd(OAc)$_2$ (2 mg, 0.008 mmol) were refluxed in 1,4-dioxane (2 ml) for 18 hours, diluted with EtOAc and filtered through a bed of silicagel (EtOAc/MeOH/ammonia:90/9/1) to yield the title compound in low purity. Further purification via preparative HPLC rendered the desired compound as a colorless foam. Yield: 50 mg (16%).

MS (ESI): 409 [M+H]$^+$ $^1$H-NMR (CDCl$_3$): δ (ppm) 8.25 (d, 1H), 8.00 (d, 2H), 6.98 (d, 2H), 6.92 (d, 1H), 4.85 (d, 1H, NH), 4.47 (m, 1H), 3.37 (dd, 4H), 2.60 (dd, 4H), 2.38 (s, 3H), 2.12 (dd, 2H), 1.38 (s, 6H), 1.57 (br s, 1H, NH), 1.19 (s, 6H), 1.02 (t, 2H).

Example 177

{4-[6-(3-Amino-3-methyl-butyl)-pyridin-3-yl]-pyrimidin-2-yl}-(2,2,6,6-tetramethyl-piperidin-4-yl)-amine

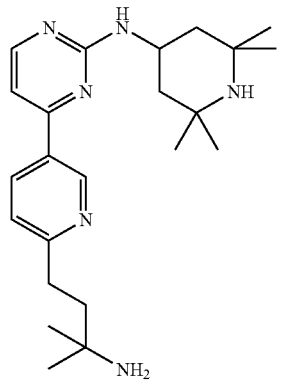

129

Step A: 3-(5-Bromo-pyridin-2-yl)-1,1-dimethyl-prop-2-ynylamine

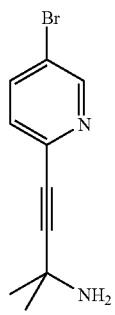

2,5-Dibromopyridine (1.19 g, 5 mmol), 1,1-dimethylpropargylamine (0.7 ml, 6 mmol), CuI (300 mg), PdCl$_2$(PPh$_3$)$_2$ (175 mg, 0.25 mmol) in triethylamine (50 ml) were refluxed for 1 hour. The reaction mixture was poured on water and extracted 3 times with EtOAc. The combined organic phases were dried over sodium sulfate, filtered and evaporated to dryness and purified via chromatography on silicagel (TBME/MeOH/ammonia:98/1.8/0.2 to 95/4.5/0.5) to give the title compound as slightly colored foam. Yield: 1.5 g (87%)

Step B: 1,1-Dimethyl-3-[5-(2-methylsulfanyl-pyrimidin-4-yl)-pyridin-2-yl]-prop-2-ynylamine

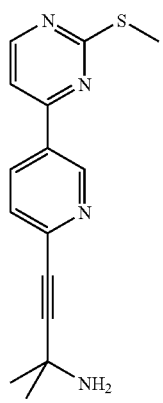

3-(5-Bromo-pyridin-2-yl)-1,1-dimethyl-prop-2-ynylamine (1.05 g, 4.4 mmol), 2-methylthio-4-tri-butylstannylpyrimidine (1.83 g, 4.4 mmol) and PdCl$_2$(PPh$_3$)$_2$ (154 mg, 0.22 mmol) in toluene (22 ml) were refluxed under argon for 2 hours. A second portion of 2-methylthio-4-tri-n-butylstannylpyrimidine (1.83 g, 4.4 mmol) was added and the mixture refluxed for 1 hour. The reaction mixture was filtered, evaporated and purified via chromatography on silicagel (TBME/MeOH/ammonia:97/2.7/0.3 to 95/4.5/0.5) to give the title compound as orange-brown solid, which was recrystallized form ether/hexanes. Yield: 500 mg (40%).

130

Step C: 3-[5-(2-Methanesulfinyl-pyrimidin-4-yl)-pyridin-2-yl]-1,1-dimethyl-prop-2-ynylamine

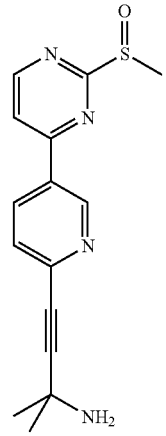

1,1-Dimethyl-3-[5-(2-methylsulfanyl-pyrimidin-4-yl)-pyridin-2-yl]-prop-2-ynylamine (500 mg, 1.76 mmol) in acetic acid/DCM (2.6 ml/8.8 ml) was treated at 0° C. with mCPBA (content 70%, 455 mg, 2.64 mmol) for 10 minutes. The reaction mixture was diluted with DCM and washed with 2N-solution of sodium carbonate. The organic phase was dried over sodium sulfate, filtered, evaporated to give the title compound as brownish crystals. Yield: 500 mg (98%).

Step D: {4-[6-(3-Amino-3-methyl-but-1-ynyl)-pyridin-3-yl]-pyrimidin-2-yl}-(2,2,6,6-tetramethyl-piperidin-4-yl)-amine

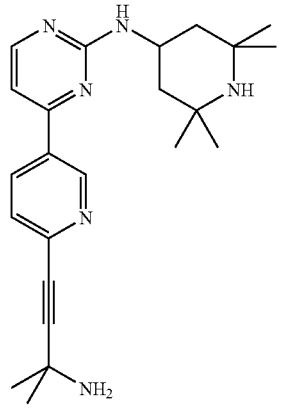

3-[5-(2-Methanesulfinyl-pyrimidin-4-yl)-pyridin-2-yl]-1,1-dimethyl-prop-2-ynylamine (500 mg, 1.76 mmol) and 4-amino-2,2,6,6-tetramethylpiperidine (0.61 ml, 3.54 mmol) were heated to 120° C. for 1 hour and the reaction mixture purified directly by chromatography on silicagel (TBME/MeOH/ammonia:95/4.5/0.5) to give the title compound as yellow crystals.

Yield: 210 mg (28%).

Step E: {4-[6-(3-Amino-3-methyl-butyl)-pyridin-3-yl]-pyrimidin-2-yl}-(2,2,6,6-tetramethyl-piperidin-4-yl)-amine {4-[6-(3-Amino-3-methyl-but-1-ynyl)-pyridin-3-yl]-pyrimidin-2-yl}-(2,2,6,6-tetramethyl-piperidin-4-yl)-amine (105 mg, 0.25 mmol) was dissolved in EtOH (100 ml) and hydrogenated at 1 atm over Pd/C (10%, 105 mg) for 2 hours at room temperature. The reaction mixture was filtered, evaporated, taken up in TBME/MeOH/ammonia (90/9/1) and passed through a bed of silicagel to give the title compound as slightly yellowish crystals, crystallized from ether. Yield: 35 mg (33%).

MS (ESI): 398 [M+H]$^{+1}$H-NMR (CDCl$_3$): δ (ppm) 9.19 (s, 1H), 8.39 (d, 1H), 8.28 (d, 1H), 7.33 (d, 1H), 7.00 (d, 1H), 5.02 (d, 1H), 4.49 (m, 1H), 2.97 (m, 2H), 2.15 (br d, 2H), 1.88 (m, 2H), 1.57 (br s, 2H, NH2), 1.40 (s, 6H), 1.22 (s, 12H), 1.10 (br t, 2H).

Example 178

[4-(4-Methylsulfanyl-phenyl)-pyrimidin-2-yl]-(2,2,6,6-tetramethyl-piperidin-4-yl)-amine

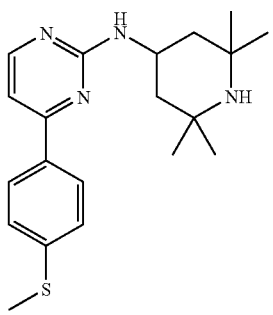

The title compound was prepared according to Method C. To a degassed suspension of (4-chloro-pyrimidin-2-yl)-(2,2,6,6-tetramethyl-piperidin-4-yl)-amine (1.07 g, 3.97 mmol) in 10 ml of 1-propanol were added bis(triphenylphosphine)palladium dichloride (112 mg, 0.16 mmol), 4-(methylthio)phenylboronic acid (1.00 g, 5.95 mmol) and 8 ml of 2N-solution of sodium carbonate. The mixture was stirred at 85° C. for 2 hours. The reaction mixture was diluted with EtOAc, filtered through Celite and washed with water. The organic layer was dried and concentrated. The solid was purified by chromatography on silicagel (EtOAc/MeOH/ammonia:66/33/1) and crystallization from n-hexane. Yield: 1.12 g (79%).

MS (ESI): 357.0 [M+H]$^{+1}$H-NMR (DMSO-d$_6$): δ (ppm) 8.32 (br d, 1H), 8.06 (d, 2H), 7.36 (d, 2H), 7.09 (d, 1H), 6.99 (br d, 1H), 4.31 (m., 1H), 2.54 (s, 3H), 1.81 (m, 2H), 1.24 (s, 6H), 1.07-1.23 (m, 3H), 1.05 (s, 6H).

Example 179

(4-Naphthalen-2-yl-pyrimidin-2-yl)-(2,2,6,6-tetramethyl-piperidin-4-yl)-amine

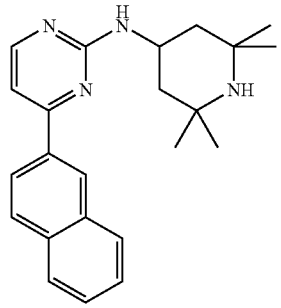

The title compound was prepared from (4-chloro-pyrimidin-2-yl)-(2,2,6,6-tetramethyl-piperidin-4-yl)-amine and 2-naphthylboronic acid according to Method C (Example 178). Yield: 142 mg (70%)

MS (ESI): 361.0 [M+H]$^{+1}$H-NMR (DMSO-d$_6$): δ (ppm) 8.75 (m, 1H), 8.41 (s, 1H), 8.27 (m, 1H), 7.95-8.06 (m, 3H), 7.57-7.63 (m, 2H), 7.30 (s, 1H), 7.06-7.16 (m, 1H), 4.27-4.48 (m, 1H), 1.72-1.98 (m, 2H), 1.32 (s, 6H), 1.10-1.30 (m, 3H), 1.06 (s, 6H).

Example 180

[4-(4-Bromo-phenyl)-pyrimidin-2-yl]-(2,2,6,6-tetramethyl-piperidin-4-yl)-amine

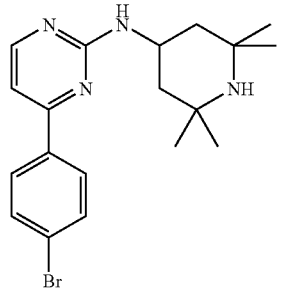

The title compound was prepared from (4-chloro-pyrimidin-2-yl)-(2,2,6,6-tetramethyl-piperidin-4-yl)-amine and 4-bromophenylboronic acid according to Method C (Example 178).

Yield: 620 mg (43%).

MS (ESI): 391.0 [M+H]$^{+1}$H-NMR (DMSO-d$_6$): δ (ppm) 8.37 (m, 1H), 8.07 (m, 2H), 7.52 (d, 2H), 7.04-7.17 (m, 2H), 4.30 (m, 1H), 1.71-1.87 (m, 2H), 1.23 (s, 6H), 1.07-1.20 (m, 3H), 1.05 (s, 6H).

Example 181

(2,2,6,6-Tetramethyl-piperidin-4-yl)-[4-(4-vinyl-phenyl)-pyrimidin-2-yl]-amine

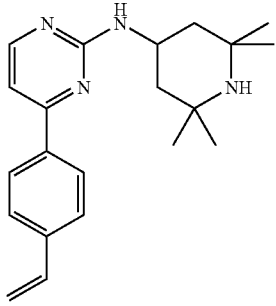

The title compound was prepared from (4-chloro-pyrimidin-2-yl)-(2,2,6,6-tetramethyl-piperidin-4-yl)-amine and vinylphenylboronic acid according to Method C (Example 178). Yield: 120 mg (64%).

MS (ESI): 337.0 [M+H]$^+$ $^1$H-NMR (DMSO-d$_6$): δ (ppm) 8.34 (m, 1H), 8.11 (m, 2H), 7.60 (d, 2H), 7.13 (d, 1H), 7.03 (m, 1H), 6.81 (dd, 1H), 5.96 (d, 1H), 5.36 (d, 1H), 4.32 (m, 1H), 1.82 (m, 2H), 1.25 (s, 6H), 1.06-1.23 (m, 3H), 1.05 (s, 6H).

Example 182

4-[2-(2,2,6,6-Tetramethyl-piperidin-4-ylamino)-pyrimidin-4-yl]-benzenesulfonamide

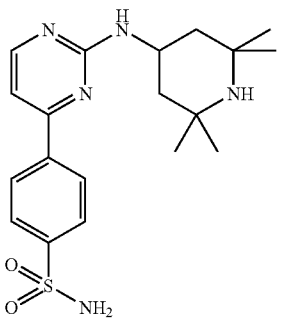

Step A: 4-(4,4,5,5-Tetramethyl-[1,3,2]dioxaborolan-2-yl)-benzenesulfonamide.

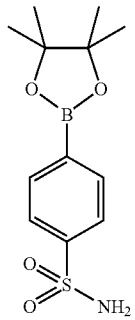

To a solution of 4-bromo-benzenesulfonamide (500 mg, 2.33 mmol) in 5 ml DMSO were added PdCl$_2$(dppf) (52 mg, 0.064 mmol), KOAc (623 mg, 6.36 mmol) and bis(pinacolato)diboron (592 mg, 2.33 mmol). The mixture was stirred at 80° C. for 16 hours. The reaction mixture was diluted with EtOAc and water and filtered through Celite. The organic layer was washed with water, dried and concentrated. The residue was triturated in ether, filtered and triturated again in 50 ml 1N-HCl to give the boronic acid ester. Yield: 406 mg (68%).

Step B: 4-[2-(2,2,6,6-Tetramethyl-piperidin-4-ylamino)-pyrimidin-4-yl]-benzenesulfonamide The title compound was prepared from (4-chloro-pyrimidin-2-yl)-(2,2,6,6-tetramethyl-piperidin-4-yl)-amine and 4-(4,4,5,5-tetramethyl-[1,3,2]dioxaborolan-2-yl)-benzenesulfonamide according to Method C (Example 178). Yield: 443 mg (86%).

MS (ESI): 388.0 [M−H]$^{-1}$ $^1$H-NMR (DMSO-d$_6$): δ (ppm) 8.39 (m, 1H), 8.23 (m, 2H), 7.88 (d, 2H), 7.12-7.21 (m, 2H), 4.25-4.37 (m, 1H), 1.72-1.92 (m, 2H), 1.02-1.31 (m, 15H).

Example 183

N-(2 Hydro-ethyl)-3-[2-(2,2,6,6-tetramethyl-piperidin-4-ylamino)-pyrimidin-4-yl]-benzenesulfonamide

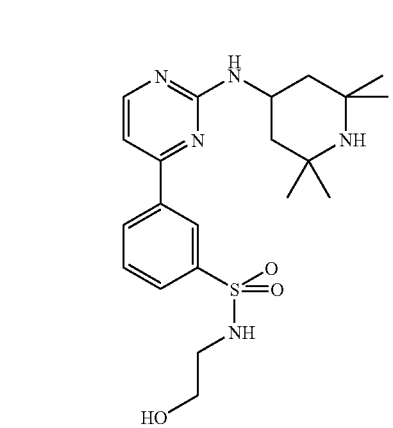

135

Step A: (4-Phenyl-pyrimidin-2-yl)-(2,2,6,6-tetramethyl-piperidin-4-yl)-amine

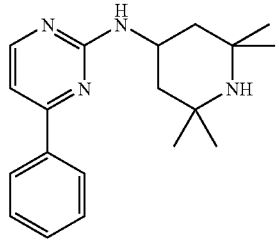

The title compound was prepared from (4-chloro-pyrimidin-2-yl)-(2,2,6,6-tetramethyl-piperidin-4-yl)-amine and phenylboronic acid according to Method C (Example 178). Yield: 190 mg (82%).

Step B: N-(2-Hydroxy-ethyl)-3-[2-(2,2,6,6-tetramethyl-piperidin-4-ylamino)-pyrimidin-4-yl]-benzenesulfonamide A solution of (4-phenyl-pyrimidin-2-yl)-(2,2,6,6-tetramethyl-piperidin-4-yl-amine (35 mg, 0.113 mmol) in 0.5 ml chlorosulfonic acid was stirred at 100° C. for 16 hours. The solution was concentrated and the residue was dissolved in 1 ml THF. To the solution were added DIEA (73 mg, 0.57 mmol) and ethanolamine (69 mg, 1.13 mmol). The reaction mixture was stirred at 60° C. for 2 hours. The solution was diluted with EtOAc and washed with aqueous NaOH and water. The organic layer was dried and concentrated. The solid was purified by preparative HPLC. Yield: 15 mg (31%).

MS (ESI): 434.0 [M+H]$^{+1}$H-NMR (DMSO-d$_6$): δ (ppm) 8.55 (m, 1H), 8.41 (m, 1H), 8.31 (m, 1H), 7.91 (d, 1H), 7.57-7.75 (m, 2H), 7.14-7.24 (m, 2H), 4.69 (br t, 1H), 4.24-4.41 (m, 1H), 3.37 (m, 2H), 2.82 (m, 2H), 1.73-1.88 (m, 2H), 1.04-1.32 (m, 15H).

Example 184

{4-[4-(3-Amino-3-methyl-butyl)-phenyl]-pyrimidin-2-yl}-(2,2,6,6-tetramethyl-piperidin-4-yl)-amine

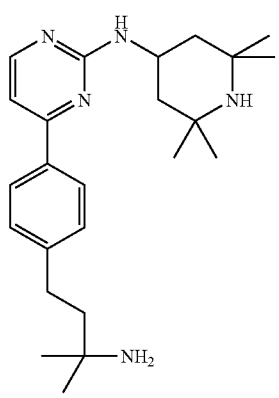

136

Step A: {4-[4-(3-Amino-3-methyl-but-1-ynyl)-phenyl]-pyrimidin-2-yl}-(2,2,6,6-tetramethyl-piperidin-4-yl)-amine

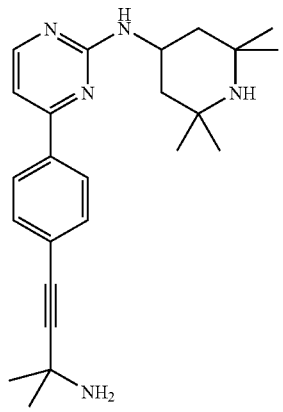

To a solution of [4-(4-bromo-phenyl)-pyrimidin-2-yl]-(2,2,6,6-tetramethyl-piperidin-4-yl)-amine (62 mg, 0.16 mmol) (Example 180) in 10 ml triethylamine were added bis(triphenylphosphine)palladium dichloride (22 mg, 0.03 mmol), 1,1-dimethyl-prop-2-ynylamine (166 µl, 1.43 mmol) and CuI (9.5 mg, 0.05 mmol). The mixture was stirred at 95° C. for 16 hours. The reaction mixture was concentrated, the residue taken up in EtOAc and the organic phase was washed with water. The organic layer was dried and concentrated. Purification using preparative HPLC gave the title compound. Yield: 26 mg (42%).

Step B: {4-[4-(3-Amino-3-methyl-butyl)-phenyl]-pyrimidin-2-yl}-(2,2,6,6-tetramethyl-piperidin-4-yl)-amine The title compound was prepared by hydrogenation of {4-[4-(3-amino-3-methyl-but-1-ynyl)-phenyl]-pyrimidin-2-yl}-(2,2,6,6-tetramethyl-piperidin-4-yl)-amine using Pd/C in EtOH.

Yield 12 mg (47%).

MS (ESI): 395.0 [M+H]$^{+1}$H-NMR (DMSO-d$_6$): δ (ppm) 8.32 (m, 1H), 8.04 (m, 2H), 7.33 (d, 2H), 7.09 (d, 1H), 6.98 (m, 1H), 4.32 (m, 1H), 2.68 (m, 2H), 1.05-1.89 (m, 27H).

Example 185

3-{4-[2-(2,2,6,6-Tetramethyl-piperidin-4-ylamino)-pyrimidin-4-yl]-phenyl}-propionic acid methyl ester

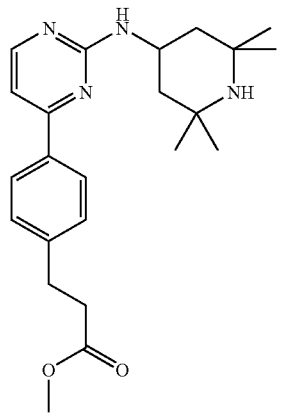

Step A: 3-{4-[2-(2,2,6,6-Tetramethyl-piperidin-4-ylamino)-pyrimidin-4-yl]-phenyl}-propionic acid

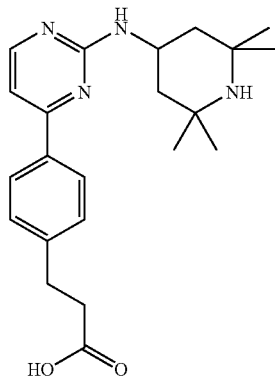

The title compound was prepared from (4-chloro-pyrimidin-2-yl)-(2,2,6,6-tetramethyl-piperidin-4-yl)-amine and 4-(2-carboxyethyl)phenylboronic acid according to Method C (Example 178). Yield: 1.4 g (100%).

Step B: 3-{4-[2-(2,2,6,6-Tetramethyl-piperidin-4-ylamino)-pyrimidin-4-yl]-phenyl}-propionic acid methyl ester The title compound was prepared using thionyl chloride followed by methanol. Yield: 24 mg (46%)
MS (ESI): 397.0 [M+H]$^{+1}$H-NMR (DMSO-d$_6$): δ (ppm) 8.86 (m, 1H), 8.35 (d, 1H), 8.03 (m, 2H), 7.24-7.84 (m, 1H), 7.36 (d, 2H), 7.16 (d, 1H), 4.37 (m, 1H), 3.58 (s, 3H), 2.92 (t, 2H), 2.68 (t, 2H), 2.06 (m, 2H), 1.35-1.59 (m, 15H).

Example 186

2-Methyl-4-{4-[2-(2,2,6,6-tetramethyl-piperidin-4-ylamino)-pyrimidin-4-yl]-phenyl}-butan-2-ol

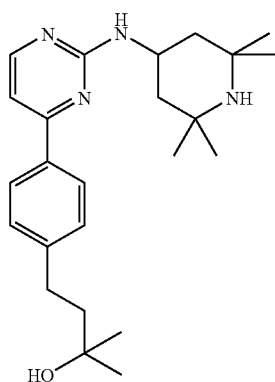

To a solution of 3-{4-[2-(2,2,6,6-tetramethyl-piperidin-4-ylamino)-pyrimidin-4-yl]-phenyl}-propionic acid methyl ester (100 mg, 0.25 mmol) (Example 185) was added an ether solution of methyllithium (505 µl, 1.6 M) at −78° C. The solution was kept at −78° C. for 1 hour and then quenched with saturated solution of ammonium chloride. Extraction with EtOAc and purification using preparative HPLC gave the title compound. Yield: 58 mg (58%).

MS (ESI): 397 [M+H]$^{+1}$H-NMR (DMSO-d$_6$): δ (ppm) 8.33 (m, 1H), 8.05 (m, 2H), 7.35 (d, 2H), 7.09 (d, 1H), 7.00 (m, 1H), 4.32 (m, 1H), 4.28 (s, 1H), 2.70 (m, 2H), 1.84 (m, 2H), 1.68 (m, 2H), 1.25 (s, 6H), 1.17 (s, 6H), 1.06-1.17 (m, 3H), 1.06 (s, 6H).S Example 187

3-{4-[2-(2,2,6,6-Tetramethyl-piperidin-4-ylamino)-pyrimidin-4-yl]-phenyl}-propionamide

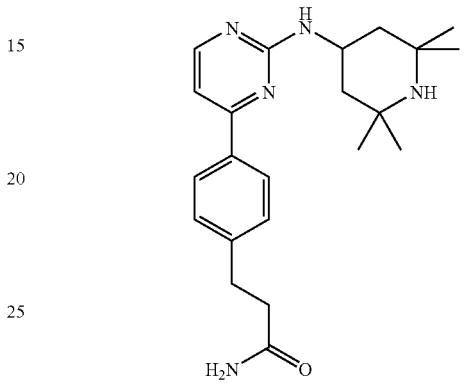

The title compound was prepared from 3-{4-[2-(2,2,6,6-tetramethyl-piperidin-4-ylamino)-pyrimidin-4-yl]-phenyl}-propionic acid (Step A of Example 185) and thionyl chloride followed by ammonia in MeOH. Yield: 5.3 mg (11%).
MS (ESI): 382 [M+H]$^{+1}$H-NMR (DMSO-d$_6$): δ (ppm) 8.70-8.96 (m, 1H), 8.35 (d, 1H), 8.04 (d, 2H), 7.67-7.92 (m, 1H), 7.35 (d, 2H), 7.30 (s, 1H), 7.16 (d, 1H), 6.77 (s, 1H), 4.38 (m, 1H), 2.87 (t, 2H), 2.40 (t, 2H), 2.05 (m, 2H), 1.24-1.67 (m, 14H).

Example 188

{4-[4-(2-Amino-ethyl)-phenyl]-pyrimidin-2-yl}-(2,2,6,6-tetramethyl-piperidin-4-yl)-amine

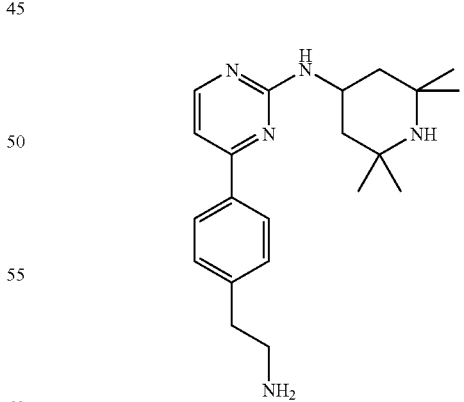

A suspension of 3-{4-[2-(2,2,6,6-tetramethyl-piperidin-4-ylamino)-pyrimidin-4-yl]-phenyl}-propionic acid (100 mg, 0.26 mmol) (Step A of Example 185), triethylamine (37 µl, 0.26 mmol) and diphenylphosphoryl azide (57 µl, 0.26 mmol) in 3 ml acetonitrile was heated for 18 hours at 70° C. Then, 1.2 ml 0.4N-HCl was added and the mixture was stirred for 1 hour at ambient temperature. The solution was diluted with water, extracted with ether and the aqueous phase was made basic with 2N-NaOH. Extraction with EtOAc and purification with preparative HPLC gave the title compound. Yield: 24 mg (26%).

MS (ESI): 353 [M+H]$^{+1}$H-NMR (DMSO-d$_6$): δ (ppm) 8.31 (d, 1H), 8.02 (d, 2H), 7.33 (d, 2H), 7.04 (d, 1H), 6.22 (m, 1H), 4.32-4.44 (m, 1H), 2.91 (t, 2H), 2.75 (t, 2H), 1.92 (dd, 2H), 1.28 (s, 6H), 1.17 (t, 2H), 1.10 (s, 6H), 1.01-1.21 (m, 3H).

Example 189

3-{4-[2-(2,2,6,6-Tetramethyl-piperidin-4-ylamino)-pyrimidin-4-yl]-phenyl}-propan-1-ol

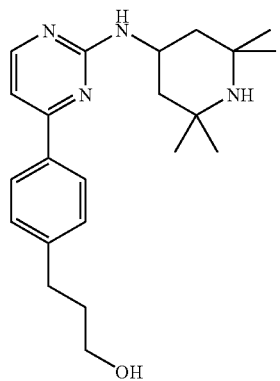

To a suspension of 3-{4-[2-(2,2,6,6-tetramethyl-piperidin-4-ylamino)-pyrimidin-4-yl]-phenyl}-propionic acid (50 mg, 0.13 mmol) (Step A of Example 185) in 1 ml THF was added LAH (1M in THF, 393 μl, 0.393 mmol). The mixture was stirred at 60° C. for 1 hour. A saturated solution of sodium sulfate was added and the aqueous phase was extracted with EtOAc. The crude product was purified using preparative HPLC. Yield: 19 mg (39%).

MS (ESI): 369 [M+H]$^{+1}$H-NMR (DMSO-d$_6$): δ (ppm) 8.31 (br d, 1H), 8.03 (br d, 2H), 7.31 (d, 2H), 7.08 (d, 1H), 6.97 (m, 1H), 4.47 (t, 1H), 4.30 (m, 1H), 3.43 (m, 2H), 2.67 (t, 2H), 1.69-1.89 (m, 4H), 1.00-1.28 (m, 15H).

Example 190

{4-[4-(3-Amino-propyl)-phenyl]-pyrimidin-2-yl}-(2,2,6,6-tetramethyl-piperidin-4-yl)-amine

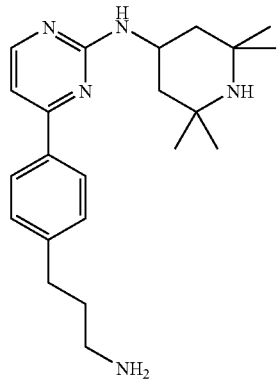

Step A: Toluene-4-sulfonic acid 3-{4-[2-(2,2,6,6-tetramethyl-piperidin-4-ylamino)-pyrimidin-4-yl]-phenyl}-propyl ester

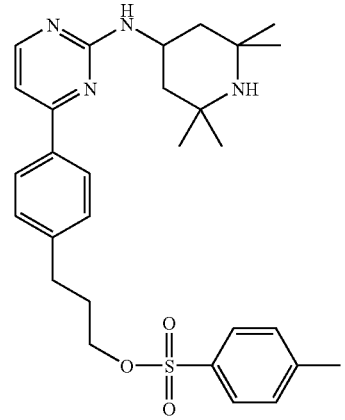

The title compound was prepared from 3-{4-[2-(2,2,6,6-tetramethyl-piperidin-4-ylamino)-pyrimidin-4-yl]-phenyl}-propan-1-ol (Example 189) and p-toluenesulfonyl chloride in pyridine. Yield: 140 mg (45%).

Step B: {4-[4-(3-Amino-propyl)-phenyl]-pyrimidin-2-yl}-(2,2,6,6-tetramethyl-piperidin-4-yl)-amine The title compound was prepared from toluene-4-sulfonic acid 3-{4-[2-(2,2,6,6-tetramethyl-piperidin-4-ylamino)-pyrimidin-4-yl]-phenyl}-propyl ester and ammonia in MeOH. Yield: 4 mg (11%).

MS (ESI): 368 [M+H]$^{+1}$H-NMR (DMSO-d$_6$): δ (ppm) 8.28 (m, 1H), 8.02 (m, 2H), 7.30 (d, 2H), 7.08 (m, 1H), 6.98 (m, 1H), 4.28 (m, 1H), 2.63 (m, 4H), 1.61-1.88 (m, 4H), 1.00-1.32 (m, 17H).

Example 191

{4-[4-(3-Methoxy-propyl)-phenyl]-pyrimidin-2-yl}-(2,2,6,6-tetramethyl-piperidin-4-yl)-amine

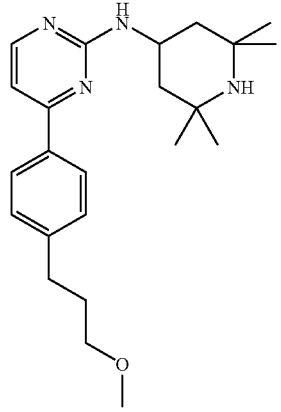

The title compound was prepared from toluene-4-sulfonic acid 3-{4-[2-(2,2,6,6-tetramethyl-piperidin-4-ylamino)-pyrimidin-4-yl]-phenyl}-propyl ester (Step A of Example 190) in MeOH. Yield: 3 mg (6%).

MS (ESI): 383.0 [M+H]$^{+1}$H-NMR (DMSO-d$_6$): δ (ppm) 8.35 (d, 1H), 8.03 (m, 2H), 7.34 (m, 3H), 7.16 (d, 1H), 4.38 (m, 1H), 3.34 (t, 2H), 3.24 (s, 3H), 2.68 (t, 2H), 2.05 (m, 2H), 1.83 (m, 2H), 1.28-1.57 (m, 15H).

Example 192

4-{4-[2-(2,2,6,6-Tetramethyl-piperidin-4-ylamino)-pyrimidin-4-yl]-phenyl}-butyronitrile

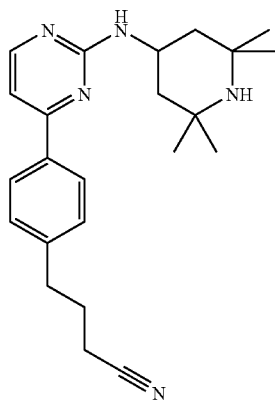

A solution of toluene-4-sulfonic acid 3-{4-[2-(2,2,6,6-tetramethyl-piperidin-4-ylamino)-pyrimidin-4-yl]-phenyl}-propyl ester (80 mg, 0.15 mmol), (Step A of Example 190), KCN (20 mg, 0.31 mmol) and a catalytic amount of potassium iodide in 2 ml DMSO was stirred for 2 hours at 100° C. The reaction mixture was diluted with EtOAc and washed with water. The crude product was purified using preparative TLC. Yield: 9 mg (16%).

MS (ESI): 378.0 [M+H]$^{+1}$H-NMR (DMSO-d$_6$): δ (ppm) 8.32 (m, 1H), 8.06 (m, 2H), 7.36 (d, 2H), 7.10 (d, 1H), 7.00 (m, 1H), 4.32 (m, 1H), 2.75 (t, 2H), 1.92 (t, 2H), 1.82 (m, 2H), 1.01-1.30 (m, 17H).

Example 193

{4-[4-(4-Amino-butyl)-phenyl]-pyrimidin-2-yl}-(2,2,6,6-tetramethyl-piperidin-4-yl)-amine

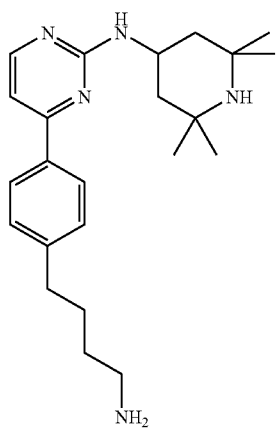

To a solution of 4-{4-[2-(2,2,6,6-tetramethyl-piperidin-4-ylamino)-pyrimidin-4-yl]-phenyl}-butyronitrile (Example 192) (37 mg, 0.10 mmol) in 2 ml THF was added LAH (1 M in THF, 294 µl, 0.294 mmol). The reaction mixture was stirred at 60° C. for 2 hours. The mixture was quenched with 0.5 ml aqueous sodium sulfate, followed by 2N-NaOH (pH 11). Extraction with EtOAc and purification using preparative HPLC gave the title compound. Yield: 16 mg (43%).

MS (ESI): 382.0 [M+H]$^{+1}$H-NMR (DMSO-d$_6$): δ (ppm) 8.31 (m, 1H), 8.04 (m, 2H), 7.32 (d, 2H), 7.08(d, 1H), 6.98 (m, 1H), 4.32 (m, 1H), 2.64 (t, 2H), 2.55 (t, 2H), 1.82 (m, 2H), 1.62 (m, 2H), 1.37 (m, 2H), 1.01-1.28 (m, 17H).

Example 194

4-{4-[2-(2,2,6,6-Tetramethyl-piperidin-4-ylamino)-pyrimidin-4-yl]-phenyl}-butan-2-one

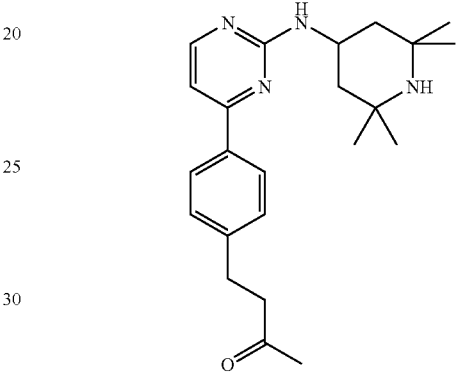

Step A: 4-[4-(4,4,5,5-Tetramethyl-[1,3,2]dioxaborolan-2-yl)-phenyl]-butan-2-one

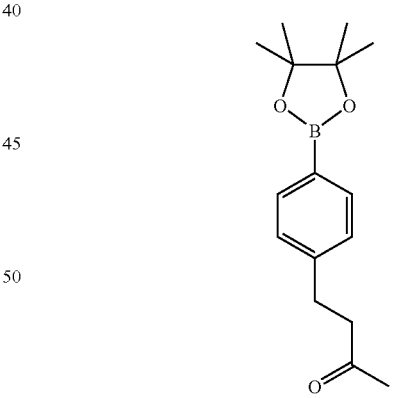

The boronic acid pinacol ester was prepared from 4-(4-bromo-phenyl)-butan-2-one and bis(pinacolato)diboron as shown in Step A of Example 182. The crude product was purified using silica gel chromatography (cyclohexane/EtOAc:6/1). Yield 330 mg (70%).

Step B: 4-{4-[2-(2,2,6,6-Tetramethyl-piperidin-4-ylamino)-pyrimidin-4-yl]-phenyl}-butan-2-one The title compound was prepared from (4-chloro-pyrimidin-2-yl)-(2,2,6,6-tetramethyl-piperidin-4-yl)-amine and 4-[4-(4,4,5,5-tetramethyl-[1,3,2]dioxaborolan-2-yl)-phenyl]-butan-2-one according to Method C (Example 178). Yield: 217 mg (71%).

MS (ESI): 381.0 [M+H]$^{+1}$H-NMR (DMSO-d$_6$): δ (ppm) 8.31 (m, 1H), 8.03 (m, 2H), 7.33 (d, 2H), 7.08(d, 1H), 7.00 (m, 1H), 4.31 (m, 1H), 2.83 (s, 4H), 2.12 (s, 3H), 1.82 (m, 2H), 1.00-1.30 (m, 15H).

Example 195

4-{4-[2-(2,2,6,6-Tetramethyl-piperidin-4-ylamino)-pyrimidin-4-yl]-phenyl}-butan-2-ol

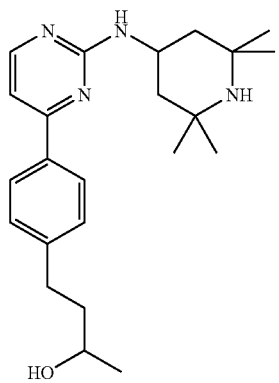

The title compound was prepared by reduction of 4-{4-[2-(2,2,6,6-tetramethyl-piperidin-4-ylamino)-pyrimidin-4-yl]-phenyl}-butan-2-one with sodium borohydride in MeOH. Yield: 196 mg (100%).

MS (ESI): 383.0 [M+H]$^{+1}$H-NMR (DMSO-d$_6$): δ (ppm) 8.33 (m, 1H), 8.05 (m, 2H), 7.33 (d, 2H), 7.10 (d, 1H), 7.01 (m, 1H), 4.50 (d, 1H), 4.33 (m, 1H), 3.63 (m, 1H), 2.60-2.79 (m, 2H), 1.84 (m, 2H), 1.66 (m, 2H), 1.02-1.30 (m, 15H), 1.12 (d, 3H).

Example 196

{4-[4-(3-Amino-butyl)-phenyl]-pyrimidin-2-yl}-(2,2,6,6-tetramethyl-piperidin-4-yl)-amine

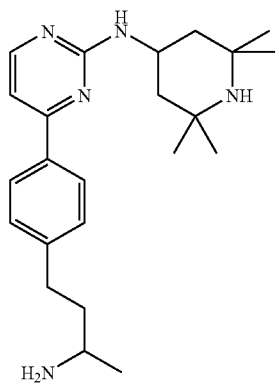

Step A: Toluene-4-sulfonic acid 1-methyl-3-{4-[2-(2,2,6,6-tetramethyl-piperidin-4-ylamino)-pyrimidin-4-yl]-phenyl}-propyl ester

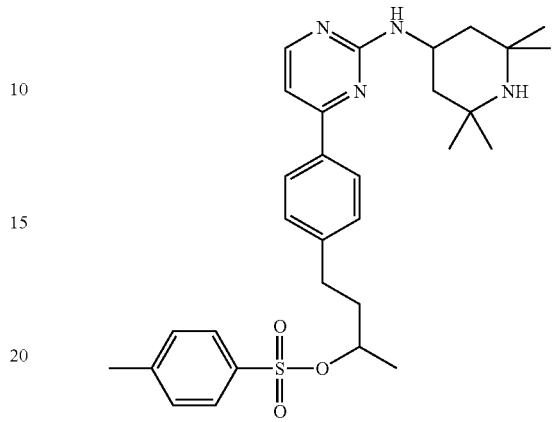

The title compound was prepared from 4-{4-[2-(2,2,6,6-tetramethyl-piperidin-4-ylamino)-pyrimidin-4-yl]-phenyl}-butan-2-ol and p-toluenesulfonyl chloride in pyridine. Yield: 182 mg (93%).

Step B: {4-[4-(3-Azido-butyl)-phenyl]-pyrimidin-2-yl}-(2,2,6,6-tetramethyl-piperidin-4-yl)-amine.

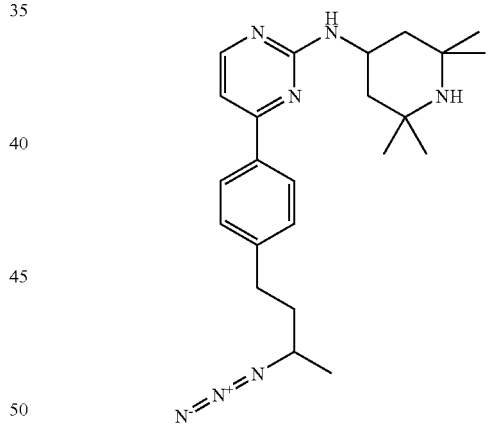

The title compound was prepared from toluene-4-sulfonic acid 1-methyl-3-{4-[2-(2,2,6,6-tetramethyl-piperidin-4-ylamino)-pyrimidin-4-yl]-phenyl}-propyl ester and sodium azide in DMF. Yield 96 mg (82%).

Step C: {4-[4-(3-Amino-butyl)-phenyl]-pyrimidin-2-yl}-(2,2,6,6-tetramethyl-piperidin-4-yl)-amine The title compound was prepared from {4-[4-(3-azido-butyl)-phenyl]-pyrimidin-2-yl}-(2,2,6,6-tetramethyl-piperidin-4-yl)-amine by hydrogenation using PtO$_2$ in MeOH. Yield: 39 mg (87%).

MS (ESI): 381.0 [M+H]$^{+1}$H-NMR (DMSO-d$_6$): δ (ppm) 8.33 (m, 1H), 8.05 (m, 2H), 7.35 (d, 2H), 7.10 (d, 1H), 7.00

(m, 1H), 4.33 (m, 1H), 2.67 (m, 3H), 1.50-1.90 (m, 4H), 1.03-1.30 (m, 17H), 1.02 (d, 3H).

Example 197

2-Methyl-4-{4-[2-(2,2,6,6-tetramethyl-piperidin-4-ylamino)-pyrimidin-4-yl]-phenyl}-butyronitrile

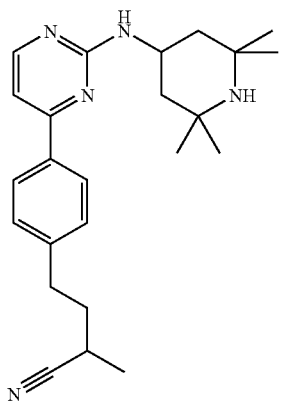

The title compound was prepared from toluene-4-sulfonic acid 1-methyl-3-{4-[2-(2,2,6,6-tetramethyl-piperidin-4-ylamino)-pyrimidin-4-yl]-phenyl}-propyl ester (Step A of Example 196) and NaCN in DMF. Yield 11 mg (72%).

MS (ESI): 392.0 [M+H]$^{+1}$H-NMR (DMSO-d$_6$): δ (ppm) 8.34 (m, 1H), 8.08 (m, 2H), 7.38 (d, 2H), 7.12 (br d, 1H), 7.03 (m, 1H), 4.33 (m, 1H), 2.70-2.87 (m, 3H), 1.76-1.95 (m, 4H), 1.30 (d, 3H), 1.04-1.28 (m, 15H).

Example 198

{4-[4-(2-Amino-propyl)-phenyl]-pyrimidin-2-yl}-(2,2,6,6-tetramethyl-piperidin-4-yl)-amine

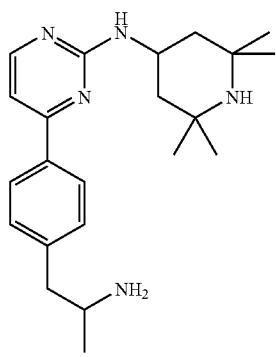

Step A: 1-[4-(4,4,5,5-Tetramethyl-[1,3,2]dioxaborolan-2-yl)-phenyl]-propan-2-one

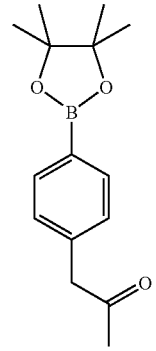

The boronic acid pinacol ester was prepared from 1-(4-bromo-phenyl)-propan-2-one and bis(pinacolato)diboron as shown in Step A of Example 182. The crude product was used without further purification.

Step B: -{4-[2-(2,2,6,6-Tetramethyl-piperidin-4-ylamino)-pyrimidin-4-yl]-phenyl}-propan-2-one

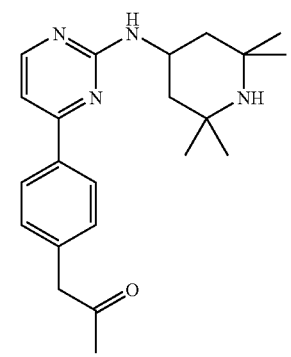

The title compound was prepared from (4-chloro-pyrimidin-2-yl)(2,2,6,6-tetramethyl-piperidin-4-yl)-amine and 1-[4-(4,4,5,5-tetramethyl-[1,3,2]dioxaborolan-2-yl)-phenyl]-propan-2-one according to Method C (Example 178). Yield: 160 mg (78%).

Step C: 1-{4-[2-(2,2,6,6-Tetramethyl-piperidin-4-ylamino)-pyrimidin-4-yl]-phenyl}-propan-2-ol

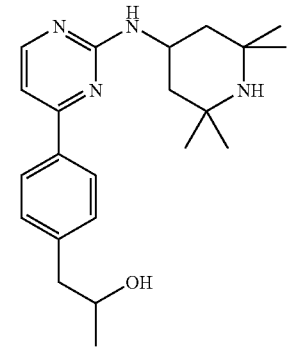

The title compound was prepared by reduction of {4-[2-(2,2,6,6-tetramethyl-piperidin-4-ylamino)-pyrimidin-4-yl]-phenyl}-propan-2-one with sodium borohydride in MeOH. Yield: 32 mg (100%).

Step D: Toluene-4-sulfonic acid 1-methyl-2-{4-[2-(2,2,6,6-tetramethyl-piperidin-4-ylamino)-pyrimidin-4-yl]-phenyl}-ethyl ester

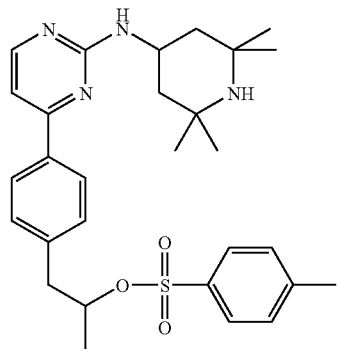

The title compound was prepared from 1-{4-[2-(2,2,6,6-tetramethyl-piperidin-4-ylamino)-pyrimidin-4-yl]-phenyl}-propan-2-ol and p-toluenesulfonyl chloride in pyridine. Yield: 177 mg (100%).

Step E: {4-[4-(2-Azido-propyl)-phenyl]-pyrimidin-2-yl}-(2,2,6,6-tetramethyl-piperidin-4-yl)-amine

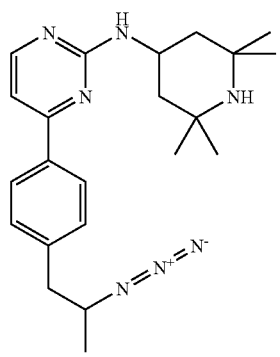

The title compound was prepared from toluene-4-sulfonic acid 1-methyl-2-{4-[2-(2,2,6,6-tetramethyl-piperidin-4-ylamino)-pyrimidin-4-yl]-phenyl}-ethyl ester and sodium azide in DMF.
Yield 84 mg (64%).

Step F: {4-[4-(2-Amino-propyl)-phenyl]-pyrimidin-2-yl}-(2,2,6,6-tetramethyl-piperidin-4-yl)-amine The title compound was prepared from {4-[4-(2-azido-propyl)-phenyl]-pyrimidin-2-yl}-(2,2,6,6-tetramethyl-piperidin-4-yl)-amine by hydrogenation using PtO$_2$ in MeOH. Yield: 38 mg (81%).

MS (ESI): 368.0 [M+H]$^{+1}$H-NMR (DMSO-d$_6$): δ (ppm) 8.33 (m, 1H), 8.06 (m, 2H), 7.32 (d, 2H), 7.11 (br d, 1H), 7.01 (m, 1H), 4.33 (m, 1H), 3.06 (m, 1H), 2.61 (br d, 2H), 1.83 (m, 2H), 1.02-1.30 (m, 17H), 0.99 (d, 3H).

Example 199

2-{4-[2-(2,2,6,6-Tetramethyl-piperidin-4-ylamino)-pyrimidin-4-yl]-phenoxymethyl}-benzonitrile

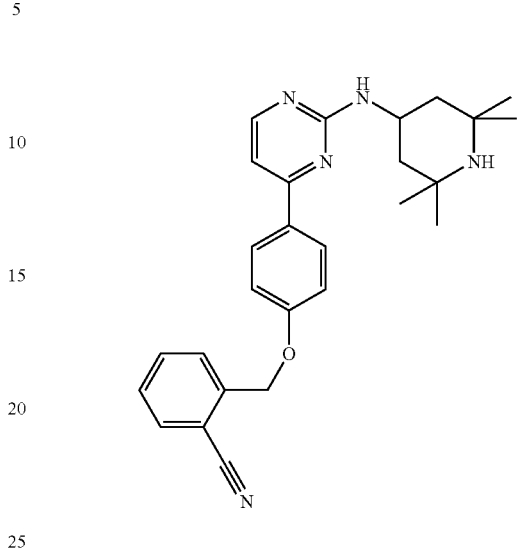

Step A: 4-[2-(2,2,6,6-Tetramethyl-piperidin-4-ylamino)-pyrimidin-4-yl]-phenol

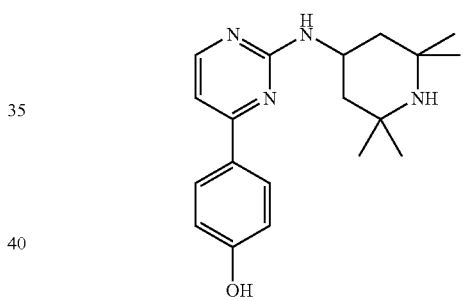

4-(tert-Butyl-dimethyl-silanyloxy)-phenylboronic ester (5.20 g, 20.6 mmol) and (4-chloro-pyrimidin-2-yl)(2,2,6,6-tetramethyl-piperidin-4-yl)-amine (5.54 g, 20.6 mmol) were reacted following the procedure given in Step C of Example 3 to give 6.48 g (19.9 mmol, 96%) of the title compound as a pale yellow solid.

MS (ESI): 327 [M+H]$^{+1}$H NMR (DMSO-d$_6$) δ (ppm): 10.0 (br s, 1H), 8.27 (d, 1H), 7.98 (d, 2H), 7.00 (d, 1H), 6.88 (br s, 1H), 6.86 (d, 2H), 4.33 (br s, 1H), 1.78-1.88 (m, 2H), 1.25 (s, 6H), 1.10-1.15 (m, 2H), 1.06 (s, 6H).

Step B: 2-{4-[2-(2,2,6,6-Tetramethyl-piperidin-4-ylamino)-pyrimidin-4-yl]-phenoxymethyl}-benzonitrile 4-[2-(2,2,6,6-Tetramethyl-piperidin-4-ylamino)-pyrimidin-4-yl]-phenol (200 mg, 0.61 mmol), potassium carbonate (102 mg, 0.74 mmol) and 2-bromomethyl benzonitrile (120 mg, 0.61 mmol) were stirred in dry DMF (5 ml) at 60° C. for 16 h. The Reaction was quenched by addition of water, The aqueous phase was extracted with ethylacetate, washed with water and brine and the crude product was purified by crystallisation from ethanol/ether. 182 mg (0.41 mmol, 68%) of yellow crystals were obtained.

MS (ESI): 442 [M+H]$^{+1}$ H NMR (DMSO-d$_6$) δ (ppm): 8.31 (d, 1H), 8.15 (d, 2H), 7.96 (d, 1H), 7.77-7.84 (m, 2H), 7.62 (ddd, 1H), 7.19 (d, 2H), 7.09 (d, 1H), 6.98 (br s, 1H), 5.36 (s, 2H), 4.34 (br s, 1H), 1.78-1.90 (m, 2H), 1.26 (s, 6H), 1.09-1.21 (m, 2H), 1.06 (s, 6H).

The following compounds (Example 200 to Example 203) were prepared analogous to Step B of Example 199, using 4-[2-(2,2,6,6-tetramethyl-piperidin-4-ylamino)-pyrimidin-4-yl]-phenol and the appropriate alkyl bromides.

Example 200

{4-[2-(2,2,6,6-Tetramethyl-piperidin-4-ylamino)-pyrimidin-4-yl]-phenoxy}-acetonitrile

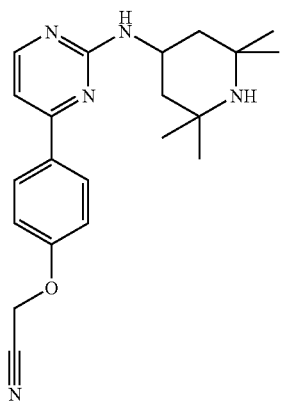

MS (ESI): 366 [M+H]$^{+1}$ H NMR (DMSO-d$_6$) δ (ppm): 8.33 (br s, 1H), 8.17 (d, 2H), 7.21 (d, 2H), 7.11 (d, 1H), 7.03 (br s, 1H), 5.29 (s, 2H), 4.34 (br s, 1H), 1.76-1.90 (m, 2H), 1.26 (s, 6H), 1.08-1.22 (m, 2H), 1.07 (s, 6H).

Example 201

{4-[4-(2-Imidazo-1-yl-ethoxy)-phenyl]-pyrimidin-2-yl}-(2,2,6,6-tetramethyl-piperidin-4-yl)-amine

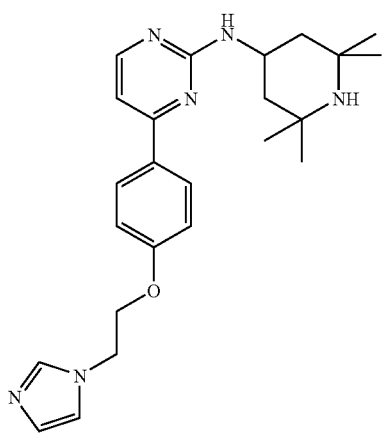

MS (ESI): 421 [M+H]$^{+1}$ H NMR (DMSO-d$_6$) δ (ppm): 9.28 (s, 1H), 8.38 (d, 1H), 8.17 (br s, 2H), 8.04-8.12 (m, 1H), 7.88 (s, 1H), 7.74 (s, 1H), 7.28 (br s, 1H), 7.12 (d, 2H), 4.69 (t, 2H), 4.50 (t, 2H), 4.43 (br s, 1H), 2.00-2.13 (m, 1H), 1.58-1.68 (m, 2H), 1.55 (s, 6H), 1.47 (s, 6H).

Example 202

4-{4-[2-(2,2,6,6-Tetramethyl-piperidin-4-ylamino)-pyrimidin-4-yl]-pheoxy}-butyronitrile

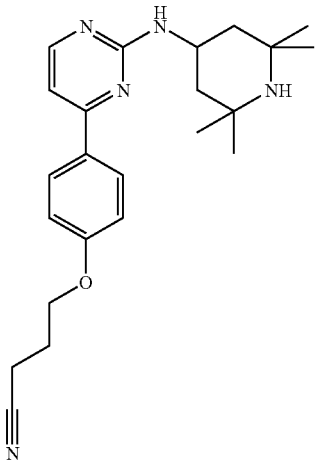

MS (ESI): 394 [M+H]$^{+1}$ H NMR (DMSO-d$_6$) δ (ppm): 8.30 (br s, 1H), 8.10 (br s, 2H), 7.07 (d, 3H), 6.96 br s, 1H), 4.32 (br s, 1H), 4.13 (t, 2H), 2.69 (t, 2H), 2.07 (quint, 2H), 1.74-1.90 (m, 2H), 1.24 (s, 6H), 1.09-1.20 (m, 2H), 1.05 (s, 6H).

Example 203

{4-[4-(Pyridin-4-ylmethoxy)-phenyl]-pyrimidin-2-yl}-(2,2,6,6-tetramethyl-piperidin-4-yl)-amine

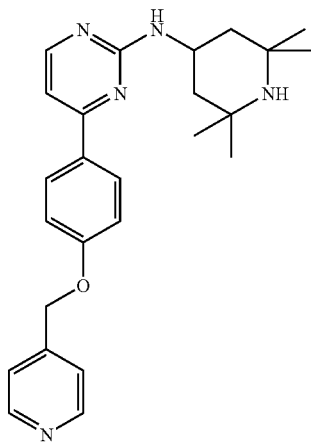

MS (ESI): 418 [M+H]$^{+1}$ H NMR (DMSO-d$_6$) δ (ppm): 8.63 (d, 2H), 8.30 (br s, 1H), 8.08-8.18 (m, 2H), 7.46 (d, 2H), 7.15

(d, 2H), 7.07 (d, 1H), 6.97 (br s, 1H), 5.30 (s, 2H), 4.33 (br s, 1H), 1.78-1.90 (m, 2H), 1.25 (s, 6H), 1.09-1.20 (m, 2H), 1.07 (s, 6H).

Indoles

Example 204

(4-Indol-1-yl-pyrimidin-2-yl)-(2,2,6,6-tetramethyl-piperidin-4-yl)-amine

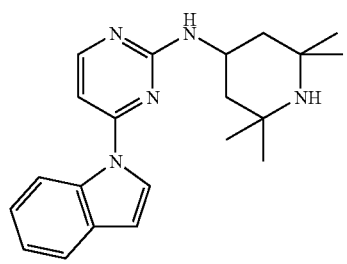

A mixture of (4-chloro-pyrimidin-2-yl)-(2,2,6,6-tetramethyl-piperidin-4-yl)-amine (200 mg, 0.74 mmol), indole (96 μl, 0.81 mmol), potassium hydroxide (63 mg, 1.10 mmol) and a few drops of Aliquat 336 were heated to 120° C. for 5 h. After cooling to room temperature the mixture was dissolved in ethylacetate, washed with water and brine and the crude product was purified by HPLC. Thus 71 mg (0.20 mmol, 27%) of the title compound were obtained.

MS (ESI): 350 [M+H]$^{+1}$H NMR (DMSO-d$_6$) δ (ppm): 8.76 (d, 1H), 8.30 (d, 1H), 8.07 (d, 1H), 7.65 (d, 1H), 7.26 (d, 1H), 7.15-7.24 (m, 2H), 6.93 (d, 2H), 6.79 (d, 1H), 4.30-4.45 (m, 1H), 1.83 (dd, 2H), 1.29 (s, 6H), 1.12-1.25 (m, 2H), 1.08 (s, 6H).

Following the procedure given in Example 204 the following compounds were prepared:

Example 205

[4-(4-Methoxy-indol-1-yl)-pyrimidin-2-yl]-(2,2,6,6-tetramethyl-piperidin-4-yl)-amine

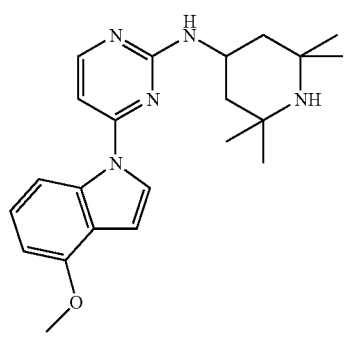

MS (ESI): 380 [M+H]$^{+1}$H NMR (DMSO-d$_6$) δ (ppm): 8.26-8.37 (m, 2H), 7.95 (d, 1H), 7.26 (d, 1H), 7.10 (t, 1H), 6.92 (d, 1H), 6.77 (s, 1H), 6.75 (d, 1H), 4.30-4.42 (m, 1H), 3.93 (s, 3H), 1.82 (dd, 2H), 1.28 (s, 6H), 1.12-1.24 (m, 2H), 1.06 (s, 6H).

Example 206

1-{1-[2-(2,2,6,6-Tetramethyl-piperidin-4-ylamino)-pyrimidin-4-yl]-1H-indol-3-yl}-ethanone

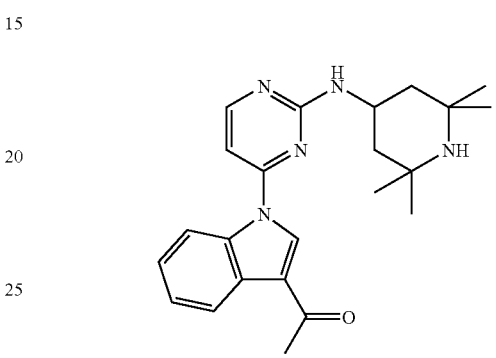

MS (EI): 391 [M]$^+$, 376 [M-CH$_3$]$^{+1}$H NMR (DMSO-d$_6$) δ (ppm): 8.97 (s, 1H), 8.70 (d, 1H), 8.42 (d, 1H), 8.29 (d, 1H), 7.46 (d, 1H), 7.34 (t, 1H), 7.28 (t, 1H), 7.17 (d, 1H), 4.30-4.41 (m, 1H), 2.59 (s, 3H), 1.85 (dd, 2H), 1.28 (s, 6H), 1.12-1.24 (m, 2H), 1.06 (s, 6H).

Example 207

[4-(5-Methoxy-indol-1-yl)-pyrimidin-2-yl]-(2,2,6,6-tetramethyl-piperidin-4-yl)-amine

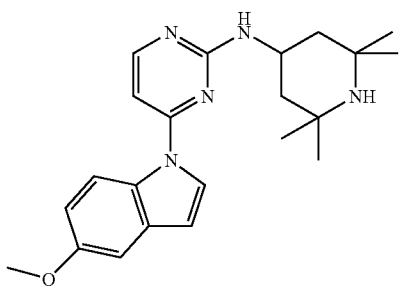

MS (ESI): 380 [M+H]$^+$, 191 [M+2H]$^{2+1}$H NMR (DMSO-d$_6$, 120° C.) δ (ppm): 8.54 (d, 1H), 8.28 (d, 1H), 7.93 (d, 1H), 7.16 (s, 1H), 6.86 (d, 1H), 6.82 (d, 1H), 6.69 (d, 1H), 6.46-6.54 (m, 1H), 4.34-4.45 (m, 1H), 3.84 (s, 3H), 1.92 (dd, 2H), 1.31 (s, 6H), 1.22 (t, 2H), 1.12 (s, 6H), 0.97 (s, 1H).

Example 208

1-[2-(2,2,6,6-Tetramethyl-piperidin-4-ylamino)-pyrimidin-4-yl]-1H-indole-3-carbonitrile

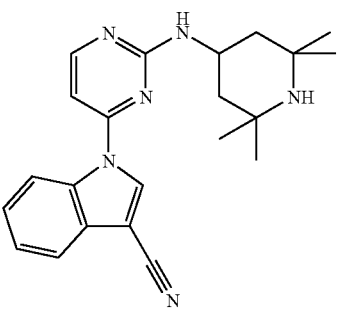

MS (EI): 375 [M+H]+, 359 [M-CH3]+ 1H NMR (DMSO-d6) δ (ppm): 9.05 (s, 1H), 8.77 (d, 1H), 8.42 (d, 1H), 7.75 (d, 1H), 7.53 (d, 1H), 7.44 (t, 1H), 7.37 (t, 1H), 7.02 (d, 1H), 4.28-4.40 (m, 1H), 1.83 (dd, 2H), 1.28 (s, 6H), 1.12-1.25 (m, 2H), 1.07 (s, 6H).

Example 209

1-[2-(2,2,6,6-Tetramethyl-piperidin-4-ylamino)-pyrimidin-4-yl]-1H-indole-3-carboxylic acid amide

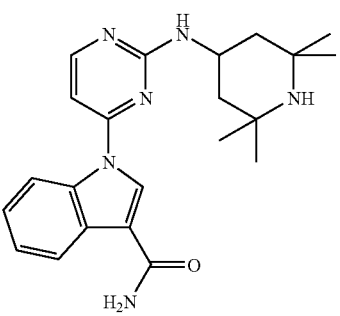

1-[2-(2,2,6,6-Tetramethyl-piperidin-4-ylamino)-pyrimidin-4-yl]-1H-indole-3-carbonitrile (Example 208, 100 mg, 0.27 mmol) was dissolved in EtOH (3 ml), treated with 10N-NaOH (1 ml) and hydrogenperoxide (30%, 1 ml) and the resulting mixture was stirred vigorously overnight. After addition of water (50 ml) the mixture was extracted with ethylacetate. Crystallisation with ether finally gave 60 mg (0.15 mmol, 57%) of the desired compound.

MS (ESI): 393 [M+H]+ 1H NMR (DMSO-d6) δ (ppm): 8.75 (s, 1H), 8.72 (d, 1H), 8.40 (d, 1H), 8.27 (d, 1H), 7.66 (br s, 1H), 7.45 (d, 1H), 7.30 (t, 1H), 7.10-7.27 (m, 2H), 6.84 (d, 1H), 1.86 (br d, 2H), 1.32 (s, 6H), 1.15-1.30 (m, 2H), 1.10 (s, 6H).

Example 210

1-[2-(2,2,6,6-Tetramethyl-piperidin-4-ylamino)-pyrimidin-4-yl]-1H-indole-4-carbonitrile

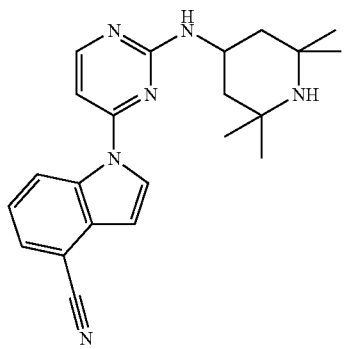

MS (EI): 374 [M]+, 359 [M-CH3]+ 1H NMR (DMSO-d6) δ (ppm): 9.05 (d, 1H), 8.34-8.40 (m, 2H), 7.75 (d, 1H), 7.43 (d, 1H), 7.34 (t, 1H), 7.02 (d, 1H), 6.95 (br s, 1H), 1.83 (dd, 2H), 1.27 (s, 6H), 1.10-1.25 (m, 2H), 1.08 (s, 6H).

Example 211

1-[2-(2,2,6,6-Tetramethyl-piperidin-4-ylamino)-pyrimidin-4-yl]-1H-indole-4-carboxylic acid amide

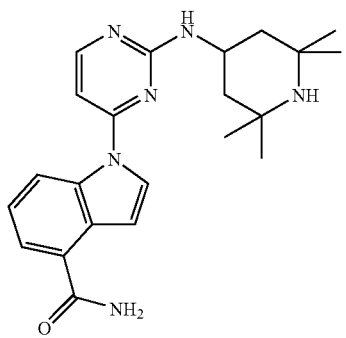

Compound was prepared from 1-[2-(2,2,6,6-Tetramethyl-piperidin-4-ylamino)-pyrimidin-4-yl]-1H-indole-4-carbonitrile as described for Example 209. Yield: 40 mg (38%).

MS (ESI): 393 [M+H]+ 1H NMR (DMSO-d6) δ (ppm): 8.90 (d, 1H), 8.33 (d, 1H), 8.18 (d, 1H), 7.92 (s, 1H), 7.64 (d, 1H), 7.38 (s, 1H), 7.33 (d, 1H), 7.25 (d, 1H), 7.21 (t, 1H), 6.97 (d, 1H), 4.30-4.43 (m, 1H), 1.85 (dd, 2H), 1.30 (s, 6H), 1.13-1.28 (m, 2H), 1.08 (s, 6H).

Example 212

[4-(1-Methyl-indol-2-yl)-pyrimidin-2-yl]-(2,2,6,6-tetramethyl-piperidin-4-yl)-amine

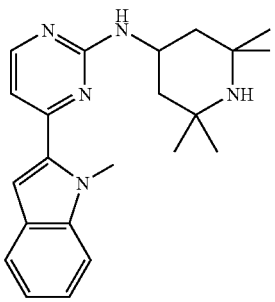

A solution of 1-methyl-indole (244 mg, 1.86 mmol) in 10 ml of THF was treated with n-butyllithium (0.74 ml of a 2.5M solution in hexanes, 1.86 mmol) at −78° C. and the mixture was stirred under argon for 2 hours. In the meantime, a solution of (4-chloro-pyrimidin-2-yl)-(2,2,6,6-tetramethyl-piperidin-4-yl)-amine (250 mg, 0.93 mmol) in 10 ml of THF was treated with n-butyllithium (0.74 ml of 2.5M solution in hexanes, 1.86 mmol) at −78° C. under argon for 15 minutes and the above solution containing the lithiated 1-methyl-indole was added with a syringe. The reaction mixture was stirred for 15 minutes at 0° C. and for 2 hours at room temperature. The reaction was quenched with saturated ammonium chloride solution (5 ml) and extracted with EtOAc. The organic layer was dried over sodium sulfate and evaporated. Purification by column chromatography on silicagel (EtOAc/MeOH/ammonia:2/1/0.02) gave the title compound. Yield: 92.5 mg (27%).

MS (ESI): 364 [M+H]$^{+1}$H-NMR (CDCl$_3$): δ (ppm) 8.28 (d, 1H), 7.62 (d, 1H), 7.55 (d, 1H), 7.25 (dd, 1H), 7.15 (s, 1H), 7.08 (dd, 1H), 7.00-7.10 (m, 2H), 4.22-4.34 (m, 1H), 4.18 (s, 3H), 1.79 (dd, 2H), 1.20 (s, 6H), 1.10 (dd, 2H), 1.02 (s, 7H).

Example 213

[4-(1H-Indol-2-yl)-pyrimidin-2-yl]-(2,2,6,6-tetramethyl-piperidin-4-yl)-amine

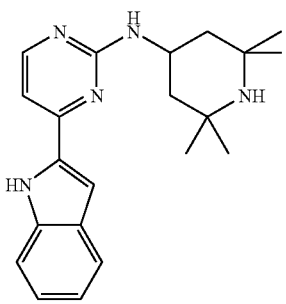

The title compound was prepared analogous to Step C of Method C starting from (4-chloro-pyrimidin-2-yl)-(2,2,6,6-tetramethyl-piperidin-4-yl)-amine and indole-2-borono-1-carboxylic acid-1-(1,1-dimethylethyl) ester, using bis(triphenylphosphine)palladium(II) dichloride as a catalyst, followed by BOC cleavage with sodium methylate in MeOH. Yield: 100 mg (85%).

MS (ESI): 350 [M+H]$^{+1}$H-NMR (CDCl$_3$): δ (ppm) 13.50 (s, 1H), 8.31 (d, 1H), 7.60 (d, 1H), 7.48 (d, 1H), 7.20 (s, 1H), 7.18 (dd, 1H), 7.08 (d, 1H), 7.02 (dd, 1H), 6.80 (s, br, 1H), 4.30-4.42 (m, 1H), 1.81 (dd, 2H), 1.40 (s, 6H), 1.04 (dd, 2H), 1.02 (s, 7H).

Example 214

[4-(1H-Indol-3-yl)-pyrimidin-2-yl]-(2,2,6,6-tetramethyl-piperidin-4-yl)-amine

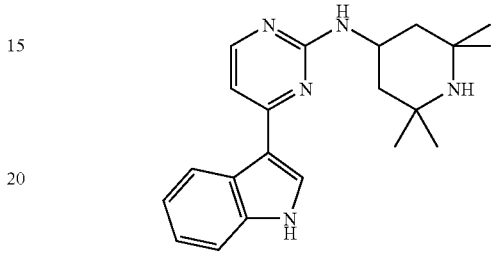

The title compound was prepared analogous to Step C of Method C, starting from (4-chloro-pyrimidin-2-yl)(2,2,6,6-tetramethyl-piperidin-4-yl)-amine and [1-(tert-butyl-dimethyl-silanyl)-1H-indol-3-yl]-boronic acid using bis(triphenylphosphine)palladium(II) dichloride as a catalyst. The TBDMS protecting group was cleaved in situ by addition of catalytic amounts of TBAF. Yield: 2.2 g (86%).

MS (ESI): 350 [M+H]$^{+1}$H-NMR (CDCl$_3$): δ (ppm) 11.69 (s, 1H), 8.72 (d, 1H), 8.20 (d, 1H), 8.10 (s, 1H), 7.42 (d, 1H), 7.15 (dd, 1H), 7.00-7.09 (m, 1H), 6.95 (d, 1H), 6.75 (d, 1H), 4.42-4.51 (m, 1H), 1.82 (dd, 2H), 1.30 (s, 6H), 1.15 (dd, 2H), 1.05 (s, 6H), 1.02 (s, 1H).

Example 215

[4-(1-Methyl-indol-3-yl)-pyrimidin-2-yl]-(2,2,6,6-tetramethyl-piperidin-4-yl)-amine

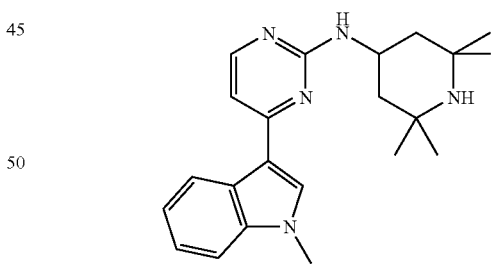

To a solution of 1-Methyl-indole (1.00 g, 3.81 mmol) in 30 ml of THF was added 1-bromo-pyrrolidine-2,5-dione (1.36 g, 3.81 mmol) and the mixture was stirred for 2 hours. The reaction mixture was poured into 200 ml of hexanes and purified by filtration over a short plug of silicagel (Ether/hexanes:1/1). The solution was concentrated close to dryness, redissolved in 25 ml of THF and cooled to −78° C. Tert.-butyllithium (5.08 ml of a 1.5M solution in pentane, 7.62 mmol) was added dropwise and stirred for 15 minutes. Then, triethylborate (0.65 ml, 3.81 mmol) was added in one portion and stirring was continued for 2 hours. The reaction was quenched with 3.5 ml of MeOH and 10 ml of water. The mixture was given into EtOAc and the aqueous layer was extracted with EtOAc. The combined organic phases were dried over sodium sulfate and evaporated to give a green suspension, which was used without further purification. The title compound was prepared analogous to Step C of Method C, starting from this crude boronic acid and (4-chloro-pyrimidin-2-yl)-(2,2,6,6-tetramethyl-piperidin-4-yl)-amine using bis(triphenylphosphine)palladium(II) dichloride as a catalyst. Yield: 327 mg (48%).

MS (ESI): 364 [M+H]$^{+1}$H-NMR (CDCl$_3$): δ (ppm) 8.62 (d, 1H), 8.20 (s, 1H), 8.10 (d, 1H), 7.50 (d, 1H), 7.21 (dd, 1H), 7.02-7.10 (m, 1H), 6.90 (d, 1H), 6.70 (d, 1H), 4.30-4.42 (m, 1H), 3.75 (s, 3H), 1.80-1.90 (m, 2H), 1.29 (s, 6H), 1.10 (dd, 2H), 1.02 (s, 6H), 1.02 (s, 1H).

Example 216

[2-(2,2,6,6-Tetramethyl-piperidin-4-ylamino)-pyrimidin-4-yl]-1H-indole-5-carbonitrile

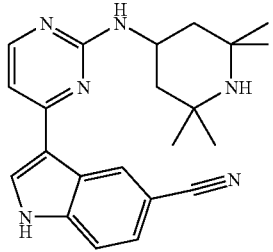

The title compound was prepared as described in Example 215, starting from 1-(tert-butyl-dimethyl-silanyl)-1H-indole-5-carbonitrile (prepared by TBDMS protection of 1H-indole-5-carbonitrile using standard procedures) and (4-chloro-pyrimidin-2-yl)-(2,2,6,6-tetramethyl-piperidin-4-yl)-amine, followed by in situ cleavage of the TBDMS protecting group with catalytic amounts of TBAF. Yield: 441 mg (26%)

MS (ESI): 375 [M+H]$^{+1}$H-NMR (CDCl$_3$): δ (ppm) 9.15 (s, 1H), 8.98 (s, 1H), 8.45 (s, 1H), 8.18 (d, 1H), 7.62 (d, 1H), 7.50 (d, 1H), 7.01 (d, 1H), 6.82 (s, 1H), 4.30-4.51 (m, 1H), 1.80 (dd, 2H), 1.20-1.35 (m, 7H), 1.15 (dd, 2H), 1.03 (s, 6H).

Example 217

3-[2-(2,2,6,6-Tetramethyl-piperidin-4-ylamino)-pyrimidin-4-yl]-1H-indole-6-carbonitrile

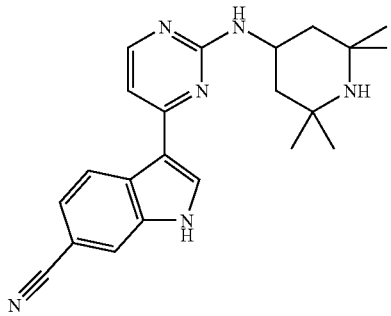

The title compound was prepared as described in Example 215, starting from 1-(tert-butyl-dimethyl-silanyl)-1H-indole-6-carbonitrile (prepared by TBDMS protection of 1H-indole-6-carbonitrile) and (4-chloro-pyrimidin-2-yl)-(2,2,6,6-tetramethyl-piperidin-4-yl)-amine, followed by in situ cleavage of the TBDMS protecting group with catalytic amounts of TBAF.

Yield: 1.04 g (59%)

MS (ESI): 375 [M+H]$^{+1}$H-NMR (CDCl$_3$): δ (ppm) 13.10 (s, 1H), 8.80-8.83 (m, 1H), 8.50 (s, 1H), 8.21 (d, 1H), 8.01 (s, 1H), 7.30-7.36 (m, 1H), 7.02 (d, 1H), 6.88 (s, 1H), 4.38-4.46 (m, 1H), 1.85 (dd, 2H), 1.30 (s, 6H), 1.25 (s, 1H), 1.13 (dd, 2H), 1.05 (s, 6H).

Example 218

[4-(5H-[1,3]Dioxolo[4,5-f]indol-7-yl)-pyrimidin-2-yl]-(2,2,6,6-tetramethyl-piperidin-4-yl)-amine

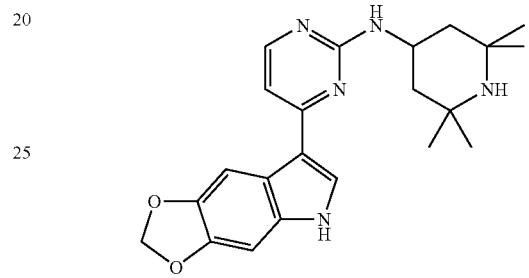

The title compound was prepared as described in Example 215, starting from 5-(tert-butyl-dimethyl-silanyl)-5H-[1,3]dioxolo[4,5-f]indole (prepared by TBDMS protection of 5H-[1,3]Dioxolo[4,5-f]indole) and (4-chloro-pyrimidin-2-yl)-(2,2,6,6-tetramethyl-piperidin-4-yl)-amine, followed by in situ cleavage of the TBDMS protecting group with catalytic amounts of TBAF. Yield: 555 mg (87%).

MS (ESI): 394 [M+H]$^{+1}$H-NMR (CDCl$_3$): δ (ppm) 11.50 (s, 1H), 8.10 (d, 1H), 8.00 (s, 1H), 7.90 (s, 1H), 6.95 (s, 1H), 6.89 (d, 1H), 6.00 (s, 1H), 5.95 (s, 2H), 4.38-4.49 (m, 1H), 1.92 (dd, 2H), 1.30 (s, 6H), 1.18 (dd, 2H), 1.10 (s, 6H), 0.95 (s, 1H).

Example 219

[4-(6-Methoxy-1H-indol-3-yl)-pyrimidin-2-yl]-(2,2,6,6-tetramethyl-piperidin-4-yl)-amine

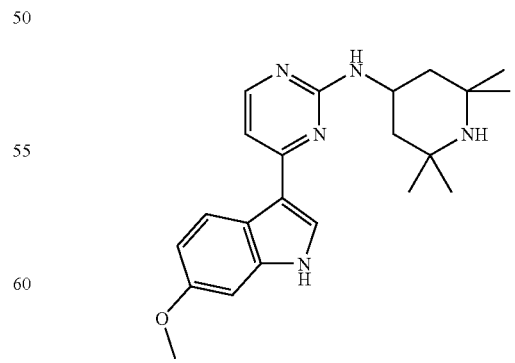

The title compound was prepared as described in Example 215, starting from 1-(tert-butyl-dimethyl-silanyl)-6-methoxy-1H-indole and (4-chloro-pyrimidin-2-yl)-(2,2,6,6-tetramethyl-piperidin-4-yl)-amine, followed by in situ cleavage of the TBDMS protecting group with catalytic amounts of TBAF. Yield: 535 mg (84%).

MS (ESI): 380 [M+H]$^{+1}$H-NMR (CDCl$_3$): δ (ppm) 11.49 (s, 1H), 8.40 (d, 1H), 8.13 (d, 1H), 7.92 (s, 1H), 7.02 (s, 1H), 6.91 (d, 1H), 6.75 (d, 1H), 5.98-6.01 (m, 1H), 4.40-4.50 (m, 1H), 3.82 (s, 3H), 1.92 (dd, 2H), 1.34 (s, 6H), 1.25 (dd, 2H), 1.12 (s, 6H), 1.12-1.25 (m, 1H).

Example 220

3-[2-(2,2,6,6-Tetramethyl-piperidin-4-ylamino)-pyrimidin-4-yl]-1H-indol-6-ol

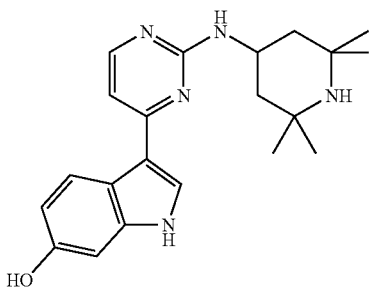

[4-(6-Methoxy-1H-indol-3-yl)-pyrimidin-2-yl]-(2,2,6,6-tetramethyl-piperidin-4-yl)-amine (150 mg, 0.4 mmol) was suspended in 6 ml of DCM under argon. After cooling to 0° C., boron tribromide (1.64 ml of a 1M solution in DCM, 1.64 mmol) was added slowly. The cooling bath was removed after 30 minutes and stirring was continued for 16 hours. The reaction was quenched by adding 8 ml of MeOH at 0° C. and the product crystallised from this solution in form of its hydrobromide salt. Yield: 155 mg (94%).

MS (ESI): 366 [M+H]$^{+1}$H-NMR (CDCl$_3$): δ (ppm) 11.30 (s, 1H), 9.50 (s, 1H), 8.60 (s, 1H), 8.20 (d, 1H), 8.12 (d, 1H), 8.09 (s, 1H), 7.70 (s, 1H), 7.11 (d, 1H), 6.89 (s, 1H), 6.70 (d, 1H), 4.50-4.61 (m, 1H), 2.17 (dd, 2H), 1.71 (dd, 2H), 1.59 (s, 6H), 1.58 (s, 1H), 1.50 (s, 6H).

Example 221

[4-(7-Methoxy-1H-indol-3-yl)-pyrimidin-2-yl]-(2,2,6,6-tetramethyl-piperidin-4-yl)-amine

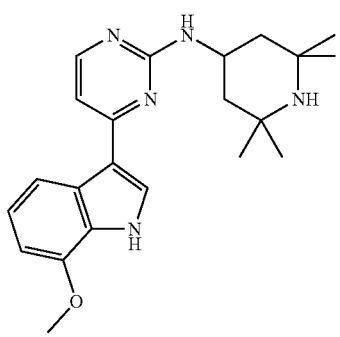

The title compound was prepared as described in Example 215, starting from 1-(tert-butyl-dimethyl-silanyl)-7-methoxy-1H-indole (prepared by TBDMS protection of 7-methoxy-1H-indole) and (4-chloro-pyrimidin-2-yl)-(2,2,6,6-tetramethyl-piperidin-4-yl)-amine, followed by in situ cleavage of the TBDMS protecting group with catalytic amounts of TBAF. Yield: 660 mg (93%).

MS (ESI): 380 [M+H]$^{+1}$H-NMR(CDCl$_3$): δ (ppm) 11.80 (s, 1H), 8.20 (d, 1H), 8.05-8.12 (m, 2H), 7.00 (d, 1H), 6.98 (s, 1H), 6.71 (d, 1H), 6.69 (d, 1H), 4.39-4.48 (m, 1H), 3.97 (s, 3H), 1.82 (dd, 2H), 1.33 (s,br, 7H), 1.13 (dd, 2H), 1.01 (s, 6H).

Example 222

3-[2-(2,2,6,6-Tetramethyl-piperidin-4-ylamino)-pyrimidin-4-yl]-1H-indol-7-ol

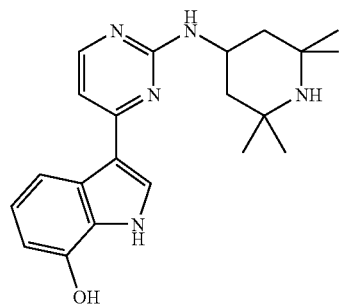

The title compound was prepared analogous to Example 220 starting from [4-(7-methoxy-1H-indol-3-yl)-pyrimidin-2-yl]-(2,2,6,6-tetramethyl-piperidin-4-yl)-amine. Yield: 129 mg (70%).

MS (ESI): 366 [M+H]$^{+1}$H-NMR (CDCl$_3$): δ (ppm) 11.40 (s, 1H), 8.53 (s, 1H), 8.10-8.18 (m, 2H), 7.92 (d, 1H), 7.70 (s, 1H), 7.12 (d, 1H), 6.98 (dd, 1H), 6.68 (d, 1H), 4.50-4.61 (m, 1H), 2.18 (dd, 2H), 1.71 (dd, 2H), 1.60 (s, 6H), 1.50 (s, 6H), 1.48 (s, 1H).

Example 223

{4-[6-(2-Amino-propyl)-1H-indol-3-yl]-pyrimidin-2-yl}-(2,2,6,6-tetramethyl-piperidin-4-yl)-amine

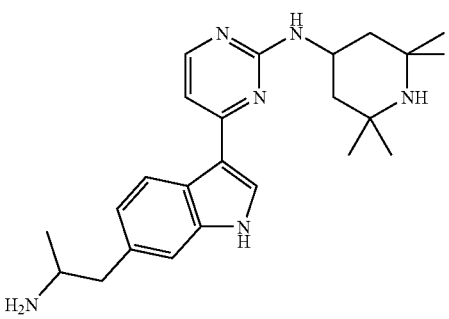

The title compound was prepared as described in Example 215, starting from {2-[1-(tert-butyl-dimethyl-silanyl)-1H-indol-6-yl]-1-methyl-ethyl}-trityl-amine (prepared by trityl and TBDMS protection of 2-(1H-Indol-6-yl)-1-methyl-ethylamine) and (4-chloro-pyrimidin-2-yl)-(2,2,6,6-tetramethyl-piperidin-4-yl)-amine, followed by in situ removal of the protecting groups with 2N-HCl. Yield: 406 mg (31%).

MS (ESI): 407 [M+H]$^{+1}$H-NMR (CDCl$_3$): δ (ppm) 9.50 (s, 1H), 8.41 (d, 1H), 8.30 (s, 1H), 8.20 (d, 1H), 7.90-8.20 (m, 3H), 7.41 (s, 1H), 7.19 (d, 1H), 7.03 (d, 1H), 4.53-4.61 (m, 1H), 3.40-3.53 (m, 1H), 3.05-3.12 (m, 1H), 2.90 (dd, 1H), 2.13 (dd, 2H), 1.80 (dd, 2H), 1.66 (s, 6H), 1.53 (s, 6H), 1.50 (s, 1H), 1.27 (d, 3H).

Example 224

{6-Methoxy-3-[2-(2,2,6,6-tetramethyl-piperidin-4-ylamino)-pyrimidin-4-yl]-indol-1-yl}-acetonitrile

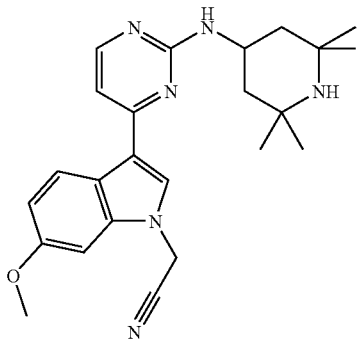

A solution of [4-(6-Methoxy-1H-indol-3-yl)-pyrimidin-2-yl]-(2,2,6,6-tetramethyl-piperidin-4-yl)-amine (150 mg, 0.40 mmol) in 2 ml of THF was added to a suspension of sodium hydride (55.3 mg, 1.38 mmol, 60% mineral dispersion) in 2 ml of THF. 0.1 ml of DMF was added and stirring was continued for 15 minutes. Bromoacetonitrile (51.9 mg, 0.43 mmol) was then added and the solution was stirred for 5 hours. The solvent was removed and the residue was purified by flash chromatography on silicagel (EtOAc/MeOH/ammonia:5/1/0.05) to give the title compound. Yield: 142 mg (88%).

MS (ESI): 419 [M+H]$^{+1}$H-NMR (CDCl$_3$): δ (ppm) 8.49 (d, 1H), 8.20 (d, 1H), 8.00 (s, 1H), 7.20 (s, 1H), 6.95 (d, 1H), 6.85 (d, 1H), 6.12 (s, 1H), 5.50 (s, 2H), 4.40-4.48 (m, 1H), 3.91 (s, 3H), 1.95 (dd, 2H), 1.32 (s,br, 7H), 1.22 (dd, 2H), 1.12 (s, 6H).

Example 225

[4-(7-Fluoro-1H-indol-3-yl)-pyrimidin-2-yl]-(2,2,6,6-tetramethyl-piperidin-4-yl)-amine

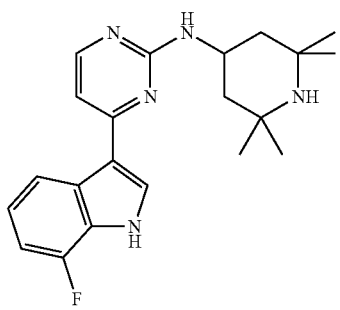

The title compound was prepared as described in Example 215, starting from 1-(tert-butyl-dimethyl-silanyl)-7-fluoro-1H-indole (prepared by TBDMS protection of 7-fluoro-1H-indole) and (4-chloro-pyrimidin-2-yl)-(2,2,6,6-tetramethyl-piperidin-4-yl)-amine, followed by in situ cleavage of the TBDMS protecting group with catalytic amounts of TBAF. Yield: 810 mg (81%).

MS (ESI): 368 [M+H]$^{+1}$H-NMR (CDCl$_3$): δ (ppm) 12.20 (s, 1H), 8.48 (d, 1H), 8.28 (s, 1H), 8.12 (d, 1H), 6.95-7.20 (m, 3H), 6.78 (d, 1H), 4.30-4.50 (m, 1H), 1.80-1.88 (m, 2H), 1.28 (s,br, 6H), 1.12 (dd, 2H), 1.10 (s, 1H), 1.05 (s, 6H).

Example 226

[4-(6-Fluoro-1H-indol-3-yl)-pyrimidin-2-yl]-(2,2,6,6-tetramethyl-piperidin-4-yl)-amine

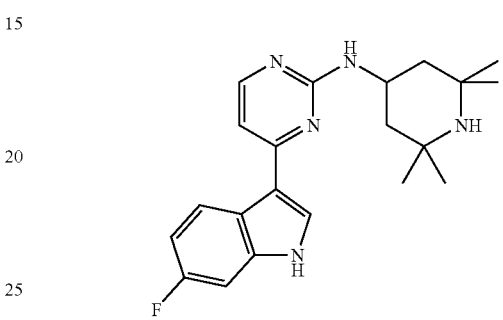

The title compound was prepared as described in Example 215, starting from 1-(tert-butyl-dimethyl-silanyl)-6-fluoro-1H-indole (prepared by TBDMS protection of 6-fluoro-1H-indole) and (4-chloro-pyrimidin-2-yl)-(2,2,6,6-tetramethyl-piperidin-4-yl)-amine, followed by in situ cleavage of the TBDMS protecting group with catalytic amounts of TBAF. Yield: 1.04 g (63%).

MS (ESI): 368 [M+H]$^{+1}$H-NMR (CDCl$_3$): δ (ppm) 11.80 (s, 1H), 8.61 (m, 1H), 8.20 (s, 1H), 8.10 (d, 1H), 7.22 (dd, 1H), 6.98 (d, 1H), 6.85 (s, 1H), 6.72 (d, 1H), 4.30-4.42 (m, 1H), 1.78-1.86 (m, 2H), 1.25 (s,br, 6H), 1.12 (dd, 2H), 1.10 (s, 1H), 1.05 (s, 6H).

Example 227

[4-(1H-Pyrrolo[2,3-b]pyridin-3-yl)-pyrimidin-2-yl]-(2,2,6,6-tetramethyl-piperidin-4-yl)-amine

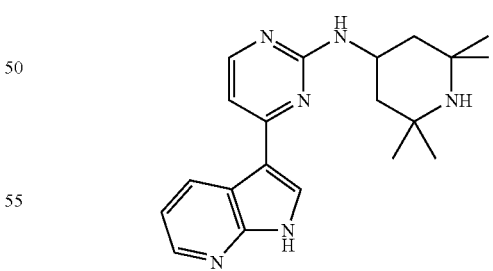

The title compound was prepared as described in Example 215, starting from 1-(tert-butyl-dimethyl-silanyl)-1H-pyrrolo[2,3-b]pyridine (prepared by TBDMS protection of 1H-pyrrolo[2,3-b]pyridine) and (4-chloro-pyrimidin-2-yl)-(2,2,6,6-tetramethyl-piperidin-4-yl)-amine, followed by in situ cleavage of the TBDMS protecting group with catalytic amounts of TBAF.

Yield: 1.60 g (63%).

MS (ESI): 351 [M+H]⁺ ¹H-NMR (DMSO): δ (ppm) 12.20 (s, 1H), 8.95 (s, broad, 1H), 8.39 (s, 1H), 8.30 (d, 1H), 8.19 (d, 1H), 7.11 (s, broad, 1H), 7.05 (d, 1H), 6.80 (d, 1H), 4.36-4.46 (m, 1H), 1.85 (dd, 2H), 1.28 (s, broad, 7H), 1.13 (dd, 2H), 1.08 (s, 6H).

Example 228

[4-(7-Chloro-1H-indol-3-yl)-pyrimidin-2-yl]-(2,2,6,6-tetramethyl-piperidin-4-yl)-amine

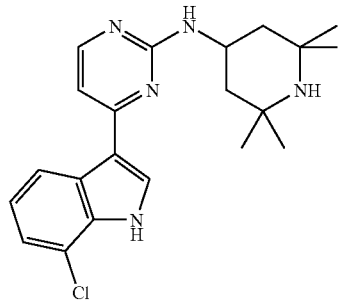

The title compound was prepared as described in Example 215, starting from 1-(tert-butyl-dimethyl-silanyl)-7-chloro-1H-indole (prepared by TBDMS protection of 7-chloro-1H-indole using standard procedures) and (4-chloro-pyrimidin-2-yl)-(2,2,6,6-tetramethyl-piperidin-4-yl)-amine, followed by in situ cleavage of the TBDMS protecting group with catalytic amounts of TBAF. Yield: 280 mg (34%).

MS (ESI): 384 [M+H]⁺ ¹H-NMR (DMSO): δ (ppm) 13.0 (s, 1H), 8.51 (d, 1H), 8.19 (d, 1H), 8.11 (s, 1H), 7.25 (d, 1H), 7.10 (t, 1H), 7.00 (d, 1H), 6.05 (d, broad, 1H), 4.41-4.49 (m, 1H), 1.95 (dd, 2H), 1.30 (s, broad, 7H), 1.20 (dd, 2H), 1.11 (s, 6H).

Example 229

[4-(6-Chloro-1H-indol-3-yl)-pyrimidin-2-yl]-(2,2,6,6-tetramethyl-piperidin-4-yl)-amine

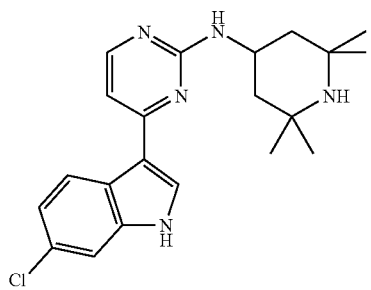

The title compound was prepared as described in Example 215, starting from 1-(tert-butyl-dimethyl-silanyl)-6-chloro-1H-indole (prepared by TBDMS protection of 6-chloro-1H-indole using standard procedures) and (4-chloro-pyrimidin-2-yl)-(2,2,6,6-tetramethyl-piperidin-4-yl)-amine, followed by in situ cleavage of the TBDMS protecting group with catalytic amounts of TBAF. Yield: 650 mg (77%).

MS (ESI): 384 [M+H]⁺ ¹H-NMR (DMSO): δ (ppm) 12.9 (s, 1H), 8.65 (d, 1H), 8.29 (s, 1H), 8.15 (d, 1H), 7.50 (s, 1H), 7.00 (d, 1H), 7.00 (m, 1H), 6.79 (d, broad, 1H), 4.41-4.49 (m, 1H), 1.85 (dd, 2H), 1.28 (s, broad, 7H), 1.12 (dd, 2H), 1.05 (s, 6H).

Example 230

(2,2,6,6-Tetramethyl-piperidin-4-yl)-[4-(6-trifluoromethyl-1H-indol-3-yl)-pyrimidin-2-yl]-amine

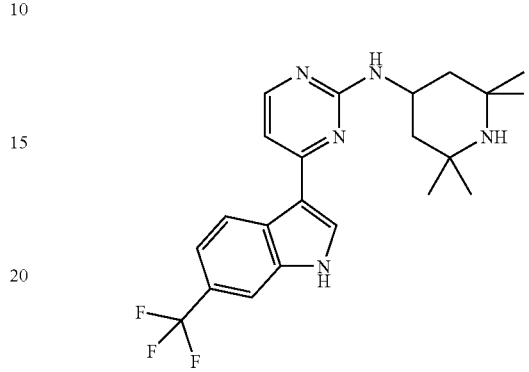

The title compound was prepared as described in Example 215, starting from 1-(tert-butyl-dimethyl-silanyl)-6-trifluoromethyl-1H-indole (prepared by TBDMS protection of 6-trifluoromethyl-1H-indole) and (4-chloro-pyrimidin-2-yl)-(2,2,6,6-tetramethyl-piperidin-4-yl)-amine, followed by in situ cleavage of the TBDMS protecting group with catalytic amounts of TBAF. Yield: 640 mg (77%).

MS (ESI): 418 [M+H]⁺ ¹H-NMR (DMSO): δ (ppm) 12.1 (s, 1H), 8.85 (m, 1H), 8.49 (s, 1H), 8.19 (d, 1H), 7.80 (s, 1H), 7.30 (m, 1H), 7.02 (d, 1H), 6.83 (d, broad, 1H), 4.40-4.50 (m, 1H), 1.85 (dd, 2H), 1.30 (s, broad, 7H), 1.14 (dd, 2H), 1.06 (s, 6H).

Example 231

[4-(7-Methyl-1H-indol-3-yl)-pyrimidin-2-yl]-(2,2,6,6-tetramethyl-piperidin-4-yl)-amine

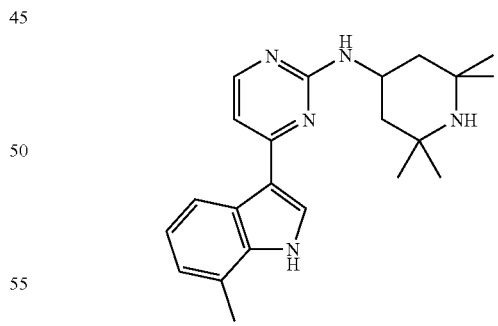

The title compound was prepared as described in Example 215, starting from 7-methyl-1-(2-trimethylsilanyl-ethoxymethyl)-1H-indole (prepared by SEM protection of 7-methyl-1H-indole using standard procedures) and (4-chloro-pyrimidin-2-yl)-(2,2,6,6-tetramethyl-piperidin-4-yl)-amine, followed by cleavage of the SEM protecting group with TBAF. Yield: 190 mg (51%).

MS (ESI): 364 [M+H]⁺ ¹H-NMR (DMSO): δ (ppm) 13.8 (s, 1H), 8.48 (m, 1H), 8.20 (d, 1H), 8.11 (d, 1H), 7.00 (d, 1H), 6.90 (m, 2H), 6.70 (d, broad, 1H), 4.40-4.50 (m, 1H), 2.50 (s, 3H), 1.87 (dd, 2H), 1.30 (s, broad, 7H), 1.15 (dd, 2H), 1.08 (s, 6H).

Example 232

2-Methyl-4-{3-[2-(2,2,6,6-tetramethyl-piperidin-4-ylamino)-pyrimidin-4-yl]-1H-indol-6-yl}-butan-2-ol

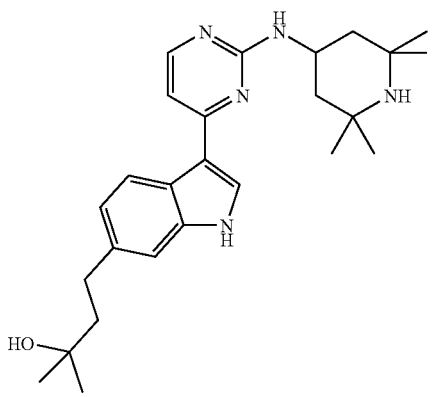

The title compound was prepared as described in Example 215, starting from 1-(tert-butyl-dimethyl-silanyl)-6-[3-(tert-butyl-dimethyl-silanyloxy)-3-methyl-butyl]-1H-indole (prepared by Raney-Nickel hydrogenation of (E)-3-(1H-Indol-6-yl)-acrylic acid methyl ester, followed by reaction with MeMgBr (Step A of Method A) and TBDMS protection according to standard procedures) and (4-chloro-pyrimidin-2-yl)-(2,2,6,6-tetramethyl-piperidin-4-yl)-amine, followed by cleavage of the TBDMS protecting groups with HF in pyridine. Yield: 57 mg (17%).

MS (ESI): 436 [M+H]$^{+1}$ H-NMR (DMSO): δ (ppm) 11.5 (s, 1H), 8.38 (d, 1H), 8.22 (d, 1H), 7.95 (d, 1H), 7.30 (s, 1H), 6.98 (d, 1H), 6.96 (d, 1H), 6.00 (s, 1H), 4.40-4.50 (m, 1H), 3.60 (s, 1H), 3.30 (dd, 2H), 1.95 (dd, 2H), 1.80 (dd, 2H), 1.36 (s, 6H), 1.20 (s, broad, 7H), 1.21 (dd, 2H), 1.18 (s, 6H).

Example 233

[4-(6,7-Difluoro-1H-indol-3-yl)-pyrimidin-2-yl]-(2,2,6,6-tetramethyl-piperidin-4-yl)-amine

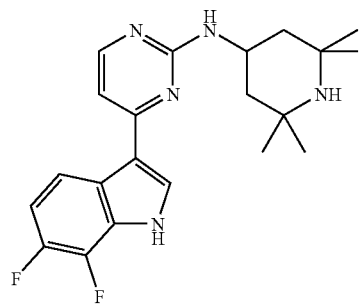

The title compound was prepared as described in Example 215, starting from SEM-protected 6,7-difluoro-1H-indole and (4-chloro-pyrimidin-2-yl)-(2,2,6,6-tetramethyl-piperidin-4-yl)-amine, followed by cleavage of the SEM-protecting group with TBAF. Yield: 100 mg (27%).

MS (ESI): 386 [M+H]$^{+1}$ H-NMR (DMSO): δ (ppm) 13.2 (s, 1H), 8.32 (dd, 1H), 8.20 (d, 1H), 8.10 (s, 1H), 7.05 (dd, 1H), 6.98 (d, 1H), 6.10 (s, 1H), 4.40-4.50 (m, 1H), 1.95 (dd, 2H), 1.32 (s, 7H), 1.22 (dd, 2H), 1.18 (s, 6H).

Example 234

2-Methyl-4-{3-[2-(2,2,6,6-tetramethyl-piperidin-4-ylamino)-pyrimidin-4-yl]-1H-indol-7-yl}-butan-2-ol

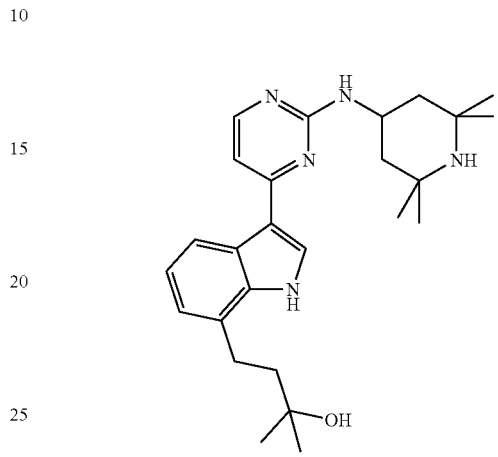

The title compound was prepared as described in Example 215, starting from 2-methyl-4-[1-(2-trimethylsilanyl-ethoxymethyl-1H-indol-7-yl]-butan-2-ol (prepared by Raney-Nickel hydrogenation of SEM-protected (E)-3-(1H-indol-7-yl)-acrylic acid methyl ester, followed by reaction with MeMgBr (Step A of Method A)) and (4-chloro-pyrimidin-2-yl)-(2,2,6,6-tetramethyl-piperidin-4-yl)-amine, followed by cleavage of the SEM-protecting group with TBAF. Yield: 220 mg (35%).

MS (ESI): 436 [M+H]$^{+1}$ H-NMR (DMSO): δ (ppm) 13.8 (s, 1H), 8.49 (d, 1H), 8.20 (d, 1H), 8.10 (d, 1H), 7.02 (d, 1H), 6.98 (m, 2H), 6.70 (d, 1H), 4.40-4.50 (m, 1H), 4.30 (s, 1H), 2.95 (dd, 2H), 1.86 (dd, 2H), 1.78 (dd, 2H), 1.40 (s, 6H), 1.31 (s, broad, 7H), 1.12 (dd, 2H), 1.05 (s, 6H).

Example 235

[4-(5,7-Difluoro-1H-indol-3-yl)-pyrimidin-2-yl]-(2,2,6,6-tetramethyl-piperidin-4-yl)-amine

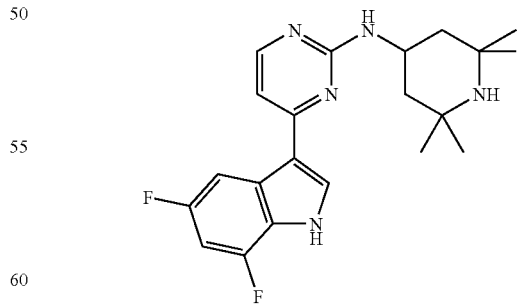

The title compound was prepared as described in Example 215, starting from SEM-protected 5,7-difluoro-1H-indole and (4-chloro-pyrimidin-2-yl)-(2,2,6,6-tetramethyl-piperidin-4-yl)-amine, followed by cleavage of the SEM-protecting group with TBAF. Yield: 260 mg (63%).

MS (ESI): 386 [M+H]$^{+1}$H-NMR (DMSO): δ (ppm) 13.2 (s, 1H), 8.19 (d, 1H), 8.19 (s, 1H), 8.12 (dd, 1H), 7.05 (d, 1H), 6.95 (dd, 1H), 6.20 (s, 1H), 4.40-4.50 (m, 1H), 1.95 (dd, 2H), 1.40 (s, 7H), 1.25 (dd, 2H), 1.18 (s, 6H).

Example 236

{4-[6-(Morpholine-4-sulfonyl)-1H-indol-3-yl]-pyrimidin-2-yl}-(2,2,6,6-tetramethylpiperidin-4-yl)-amine

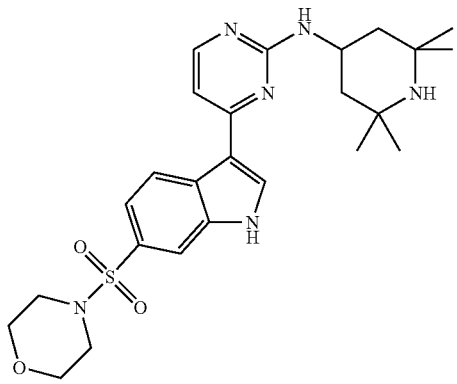

The title compound was prepared as described in Example 215, starting from TBDMS-protected 6-(morpholine-4-sulfonyl)-1H-indole (prepared by Batcho-Leimgruber synthesis starting from morpholine and 4-methyl-3-nitro-benzenesulfonyl chloride, J. Org. Chem. 1991, 56, 4576) and (4-chloro-pyrimidin-2-yl)-(2,2,6,6-tetramethyl-piperidin-4-yl)-amine, followed by cleavage of the TBDMS protecting group with TBAF. Yield: 220 mg (15%).

MS (ESI): 499 [M+H]$^{+1}$H-NMR (DMSO): δ (ppm) 13.0 (s, 1H), 8.90 (m, 1H), 8.51 (s, 1H), 8.20 (d, 1H), 7.88 (s, 1H), 7.42 (m, 1H), 7.02 (d, 1H), 6.82 (d, 1H), 4.40-4.50 (m, 1H), 3.62 (m, 4H), 2.88 (m, 4H), 1.86 (dd, 2H), 1.31 (s, broad, 7H), 1.12 (dd, 2H), 1.08 (s, 6H).

Example 237

[4-(5-Fluoro-7-methyl-1H-indol-3-yl)-pyrimidin-2-yl]-(2,2,6,6-tetramethyl-piperidin-4-yl)-amine

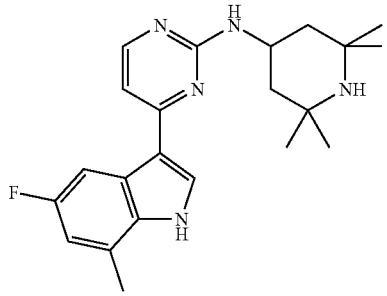

The title compound was prepared as described in Example 215, starting from SEM-protected 5-Fluoro-7-methyl-1H-indole (prepared by Sugasawa synthesis starting from 4-fluoro-2-methyl-phenylamine, J. Med. Chem. 1990, 33, 2777) and (4-chloro-pyrimidin-2-yl)-(2,2,6,6-tetramethyl-piperidin-4-yl)-amine, followed by cleavage of the SEM protecting group with TBAF. Yield: 2.00 g (69%).

MS (ESI): 382 [M+H]$^{+1}$H-NMR (DMSO): δ (ppm) 12.9 (s, 1H), 8.15 (d, 1H), 8.09 (s, 1H), 8.07 (s, 1H), 6.95 (d, 1H), 6.82 (d, 1H), 6.05 (s, 1H), 4.40-4.50 (m, 1H), 2.50 (s, 3H), 1.95 (dd, 2H), 1.32 (s, 7H), 1.22 (dd, 2H), 1.12 (s, 6H).

Example 238

3-[2-(2,2,6,6-Tetramethyl-piperidin-4-ylamino)-pyrimidin-4-yl]-1H-indole-6-sulfonic acid dimethylamide

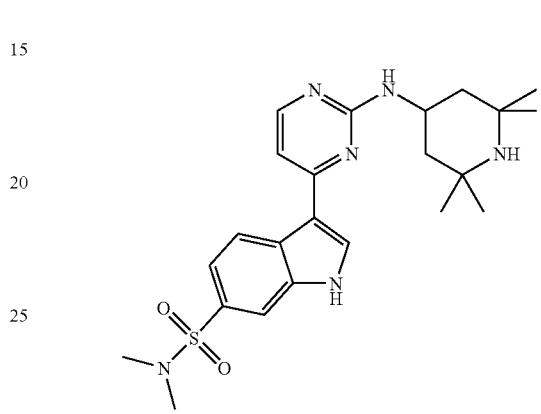

The title compound was prepared as described in Example 215, starting from TBDMS-protected 1H-indole-6-sulfonic acid dimethylamide and (4-chloro-pyrimidin-2-yl)-(2,2,6,6-tetramethyl-piperidin-4-yl)-amine, followed by cleavage of the TBDMS protecting group with TBAF. Yield: 150 mg (16%).

MS (ESI): 457 [M+H]$^{+1}$H-NMR (DMSO): δ (ppm) 13.1 (s, 1H), 8.75 (d, 1H), 8.32 (s, 1H), 8.21 (d, 1H), 7.92 (s, 1H), 7.45 (d, 1H), 7.10 (d, 1H), 6.15 (s, broad, 1H), 4.40-4.50 (m, 1H), 2.70 (s, 6H), 1.97 (dd, 2H), 1.35 (s, 7H), 1.22-1.88 (m, 2H), 1.12 (s, 6H).

Example 239

3-[2-(2,2,6,6-Tetramethyl-piperidin-4-ylamino)-pyrimidin-4-yl]-1H-indole-7-carbonitrile

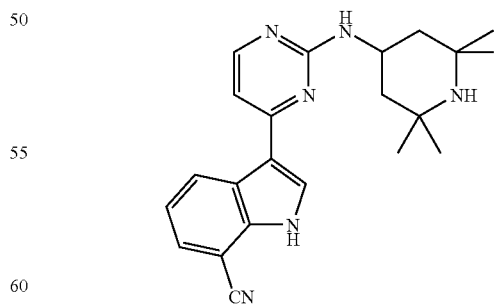

The title compound was prepared as described in Example 215, starting from SEM-protected 1H-indole-7-carbonitrile and (4-chloro-pyrimidin-2-yl)-(2,2,6,6-tetramethyl-piperidin-4-yl)-amine, followed by cleavage of the SEM-protecting group with TBAF. Yield: 10 mg (6%).

MS (ESI): 375 [M+H]+ 1H-NMR (DMSO): δ (ppm) 13.3 (s, 1H), 8.80 (d, 1H), 8.21 (d, 1H), 8.20 (s, 1H), 7.60 (d, 1H), 7.22 (t, 1H), 7.00 (d, 1H), 6.12 (s, broad, 1H), 4.40-4.50 (m, 1H), 1.92 (dd, 2H), 1.30 (s, broad, 6H), 1.21 (s, 1H), 1.15 (dd, 2H), 1.10 (s, 6H).

Example 240a

[4-(7-Nitro-1H-indol-3-yl)-pyrimidin-2-yl]-(2,2,6,6-tetramethyl-piperidin-4-yl)-amine

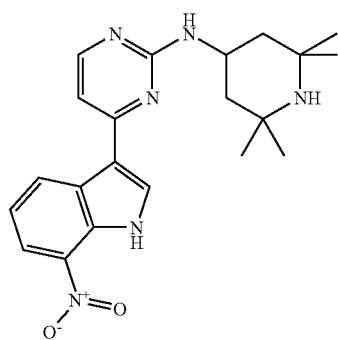

To a suspension of 1.60 g (40 mmol) sodium hydride in DMF (20 ml) was added 3-acetyl-7-nitroindol (*Org. Lett.* 2000, 2, 1485-1487). After stirring at room temperature for 60 minutes, 6.08 g (36.5 mmol) SEM-chloride was added. Stirring was continued for 16 hours. Then the reaction mixture was poured on icewater, the aqueous phase was extracted twice with ethylacete, the organic phase was dried (NaSO4) and evaporated. Crystallisation from ethanol gave 9.26 g (27.7 mmol, 83%) of the SEM protected indole.

1 g of the material described above was dissolved in dimethyformamide-dimethylacetal and heated under reflux for 24 hours. Evaporation of the excess DMF-dimethylacetal gave a crude enamino-ketone which was dissolved in 40 ml 1-butanol and treated with 2.27 g (7.7 mmol) of tetramethylpiperidyl-guanidine hemisulfate and 2.13 g (15.3 mmol) potassium carbonate. The reaction mixture was heated under reflux for 16 hours, then 200 ml water was added and the mixture was extracted into ethylacetate. Removal of the solvent yielded the crude product which was further purified by crystallisation from ether. Thus a total of 0.38 g (0.7 mmol, 28%) pyrimidine was obtained.

To 0.38 g of SEM protected indolyl-pyrimidine in 30 ml tetrahydrofuran 1.0 ml tetrabutylammonium fluoride (1.0 M in THF) was added. The mixture was stirred at 60° C. for 16 hours, poured onto water and extracted with ethylacetate. Removal of the solvent and crystallisation from ether yielded 0.15 g (3.9 mmol, 54%) of the title compound.

MS (ESI+): 395 [M+H]+ 1H NMR (DMSO-d6): δ (ppm) 9.08 (d, 1H), 8.25 (d, 1H), 8.23 (s, 1H), 8.18 (d, 1H), 7.33 (t, 1H), 7.06 (d, 1H), 6.18 (d, 1H), 4.50-4.37 (m, 1H), 1.95 (dd, 2H), 1.32 (s, 6H), 1.22 (t, 2H), 1.12 (s, 6H).

Example 240b

3-[2-(2,2,6,6-Tetramethyl-piperidin-4-ylamino)-pyrimidin-4-yl]-1H-indol-7-ylamine

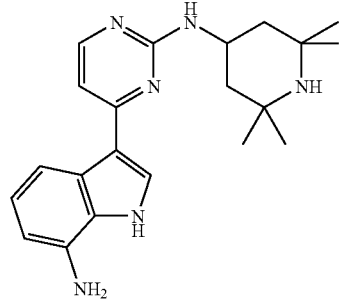

0.14 g (0.36 mmol) of Example 240a was hydrogenated over Pd/C in 20 ml of methanol. The residue obtained after removal of catalyst and solvent was further purified by RP-HPLC.

Yield: 0.08 mg (0.22 mmol, 61%).

MS (ESI+): 365 [M+H]+

Example 240c

N-{3-[2-(2,2,6,6-Tetramethyl-piperidin-4-ylamino)-pyrimidin-4-yl]-1H-indol-7-yl}-acetamide

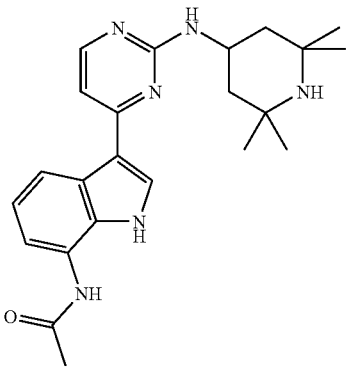

60 mg (0.167 mmol) of compound 240b was dissolved in 5 ml pyridine and 18 mg acetanhydride was added. Stirring at room temperature was continued for 18 hours. The reaction mixture was poured onto water and extracted with ethylacetate. Purification by RP-HPLC gave 0.033 mg (0.081 mmol, 49%) of the title compound.

MS (ESI+): 407 [M+H]+ 1H NMR (DMSO-d6): δ (ppm) 9.94 (s, 1H), 8.44 (d, 1H), 8.22 (s, 1H), 8.14 (d, 1H), 7.40 (d, 1H), 7.05-6.97 (m, 2H), 6.75 (d, 1H), 4.50-440 (m, 1H), 2.16 (s, 3H), 1.90-1.81 (m, 2H), 1.40-1.10 (m, 8H), 1.08 (s, 6H).

Example 240d

[4-(7-Bromo-1H-indol-3-yl)-pyrimidin-2-yl]-(2,2,6,6-tetramethyl-piperidin-4-yl)-amine

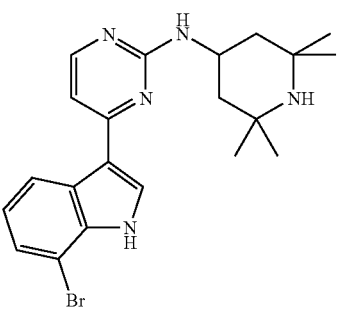

The title compound was prepared as described in Example 240a, starting from 7-Bromo-1H-indole. Yield: 15 mg (40%).

MS (ESI$^+$): 426 [M+H]$^{+1}$H NMR (DMSO-d$_6$): δ (ppm) 12.95 (s, 1H), 8.70 (d, 1H), 8.29 (s, 1H), 8.17 (d, 1H), 7.42 (d, 1H), 7.07 (d, 1H), 7.06-6.94 (m, 1H), 6.80 (d, 1H), 4.53-4.32 (m, 1H), 1.85 (d, 2H), 1.30 (s, 6H), 1.16 (t, 2H), 1.08 (s, 6H).

Example 240e

[4-(1H-Pyrrolo[3,2-h]quinolin-3-yl)-pyrimidin-2-yl]-(2,2,6,6-tetramethyl-piperidin-4-yl)-amine

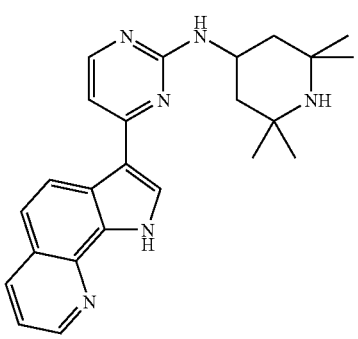

The title compound was prepared as described in Example 240a, starting from 1H-pyrrolo[3,2-h]quinoline. Yield: 15 mg (4%).

MS (ESI): 401 [M+H]$^{+1}$H-NMR (DMSO): δ (ppm) 13.4 (s, 1H), 8.89-8.91 (m, 2H), 8.49 (d, 1H), 8.31 (s, 1H), 8.20 (d, 1H), 7.52 (dd, 1H), 7.51-7.60 (m, 1H), 7.11 (d, 1H), 6.82 (s, broad, 1H), 4.48-4.52 (m, 1H), 1.90 (dd, 2H), 1.40 (s, broad, 7H), 1.15 (dd, 2H), 1.09 (s, 6H).

Example 241

Morpholin-4-yl-{3-[2-(2,2,6,6-tetramethyl-piperidin-4-ylamino)-pyrimidin-4-yl]-1H-indol-6-yl}-methanone

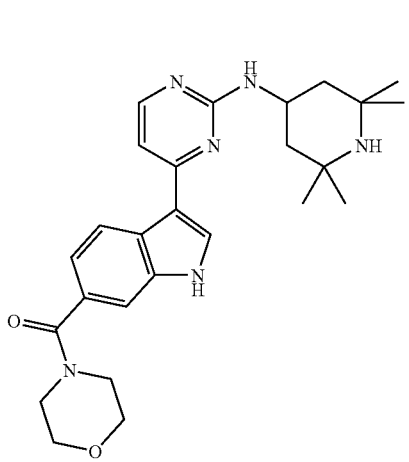

Step A: [3-[2-(2,2,6,6-Tetramethyl-piperidin-4-ylamino)-pyrimidin-4-yl]-1-(2-trimethylsilanyl-ethoxymethyl)-1H-indol-6-yl]-methanol

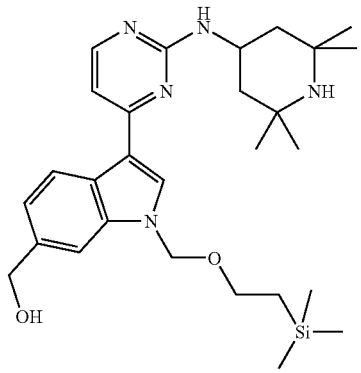

[3-[2-(2,2,6,6-Tetramethyl-piperidin-4-ylamino)-pyrimidin-4-yl]-1-(2-trimethylsilanyl-ethoxymethyl)-1H-indol-6-yl]-methanol was prepared as described in Example 215, starting from 6-(tert-butyl-dimethyl-silanyloxymethyl)-1-(2-trimethylsilanyl-ethoxymethyl)-1H-indole and (4-chloro-pyrimidin-2-yl)-(2,2,6,6-tetramethyl-piperidin-4-yl)-amine, followed by selective cleavage of the TBDMS-protecting group with TBAF. Yield: 7.1 g (93%).

Step B: 3-[2-(2,2,6,6-Tetramethyl-piperidin-4-ylamino)-pyrimidin-4-yl]-1-(2-trimethylsilanyl-ethoxymethyl)-1H-indole-6-carboxylic acid

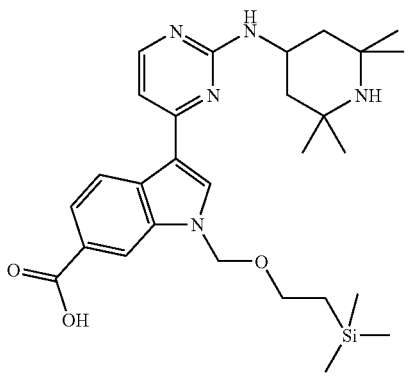

To a solution of [3-[2-(2,2,6,6-Tetramethyl-piperidin-4-ylamino)-pyrimidin-4-yl]1-(2-trimethylsilanyl-ethoxymethyl)-1H-indol-6-yl]-methanol (7.20 g, 14.1 mmol) in DMSO (35 ml) and Et₃N (31.4 ml, 226 mmol) was added a solution of sulfur trioxide pyridine complex (6.73 g, 42.3 mmol) in DMSO (35 ml). After stirring for 2 h at room temperature, the reaction mixture was poured into EtOAc and the organic phase was washed with water. The organic layer was dried and concentrated. The crude product was dissolved in tert-butanol (645 ml) and 2-methyl-2-butene (100 ml). Then sodium dihydrogenphosphate (4.19 g, 35.0 mmol) dissolved in water (50 ml) was added followed by sodium chlorite (7.91 g, 70.0 mmol) dissolved in water (75 ml) The reaction mixture was stirred overnight and concentrated and diluted with EtOAc upon which a yellow solid was obtained which was used without further purification. Yield: 5.00 g (69%).

Step C: Morpholin-4-yl-{3-[2-(2,2,6,6-tetramethyl-piperidin-4-ylamino)-pyrimidin-4-yl]-1H-indol-6-yl}-methanone A suspension of 3-[2-(2,2,6,6-Tetramethyl-piperidin-4-ylamino)-pyrimidin-4-yl]-1-(2-trimethylsilanyl-ethoxymethyl)-1H-indole-6-carboxylic acid (542 mg, 1.0 mmol) in dichloroethane was treated with 3 equivalents of thionyl chloride. A drop of DMF was added and the clear solution was stirred at room temperature for 10 min. This solution was added to a solution of morpholine (1.30 g, 14.9 mmol) in dichloroethane containing DMAP (5.00 mg). After 2 h the reaction mixture was given into a saturated bicarbonate solution, extracted with DCM and dried over sodium sulfate. After removal of the solvent the yellow residue was dissolved in THF and treated with 10 equivalents of TBAF under reflux for 8 h. The reaction mixture was given into EtOAc, washed with 2.5M NaOH, dried over sodium sulfate and concentrated. Purification via chromatography on silicagel (EtOAc/MeOH/ammonia:95/4/1 to 80/19/1) gave the title compound as a white solid. Yield: 250 mg (54%).

MS (ESI): 463 [M+H]$^{+1}$H-NMR (DMSO): δ (ppm) 13.0 (s, 1H), 8.70 (d, 1H), 8.32 (s, 1H), 8.15 (d, 1H), 7.50 (s, 1H), 7.10 (m, 1H), 7.01 (d, 1H), 6.78 (d, 1H), 4.40-4.50 (m, 1H), 3.65 (m, 4H), 3.52 (m, 4H), 1.85 (dd, 2H), 1.31 (s, broad, 7H), 1.12 (dd, 2H), 1.07 (s, 6H).

Example 242

3-[2-(2,2,6,6-Tetramethyl-piperidin-4-ylamino)-pyrimidin-4-yl]-1H-indole-7-sulfonic acid methylamide

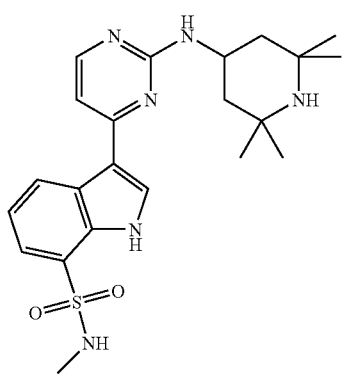

The title compound was prepared as described in Example 215, starting from SEM-protected 1H-indole-7-sulfonic acid methylamide and (4-chloro-pyrimidin-2-yl)(2,2,6,6-tetramethyl-piperidin-4-yl)-amine, followed by cleavage of the SEM-protecting groups with TBAF. Yield: 70 mg (5%).

MS (ESI): 443 [M+H]$^{+1}$H-NMR (DMSO): δ (ppm) 12.8 (s, 1H), 8.87 (d, 1H), 8.21 (d, 1H), 8.19 (s, 1H), 7.62 (d, 1H), 7.51 (s, 1H), 7.29 (dd, 1H), 7.00 (s, 1H), 6.12 (s, 1H), 4.40-4.50 (m, 1H), 2.52 (s, 3H), 1.95 (dd, 2H), 1.32 (s, 7H), 1.21 (dd, 2H), 1.12 (s, 6H).

Example 243

(5-Aza-spiro[3.5]non-yl)-[4-(chloro-1H-indol-3-yl)-pyrimidin-2-yl]-amine

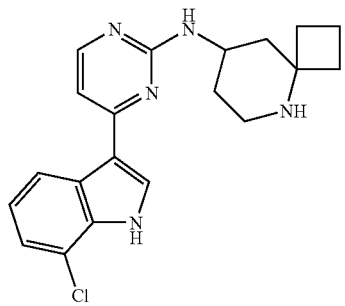

Step A: 7-Chloro-3-(2-chloro-pyrimidin-4-yl)-1H-indole

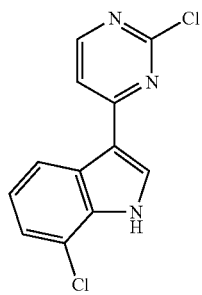

The title compound was prepared analogous to Step B of Method A, starting from 2,4-dichloropyrimidine, [1-(tert-Butyl-dimethyl-silanyl)-7-chloro-1H-indole-3-yl]-boronic acid (prepared analogous as described in Example 215).

Step B: (5-Aza-spiro[3.5]non-yl)-[4-(chloro-1H-indol-3-yl)-pyrimidin-2-yl]-amine The title compound of Step A (56 mg, 0.2 mmol) and 8-Amino-5-aza-spiro[3.5]nonane-5-carboxylic acid tert-butylester (76 mg, 0.3 mmol) (prepared as described in Example 161b) were dissolved in 5 ml dioxane and 0.5 ml DIEA. This mixture was refluxed for 48 hours. The solvent was removed and the residue was BOC-deprotected with 4N-HCl in dioxane. Again the solvent was removed and the residue was purified by flash chromatography on silicagel (DCM/methanol/ammonia:9/1/0.1) to give the racemic title compound. Yield: 10 mg (36%).

MS (ESI): 368 [M+H]$^{+1}$H-NMR (DMSO-d$_6$, 120° C.): δ (ppm) 8.45 (d, 1H), 8.25 (m, 2H), 7.30 (d, 1H), 7.15-7.10 (m, 2H), 4.25-4.15 (m, 1H), 3.35-3.30 (m,1H), 3.05-2.95 (m, 1H), 2.50-2.30 (m, 4H), 2.20-2.15 (m, 1H), 2.10-1.80 (m, 5H).

Example 244

[4-(7-Chloro-1H-indol-3-yl)-pyrimidin-2-yl](2,2-dimethyl-piperidin-4-yl)-amine

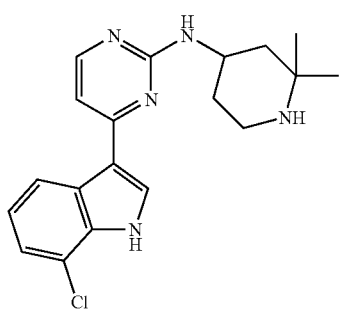

Step A: 4-Amino-2,2-dimethyl-piperidine-1-carboxylic acid tert-butyl ester

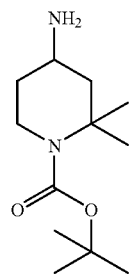

The title compound was prepared analogous to Step A of Example 161b, starting from 2,2-dimethyl-4-oxo-piperidine-1-carboxylic acid tert-butyl ester (EP 685468)

Step B: [4-(7-Chloro-1H-indol-3-yl)-pyrimidin-2-yl]-(2,2-dimethyl-piperidin-4-yl)-amine The racemic title compound was prepared as described in Step B of Example 243.

MS (ESI): 356[m+H]$^{+1}$H-NMR (DMSO-d$_6$, 120° C.): δ (ppm) 8.45 (d, 1H), 8.30 (d, 1H), 8.15 (s, 1H), 7.30 (d, 1H), 7.15 (t, 1H), 7.10 (d, 1H), 6.55-6.50 (m, 1NH), 4.40-4.30 (m, 1H), 3.30-3.20 (m, 2H), 2.25-2.10 (m, 2H), 1.75-1.60 (m, 2H), 1.45 (s, 3H), 1.40 (s, 3H).

Example 245

[4-(7-Fluoro-1H-indol-3-yl)-pyrimidin-2-yl]-(2,2-dimethyl-piperidin-4-yl)-amine

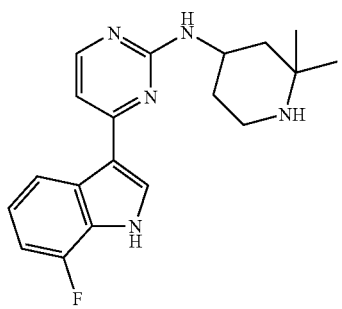

The racemic title compound was prepared as described in Example 244, starting from 7-Fluoro-3-(2-chloro-pyrimidin-4-yl)-1H-indole.

MS (ESI): 340 [M+H]$^{+1}$H-NMR (DMSO-d$_6$, 120° C.): δ (ppm) 8.30 (d, 1H), 8.20 (d, 1H), 8.10 (m, 1H), 7.15-7.05 (m, 1H), 7.05 (d, 1H), 7.00 (dxd, 1H), 6.55-6.50 (m, 1NH), 4.40-4.30 (m, 1H), 3.35-3.25 (m, 2H), 2.25-2.10 (m, 2H), 1.75-1.60 (m, 2H), 1.50 (s, 3H), 1.45 (s, 3H).

Example 246

(1-Aza-spiro[5.5]undec-4-yl)-[4-(7-fluoro-1H-indol-3-yl)-pyrimidin-2-yl]-amine

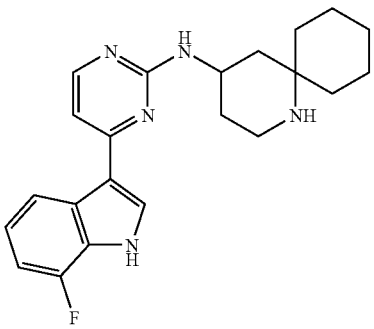

Step A:
4-Amino-1-aza-spiro[5.5]undecane-1-carboxylic acid tert-butyl ester

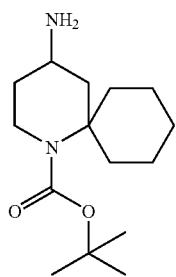

The title compound was prepared analogous to Step A of Example 161b, starting from 4-Oxo-1-aza-spiro[5.5]undecane-1-carboxylic acid tert-butyl ester (*Tetrahedron Letters* 42, 4815 (2001)).

Step B: (1-Aza-spiro[5.5]undec-4-yl)[4-(7-fluoro-1H-indol-3-yl)-pyrimidin-2-yl]-amine The racemic title compound was prepared as described in Example 244, starting from 7-Fluoro-3-(2-chloro-pyrimidin-4-yl)-1H-indole and 4-amino-1-aza-spiro[5.5]undecane-1-carboxylic acid tert-butyl ester from step A.

MS (ESI): [M+H]$^{+1}$ H-NMR (DMSO-d$_6$, 120° C.): δ (ppm) 8.30 (d, 1H), 8.20 (d, 1H), 8.15 (s, 1H), 4.40-4.30 (m, 1H), 3.30-3.20 (m, 2H), 2.45-2.40 (m, 1H), 2.25-2.20 (m, 1H), 2.15-2.05 (m, 1H), 1.95-1.80 (m, 4H), 1.80-1.70 (m, 2H), 1.65-1.45 (m, 4H), 1.45-1.40 (m, 1H).

Example 247 trans-(2,6-Dimethyl-piperidin-4-yl)-[4-(1H-indol-3-yl)-pyrimidin-2-yl]-amine

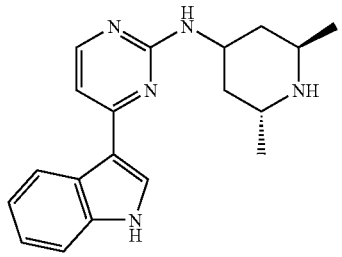

The racemic title compound was prepared analogous to Method A, starting from 2,4-dichloropyrimidine, [1-(tert-butyl-dimethyl-silanyl)-1H-indole-3-yl]boronic acid (prepared by the procedure described in Example 215) and trans-2,6-dimethyl-piperidin-4-yl amine (see step A of Example 161c and WO-97/36871).

MS (ESI): 322.3 [M+H]$^{+1}$ H-NMR (DMSO-d$_6$): δ (ppm) 8.62 (br d, 1H), 8.21 (s, 1H), 8.12 (br d, 1H), 7.45 (br d, 1H), 7.03-7.22 (m, 2H), 6.98 (d, 1H), 6.72 (br d, 1H), 4.25 (br m, 1H), 3.33 (br m, 1H), 3.05 (br m, 1H), 1.9-2.0 (m, 2H), 0.9-1.9 (m, 8H).

Example 248

[4-(7-Chloro-1H-indol-3-yl)-pyrimidin-2-yl]-trans-(2,6-dimethyl-piperidin-4-yl)-amine

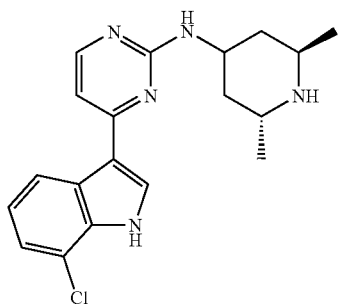

The racemic title compound was prepared analogous to Method A, starting from 2,4-dichloropyrimidine, [1-(tert-butyl-dimethyl-silanyl)-7-chloro-1H-indole-3-yl]boronic acid (prepared by the procedure described in Example 215) and trans-2,6-dimethyl-piperidin-4-yl amine (see step A of Example 161c and WO-97/36871).

MS (ESI): 356.2 [M+H]$^{+1}$ H-NMR (DMSO-d$_6$): δ (ppm) 8.62 (br m, 1H), 8.32 (s, 1H), 8.17 (br d, 1H), 7.28 (d, 1H), 7.1 (br m, 1H), 7.07 (d, 1H), 6.83 (br d, 1H), 4.28 (br m, 1H), 3.35 (br m, 1H), 3.05 (br m, 1H), 1.9-2.0 (m, 2H), 0.9-1.9 (br m, 8H).

Example 249 trans-(2,6-Dimethyl-piperidin-4-yl)-[4-(7-fluoro-1H-indol-3-yl)-pyrimidin-2-yl]-amine

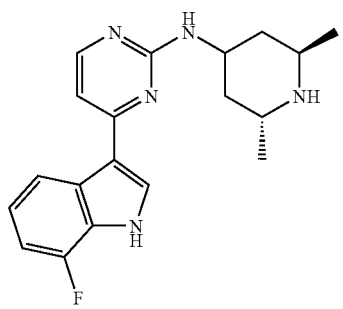

The racemic title compound was prepared analogous to Method A, starting from 2,4-dichloropyrimidine, [1-(tert-butyl-dimethyl-silanyl)-7-fluoro-1H-indole-3-yl]boronic acid (prepared by the procedure described in Example 215) and trans-2,6-dimethyl-piperidin-4-yl amine (see step A of Example 161c and WO-97/36871).

MS (ESI): 340.3 [M+H]$^{+1}$H-NMR (DMSO-d$_6$): δ (ppm) 8.45 (br m, 1H), 8.3 (s, 1H), 8.15 (br d, 1H), 6.96-7.1 (m, 3H), 4.25 (br m, 1H), 3.35 (br m, 1H), 3.05 (br m, 1H), 1.88-1.98 (m, 2H), 0.9-1.85 (m, 8H).

Example 250

((2R,4R,6S)-2,6-Dimethyl-piperidin-4-yl)-[4-(7-fluoro-1H-indol-3-yl)-pyrimidin-2-yl]-amine

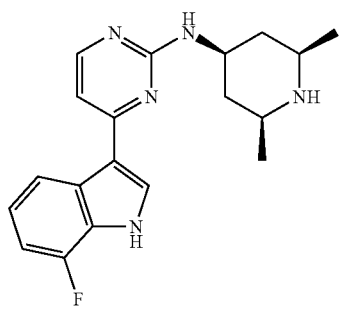

The title compound was prepared analogous to Method A, starting from 2,4-dichloropyrimidine, [1-(tert-butyl-dimethyl-silanyl)-7-chloro-1H-indole-3-yl]boronic acid (prepared by the procedure described in Example 215) and cis-2,6-dimethyl-piperidin-4-yl amine (separated from the trans-isomer as described in WO-97/36871). The (2,R4,R6S)-isomer was separated from the diastereomeric mixture by preparative HPLC chromatography. The stereochemical assignment is based on NOE-experiments (data not shown).

MS (ESI): 340.3 [M+H]$^{+1}$H-NMR (DMSO-d$_6$): δ (ppm) 12.03 (s, 1H), 8.43 (br m, 1H), 8.32 (br s, 1H), 8.16 (br d, 1H), 6.98-7.14 (m, 4H), 6.88 (br d, 1H), 3.9 (br m, 1H), 2.65-2.85 (br m, 2H), 1.8-2.08 (br m, 2H), 0.92-1.1 (br m, 2H) overlapping 1.04 (d, 6H).

Example 251

((2R,4S,6S)-2,6-Dimethyl-piperidin-4-yl)-[4-(7-fluoro-1H-indol-3-yl)-pyimidin-2-yl]-amine

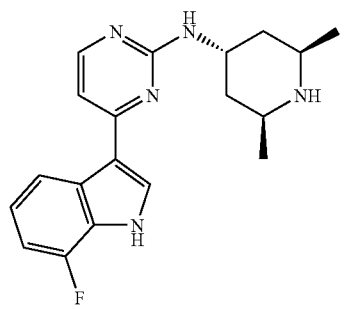

The title compound was separated as the (2R,4S,6S)-isomer from the diastereomeric mixture of Example 250 by preparative HPLC chromatography. The stereochemical assignment is based on NOE-experiments (data not shown).

MS (ESI): 340.3 [M+H]$^{+1}$H-NMR (DMSO-d$_6$): δ (ppm) 12.2 (s, 1H), 8.43 (br s, 1H), 8.31 (s, 1H), 8.18 (d, 1H), 7.0-7.17 (m, 4H), 6.81 (br d, 1H), 4.28 (br m, 1H), 3.05 (m, 2H), 1.8-1.9 (m, 2H), 1.15-1.35 (m, 2H), 0.98 (d, 6H).

Example 252

[4-(5-Fluoro-1H-indol-3-yl)-pyrimidin-2-yl]-(2,2,6,6-tetramethyl-piperidin-4-yl)-amine

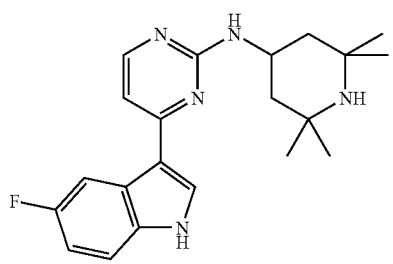

The title compound was prepared as described in Example 215, starting from 5-fluoro-1-(2-trimethylsilanyl-ethoxymethyl)-1H-indole (prepared by SEM protection of 5-fluoro-1H-indole using standard procedures) and (4-chloro-pyrimidin-2-yl)-(2,2,6,6-tetramethyl-piperidin-4-yl)-amine, followed by cleavage of the SEM protecting group with TBAF.

MS (ESI): 368.3 [M+H]$^{+1}$H-NMR (DMSO-d$_6$): δ (ppm) 8.27-8.5 (br m, 2H), 8.13 (br d, 1H), 7.45 (m, 1H), 6.95-7.07 (br m, 2H), 6.8 (br s, 1H), 4.45 (br m, 1H), 1.8-1.9 (m, 2H), 1.0-1.4 (m, 14H).

Example 253

[4-(6-Chloro-5-fluoro-1H-indol-3-yl)-pyrimidin-2-yl]-(2,2,6,6-tetramethyl-piperidin-4-yl)-amine

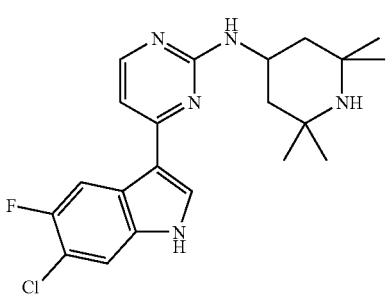

The title compound was prepared as described in Example 215, starting from 6-chloro-5-fluoro-1-(2-trimethylsilanyl-ethoxymethyl-1H-indole (prepared by SEM protection of 6-chloro-5-fluoro-1H-indole using standard procedures) and (4-chloro-pyrimidin-2-yl)-(2,2,6,6-tetramethyl-piperidin-4-yl)-amine, followed by cleavage of the SEM protecting group with TBAF.

MS (ESI): 402.2 [M+H]$^{+1}$H-NMR (DMSO-d$_6$, 120° C.): δ (ppm) 8.45 (d, 1H), 8.17 (m, 2H), 7.6 (d, 1H), 6.95 (d, 1H), 6.14 (br m, 1H), 4.45 (br m, 1H), 1.88-1.97 (m, 2H), 1.32 (s, 6H), 1.14-1.26 (m, 2H), 1.12 (s, 6H).

Example 254

[4-(7-Chloro-5-fluoro-1H-indol-3-yl)-pyrimidin-2-yl]-(2,2,6,6-tetramethyl-piperidin-4-yl)-amine

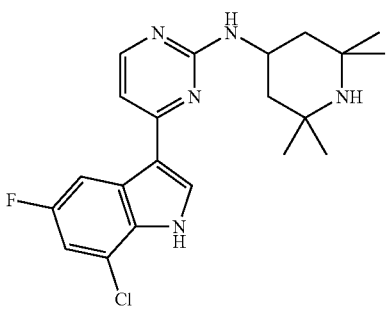

The title compound was prepared as described in Example 215, starting from 7-chloro-5-fluoro-1-(2-trimethylsilanyl-ethoxymethyl 1H-indole (prepared by SEM protection of 7-chloro-5-fluoro-1H-indole using standard procedures) and (4-chloro-pyrimidin-2-yl)-(2,2,6,6-tetramethyl-piperidin-4-yl)-amine, followed by cleavage of the SEM protecting group with TBAF.

MS (ESI): 402.2 [M+H]$^{+1}$H-NMR (DMSO-d$_6$): δ (ppm) 8.3 (br m, 1H), 8.2 (br m, 2H), 7.16 (br m, 1H), 7.0 (br m, 1H), 6.15 (br m, 1H), 4.45 (br m, 1H), 1.88-1.97 (m, 2H), 1.1-1.4 (m, 14H).

Example 255

[4-(6-Chloro-7-fluoro-1H-indol-3-yl)-pyrimidin-2-yl]-(2,2,6,6-tetramethyl-piperidin-4-yl)-amine

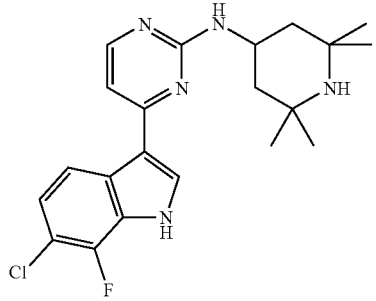

The title compound was prepared as described in Example 215, starting from 6-chloro-7-fluoro-1-(2-trimethylsilanyl-ethoxymethyl-1H-indole (prepared by SEM protection of 6-chloro-7-fluoro-1H-indole using standard procedures) and (4-chloro-pyrimidin-2-yl)(2,2,6,6-tetramethyl-piperidin-4-yl)-amine, followed by cleavage of the SEM protecting group with TBAF.

MS (ESI): 402.2 [M+H]$^{+1}$H-NMR (DMSO-d$_6$): δ (ppm) 8.48 (br m, 1H), 8.38 (s, 1H), 8.19 (br d, 1H), 7.1 (br m, 1H), 7.06 (d, 1H), 6.88 (br m, 1H), 4.4 (br m, 1H), 1.8-1.95 (m, 2H), 1.0-1.65 (m, 14H).

The following Examples (256 to 263) were prepared by the General Procedure for the Heck olefination of chloro-indole derivatives with the appropriate olefins, outlined below for Example 256.

Example 256

(E)-4-{5-Fluoro-3-[2-(2,2,6,6-tetramethyl-piperidin-4-ylamino)-pyrimidin-4-yl]-1H-indol-6-yl}-2-methyl-but-3-en-2-ol

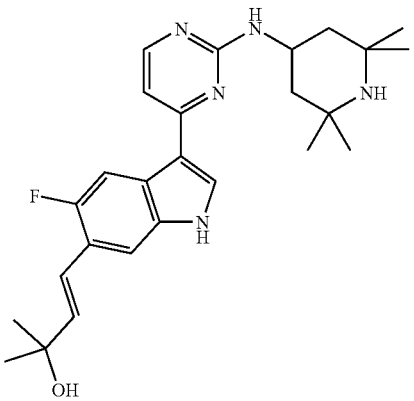

The SEM-protected intermediate {4-[6-Chloro-5-fluoro-1-(2-trimethylsilanyl-ethoxymethyl)-1H-indol-3-yl]-pyrimidin-2-yl}-(2,2,6,6-tetramethyl-piperidin-4-yl)-amine, obtained from Example 253, (200 mg, 0.38 mmol) was suspended in 2 ml of dioxane and mixed with 5 equivalents of 2-methyl-but-3-en-2-ol and 5 equivalents of dicyclohexyl-methyl-amine. To this mixture, 0.03 equivalents of Pd(t-

Bu$_3$P)$_2$ were added and the vial was closed with a pressure-tight septum. The vial was then placed in a Smith-Creator™ microwave reactor and heated at 16° C. for 600 seconds. After cooling, the formed precipitate was filtered-off, redissolved in methanol and filtered through a pad of silicagel to remove the catalyst. The solution was evaporated to give crude (E)-4-[5-Fluoro-3-[2-(2,2,6,6-tetramethyl-piperidin-4-ylamino)-pyrimidin-4-yl]-1-(2-trimethylsilanyl-ethoxymethyl)-1H-indol-6-yl]-2-methyl-but-3-en-2-ol which was subsequently treated with TBAF in THF to remove the SEM protecting group. After purification by preparative HPLC chromatography the desired title product was obtained.

Yield: 40%.

MS (ESI): 452.3 [M+H]$^{+1}$H-NMR (DMSO-d$_6$): δ (ppm) 8.25-8.4 (br m, 2H), 8.14 (br d, 1H), 7.56 (d, 1H), 6.98 (d, 1H), 6.7-6.85 (br m, 2H), 6.46 (d, 1H), 4.76 (s, 1H), 4.48 (br m, 1H), 1.8-1.88 (m, 2H), 1.0-1.4 (m, 20H).

Example 257

(E)-3-{5-Fluoro-3-[2-(2,2,6,6-tetramethyl-piperidin-4-ylamino)-pyrimidin-4-yl]-1H-indol-6-yl}-acrylonitrile

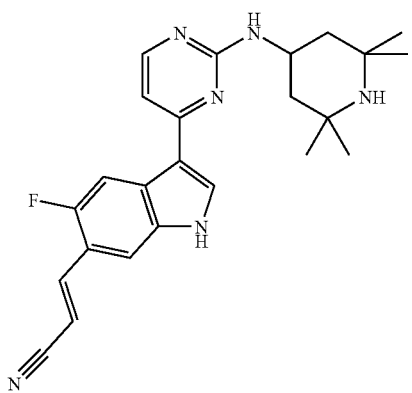

The title compound was prepared by the general Heck procedure described in Example 256, using the SEM-protected intermediate of Example 253 and acrylonitrile, followed by TBAF deprotection of the SEM group.

MS (ESI): 419.3 [M+H]$^{+1}$H-NMR (DMSO-d$_6$): δ (ppm) 8.48 (br s, 1H), 8.17 (br d, 1H), 7.83 (br d, 1H), 7.76 (d, 1H), 6.96-7.06 (br m, 2H), 6.85 (br m, 1H), 6.43 (d, 1H), 4.45 (br m, 1H), 1.77-1.88 (m, 2H), 1.0-1.4 (m, 14H).

Example 258

(E)-4-{5-Fluoro-3-[2-(2,2,6,6-tetramethyl-piperidin-4-ylamino)-pyrimidin-4-yl]-1H-indol-7-yl}-2-methyl-but-3-en-2-ol

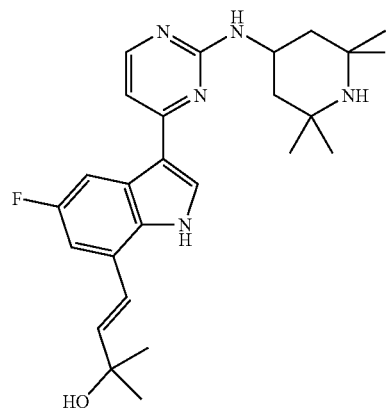

The title compound was prepared by the general Heck procedure described in Example 256, using the SEM-protected intermediate of Example 254 and 2-methyl-but-3-en-2-ol, followed by TBAF deprotection of the SEM group.

MS (ESI): 452.3 [M+H]$^{+1}$H-NMR (DMSO-d$_6$): δ (ppm) 8.1-8.4 (br m, 3H), 7.20 (br d, 1H), 7.05 (m, 2H), 6.8 (br s, 1H), 6.6 (m, 1H), 4.7 (br s, 1H), 4.5 (br s, 1H), 1.8-1.9 (m, 2H), 1.05-1.45 (br m, 20H).

Example 259

(E)-3-{3-[2-(2,2,6,6-Tetramethyl-piperidin-4-ylamino)-pyrimidin-4-yl]-1H-indol-6-yl}-acrylonitrile

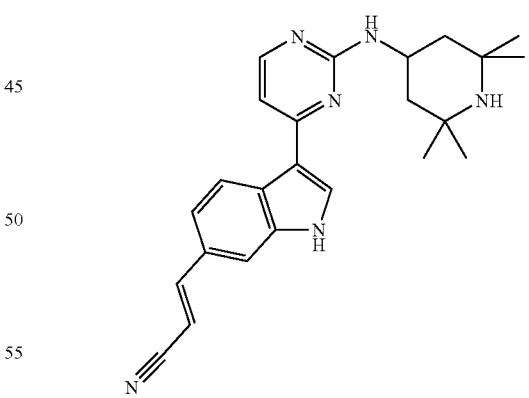

The title compound was prepared by the general Heck procedure described in Example 256, using the SEM-protected intermediate of Example 229 and acrylonitrile, followed by TBAF deprotection of the SEM group.

MS (ESI): 401.3 [M+H]$^{+1}$H-NMR (DMSO-d$_6$): δ (ppm) 8.65 (br m, 1H), 8.37 (br s, 1H), 8.17 (br d, 1H), 7.78 (d, 1H), 7.72 (br s, 1H), 7.4 (br m, 1H), 7.04 (br d, 1H), 6.8 (br m, 1H), 6.44 (d, 1H), 4.45 (br m, 1H), 1.8-1.95 (m, 2H), 1.0-1.4 (m, 14H).

Example 260

{4-[6-((E)-2-Imidazol-1-yl-vinyl)-1H-indol-3-yl]-pyrimidin-2-yl}-(2,2,6,6-tetramethyl-piperidin-4-yl)-amine

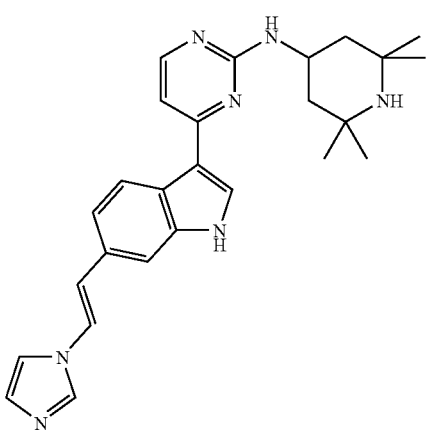

The title compound was prepared by the general Heck procedure described in Example 256, using the SEM-protected intermediate of Example 229 and 1-vinyl-1H-imidazole, followed by TBAF deprotection of the SEM group.

MS (ESI): 442.3 [M+H]$^{+1}$H-NMR (DMSO-d$_6$): δ (ppm) 8.62 (br d, 1H), 8.22 (br s, 1H), 8.15 (br d, 1H), 8.07 (br s, 1H), 7.84 (d, 1H), 7.75 (br s, 1H), 7.54 (br s, 1H), 7.25 (br d, 1H), 7.17 (d, 1H), 7.06 (br s, 1H), 702 (d, 1H), 6.75 (br d, 1H), 4.47 (br m, 1H), 1.9-1.95 (m, 2H), 1.05-1.45 (m, 14H).

Example 261

(E)-3-{3-[2-(2,2,6,6-Tetramethyl-piperidin-4-ylamino)-pyrimidin-4-yl]-1H-indol-7-yl}-acrylonitrile

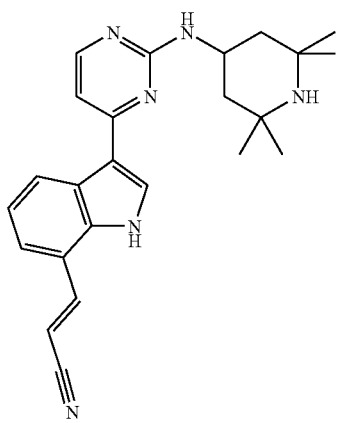

The title compound was prepared by the general Heck procedure described in Example 256, using the SEM-protected intermediate of Example 228 and acrylonitrile, followed by TBAF deprotection of the SEM group.

MS (ESI): 401.3 [M+H]$^{+1}$H-NMR (DMSO-d$_6$): δ (ppm) 8.66 (br d, 1H), 8.32 (br s, 1H), 8.17 (d, 1H), 7.28 (br d, 1H), 7.0-7.2 (br m, 3H), 6.8 (br d, 1H), 6.57 (d, 1H), 4.45 (br m, 1H), 1.8-1.9 (m, 2H), 1.0-1.4 (m, 14H).

Example 262

(E)-N,N-Dimethyl-3-{3-[2-(2,2,6,6-tetramethyl-piperidin-4-ylamino)-pyrimidin-4-yl]-1H-indol-7-yl}-acrylamide

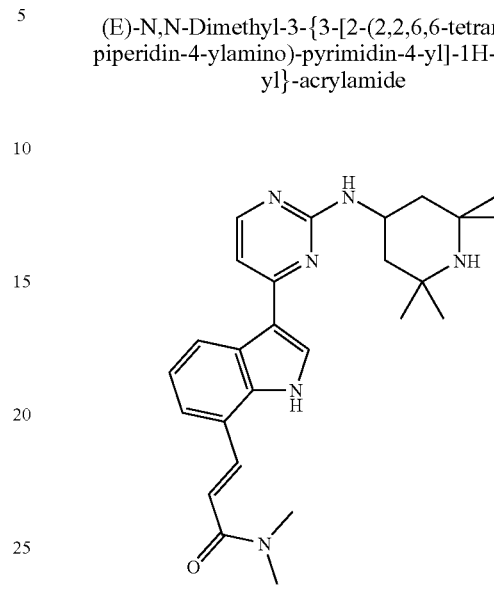

The title compound was prepared by the general Heck procedure described in Example 256, using the SEM-protected intermediate of Example 228 and N,N-dimethyl-acrylamide, followed by TBAF deprotection of the SEM group.

MS (ESI): 447.3 [M+H]$^{+1}$H-NMR (DMSO-d$_6$): δ (ppm) 8.72 (br d, 1H), 8.27 (s, 1H), 8.16 (br d, 1H), 8.06 (d, 1H), 7.68 (br d, 1H), 7.3 (d, 1H), 7.1 (br s, 1H), 7.06 (d, 1H), 6.76 (br d, 1H), 4.46 (br m, 1H), 3.23 (s, 3H), 3.0 (s, 3H), 1.8-1.9 (m, 2H), 1.0-1.4 (m, 14H).

Example 263

(E)-2-Methyl-3-{3-[2-(2,2,6,6-tetramethyl-piperidin-4-ylamino)-pyrimidin-4-yl]-1H-indol-7-yl}-acrylonitrile

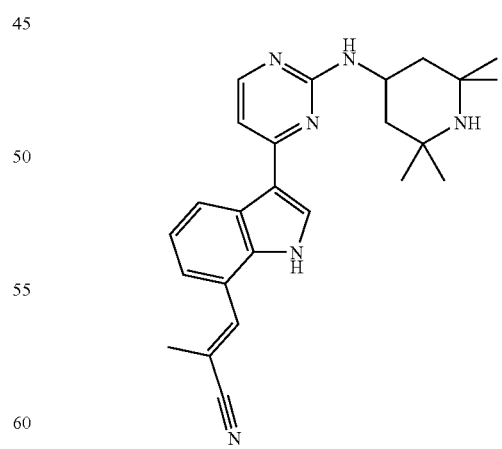

The title compound was prepared by the general Heck procedure described in Example 256, using the SEM-protected intermediate of Example 228 and 2-methyl-acrylonitrile, followed by TBAF deprotection of the SEM group. The formation of about 20% of the (Z)-Isomer was also observed.

MS (ESI): 415.3 [M+H]⁺ ¹H-NMR (DMSO-d₆): δ (ppm) 8.75 (br m, 1H), 8.32 (s, 1H), 8.16 (br m, 1H), 7.80 (s, 1H), 7.32 (br d, 1H), 7.15 (br m, 1H), 7.05 (br d, 1H), 6.8 (br d, 1H), 4.45 (br m, 1H), 2.18 (s, 3H), 1.8-1.95 (m, 2H), 1.05-1.4 (m, 14H).

Example 264

4-{5-Fluoro-3-[2-(2,2,6,6-tetramethyl-piperidin-4-ylamino)-pyrimidin-4-yl]-1H-indol-6-yl}-2-methyl-butan-2-ol

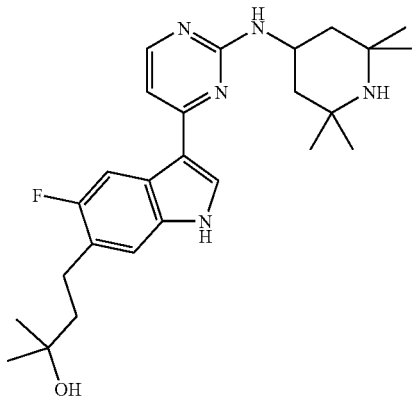

The title compound was prepared by catalytic hydrogenation of Example 256 with Pd/C in methanol.

MS (ESI): 454.3 [M+H]⁺ ¹H-NMR (DMSO-d₆): δ (ppm) 8.2-8.35 (br m, 2H), 8.13 (br d, 1H), 7.28 (br d, 1H), 6.97 (br d, 1H), 6.75 (br m, 1H), 4.45 (br m, 1H), 4.3 (s, 1H), 2.7-2.8 (m, 2H), 1.8-1.9 (m, 2H), 1.65-1.75 (m, 2H), 1.0-1.4 (m, 20H).

Example 265

3-{5-Fluoro-3-[2-(2,2,6,6-tetramethyl-piperidin-4-ylamino)-pyrimidin-4-yl]-1H-indol-6-yl}-propionitrile

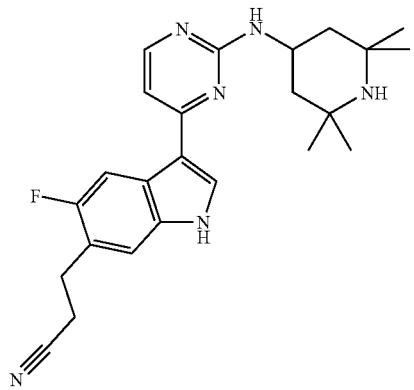

The title compound was prepared by catalytic hydrogenation of Example 257 with Pd/C in methanol.

MS (ESI): 421.3 [M+H]⁺ ¹H-NMR (DMSO-d₆): δ (ppm) 8.25-8.45 (br m, 2H), 8.15 (br d, 1H), 7.43 (br d, 1H), 6.99 (br d, 1H), 4.45 (br m, 1H), 3.04 (t, 2H), 2.86 (t, 2H), 1.8-1.9 (m, 2H), 1.0-1.4 (m, 14H).

Example 266

3-{7-Fluoro-3-[2-(2,2,6,6-tetramethyl-piperidin-4-ylamino)-pyrimidin-4-yl]-1H-indol-6-yl}-propionitrile

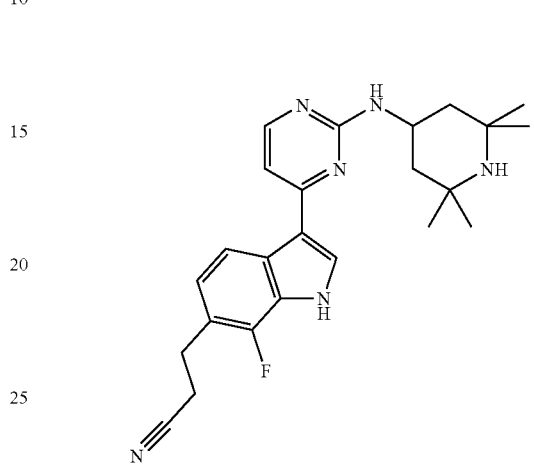

The title compound was prepared by the general Heck procedure described in Example 256, using the SEM-protected intermediate of Example 255 and acrylonitrile, followed by TBAF deprotection of the SEM group and catalytic hydrogenation with Pd/C in methanol.

MS (ESI): 421.3 [M+H]⁺ ¹H-NMR (DMSO-d₆): δ (ppm) 8.4 (br d, 1H), 8.27 (s, 1H), 8.15 (br d, 1H), 6.73-7.07 (br m, 3H), 4.43 (br m, 1H), 3.06 (br t, 2H), 2.86 (br t, 2H), 1.8-1.9 (m, 2H), 1.05-1.45 (m, 14H).

Example 267

4-{5-Fluoro-3-[2-(2,2,6,6-tetramethyl-piperidin-4-ylamino)-pyrimidin-4-yl]-1H-indol-7-yl}-2-methyl-butan-2-ol

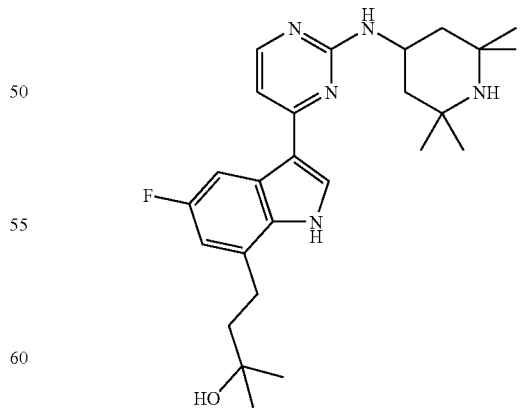

The title compound was prepared by catalytic hydrogenation of Example 258 with Pd/C in methanol.

MS (ESI): 454.3 [M+H]⁺ ¹H-NMR (DMSO-d₆): δ (ppm) 8.27 (s, 1H), 8.20 (s, 1H), 8.05-8.25 (br m, 2H), 7.0 (br d, 1H), 6.82 (br d, 1H), 6.72 (br m, 1H), 4.45 (br m, 1H), 2.93 (m, 2H), 1.72-1.88 (m, 4H), 1.0-1.4 (m, 14H).

Example 268

3-{3-[2-(2,2,6,6-Tetramethyl-piperidin-4-ylamino)-pyrimidin-4-yl]-1H-indol-6-yl}-propionitrile

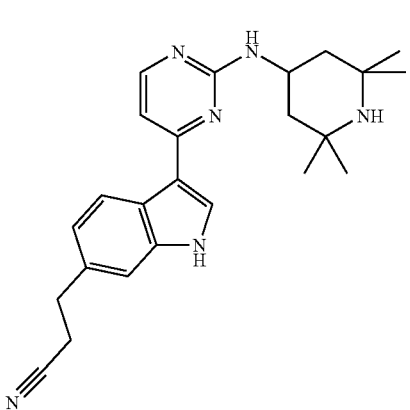

The title compound was prepared by catalytic hydrogenation of Example 259 with Pd/C in methanol.

MS (ESI): 403.3 [M+H]$^{+1}$H-NMR (DMSO-d$_6$): δ (ppm) 8.53 (br m, 1H), 8.24 (br d, 1H), 8.16 (br d, 1H), 7.48 (s, 1H), 7.0-7.15 (m, 3H), 4.5 (br m, 1H), 3.0 (t, 2H), 2.87 (t, 2H), 2.0-2.15 (m, 2H), 1.2-1.65 (m, 14H).

Example 269

{4-[6-(2-Imidazol-1-yl-ethyl)-1H-indol-3-yl]-pyrimidin-2-yl}-(2,2,6,6-tetramethyl-piperidin-4-yl)-amine

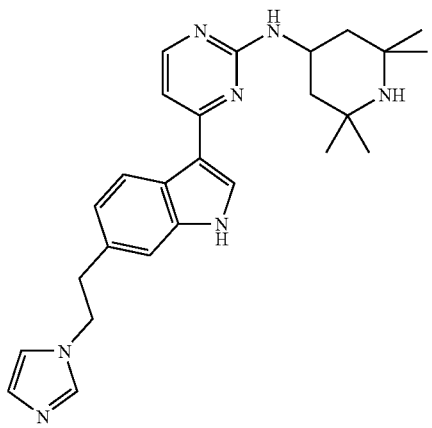

The title compound was prepared by catalytic hydrogenation of Example 260 with Pd/C in methanol.

MS (ESI): 444.3 [M+H]$^{+1}$H-NMR (DMSO-d$_6$, 120° C.): δ (ppm) 8.42 (d, 1H), 8.15 (d, 1H), 8.01 (s, 1H), 7.46 (br s, 1H), 7.24 (br s, 1H), 7.06 (br s, 1H), 6.92-6.96 (m, 2H), 6.86 (br s, 1H), 5.95 (br m, 1H), 4.45 (br m, 1H), 4.28 (t, 2H), 3.17 (t, 3H), 1.9-1.97 (m, 2H), 1.32 (s, 6H), 1.14-1.24 (m, 2H), 1.12 (s, 6H).

Example 270

3-{3-[2-(2,2,6,6-Tetramethyl-piperidin-4-ylamino)-pyrimidin-4-yl]-1H-indol-7-yl}-propionitrile

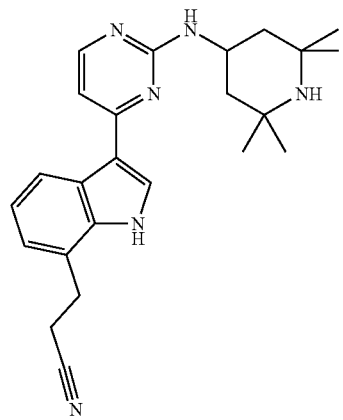

The title compound was prepared by catalytic hydrogenation of Example 261 with Pd/C in methanol.

MS (ESI): 403.3 [M+H]$^{+1}$H-NMR (DMSO-d$_6$): δ (ppm) 8.57 (br d, 1H), 8.28 (br s, 1H), 8.14 (br d, 1H), 7.11 (br d, 1H), 7.0-7.07 (m, 2H), 6.74 (br d, 1H), 4.46 (br m, 1H), 3.21 (t, 2H), 2.9 (t, 2H), 1.8-1.9 (m, 2H), 1.05-1.4 (m, 14H).

Example 271

N,N-Dimethyl-3-{3-[2-(2,2,6,6-tetramethyl-piperidin-4-ylamino)-pyrimidin-4-yl]-1H-indol-7-yl}-propionamide

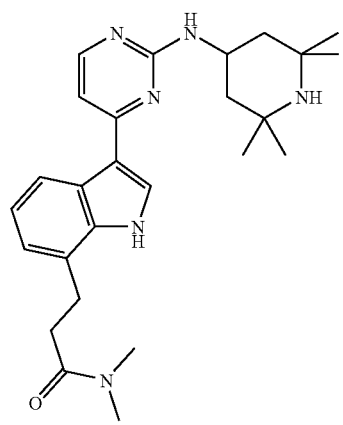

The title compound was prepared by catalytic hydrogenation of Example 262 with Pd/C in methanol.

MS (ESI): 449.3 [M+H]$^{+1}$H-NMR (DMSO-d$_6$): δ (ppm) 8.95 (br s, 1H), 8.45 (br s, 1H), 8.23 (br d, 1H), 8.17 (br d, 1H), 7.88 (br s, 1H), 6.95-7.2 (m, 3H), 4.55 (br m, 1H), 3.11 (br t, 2H), 2.95 (s, 3H), 2.86 (s, 3H), 2.71 (br t, 2H), 2.05-2.15 (m, 2H), 1.35-1.6 (m, 14H).

Example 272

2-Methyl-3-{3-[2-(2,2,6,6-tetramethyl-piperidin-4-ylamino)-pyrimidin-4-yl]-1H-indol-7-yl}-propionitrile

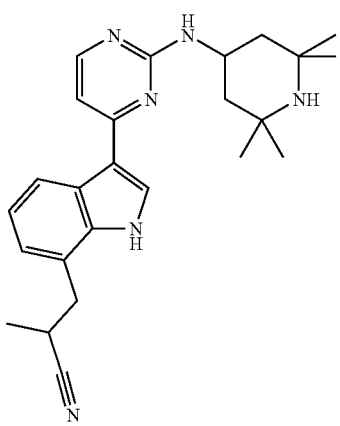

The title compound was prepared by catalytic hydrogenation of Example 263 with Pd/C in methanol.

MS (ESI): 417.3 [M+H]$^+$ $^1$H-NMR (DMSO-d$_6$): δ (ppm) 8.58 (d, 1H), 8.27 (s, 1H), 8.1.4 (br d, 1H), 7.0-7.12 (m, 3H), 6.73 (br d, 1H), 4.45 (br m, 1H), 3.1-3.25 (m, 3H), 1.80-1.90 (m, 2H), 1.05-1.35 (m, 17H).

The Agents of the Invention, as defined above, e.g., of formula I, II and III particularly as exemplified, in free or pharmaceutically acceptable acid addition salt form, exhibit pharmacological activity and are useful as pharmaceuticals, e.g. for therapy, in the treatment of diseases and conditions as hereinafter set forth.

In particular Agents of the Invention are potent inhibitors of IKK and thus have potential for pharmaceutical use for treatment of diseases and medical conditions mediated by IKK. In particular, as inhibitors of IKK, the Agents of the invention can act to inhibit or even block NFκB activated gene expression and thus act to inhibit production of inflammatory cytokines, such as TNF-α and IL-1, and also to potentially block the effects of these cytokines on their target cells. These and other pharmacological activities of the Agents of the Invention as may be demonstrated in standard test methods, for example as described below:

Experimental Procedures—IκB Kinase Assay and IκB Degradation Assay

Expression and purification of recombinant IκBα substrate. The cDNA encoding human IκBα was cloned into the vector pET17b (Novagen, Inc., Madison, Wis., U.S.A.) and recombinant IκBα protein was expressed in E. coli strain BL21 DE3 pLysS (Novagen, Inc., Madison, Wis., U.S.A.) according to the suppliers specifications and purified as follows (all steps at 0-4° C.). 3 g of wet cell pellet was resuspended in 10 ml of 50 mM Tris/HCl buffer at pH 8.0, containing 1 mM DTE, and sonicated on ice (3×1 min). The resulting homogenate was centrifuged in a Beckman JA-20 rotor (Beckmann Instruments, Fullerton, Calif., U.S.A.) at 15,000 rpm for 15 minutes and the IκBα protein was precipitated from the supernatant by addition of 15% (w/v) ammonium sulfate. After incubation for 15 minutes and centrifugation in a Beckman JA-20 rotor at 14,000 rpm for 12 minutes, the pellet was dissolved in 20 ml of 50 mM Tris/HCl at pH 8.0, containing 1 mM DTE, and loaded onto a 35 ml Q-Sepharose Fast Flow column (Amersham Pharmacia Biotech AB, Uppsala, Sweden) equilibrated with the same buffer. Bound proteins were eluted with a linear gradient of 0-1 M NaCl. IκBα-containing fractions, which eluted between 0.55 and 0.6 M salt, were pooled, frozen by dripping the solution into liquid nitrogen, and stored at −80° C. Typical yields were 2-7 mg of pure protein per liter of E. coli cell culture.

Purification of IκB kinase. IκB kinase was purified from TNFα-stimulated HeLa cells. HeLa cells were maintained in RPMI 1640 medium (GIBCO BRL, Life Technologies AG, Basel, Switzerland) supplemented with 5% fetal calf serum, 446 mg/l L-alanyl-L-glutamine, 50 µM mercaptoethanol. For 12 hours prior to stimulation, the cells were starved in serum-free RPMI 1640 medium supplemented with L-alanyl-L-glutamine, 50 µM mercaptoethanol, 100 IU/ml penicilline (GIBCO BRL, Life Technologies AG, Basel, Switzerland) and 100 µg/ml streptomycine (GIBCO BRL, Life Technologies AG, Basel, Switzerland). The starved cells were stimulated with 50 ng/ml TNFα for 5 min at 37° C., immediately chilled to 4° C. and collected by centrifugation. All subsequent steps were carried out at 4° C. or on ice. HeLa cells were suspended in ice-cold extraction buffer (10 mM Tris/HCl at pH 7.5, containing 10 mM KCl, 1 mM EDTA, 1 mM DTE and 100 µg/ml PMSF) and lysed by 20 strokes in a dounce homogenizer with a pistil B. Centrifugation in a Beckman JA-20 rotor for 30 minutes at 12,000 rpm and then in a Beckman Ti 45 rotor at 42,000 rpm for 2 hours yielded the post-ribosomal supernatant from which the proteins were precipitated with ammonium sulfate in a stepwise manner: addition of ammonium sulfate to a concentration of 8% (w/v), incubation for 15 min and centrifugation in a Beckman JA-20 rotor at 14,000 rpm was followed by a second precipitation step at 31% (w/v) ammonium sulfate. After an incubation period of 15 min and centrifugation in a Beckman JA-20 rotor at 14,000 rpm the latter pellet was dissolved in 50 ml of 25 mM Tris/HCl buffer at pH 8.0, containing 1 mM DTE, and dialyzed extensively against the same buffer. The protein solution was then loaded onto a 300 ml Q-Sepharose Fast Flow column which was equilibrated with the above dialysis buffer. Bound proteins were eluted with a gradient of 0-1 M NaCl. IκB kinase activity, which eluted from the column between 300 mM and 350 mM NaCl, was concentrated by ultrafiltration with Amicon PM 10 filters (Amicon, Inc., Beverly, Mass., U.S.A.). The concentrated protein solution was then passed over a Sephacryl S300 column (Amersham Pharmacia Biotech AB, Uppsala, Sweden) developed in 25 mM Tris/HCl buffer at pH 8.0, containing 150 mM NaCl and 1 mM DTE. The IκB kinase-containing fractions were pooled, loaded onto a MonoQ column (Amersham Pharmacia Biotech AB, Uppsala, Sweden) and eluted with a linear gradient of 0.15-0.5 M NaCl in 25 mM Tris/HCl, pH 8.0, 1 mM DTE. Purified IkB kinase was stored frozen at −80° C. until further use.

IκB kinase activity assay. Nunc-ImmunoPlates MaxiSorp (Life Technologies AG, Basel, Switzerland) were coated for 2 hours at room temperature with 50 µl/well of 25 µM IκBα in 50 mM Tris/HCl at pH 8.0, 1 mM DTE. After blocking for 1 hour with a solution of 2% (w/v) BSA in PBS buffer, the plates were washed 5 times with PBS containing 0.05% (v/v) Tween 20. The kinase reaction was done in 50 mM Tris/HCl buffer at pH 8.0, containing 10 mM MgCl$_2$ and 1 mM DTE. The substrate ATP was used at a concentration of 10 µM and the reaction started by the addition of the purified IκB kinase. For measuring the inhibition of IκB kinase by compounds, the test compounds were dissolved in DMSO and added to the enzyme reaction prior to addition of the kinase. After 20-90 minutes at room temperature the reaction was terminated by washing with PBS/0.05% (v/v) Tween 20. The phosphorylated IκBα was then detected using a phospho-specific IκBα (Ser32) antibody (New England Biolabs, Beverly, Mass., U.S.A., cat. # 9041S) in combination with a horseradish peroxidase conjugated anti-rabbit IgG antibody (Santa Cruz Biotechnology, Santa Cruz, Calif., U.S.A.) and employment of BM Blue POD substrate (Roche Diagnostics AG, Basel, Switzerland) as follows. The first, phospho-specific IκBα antibody was diluted 1:1500 with PBS, 2% (w/v) BSA, 0.05% (v/v) Tween 20 and added to the wells. After incubation for 1 hour at room temperature, the plates were washed 5 times with PBS containing 0.05% (v/v) Tween 20. The second antibody, diluted 1:3000 with PBS, 2% (w/v) BSA, 0.05% (v/v) Tween 20, was then added to the wells and the plates allowed to incubate for 1 hour at room temperature. Following 5 washing steps with PBS, 2% (w/v) BSA, 0.05% (v/v) Tween 20, 50 µl BM Blue POD substrate was added to each well. The color reaction was stopped by addition of 50 µl of 2.25 M $H_2SO_4$ and the absorbance of the wells measured at 450 nm versus 650 nm. Each compound was tested twice in duplicate and calculation of $IC_{50}$ values were done using the GraphPad Prism software (GraphPad Software, Inc., San Diego, Calif., U.S.A.). Agents of the invention typically have $IC_{50}$ values when measured in the above assay in the range from 20 to 1000 nM.

IκBα degradation assay. THP-1 cells were maintained in RPMI 1640 medium with Glutamax-I (GIBCO BRL, Life Technologies AG, Basel, Switzerland) supplemented with 10% fetal calf serum, 100 U/ml penicilline and 100 µg/ml streptomycine. For the assay, the cells were transferred to 96-well plates (Nunc, Life Technologies AG, Basel, Switzerland, cat. #245128) at a density of 600 000 cells/well and stimulated with 10 ng/ml TNFα for 12 minutes at room temperature. For measuring the inhibition of TNFα-stimulated IκBα degradation by compounds, the test compounds were dissolved in DMSO and added to the cell suspension prior to addition of TNFα. Following incubation, the plates were centrifuged at 1200 rpm in a Heraeus Megafuge 2.0R (Heraeus AG, Zuerich, Switzerland), the supernatants discarded, and the cell pellet dissolved in 50 µl/well Laemmli sample buffer (Bio-Rad Laboratories AG, Glattbrugg, Switzerland, cat. #161-0737) supplemented with 5% (v/v) 2-mercaptoethanol. The concentration of IκBα in the individual samples was analyzed by Western blotting using NOVEX 10% Tris-Glycine gels (Invitrogen, Life Technologies AG, Basel, Switzerland) and the ECL+Plus Western blotting detection reagents (Amersham Pharmacia Biotech AB, Uppsala, Sweden) according to the manufacturer's specifications. The primary antibody was an anti-IκBα antibody (Santa Cruz Biotechnology, Santa Cruz, Calif., U.S.A., cat. # sc-371) diluted 1:1000 and the secondary antibody a goat anti-rabbit IgG HRP-conjugated antibody (Bio-Rad Laboratories AG, Glattbrugg, Switzerland, cat. #172-1019). Each compound was tested in duplicate and estimation of $IC_{50}$ values were done based on densitometric scanning or visual inspection. Agents of the invention typically have $IC_{50}$ values when measured in the above assay in the range from 0.5 to 30 µM.

Assay for Inhibition of TNF-α Release from hPBMCs

Human peripheral blood mononuclear cells (hPBMCs) are prepared from the peripheral blood of healthy volunteers using ficoll-hypaque density separation according to the method of Hansell et al., J. Imm. Methods (1991) 145: 105. and used at a concentration of $10^5$ cells/well in RPMI 1640 plus 10% FCS. Cells are incubated with serial dilutions of the test compounds for 30 minutes at 37° C. prior to the addition of IFNg (100 U/ml) and LPS (5 mg/ml) and subsequently further incubated for three hours. Incubation is terminated by centrifugation at 1400 RPM for 10 min. TNF-α in the supernatant is measured using a commercial ELISA (Innotest hTNFa, available from innogenetics N.V., Zwijnaarde, Belgium). Agents of the Invention are tested at concentrations of from 0 to 10 mM. Exemplified Agents of the Invention typically suppress TNF release in this assay with $IC_{50}$ values raging from about 100 nM to about 3000 nM or less when tested in this assay.

Assay for Inhibition of TNF-α Production in LPS Stimulated Mice

Injection of lipopolysaccharide (LPS) induces a rapid release of soluble tumour necrosis factor (TNF-α) into the periphery. This model is be used to analyse prospective blockers of TNF release in vivo.

LPS (20 mg/kg) is injected i.v. into OF1 mice (female, 8 week old). One (1) hour later blood is withdrawn from the animals and TNF levels are analysed in the plasma by an ELISA method using an antibody to TNF-α. Using 20 mg/kg of LPS levels of up to 15 ng of TNF-α/ml plasma are usually induced. Compounds to be evaluated are given either orally or s.c. 1 to 4 hours prior to the LPS injection. Inhibition of LPS-induced TNF-release is taken as the readout.

Agents of the Invention typically inhibit TNF production to the extent of up to about 50% or more in the above assay when administered at 30 mg/kg p.o., i.v. or s.c.

As indicated in the above assays Agents of the Invention are potent inhibitors of TNF-α release. Accordingly, the Novel Compounds have pharmaceutical utility as follows:

Agents of the Invention are useful for the prophylaxis and treatment of diseases or pathological conditions mediated by cytokines such as TNFα and IL-1, e.g., inflammatory conditions, autoimmune diseases, severe viral infections, and organ or tissue transplant rejection, e.g. for the treatment of recipients of heart, lung, combined heart-lung, liver, kidney, pancreatic, skin or corneal transplants and for the prevention of graft-versus-host disease, such as following bone marrow transplants. In addition, Agents of the Invention are useful for the treatment of cancer.

Agents of the Invention are particularly useful for the treatment, prevention, or amelioration of autoimmune disease and of inflammatory conditions, in particular inflammatory conditions with an aetiology including an autoimmune component such as arthritis (for example rheumatoid arthritis, arthritis chronica progrediente and arthritis deformans) and rheumatic diseases. Specific auto-immune diseases for which Agents of the Invention may be employed include autoimmune haematological disorders (including e.g. hemolytic anaemia, aplastic anaemia, pure red cell anaemia and idiopathic thrombocytopenia), systemic lupus erythematosus, polychondritis, sclerodoma, Wegener granulamatosis, dermatomyositis, chronic active hepatitis, myasthenia gravis, psoriasis, Steven-Johnson syndrome, idiopathic sprue, autoimmune inflammatory bowel disease (including e.g. ulcerative colitis and Crohn's disease), endocrine ophthalmopathy, Graves disease, sarcoidosis, multiple sclerosis, primary biliary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minimal change nephropathy).

Agents of the Invention are also useful for the treatment, prevention, or amelioration of asthma, bronchitis, pneumoconiosis, pulmonary emphysema, and other obstructive or inflammatory diseases of the airways.

Agents of the Invention are useful for treating undesirable acute and hyperacute inflammatory reactions which are mediated by TNF, especially by TNFα, e.g., acute infections, for example septic shock (e.g., endotoxic shock and adult respiratory distress syndrome), meningitis, pneumonia; and severe burns; and for the treatment of cachexia or wasting syndrome associated with morbid TNF release, consequent to infection, cancer, or organ dysfunction, especially AIDS-related cachexia, e.g., associated with or consequential to HIV infection.

Agents of the Invention are also useful for the treatment of neurodegenerative diseases, such as Alzheimer's disease, acute encephalitis, brain injury, multiple sclerosis including demyelation and oligiodendrocyte loss in multiple sclerosis and inflammatory nervous system diseases, such as neuroinflammatory and stroke.

Advantageously treatment with Agents of the Invention may result in inhibition of COX-2 activity and as such the Agents of the Invention conveniently have the following additional uses. Thus the Agents of the Invention are particularly useful for the treatment of cyclooxygenase dependent disorders in mammals, including inflammation, pyresis, pain, osteoarthritis, rheumatoid arthritis, migraine headache, neurodegenerative diseases (such as multiple sclerosis), Alzheimer's disease, osteoporosis, asthma, lupus and psoriasis.

The Agents of the Invention are further useful for the treatment of neoplasia particularly neoplasia that produce prostaglandins or express cyclooxygenase, including both benign and cancerous tumors, growths and polyps. Compounds of the present invention may be employed for the treatment of any neoplasia as for example recited in International Patent Application Publication No. WO 98/16227, published 23 Apr. 1998, in particular epithelium cell-derived neoplasia. Compounds of the present invention are in particular useful for the treatment of liver, bladder, pancreas, ovarian, prostate, cervical, lung and breast cancer and, especially gastrointestinal cancer, for example cancer of the colon, and skin cancer, for example squamus cell or basal cell cancers and melanoma.

The term "treatment" as used herein is to be understood as including both therapeutic and prophylactic modes of therapy, e.g. in relation to the treatment of neoplasia, therapy to prevent the onset of clinically or preclinically evident neoplasia, or for the prevention of initiation of malignant cells or to arrest or reverse the progression of premalignant to malignant cells, as well as the prevention or inhibition of neoplasia growth or metastasis. In this context, the present invention is, in particular, to be understood as embracing the use of compounds of the present invention to inhibit or prevent development of skin cancer, e.g. squamus or basal cell carcinoma consequential to UV light exposure, e.g. resultant from chronic exposure to the sun.

The Agents of the Invention may also be used in ocular applications which include the treatment of ocular disorders, in particular of ocular inflammatory disorders, of ocular pain including pain associated with ocular surgery such as PRK or cataract surgery, of ocular allergy, of photophobia of various etiology, of elevated intraocular pressure (in glaucoma) by inhibiting the production of trabecular meshwork inducible glucocorticoid response (TIGR) protein, and of dry eye disease.

Agents of the Invention are particularly useful for treating diseases of bone metabolism including osteoarthritis, osteoporosis and other inflammatory arthritides.

For the above indications the appropriate dosage will, of course, vary depending, for example, on the particular Agent of the Invention employed, the subject to be treated, the mode of administration and the nature and severity of the condition being treated. However, in general, satisfactory results in animals are obtained at daily dosages of from about 1 to about 50 mg/kg/day p.o. In larger mammals, for example humans, an indicated daily dosage is in the range of from about 50 to about 750 mg of an Agent of the Invention administered orally once or, more suitably, in divided dosages two to four times/day.

The Agents of the Invention may be administered by any conventional route, e.g. orally, for example in the form of solutions for drinking, tablets or capsules or parenterally, for example in the form of injectable solutions or suspensions. Normally for systemic administration oral dosage forms are preferred, although for some indications the Agents of the Invention may also be administered topically or dermally, e.g. in the form of a dermal cream or gel or like preparation or, for the purposes of application to the eye, in the form of an ocular cream, gel or eye-drop preparation; or may be administered by inhalation, e.g., for treating asthma. Suitable unit dosage forms for oral administration comprise e.g. from 25 to 250 mg of Agent of the Invention per unit dosage.

In accordance with the foregoing the present invention also provides in a further series of embodiments:

A. A method of inhibiting production of soluble TNF, especially TNFα, or of reducing inflammation in a subject (i.e., a mammal, especially a human) in need of such treatment which method comprises administering to said subject an effective amount of an Agent of the Invention, or a method of treating any of the above mentioned conditions, particularly a method of treating an inflammatory or autoimmune disease or condition, e.g. rheumatoid arthritis, or alleviating one or more symptoms of any of the above mentioned conditions.

B. An Agent of the Invention for use as a pharmaceutical, e.g. for use as an immunosuppressant or antiinflammatory agent or for use in the prevention, amelioration on treatment of any disease or condition as described above, e.g., an autoimmune or inflammatory disease or condition.

C. A pharmaceutical composition comprising an Agent of the Invention in association with a pharmaceutically acceptable diluent or carrier, e.g., for use as an immunosuppressant or anti-inflammatory agent or for use in the prevention, amelioration or treatment of any disease or condition as described above, e.g., an autoimmune or inflammatory disease or condition.

D. Use of an Agent of the Invention in the manufacture of a medicament for use as an immunosuppressant or anti-inflammatory agent or for use in the prevention, amelioration or treatment of any disease or condition as described above, e.g., an autoimmune of inflammatory disease or condition.

The invention claimed is:

1. A compound of formula IIIa or formula IIIb or a pharmaceutically-acceptable salt, thereof:

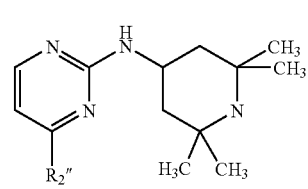

IIIa

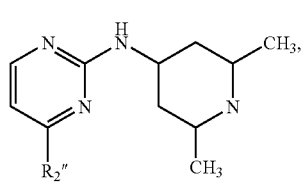

IIIb wherein

R$_2$" is phenyl, thiophenyl, benzthiophenyl, pyridinyl, naphthalenyl or indolyl, wherein any of which is/are optionally substituted by one-to-three substituents R$_{20}$, where each R$_{20}$ is independently selected from I, Br, Cl, F, and R$_{23}$, wherein R$_{23}$ is selected from OH, CN, NO$_2$, —C(O)—R$_x$, —O—C(O)—R$_x$, —S(O)—R$_x$, —S(O)$_2$—R$_x$, —CH$_2$—O—R$_x$, —NH—C(O)—R$_x$, and R$_{24}$, where R$_{24}$ is selected from linear- or branched-C$_1$-C$_7$-alkyl, C$_3$-C$_{10}$-cycloalkyl, C$_3$-C$_{10}$-cycloalkyl-linear- or branched-C$_1$-C$_7$-alkyl, linear- or branched-C$_2$-C$_7$-alkene, linear- or branched-C$_2$-C$_7$-alkyne, linear- or branched-C$_1$-C$_7$-alkoxy, linear- or branched-C$_1$-C$_7$-thioalkoxy, linear- or branched-C$_2$-C$_7$-alkenyloxy, linear- or branched-C$_2$-C$_7$-thioalkenyloxy, linear- or branched-C$_2$-C$_7$-alkynyloxy, linear- or branched-C$_2$-C$_7$-thioalkynyloxy, carbocyclic aryl, heteroaryl, heterocycloalkyl, and NH$_2$, wherein each R$_{24}$ may be substituted by one or two substituents independently selected from linear- or branched-C$_1$-C$_7$-alkyl, carbocyclic aryl, heteroaryl, carbocyclic aryl-linear- or branched-C$_1$-C$_7$-alkyl, heteroaryl-linear- or branched-C$_1$-C$_7$-alkyl, heterocycloalkyl or heterocycloalkyl-linear- or branched-C$_1$-C$_7$-alkyl, and wherein each R$_{23}$ is optionally substituted by one-to-four substituents independently selected from I, Br, Cl, F, and R$_{25}$, where R$_{25}$ is selected from OH, CN, NO$_2$, —C(O)—R$_x$, —O—C(O)—R$_x$, —S(O)—R$_x$, —O—S(O)—R$_x$,—CH$_2$—O—R$_x$, —NH—C(O)—R$_x$, and R$_{26}$, where R$_{26}$ is selected from linear- or branched-C$_1$-C$_7$-alkyl, C$_3$-C$_{10}$-cycloalkyl, C$_3$-C$_{10}$-cycloalkyl-linear- or branched-C$_1$-C$_7$-alkyl, linear- or branched-C$_2$-C$_7$-alkene, linear- or branched-C$_2$-C$_7$-alkyne, linear- or branched-C$_1$-C$_7$alkoxy, linear- or branched-C$_1$-C$_7$-thioalkoxy, linear- or branched-C$_2$-C$_7$-alkenyloxy, linear- or branched-C$_2$-C$_7$-thioalkenyloxy, linear- or branched-C$_2$-C$_7$-alkynyloxy, linear- or branched-C$_2$-C$_7$-thioalkynyloxy, carbocyclic aryl, heteroaryl, heterocycloalkyl, and NH$_2$, where each R$_{26}$ may be substituted by one or two substituents independently selected from linear- or branched-C$_1$-C$_7$-alkyl, carbocyclic aryl, heteroaryl, carbocyclic aryl- linear- or branched-C$_1$-C$_7$-alkyl, heteroaryl-linear- or branched-C$_1$-C$_7$-alkyl,heterocycloalkyl or heterocycloalkyl- linear- or branched-C$_1$C$_7$-alkyl and wherein each R$_{25}$is optionally substituted by one-to-three substituents R$_{27}$ independently selected from I, Br, Cl, F and R$_{28}$, where R$_{28}$is selected from OH, CN, NO$_2$, —C(O)—R$_x$, —O—C(O)R$_x$, —S(O)—R$_x$, —O—S(O)—R$_x$, —CH$_2$—O—R$_x$, —NH—C(O)—R$_x$, linear- or branched-C$_1$-C$_7$-alkyl, C$_3$-C$_{10}$-cycloalkyl, C$_3$-C$_{10}$-cycloalkyl-linear- or branched-C$_1$-C$_7$-alkyl, linear- or branched-C$_1$-C$_7$-alkoxy, linear- or branched-C$_1$-C$_7$-thioalkoxy, carbocyclic aryl, heteroaryl, heterocycloalkyl, and NH$_2$, where each R$_{27}$ may be substituted by one or two substituents independently selected from linear- or branched-C$_1$-C$_7$-alkyl, carbocyclic aryl, heteroaryl, carbocyclic aryl- linear- or branched-C$_1$-C$_7$-alkyl, heteroaryl-linear- or branched-C$_1$-C$_7$-alkyl, heterocycloalkyl and heterocycloalkyl linear- or branched-C$_1$-C$_7$-alkyl;

wherein

R$_x$ is OH, linear- or branched-C$_1$-C$_7$-alkoxy, linear- or branched-C$_1$-C$_7$-thioalkoxy, carbocyclic aryloxy, heteroaryloxy, thio-carbocyclic aryloxy, thio-heteroaryloxy, carbocyclic aryl-linear- or branched-C$_1$-C$_7$-alkoxy, carbocyclic-aryl-linear- or branched C$_1$-C$_7$-thioalkoxy, heteroaryl-linear- or branched-C$_1$-C$_7$-alkoxy, heteroaryl-linear- or C$_1$-C$_7$-thioalkoxy, or NH$_2$, any of which may be substituted by one or two substituents independently selected from linear- or branched-C$_1$-C$_7$-alkyl, carbocyclic aryl, heteroaryl, carbocyclic aryl-linear- or branched-C$_1$-C$_7$-alkyl, heteroaryl -linear- or branched-C$_1$-C$_7$-alkyl, heterocycloalkyl and heterocycloalkyl -linear- or branched-C$_1$-C$_7$-alkyl;

carbocyclic aryl is a mono-, bi- or tricyclic aryl selected from phenyl, phenyl that is substituted by one, two or three substituents selected from linear- or branched-C$_1$-C$_7$-alkyl, linear- or branched-C$_1$-C$_7$-alkoxy, linear- or branched-C$_1$-C$_7$-thioalkoxy, phenyl, hydroxy, I, Br, Cl, F, cyano, trifluoromethyl, linear- or branched-C$_2$-C$_7$-alkylenedioxy; oxy-C$_2$-C$_3$-alkylene; 1- or 2-naphthyl; and 1- or 2-phenanthrenyl;

heterocycloalkyl is a mono- bi- or tricyclic moiety comprising from 3-to 18 ring atoms, wherein 1-to-3 ring atoms is/are independently selected from O, S and N, and the remaining ring atoms are carbon atoms, which ring(s) is/are saturated or comprise(s) one or more unsaturated alkenyl or alkynyl bonds; and heteroaryl is a mono- or bicyclic heteroaryl selected from pyridyl, indolyl, quinoxalinyl, quinolinyl, isoquinolinyl, benzothienyl, benzofuranyl, benzopranyl, benzothiophenyl, benzothiopyranyl, furanyl, pyrrolyl, thiazolyl, oxazolyl, isoxazolyl, triazolyl, tetrazolyl, pyrazolyl, imidazolyl and thienyl.

2. A pharmaceutical composition comprising a therapeutically-effective and TNF-α release-inhibiting amount of a compound according to claim 1, or a pharmaceutically-acceptable salt thereof, in association with a pharmaceutically-acceptable diluent or carrier.

3. A compound selected from the group consisting of:

2-methyl-4-{5-[2-(2,2,6,6-tetramethyl-piperidin-4-ylamino)-pyrimidin-4-yl]-thiophen-2-yl}-butan-2-ol;

4-{5-[5-methoxy-2-(2,2,6,6-tetramethyl-piperidin-4-ylamino)-pyrimidin-4-yl]-thiophen-2-yl}-2-methyl-butan-2-ol;

{4-[5-(4-methoxy-butyl)-thiophen-2-yl]-pyrimidin-2-yl}-(2,2,6,6-tetramethyl-piperidin-4-yl)-amine hydrochloride;

(E)-4-{5-[2-(2,2,6,6-tetramethyl-piperidin-4-ylamino)-pyrimidin-4-yl]-thiophen-2-yl}-but-3-en-2-ol;

{4-[5-(3-amino-3-methyl-but-1-ynyl)-thiophen-2-yl]-pyrimidin-2-yl}-(2,2,6,6-tetramethyl-piperidin-4-yl)-amine;

(E)-2-methyl-4-{5-[2-(2,2,6,6-tetramethyl-piperidin-4-ylamino)-pyrimidin-4-yl]-thiophen-2-yl}-but-3-en-2-ol;

1-{5-[2-(2,2,6,6-tetramethyl-piperidin-4-ylamino)-pyrimidin-4-yl]-thiophen-2-yl}-propan-2-ol;

2-methyl-1-{5-[2-(2,2,6,6-tetramethyl-piperidin-4-ylamino)-pyrimidin-4-yl]-thiophen-2-yl}-propan-2-ol;

2,2,N-trimethyl-3-{5-[2-(2,2,6,6-tetramethyl-piperidin-4-ylamino)-pyrimidin-4-yl]-thiophen-2-yl}-propionamide;

2-methyl-4-{3-[2-(2,2,6,6-tetramethyl-piperidin-4-ylamino)-pyrimidin-4-yl]-pyrrol-1-yl}-butan-2-ol;
2-(2-{5-[2-(2,2,6,6-tetramethyl-piperidin-4-ylamino)-pyrimidin-4-yl]-thiophen-2-ylmethyl}-cyclopropyl)-propan-2-ol;
2,3,3-trimethyl-5-{5-[2-(2,2,6,6-tetramethyl-piperidin-4-ylamino)-pyrimidin-4-yl]-thiophen-2-yl}-pentan-2-ol;
2-((1R,2R)-2-{5-[2-(2,2,6,6-tetramethyl-piperidin-4-ylamino)-pyrimidin-4-yl]-thiophen-2-yl}-cyclopropyl)-propan-2-ol;
2-((1S,2S)-2-{5-[2-(2,2,6,6-tetramethyl-piperidin-4-ylamino)-pyrimidin-4-yl]-thiophen-2-yl}-cyclopropyl)-propan-2-ol;
2-ethoxy-2-methyl-1-{5-[2-(2,2,6,6-tetramethyl-piperidin-4-ylamino)-pyrimidin-4-yl]-thiophen-2-yl}-propan-1-one;
{4-[5-(3-methoxy-propyl)-thiophen-2-yl]-pyrimidin-2-yl}-(2,2,6,6-tetramethyl-piperidin-4-yl)-amine;
2'-{5-[2-(2,2,6,6-tetramethyl-piperidin-4-ylamino)-pyrimidin-4-yl]-thiophen-2-yl}-bicyclopropyl-1-ol;
4-{3-methoxy-5-[2-(2,2,6,6-tetramethyl-piperidin-4-ylamino)-pyrimidin-4-yl]-thiophen-2-yl}-2-methyl-butan-2-ol;
{4-[5-(2-amino-2-methyl-propyl)-thiophen-2-yl]-pyrimidin-2-yl}-(2,2,6,6-tetramethyl-piperidin-4-yl)-amine;
2,2-difluoro-3-methyl-1-{5-[2-(2,2,6,6-tetramethyl-piperidin-4-ylamino)-pyrimidin-4-yl]-thiophen-2-yl}-butane-1,3-diol;
2,3,3-trimethyl-4-{5-[2-(2,2,6,6-tetramethyl-piperidin-4-ylamino)-pyrimidin-4-yl]-thiophen-2-yl}-butan-2-ol;
[4-(5-benzyloxy-thiophen-2-yl)-pyrimidin-2-yl]-(2,2,6,6-tetramethyl-piperidin-4-yl)-amine;
[4-(5-butyl-thiophen-2-yl)-pyrimidin-2-yl]-(2,2,6,6-tetramethyl-piperidin-4-yl)-amine;
[4-(5-propoxy-thiophen-2-yl)-pyrimidin-2-yl]-(2,2,6,6-tetramethyl-piperidin-4-yl)-amine;
{4-[5-(2-methoxy-ethoxy)-thiophen-2-yl]-pyrimidin-2-yl}-(2,2,6,6-tetramethyl-piperidin-4-yl)-amine;
{4-[5-(2-dimethylamino-ethoxy)-thiophen-2-yl]-pyrimidin-2-yl}-(2,2,6,6-tetramethyl-piperidin-4-yl)-amine (dihydrochloride);
[4-(5-pyridin-4-yl-thiophen-2-yl)-pyrimidin-2-yl]-(2,2,6,6-tetramethyl-piperidin-4-yl)-amine;
1-methyl-4-{5-[2-(2,2,6,6-tetramethyl-piperidin-4-ylamino)-pyrimidin-4-yl]-thiophen-2-yl}-piperidin-4-ol;
[4-(5-pyridin-3-yl-thiophen-2-yl)-pyrimidin-2-yl]-(2,2,6,6-tetramethyl-piperidin-4-yl)-amine;
[4-(5-pyridin-2-yl-thiophen-2-yl)-pyrimidin-2-yl]-(2,2,6,6-tetramethyl-piperidin-4-yl)-amine;
[4-(5-Piperazin-4-yl-thiophen-2-yl)-pyrimidin-2-yl]-(2,2,6,6-tetramethyl-piperidin-4-yl)-amine;
4-(5-{2-[(8-aza-bicyclo[3.2.1]oct-3-yl)exo-amino]-pyrimidin-4-yl}-thiophen-2-yl)-1-methyl-piperidin-4-ol;
8-aza-bicyclo[3.2.1]oct-3-yl-[4-(5-piperazin-1-yl-thiophen-2-yl)-pyrimidin-2-yl]-exo-amine;
{4-[5-((E)-3-amino-3-methyl-but-1-enyl)-thiophen-2-yl]-pyrimidin-2-yl}-(2,2,6,6-tetramethyl-piperidin-4-yl)-amine;
{4-[5-(3-amino-3-methyl-butyl)-thiophen-2-yl]-pyrimidin-2-yl}-(2,2,6,6-tetramethyl-piperidin-4-yl)-amine;
2-methyl-4-{5-[2-(2,2,6,6-tetramethyl-piperidin-4-ylamino)-pyrimidin-4-yl]-thiophen-2-yl}-but-3-yn-2-ol;
{4-[5-(3-RS-methyl-piperazin-1-yl)-thiophen-2-yl]-pyrimidin-2-yl}(2,2,6,6-tetramethyl-piperidin-4-yl)-amine;
5-[2-(2,2,6,6-tetramethyl-piperidin-4-ylamino)-pyrimidin-4-yl]-thiophene-2-sulfonic acid amide;
5-[2-(2,2,6,6-tetramethyl-piperidin-4-ylamino)-pyrimidin-4-yl]-thiophene-2-carboxylic acid ((S)-1-carbamoyl-2-phenyl-ethyl)-amide;
(S)-3-phenyl-2-({5-[2-(2,2,6,6-tetramethyl-piperidin-4-ylamino)-pyrimidin-4-yl]-thiophene-2-carbonyl}-amino)-propionic acid methyl ester;
(R)-3-phenyl-2-({5-[2-(2,2,6,6-tetramethyl-piperidin-4-ylamino)-pyrimidin-4-yl]-thiophene-2-carbonyl}-amino)-propionic acid methyl ester;
2-benzyl-1-{5-[2-(2,2,6,6-tetramethyl-piperidin-4-ylamino)-pyrimidin-4-yl]-thiophene-2-carbonyl}-piperidin-4-one;
1-{5-[2-(2,2,6,6-tetramethyl-piperidin-4-ylamino)-pyrimidin-4-yl]-thiophene-2-carbonyl}-piperidine-4-carboxylic acid isopropylamide;
biphenyl-4-yl-({5-[2-(2,2,6,6-tetramethyl-piperidin-4-ylamino)-pyrimidin-4-yl]-thiophene-2-carbonyl}-amino)-acetic acid methyl ester;
(2S,4R)-4-hydroxy-1-{5-[2-(2,2,6,6-tetramethyl-piperidin-4-ylamino)-pyrimidin-4-yl]-thiophene-2-carbonyl}-pyrrolidine-2-carboxylic acid benzyl ester;
5-[2-(2,2,6,6-tetramethyl-piperidin-4-ylamino)-pyrimidin-4-yl]-thiophene-2-carboxylic acid phenethylamide;
[4-(1H-indol-3-yl)-piperidin-1-yl]-{5-[2-(2,2,6,6-tetramethyl-piperidin-4-ylamino)-pyrimidin-4-yl]-thiophen-2-yl}-methanone;
(4-[2,2']bithiophenyl-5-yl-5-methyl-pyrimidin-2-yl)-(2,2,6,6-tetramethyl-piperidin-4-yl)-amine;
1-{5'-[5-methyl-2-(2,2,6,6-tetramethyl-piperidin-4-ylamino)-pyrimidin-4-yl]-[2,2']bithiophenyl-5-yl}-ethanone;
{4-[5'-(1-amino-ethyl)-[2,2']bithiophenyl-5-yl]-5-methyl-pyrimidin-2-yl}-(2,2,6,6-tetramethyl-piperidin-4-yl)-amine;
[5-bromo-4-(4,5,6,7-tetrahydro-benzo[b]thiophen-2-yl)-pyrimidin-2-yl]-(2,2,6,6-tetramethyl-piperidin-4-yl)-amine;
N-(2-{5-[5-bromo-2-(2,2,6,6-tetramethyl-piperidin-4-ylamino)-pyrimidin-4-yl]-thiophen-2-yl}-ethyl)-acetamide;
{4-[5-(2-amino-ethyl)-thiophen-2-yl]-5-bromo-pyrimidin-2-yl}-(2,2,6,6-tetramethyl-piperidin-4-yl)-amine;
{5-bromo-4-[5-(2-dimethylamino-ethyl)-thiophen-2-yl]-pyrimidin-2-yl}-(2,2,6,6-tetramethyl-piperidin-4-yl)-amine;
1-(4-{5-[2-(2,2,6,6-tetramethyl-piperidin-4-ylamino)-pyrimidin-4-yl]-thiophen-2-yl}-phenyl)-ethanone O-methyl-oxime;
(4-{5-[4-((Z)-1-methyl-propenyl)-phenyl]-thiophen-2-yl}-pyrimidin-2-yl)-(2,2,6,6-tetramethyl-piperidin-4-yl)-amine;
(4-{5-[4-(1-amino-ethyl)-phenyl]-thiophen-2-yl}-pyrimidin-2-yl)-(2,2,6,6-tetramethyl-piperidin-4-yl)-amine;
[5-bromo-4-(5-chloro-thiophen-2-yl)-pyrimidin-2-yl]-(2,2,6,6-tetramethyl-piperidin-4-yl)-amine;
4-{5-[5-bromo-2-(2,2,6,6-tetramethyl-piperidin-4-ylamino)-pyrimidin-4-yl]-thiophen-2-yl}-butyric acid methyl ester;
4-{5-[5-bromo-2-(2,2,6,6-tetramethyl-piperidin-4-ylamino)-pyrimidin-4-yl]-thiophen-2-yl}-butan-1-ol;
{4-[5'-(1-amino-ethyl)-[2,2']bithiophenyl-5-yl]-pyrimidin-2-yl}-(2,2,6,6-tetramethyl-piperidin-4-yl)-amine;
{4-[5-(3-aminomethyl-phenyl)-thiophen-2-yl]-pyrimidin-2-yl}-(2,2,6,6-tetramethyl-piperidin-4-yl)-amine;

{4-[5-(4-dimethylaminomethyl-phenyl)-thiophen-2-yl]-pyrimidin-2-yl}-(2,2,6,6-tetramethyl-piperidin-4-yl)-amine;
(4-{5-[(2-piperidin-1-yl-ethylamino)-methyl]-thiophen-2-yl}-pyrimidin-2-yl)-(2,2,6,6-tetramethyl-piperidin-4-yl)-amine;
[4-(5-{[methyl-(2-piperidin-1-yl-ethyl)-amino]-methyl}-thiophen-2-yl)-pyrimidin-2-yl]-(2,2,6,6-tetramethyl-piperidin-4-yl)-amine;
2-methyl-5-{5-[2-(2,2,6,6-tetramethyl-piperidin-4-ylamino)-pyrimidin-4-yl]-thiophen-2-yl}-pentan-2-ol;
{4-[5-(2-isopropylamino-ethyl)-thiophen-2-yl]-pyrimidin-2-yl}-(2,2,6,6-tetramethyl-piperidin-4-yl)-amine;
(2-{5-[2-(2,2,6,6-tetramethyl-piperidin-4-ylamino)-pyrimidin-4-yl]-thiophen-2-yl}-ethyl)-urea;
{5-[2-(2,2,6,6-tetramethyl-piperidin-4-ylamino)-pyrimidin-4-yl]-thiophen-2-ylmethyl}-urea;
N-{5-[2-(2,2,6,6-tetramethyl-piperidin-4-ylamino)-pyrimidin-4-yl]-thiophen-2-ylmethyl}-methanesulfonamide;
N-{5'-[2-(2,2,6,6-tetramethyl-piperidin-4-ylamino)-pyrimidin-4-yl]-[2,2']bithiophenyl-5-ylmethyl}-methanesulfonamide;
[4-(5'-dimethylaminomethyl-[2,2']bithiophenyl-5-yl)-pyrimidin-2-yl]-(2,2,6,6-tetramethyl-piperidin-4-yl)-amine;
{5'-[2-(2,2,6,6-tetramethyl-piperidin-4-ylamino)-pyrimidin-4-yl]-[2,2']bithiophenyl-5-ylmethyl}-urea;
2-methoxy-N-{5'-[2-(2,2,6,6-tetramethyl-piperidin-4-ylamino)-pyrimidin-4-yl]-[2,2']bithiophenyl-5-ylmethyl}-acetamide;
3-{3-methyl-5-[2-(2,2,6,6-tetramethyl-piperidin-4-ylamino)-pyrimidin-4-yl]-thiophen-2-yl}-propionamide;
{4-[5-(3-amino-3-ethyl-pentyl)-thiophen-2-yl]-pyrimidin-2-yl}-(2,2,6,6-tetramethyl-piperidin-4-yl)-amine;
{4-[5-(2-methanesulfinyl-ethyl)-thiophen-2-yl]-pyrimidin-2-yl}-(2,2,6,6-tetramethyl-piperidin-4-yl)-amine;
{4-[5-(3-methylsulfanyl-propyl)-thiophen-2-yl]-pyrimidin-2-yl}(2,2,6,6-tetramethyl-piperidin-4-yl)-amine;
{4-[5-(4-methanesulfonyl-butyl)-thiophen-2-yl]-pyrimidin-2-yl}-(2,2,6,6-tetramethyl-piperidin-4-yl)-amine;
1-{5-[2-(2,2,6,6-tetramethyl-piperidin-4-ylamino)-pyrimidin-4-yl]-thiophen-2-yl}-pentan-3-ol:
{4-[5-(1-amino-cyclohexylethynyl)-thiophen-2-yl]-pyrimidin-2-yl}-(2,2,6,6-tetramethyl-piperidin-4-yl)-amine;
(4-{5-[2-(1-amino-cyclohexyl)-ethyl]-thiophen-2-yl}-pyrimidin-2-yl)-(2,2,6,6-tetramethyl-piperidin-4-yl)-amine;
1-(2-{5-[2-(2,2,6,6-tetramethyl-piperidin-4- ylamino)-pyrimidin-4-yl]-thiophen-2-yl}-ethyl)-cyclobutanol;
phenyl-(4-{5-[2-(2,2,6,6-tetramethyl-piperidin-4-ylamino)-pyrimidin-4-yl]-thiophen-2-yl}-butyrylamino)-acetic acid methyl ester;
{4-[5-(5-phenyl-pentyl)-thiophen-2-yl]-pyrimidin-2-yl}-(2,2,6,6-tetramethyl-piperidin-4-yl)-amine;
(benzyl-{5-[2-(2,2,6,6-tetramethyl-piperidin-4-ylamino)-pyrimidin-4-yl]-thiophen-2-ylmethyl}-amino)-acetic acid ethyl ester;
1-(benzyl-{5-[2-(2,2,6,6-tetramethyl-piperidin-4-ylamino)-pyrimidin-4-yl]-thiophen-2-ylmethyl}-amino)-2-methyl-propan-2-ol;
1-phenyl-3-{5-[2-(2,2,6,6-tetramethyl-piperidin-4-ylamino)-pyrimidin-4-yl]-thiophen-2-yl}-propan-1-ol;
3-ethyl-1-{5-[2-(2,2,6,6-tetramethyl-piperidin-4-ylamino)-pyrimidin-4-yl]-thiophen-2yl}-pentan-3-ol;
3-({5-[2-(2,2,6,6-tetramethyl-piperidin-4-ylamino)-pyrimidin-4-yl]-thiophen-2-ylmethyl}-amino)-propionitrile;
3-(benzyl-{5-[2-(2,2,6,6-tetramethyl-piperidin-4-ylamino)-pyrimidin-4-yl]-thiophen-2-ylmethyl}-amino)-propionitrile;
3-(methyl-{5-[2-(1,2,2,6,6-pentamethyl-piperidin-4-ylamino)-pyrimidin-4-yl]-thiophen-2-ylmethyl}-amino)-propionitrile;
N-(2-cyano-ethyl)-N-{5-[2-(2,2,6,6-tetramethyl-piperidin-4-ylamino)-pyrimidin-4-yl]-thiophen-2-ylmethyl}-acetamide;
1-{5-[2-(2,2,6,6-tetramethyl-piperidin-4-ylamino)-pyrimidin-4-yl]-thiophen-2-yl}-ethanone;
{4-[5-(4-chloro-phenyl)-thiophen-2-yl]-pyrimidin-2-yl}-(2,2,6,6-tetramethyl-piperidin-4-yl)-amine;
3-methyl-5-[2-(2,2,6,6-tetramethyl-piperidin-4-ylamino)-pyrimidin-4-yl]-thiophene-2-carbonitrile;
(4-[2,2']bithiophenyl-5-yl-pyrimidin-2-yl)-(2,2,6,6-tetramethyl-piperidin-4-yl)-amine;
[4-(5-isopropenyl-thiophen-2-yl)-pyrimidin-2-yl]-(2,2,6,6-tetramethyl-piperidin-4-yl)-amine;
{4-[5-(2-amino-ethyl)-thiophen-2-yl]-pyrimidin-2-yl}-(2,2,6,6-tetramethyl-piperidin-4-yl)-amine;
[4-(4,5,6,7-tetrahydro-benzo[b]thiophen-2-yl)-pyrimidin-2-yl]-(2,2,6,6-tetramethyl-piperidin-4-yl)-amine;
4-chloro-2-((E)-2-{5-[2-(2,2,6,6-tetramethyl-piperidin-4-ylamino)-pyrimidin-4-yl]-thiophen-2-yl}-vinyl)-benzonitrile;
2-[2-(2,2,6,6-tetramethyl-piperidin-4-ylamino)-pyrimidin-4-yl]-4,5,6,7-tetrahydro-benzo[b]thiophen-4-ol;
(2,2,6,6-tetramethyl-piperidin-4-yl)-(4-thieno[3,2-c]pyridin-2-yl-pyrimidin-2-yl)-amine;
(4-chloro-phenyl)-{5-[2-(2,2,6,6-tetramethyl-piperidin-4-ylamino)-pyrimidin-4-yl]-thiophen-2-yl}-methanol;
N-(2-{5-[2-(2,2,6,6-tetramethyl-piperidin-4-ylamino)-pyrimidin-4-yl]-thiophen-2-yl}-ethyl)-acetamide;
{4-[5-(2-dimethylamino-ethyl)-thiophen-2-yl]-pyrimidin-2-yl}-(2,2,6,6-tetramethyl-piperidin-4-yl)-amine;
1-(4-{5-[2-(2,2,6,6-tetramethyl-piperidin-4-ylamino)-pyrimidin-4-yl]-thiophen-2-yl}-phenyl)-ethanone;
3-methyl-5-[2-(2,2,6,6-tetramethyl-piperidin-4-ylamino)-pyrimidin-4-yl]-thiophene-2-carboxylic acid methyl ester;
[4-(5-chloro-thiophen-2-yl)-pyrimidin-2-yl]-(2,2,6,6-tetramethyl-piperidin-4-yl)-amine
4-{5-[2-(2,2,6,6-tetramethyl-piperidin-4-ylamino)-pyrimidin-4-yl]-thiophen-2-yl}-butyric acid methyl ester;
4-{5-[2-(2,2,6,6-tetramethyl-piperidin-4-ylamino)-pyrimidin-4-yl]-thiophen-2-yl}-butyric acid;
5-[2-(2,2,6,6-tetramethyl-piperidin-4-ylamino)-pyrimidin-4-yl]-thiophene-2-carboxylic acid benzylamide;
[4-(5-nitro-thiophen-2-yl)-pyrimidin-2-yl]-(2,2,6,6-tetramethyl-piperidin-4-yl)-amine;
{4-[5-(4-methoxy-phenyl)-thiophen-2-yl]-pyrimidin-2-yl}-(2,2,6,6-tetramethyl-piperidin-4-yl)-amine;
4-{5-[2-(2,2,6,6-tetramethyl-piperidin-4-ylamino)-pyrimidin-4-yl]-thiophen-2-yl}-phenol;
1-{5'-[2-(2,2,6,6-tetramethyl-piperidin-4-ylamino)-pyrimidin-4-yl]-[2,2']bithiophenyl-5-yl}-ethanone;
{4-[5-(2-methoxy-phenyl)-thiophen-2-yl]-pyrimidin-2-yl}-(2,2,6,6-tetramethyl-piperidin-4-yl)-amine;
{5-[2-(2,2,6,6-tetramethyl-piperidin-4-ylamino)-pyrimidin-4-yl]-thiophen-2-yl}-methanol;
5-[2-(2,2,6,6-tetramethyl-piperidin-4-ylamino)-pyrimidin-4-yl]-thiophene-2-carboxylic acid (2-amino-ethyl)-amide;

4-{5-[2-(2,2,6,6-tetramethyl-piperidin-4-ylamino)-pyrimidin-4-yl]-thiophen-2-yl}-butan-1-ol;
{4-[5-(3-methoxy-phenyl)-thiophen-2-yl]-pyrimidin-2-yl}-(2,2,6,6-tetramethyl-piperidin-4-yl)-amine;
4-{5-[2-(2,2,6,6-tetramethyl-piperidin-4-ylamino)-pyrimidin-4-yl]-thiophen-2-yl}-benzenesulfonamide;
3-{5-[2-(2,2,6,6-tetramethyl-piperidin-4-ylamino)-pyrimidin-4-yl]-thiophen-2-yl}-benzonitrile;
4-{5-[2-(2,2,6,6-tetramethyl-piperidin-4-ylamino)-pyrimidin-4-yl]-thiophen-2-yl}-benzoic acid methyl ester;
(4-{5-[2-(2,2,6,6-tetramethyl-piperidin-4-ylamino)-pyrimidin-4-yl]-thiophen-2-yl}-phenyl)-methanol;
(3-{5-[2-(2,2,6,6-tetramethyl-piperidin-4-ylamino)-pyrimidin-4-yl]-thiophen-2-yl}-phenyl)-methanol;
N-(3-{5-[2-(2,2,6,6-tetramethyl-piperidin-4-ylamino)-pyrimidin-4-yl]-thiophen-2-yl}-phenyl)-acetamide;
{4-[5-(3-amino-phenyl)-thiophen-2-yl]-pyrimidin-2-yl}-(2,2,6,6-tetramethyl-piperidin-4-yl)-amine;
1-(3-{5-[2-(2,2,6,6-tetramethyl-piperidin-4-ylamino)-pyrimidin-4-yl]-thiophen-2-yl}-phenyl)-ethanone;
5'-[2-(2,2,6,6-tetramethyl-piperidin-4-ylamino)-pyrimidin-4-yl]-[2,2']bithiophenyl-5-sulfonic acid amide;
{4-[5-(1-amino-ethyl)-thiophen-2-yl]-pyrimidin-2-yl}-(2,2,6,6-tetramethyl-piperidin-4-yl)-amine;
3-{5-[2-(2,2,6,6-tetramethyl-piperidin-4-ylamino)-pyrimidin-4-yl]-thiophen-2-yl}-propan-1-ol;
3-{5-[2-(2,2,6,6-tetramethyl-piperidin-4-ylamino)-pyrimidin-4-yl]-thiophen-2-yl}-propionic acid methyl ester;
{4-[5-(4-amino-butyl)-thiophen-2-yl]-pyrimidin-2-yl}-(2,2,6,6-tetramethyl-piperidin-4-yl)-amine;
5-[2-(2,2,6,6-tetramethyl-piperidin-4-ylamino)-pyrimidin-4-yl]-thiophene-2-carbonitrile;
[4-(5-aminomethyl-thiophen-2-yl)-pyrimidin-2-yl]-(2,2,6,6-tetramethyl-piperidin-4-yl)-amine;
{4-[5-(4-aminomethyl-phenyl)-thiophen-2-yl]-pyrimidin-2-yl}-(2,2,6,6-tetramethyl-piperidin-4-yl)-amine;
{5'-[2-(2,2,6,6-tetramethyl-piperidin-4-ylamino)-pyrimidin-4-yl]-[2,2']bithiophenyl-5-yl}-methanol;
2-methyl-1-{5-[2-(2,2,6,6-tetramethyl-piperidin-4-ylamino)-pyrimidin-4-yl]-thiophen-2-yl}-propan-1-ol;
3-{5-[2-(2,2,6,6-tetramethyl-piperidin-4-ylamino)-pyrimidin-4-yl]-thiophen-2-yl}-propionamide;
{4-[5-(3-amino-propyl)-thiophen-2-yl]-pyrimidin-2-yl}-(2,2,6,6-tetramethyl-piperidin-4-yl)-amine;
4-{5-[2-(2,2,6,6-tetramethyl-piperidin-4-ylamino)-pyrimidin-4-yl]-thiophen-2-yl}-butan-2-ol;
[4-(5'-aminomethyl-[2,2']bithiophenyl-5-yl)-pyrimidin-2-yl]-(2,2,6,6-tetramethyl-piperidin-4-yl)-amine;
3-{3-methyl-5-[2-(2,2,6,6-tetramethyl-piperidin-4-ylamino)-pyrimidin-4-yl]-thiophen-2-yl}-propionic acid methyl ester;
acetic acid 2-methyl-2-nitro-1-{5-[2-(2,2,6,6-tetramethyl-piperidin-4-ylamino)-pyrimidin-4-yl]-thiophen-2-yl}-propyl ester;
6-{5-[2-(2,2,6,6-tetramethyl-piperidin-4-ylamino)-pyrimidin-4-yl]-thiophen-2-yl}-hexanenitrile;
{4-[5-(6-amino-hexyl)-thiophen-2-yl]-pyrimidin-2-yl}-(2,2,6,6-tetramethyl-piperidin-4-yl)-amine;
1-{5-[2-(2,2,6,6-tetramethyl-piperidin-4-ylamino)-pyrimidin-4-yl]-thiophen-2-yl}-pentan-3-one;
1-phenyl-3-{5-[2-(2,2,6,6-tetramethyl-piperidin-4-ylamino)-pyrimidin-4-yl]-thiophen-2-yl-propan-1-one;
4-(4-benzo[b]thiophen-2-yl-pyrimidin-2-ylamino)-2,2,6,6-tetramethyl-piperidin-4-ol;
(4-benzo[b]thiophen-2-yl-pyrimidin-2-yl)-(1,2,2,6,6-pentamethyl-piperidin-4-yl)-amine;
(4-benzo[b]thiophen-2-yl-pyrimidin-2-yl)-(1-benzyl-piperidin-4-yl)-amine;
(4-benzo[b]thiophen-2-yl-pyrimidin-2-yl)-piperidin-4-yl-amine;
3-[4-(4-benzo[b]thiophen-2-yl-pyrimidin-2-ylamino)-piperidin-1-yl]-propionitrile;
[4-(6-methoxy-benzo[b]thiophen-2-yl)-pyrimidin-2-yl]-(2,2,6,6-tetramethyl-piperidin-4-yl)-amine;
2-[2-(2,2,6,6-tetramethyl-piperidin-4-ylamino)-pyrimidin-4-yl]-benzo[b]thiophen-6-ol;
[4-(6-ethoxy-benzo[b]thiophen-2-yl)-pyrimidin-2-yl]-(2,2,6,6-tetramethyl-piperidin-4-yl)-amine;
[4-(6-allyloxy-benzo[b]thiophen-2-yl)-pyrimidin-2-yl]-(2,2,6,6-tetramethyl-piperidin-4-yl)-amine;
[4-(6-oxiranylmethoxy-benzo[b]thiophen-2-yl)-pyrimidin-2-yl]-(2,2,6,6-tetramethyl-piperidin-4-yl)-amine;
1-isopropylamino-3-{2-[2-(2,2,6,6-tetramethyl-piperidin-4-ylamino)-pyrimidin-4-yl]-benzo[b]thiophen-6-yloxy}-propan-2-ol;
[4-(6-methoxy-benzo[b]thiophen-2-yl)-5-methyl-pyrimidin-2-yl]-(2,2,6,6-tetramethyl-piperidin-4-yl)-amine;
1-isopropylamino-3-{2-[5-methyl-2-(2,2,6,6-tetramethyl-piperidin-4-ylamino)-pyrimidin-4-yl]-benzo[b]thiophen-6-yloxy}-propan-2-ol;
[1-(3-amino-propyl)-piperidin-4-yl]-(4-benzo[b]thiophen-2-yl-pyrimidin-2-yl)-amine;
(5-aza-spiro[3.5]non-8-yl)-(4-benzo[b]thiophen-2-yl-pyrimidin-2-yl)-amine;
(4-benzo[b]thiophen-2-yl-pyrimidin-2-yl)-trans-(2,6-dimethyl-piperidin-4-yl)-amine;
[4-(3-methyl-benzo[b]thiophen-2-yl)-pyrimidin-2-yl]-(2,2,6,6-tetramethyl-piperidin-4-yl)-amine;
[4-(5-methyl-benzo[b]thiophen-2-yl)-pyrimidin-2-yl]-(2,2,6,6-tetramethyl-piperidin-4-yl)-amine;
[4-(7-methoxy-benzo[b]thiophen-2-yl)-pyrimidin-2-yl]-(2,2,6,6-tetramethyl-piperidin-4-yl)-amine;
(4-benzo[b]thiophen-5-yl-pyrimidin-2-yl)-(2,2,6,6-tetramethyl-piperidin-4-yl)-amine;
(4-benzo[b]thiophen-2-yl-pyrimidin-2-yl)-(2,2,6,6-tetramethyl-piperidin-4-yl)-amine;
2-[2-(2,2,6,6-tetramethyl-piperidin-4-ylamino)-pyrimidin-4-yl]-benzo[b]thiophene-7-carboxylic acid (2-diethylamino-ethyl)-amide;
8-aza-bicyclo[3.2.1]oct-3-yl-(4-benzo[b]thiophen-2-yl-pyrimidin-2-yl)-endo-amine;
8-aza-bicyclo[3.2.1]oct-3-yl-(4-benzo[.b.]thiophen-2-yl-pyrimidin-2-yl)-exo-amine;
(2R,4R)-4-(4-benzo[b]thiophen-2-yl-pyrimidin-2-ylamino)-piperidine-2-carboxylic acid methyl ester;
(4-benzo[b]thiophen-2-yl-5-methyl-pyrimidin-2-yl)-(2,2,6,6-tetramethyl-piperidin-4-yl)-amine;
[4-(4-pyridin-4-yl-phenyl)-pyrimidin-2-yl]-(2,2,6,6-tetramethyl-piperidin-4-yl)-amine;
1-methyl-4-{4-[2-(2,2,6,6-tetramethyl-piperidin-4-ylamino)-pyrimidin-4-yl]-phenyl}-piperidin-4-ol;
[4-(4-pyridin-3-yl-phenyl)-pyrimidin-2-yl]-(2,2,6,6-tetramethyl-piperidin-4-yl)-amine;
[4-(4-pyridin-2-yl-phenyl)-pyrimidin-2-yl]-(2,2,6,6-tetramethyl-piperidin-4-yl)-amine;
{4-[4-(4-methyl-piperazin-1-yl)-phenyl]-pyrimidin-2-yl}-(2,2,6,6-tetramethyl-piperidin-4-yl)-amine;
{4-[6-(3-amino-3-methyl-butyl)-pyridin-3-yl]-pyrimidin-2-yl}-(2,2,6,6-tetramethyl-piperidin-4-yl)-amine;
[4-(4-methylsulfanyl-phenyl)-pyrimidin-2-yl]-(2,2,6,6-tetramethyl-piperidin-4-yl)-amine;
(4-naphthalen-2-yl-pyrimidin-2-yl)-(2,2,6,6-tetramethyl-piperidin-4-yl)-amine;

[4-(4-bromo-phenyl)-pyrimidin-2-yl]-(2,2,6,6-tetram-ethyl-piperidin-4-yl)-amine;
(2,2,6,6-tetramethyl-piperidin-4-yl)-[4-(4-vinyl-phenyl)-pyrimidin-2-yl]-amine;
4-[2-(2,2,6,6-tetramethyl-piperidin-4-ylamino)-pyrimidin-4-yl]-benzenesulfonamide;
N-(2-hydroxy-ethyl)-3-[2-(2,2,6,6-tetramethyl-piperidin-4-ylamino)-pyrimidin-4-yl]-benzenesulfonamide;
{4-[4-(3-amino-3-methyl-butyl)-phenyl]-pyrimidin-2-yl}-(2,2,6,6-tetramethyl-piperidin-4-yl)-amine;
3-{4-[2-(2,2,6,6-tetramethyl-piperidin-4-ylamino)-pyrimidin-4-yl]-phenyl}-propionic acid methyl ester;
2-methyl-4-{-[2-(2,2,6,6-tetramethyl-piperidin-4-ylamino)-pyrimidin-4-yl]-phenyl}-butan-2-ol;
3-{4-[2-(2,2,6,6-tetramethyl-piperidin-4-ylamino)-pyrimidin-4-yl]-phenyl}-propionamide;
{4-[4-(2-amino-ethyl)-phenyl]-pyrimidin-2-yl}-(2,2,6,6-tetramethyl-piperidin-4-yl)-amine;
3-{4-[2-(2,2,6,6-tetramethyl-piperidin-4-ylamino)-pyrimidin-4-yl]-phenyl}-propan-1-ol;
{4-[4-(3-amino-propyl)-phenyl]-pyrimidin-2-yl}-(2,2,6,6-tetramethyl-piperidin-4-yl)-amine;
{4-[4-(3-methoxy-propyl)-phenyl]-pyrimidin-2-yl}-(2,2,6,6-tetramethyl-piperidin-4-yl)-amine;
4-{4-[2-(2,2,6,6-tetramethyl-piperidin-4-ylamino)-pyrimidin-4-yl]-phenyl}-butyronitrile;
{4-[4-(4-amino-butyl)-phenyl]-pyrimidin-2-yl}-(2,2,6,6-tetramethyl-piperidin-4-yl)-amine;
4-{4-[2-(2,2,6,6-tetramethyl-piperidin-4-ylamino)-pyrimidin-4-yl]-phenyl}-butan-2-one;
4-{4-[2-(2,2,6,6-tetramethyl-piperidin-4-ylamino)-pyrimidin-4-yl]-phenyl}-butan-2-ol;
{4-[4-(3-amino-butyl)-phenyl]-pyrimidin-2-yl}-(2,2,6,6-tetramethyl-piperidin-4-yl)-amine;
2-methyl-4-{4-[2-(2,2,6,6-tetramethyl-piperidin-4-ylamino)-pyrimidin-4-yl]-phenyl}-butyronitrile;
{4-[4-(2-amino-propyl)-phenyl]-pyrimidin-2-yl}-(2,2,6,6-tetramethyl-piperidin-4-yl)-amine;
2-{4-[2-(2,2,6,6-tetramethyl-piperidin-4-ylamino)-pyrimidin-4-yl]-phenoxymethyl}-benzonitrile;
{4-[2-(2,2,6,6-tetramethyl-piperidin-4-ylamino)-pyrimidin-4-yl]-phenoxy}-acetonitrile;
{4-[4-(2-imidazol-1-yl-ethoxy)-phenyl]-pyrimidin-2-yl}-(2,2,6,6-tetramethyl-piperidin-4-yl)-amine;
4-{4-[2-(2,2,6,6-tetramethyl-piperidin-4-ylamino)-pyrimidin-4-yl]-phenoxy}-butyronitrile;
{4-[4-(pyridin-4-ylmethoxy)-phenyl]-pyrimidin-2-yl}-(2,2,6,6-tetramethyl-piperidin-4-yl)-amine;
(4-indol-1-yl-pyrimidin-2-yl)-(2,2,6,6-tetramethyl-piperidin-4-yl)-amine;
[4-(4-methoxy-indol-1-yl)-pyrimidin-2-yl]-(2,2,6,6-tetramethyl-piperidin-4-yl)-amine;
1-{1-[2-(2,2,6,6-tetramethyl-piperidin-4-ylamino)-pyrimidin-4-yl]-1H-indol-3-yl}-ethanone;
[4-(5-methoxy-indol-1-yl)-pyrimidin-2-yl]-(2,2,6,6-tetramethyl-piperidin-4-yl)-amine;
1-[2-(2,2,6,6-tetramethyl-piperidin-4-ylamino)-pyrimidin-4-yl]-1H-indole-3-carbonitrile;
1-[2-(2,2,6,6-tetramethyl-piperidin-4-ylamino)-pyrimidin-4-yl]-1H-indole-3-carboxylic acid amide;
1-[2-(2,2,6,6-tetramethyl-piperidin-4-ylamino)-pyrimidin-4-yl]-1H-indole-4-carbonitrile;
1-[2-(2,2,6,6-tetramethyl-piperidin-4-ylamino)-pyrimidin-4-yl]-1H-indole-4-carboxylic acid amide;
[4-(1-methyl-indol-2-yl)-pyrimidin-2-yl]-(2,2,6,6-tetramethyl-piperidin-4-yl)-amine;
[4-(1H-indol-2-yl)-pyrimidin-2-yl]-(2,2,6,6-tetramethyl-piperidin-4-yl)-amine;
[4-(1H-indol-3-yl)-pyrimidin-2-yl]-(2,2,6,6-tetramethyl-piperidin-4-yl)-amine;
[4-(1-methyl-indol-3-yl)-pyrimidin-2-yl]-(2,2,6,6-tetramethyl-piperidin-4-yl)-amine;
[2-(2,2,6,6-tetramethyl-piperidin-4-ylamino)-pyrimidin-4-yl]-1H-indole-5-carbonitrile;
3-[2-(2,2,6,6-tetramethyl-piperidin-4-ylamino)-pyrimidin-4-yl]-1H-indole-6-carbonitrile;
[4-(5H-[1,3]dioxolo[4,5-f]indol-7-yl)-pyrimidin-2-yl]-(2,2,6,6-tetramethyl-piperidin-4-yl)-amine;
[4-(6-methoxy-1H-indol-3-yl)-pyrimidin-2-yl]-(2,2,6,6-tetramethyl-piperidin-4-yl)-amine;
3-[2-(2,2,6,6-tetramethyl-piperidin-4-ylamino)-pyrimidin-4-yl]-1H-indol-6-ol;
[4-(7-methoxy-1H-indol-3-yl)-pyrimidin-2-yl]-(2,2,6,6-tetramethyl-piperidin-4-yl)-amine;
3-[2-(2,2,6,6-tetramethyl-piperidin-4-ylamino)-pyrimidin-4-yl]-1H-indol-7-ol;
{4-[6-(2-amino-propyl)-1H-indol-3-yl]-pyrimidin-2-yl}-(2,2,6,6-tetramethyl-piperidin-4-yl)-amine
{6-methoxy-3-[2-(2,2,6,6-tetramethyl-piperidin-4-ylamino)-pyrimidin-4-yl]-indol-1-yl}-acetonitrile
[4-(7-fluoro-1H-indol-3-yl)-pyrimidin-2-yl]-(2,2,6,6-tetramethyl-piperidin-4-yl)-amine;
[4-(6-fluoro-1H-indol-3-yl)-pyrimidin-2-yl]-(2,2,6,6-tetramethyl-piperidin-4-yl)-amine;
[4-(1H-pyrrolo[2,3-b]pyridin-3-yl)-pyrimidin-2-yl]-(2,2,6,6-tetramethyl-piperidin-4-yl)-amine;
[4-(7-chloro-1H-indol-3-yl)-pyrimidin-2-yl]-(2,2,6,6-tetramethyl-piperidin-4-yl)-amine;
[4-(6-chloro-1H-indol-3-yl)-pyrimidin-2-yl]-(2,2,6,6-tetramethyl-piperidin-4-yl)-amine;
(2,2,6,6-tetramethyl-piperidin-4-yl)-[4-(6-trifluoromethyl-1H-indol-3-yl)-pyrimidin-2-yl]-amine;
[4-(7-methyl-1H-indol-3-yl)-pyrimidin-2-yl]-(2,2,6,6-tetramethyl-piperidin-4-yl)-amine;
2-methyl-4-{3-[2-(2,2,6,6-tetramethyl-piperidin-4-ylamino)-pyrimidin-4-yl]-1H-indol-6-yl}-butan-2-ol;
[4-(6,7-difluoro-1H-indol-3-yl)-pyrimidin-2-yl]-(2,2,6,6-tetramethyl-piperidin-4-yl)-amine;
2-methyl-4-{3-[2-(2,2,6,6-tetramethyl-piperidin-4-ylamino)-pyrimidin-4-yl]-1H-indol-7-yl}-butan-2-ol;
[4-(5,7-difluoro-1H-indol-3-yl pyrimidin-2-yl]-(2,2,6,6-tetramethyl-piperidin-4-yl)-amine;
{4-[6-(morpholine-4-sulfonyl)-1H-indol-3-yl]-pyrimidin-2-yl}-(2,2,6,6-tetramethyl-piperidin-4-yl)-amine;
[4-(5-fluoro-7-methyl-1H-indol-3-yl)-pyrimidin-2-yl]-(2,2,6,6-tetramethyl-piperidin-4-yl)-amine;
3-[2-(2,2,6,6-tetramethyl-piperidin-4-ylamino)-pyrimidin-4-yl]-1H-indole-6-sulfonic acid dimethylamide;
3-[2-(2,2,6,6-tetramethyl-piperidin-4-ylamino)-pyrimidin-4-yl]-1H-indole-7-carbonitrile;
[4-(7-nitro-1H-indol-3-yl)-pyrimidin-2-yl]-(2,2,6,6-tetramethyl-piperidin-4-yl)-amine;
3-[2-(2,2,6,6-tetramethyl-piperidin-4-ylamino)-pyrimidin-4-yl]-1H-indol-7-ylamine;
N-{3-[2-(2,2,6,6-tetramethyl-piperidin-4-ylamino)-pyrimidin-4-yl]-1H-indol-7-yl}-acetamide;
[4-(7-bromo-1H-indol-3-yl)-pyrimidin-2-yl]-(2,2,6,6-tetramethyl-piperidin-4-yl)-amine;
[4-(1H-pyrrolo[3,2-h]quinolin-3-yl)-pyrimidin-2-yl]-(2,2,6,6-tetramethyl-piperidin-4-yl)-amine;
morpholin-4-yl-{3-[2-(2,2,6,6-tetramethyl-piperidin-4-ylamino)-pyrimidin-4-yl]-1H-indol-6-yl}-methanone;

3-[2-(2,2,6,6-tetramethyl-piperidin-4-ylamino)-pyrimidin-4-yl]-1H-indole-7-sulfonic acid methylamide;
(5-aza-spiro[3.5]non-yl)-[4-(chloro-1H-indol-3-yl)-pyrimidin-2-yl]-amine;
[4-(7-chloro-1H-indol-3-yl)-pyrimidin-2-yl]-(2,2-dimethyl-piperidin-4-yl)-amine;
[4-(7-fluoro-1H-indol-3-yl)-pyrimidin-2-yl]-(2,2-dimethyl-piperidin-4-yl)-amine;
(1-aza-spiro[5.5]undec-4-yl)-[4-(7-fluoro-1H-indol-3-yl)-pyrimidin-2-yl]-amine;
trans-(2,6-dimethyl-piperidin-4-yl)-[4-(1H-indol-3-yl)-pyrimidin-2-yl]-amine;
[4-(7-chloro-1H-indol-3-yl)-pyrimidin-2-yl]-trans-(2,6-dimethyl-piperidin-4-yl)-amine;
trans-(2,6-dimethyl-piperidin-4-yl)-[4-(7-fluoro-1H-indol-3-yl)-pyrimidin-2-yl]-amine;
((2R,4R,6S)-2,6-dimethyl-piperidin-4-yl)-[4-(7-fluoro-1H-indol-3-yl)-pyrimidin-2-yl]-amine;
((2R,4S,6S)-2,6-dimethyl-piperidin-4-yl)-[4-(7-fluoro-1H-indol-3-yl)-pyrimidin-2-yl]-amine;
[4-(5-fluoro-1H-indol-3-yl)-pyrimidin-2-yl]-(2,2,6,6-tetramethyl-piperidin-4-yl)-amine;
[4-(6-chloro-5-fluoro-1H-indol-3-yl)-pyrimidin-2-yl]-(2,2,6,6-tetramethyl-piperidin-4-yl)-amine;
[4-(7-chloro-5-fluoro-1H-indol-3-yl)-pyrimidin-2-yl]-(2,2,6,6-tetramethyl-piperidin-4-yl)-amine;
[4-(6-chloro-7-fluoro-1H-indol-3-yl)-pyrimidin-2-yl]-(2,2,6,6-tetramethyl-piperidin-4-yl)-amine;
(E)-4-{5-fluoro-3-[2-(2,2,6,6-tetramethyl-piperidin-4-ylamino)-pyrimidin-4-yl]-1H-indol-6-yl}-2-methyl-but-3-en-2-ol;
(E)-3-{5-fluoro-3-[2-(2,2,6,6-tetramethyl-piperidin-4-ylamino-pyrimidin-4-yl]-1H-indol-6-yl}-acrylonitrile;
(E)-4-{5-fluoro-3-[2-(2,2,6,6-tetramethyl-piperidin-4-ylamino)-pyrimidin-4-yl]-1H-indol-7-yl}-2-methyl-but-3-en-2-ol;
(E)-3-{3-[2-(2,2,6,6-tetramethyl-piperidin-4-ylamino)-pyrimidin-4-yl]-1H-indol-6-yl}-acrylonitrile;
{4-[6-((E)-2-imidazol-1-yl-vinyl)-1H-indol-3-yl]-pyrimidin-2-yl}-(2,2,6,6-tetramethyl-piperidin-4-yl)-amine;
(E)-3-{3-[2-(2,2,6,6-tetramethyl-piperidin-4-ylamino)-pyrimidin-4-yl]-1H-indol-7-yl}-acrylonitrile;
(E)-N,N-dimethyl-3-{3-[2-(2,2,6,6-tetramethyl-piperidin-4-ylamino)-pyrimidin-4-yl]-1H-indol-7-yl}-acrylamide;
(E)-2-methyl-3-{3-[2-(2,2,6,6-tetramethyl-piperidin-4-ylamino)-pyrimidin-4-yl]-1H-indol-7-yl}-acrylonitrile;
4-{5-fluoro-3-[2-(2,2,6,6-tetramethyl-piperidin-4-ylamino)-pyrimidin-4-yl]-1H-indol-6-yl}-2-methyl-butan-2-ol;
3-{5-fluoro-3-[2-(2,2,6,6-tetramethyl-piperidin-4-ylamino)-pyrimidin-4-yl]-1H-indol-6-yl}-propionitrile;
3-{7-fluoro-3-[2-(2,2,6,6-tetramethyl-piperidin-4-ylamino)-pyrimidin-4-yl]-1H-indol-6-yl}-propionitrile;
4-{5-fluoro-3-[2-(2,2,6,6-tetramethyl-piperidin-4-ylamino)-pyrimidin-4-yl]-1H-indol-7-yl}-2-methyl-butan-2-ol;
3-{3-[2-(2,2,6,6-tetramethyl-piperidin-4-ylamino)-pyrimidin-4-yl]-1H-indol-6-yl}-propionitrile;
{4-[6-(2-imidazol-1-yl-ethyl)-1H-indol-3-yl]-pyrimidin-2-yl}-(2,2,6,6-tetramethyl-piperidin-4-yl)-amine;
3-{3-[2-(2,2,6,6-tetramethyl-piperidin-4-ylamino)-pyrimidin-4-yl]-1H-indol-7-yl}-propionitrile;
N,N-dimethyl-3-{3-[2-(2,2,6,6-tetramethyl-piperidin-4-ylamino)-pyrimidin-4-yl]-1H-indol-7-yl}-propionamide; and
2-methyl-3-{3-[2-(2,2,6,6-tetramethyl-piperidin-4-ylamino)-pyrimidin-4-yl]-1H-indol-7-yl}-propionitrile;
and a pharmaceutically-acceptable salt of any thereof.

4. A method for the treatment of conditions mediated by TNFα, selected from rheumatoid arthritis, arthritis chronica progrediente, arthritis deformans, hemolytic anaemia, aplastic anaemia, pure red cell anaemia, idiopathic thrombocytopenia, systemic lupus erythematosus, polychondritis, scleroderma, Wegener granulomatosis, dermatomyositis, chronic active hepatitis, myasthenia gravis, psoriasis, Steven-Johnson syndrome, idiopathic sprue, ulcerative colitis, Crohn+s disease, endocrine ophthalmopathy, Graves disease, sarcoidosis, multiple sclerosis, primary biliary cirrhosis, diabetes mellitus type I, uveitis, keratoconjuctivitis sicca, vernal keratoconjunctivitis, interstitial lung fibrosis, psoriatic arthritis, glomerulonephritis, asthma, bronchitis, pneumoconiosis, pulmonary emphysema, septic shock, meningitis, pneumonia, severe burns, and AIDS-related chachexia which method comprises administering to a patient in need of such treatment a therapeutically-effective and TNFα-inhibiting amount of a compound according to claim 1, or a pharmaceutically-acceptable salt thereof.

5. A pharmaceutical composition comprising a therapeutically-effective and TNF-α release-inhibiting amount of a compound according to claim 3, or a pharmaceutically-acceptable salt thereof, in association with a pharmaceutically-acceptable diluent or carrier.

6. A method for the treatment of conditions mediated by TNFα selected from rheumatoid arthritis, arthritis chronica progrediente, arthritis deformans, hemolytic anaemia, aplastic anaemia, pure red cell anaemia, idiopathic thrombocytopenia, systemic lupus erythematosus, polychondritis, scleroderma, Wegener granulomatosis, dermatomyositis, chronic active hepatitis, myasthenia gravis, psoriasis, Steven-Johnson syndrome, idiopathic sprue, ulcerative colitis, Crohn's disease, endocrine ophthalmopathy, Graves disease, sarcoidosis, multiple sclerosis, primary biliary cirrhosis, diabetes mellitus type I, uveitis, keratoconjuctivitis sicca, vernal keratoconjunctivitis, interstitial lung fibrosis, psoriatic arthritis, glomerulonephritis, asthma, bronchitis, pneumoconiosis, pulmonary emphysema, septic shock, meningitis, pneumonia, severe burns, and AIDS-related chachexia, which method comprises administering to a patient in need of such treatment a therapeutically-effective and TNFα-inhibiting amount of a compound according to claim 3, or a pharmaceutically-acceptable salt thereof.

* * * * *

UNITED STATES PATENT AND TRADEMARK OFFICE
CERTIFICATE OF CORRECTION

PATENT NO. : 7,615,562 B2  Page 1 of 1
APPLICATION NO. : 10/552317
DATED : November 10, 2009
INVENTOR(S) : Bollbuck et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 796 days.

Signed and Sealed this

Nineteenth Day of October, 2010

David J. Kappos
*Director of the United States Patent and Trademark Office*